US008183239B2

(12) United States Patent
Bonaventure et al.

(10) Patent No.: US 8,183,239 B2
(45) Date of Patent: May 22, 2012

(54) SUBSTITUTED PIPERAZINES AND PIPERIDINES AS MODULATORS OF THE NEUROPEPTIDE Y2 RECEPTOR

(75) Inventors: Pascal Bonaventure, San Diego, CA (US); Nicholas I. Carruthers, Poway, CA (US); Wenying Chai, San Diego, CA (US); Curt A. Dvorak, San Diego, CA (US); Jill A. Jablonowski, San Diego, CA (US); Dale A. Rudolph, San Diego, CA (US); Mark Seierstad, San Diego, CA (US); Chandravadan R. Shah, San Diego, CA (US); Devin M. Swanson, La Jolla, CA (US); Victoria D. Wong, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 301 days.

(21) Appl. No.: 11/553,556

(22) Filed: Oct. 27, 2006

(65) Prior Publication Data

US 2007/0100141 A1    May 3, 2007

Related U.S. Application Data

(60) Provisional application No. 60/731,773, filed on Oct. 31, 2005.

(51) Int. Cl.
| | |
|---|---|
| *A61K 31/495* | (2006.01) |
| *A61K 31/496* | (2006.01) |
| *A61K 31/5377* | (2006.01) |
| *C07D 211/34* | (2006.01) |
| *C07D 211/58* | (2006.01) |
| *C07D 213/56* | (2006.01) |
| *C07D 295/15* | (2006.01) |
| *C07D 401/04* | (2006.01) |
| *A61K 31/451* | (2006.01) |
| *A61K 31/454* | (2006.01) |
| *C07D 401/12* | (2006.01) |
| *C07D 417/12* | (2006.01) |

(52) U.S. Cl. ........... 514/235.8; 514/253.01; 514/253.13; 514/254.03; 514/254.1; 514/254.11; 514/255.03; 544/121; 544/360; 544/364; 544/367; 544/372; 544/374; 544/377; 544/379; 544/393; 544/238; 544/295; 544/322; 546/194; 546/208; 546/210; 546/234; 546/257; 546/265; 546/276.7; 546/209; 548/453

(58) Field of Classification Search ........... 544/360, 544/393
See application file for complete search history.

(56) References Cited

U.S. PATENT DOCUMENTS

| | | | | |
|---|---|---|---|---|
| 4,616,086 A | * | 10/1986 | Witte et al. | 544/383 |
| 5,177,087 A | * | 1/1993 | Goto et al. | 514/331 |
| 6,552,022 B1 | | 4/2003 | Daugan | |
| 6,777,414 B1 | | 8/2004 | Ohkura et al. | |
| 6,906,073 B2 | * | 6/2005 | Du Bois et al. | 514/252.13 |
| 7,317,025 B2 | | 1/2008 | Carruthers et al. | |
| 2007/0043079 A1 | | 2/2007 | Habashita et al. | |
| 2007/0099934 A1 | | 5/2007 | Lieven et al. | |
| 2007/0191383 A1 | | 8/2007 | Meerpoel et al. | |
| 2007/0249620 A1 | | 10/2007 | Kurata et al. | |

FOREIGN PATENT DOCUMENTS

| | | |
|---|---|---|
| EP | 1 161 862 A2 | 1/2006 |
| WO | WO 93/14077 A1 | 7/1993 |
| WO | WO 01/64645 A2 | 9/2001 |
| WO | WO 02/20501 A2 | 3/2002 |
| WO | WO 02/42271 A2 | 5/2002 |
| WO | WO 02/081460 A1 | 10/2002 |
| WO | WO 02/083137 A1 | 10/2002 |
| WO | WO 2004/017969 A1 | 3/2004 |
| WO | WO 2004/092136 A1 | 10/2004 |
| WO | WO 2005/030754 A1 | 4/2005 |
| WO | WO 2005/085226 A1 | 9/2005 |

OTHER PUBLICATIONS

Testa et al. Pure Appl. Chem. vol. 76, pp. 907-914 (2004).*

(Continued)

*Primary Examiner* — Emily Bernhardt
(74) *Attorney, Agent, or Firm* — Samuel M. Kais

(57) ABSTRACT

The invention provides novel non-peptidic NPY Y2 receptor inhibitors useful in treating or preventing: anxiolytic disorders or depression; injured mammalian nerve tissue; conditions responsive to treatment through administration of a neurotrophic factor; neurological disorders; bone loss; substance related disorders; sleep/wake disorders; cardiovascular disease; obesity; or an obesity-related disorder. Compounds of the invention are also useful in modulating endocrine functions, particularly endocrine functions controlled by the pituitary and hypothalamic glands, and are therefore useful in the treatment or prevention of inovulation and infertility. The compounds of the present invention are of the formula (I)

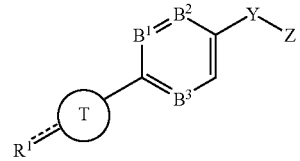

where Ring T is a heterocycloalkyl ring selected from the group consisting of:

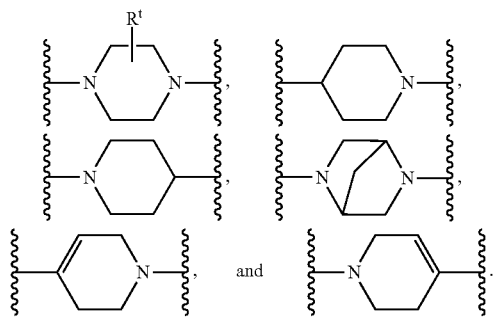

35 Claims, No Drawings

OTHER PUBLICATIONS

Bagshawe et al., Drug Dev Res 1995 vol. 34 pp. 220-230.
Baldock, P. A. J. Clin. Invest. 2002, vol. 109 pp. 915-921.
Batterham, R. L. et al Nature 2002 vol. 418, pp. 650-654.
Berge et al., J. Pharm Sci 1977 vol. 66 pp. 1-19.
Bertolini et al J Med Chem 1997 vol. 40 pp. 2011-2016.
Bodor et al., Adv Drug Res 1984 vol. 13 pp. 224-331.
Bungaard et al., Design of Prodrugs 1985 Ed. H. Bungaard Elsevier.
Castan, I. et a Endocrinology 1992 vol. 131(4) pp. 1970-1976.
Clark, J. T. et al.Endocrinology 1984 vol. 115(1) pp. 427-429.
Colmers "The Biology of Neuropeptide and Related Peptides" Colmers W.F. and Wahlestedt C. Eds. Humana Press Totowa N.J. 1993.
Cooper Jr. Bloom F.E. Roth R.H. Eds. "The Biochemical Basis of Neuropharmacology" $6^{th}$ Ed. Oxford University Press, New York, N.Y. 1991.
Doods, H., et al. Eur. J. Pharmacol. 1999 vol. 384 pp. R3-R5.
Epstein, J.W. et al. J. Med. Chem. 1981 vol. 24 pp. 481-490.
Fleisher et al. Adv Drug Deliv Rev 1996 vol. 19 pp. 115-130.
Flood, J. F. et al. Brain Res. 1987 vol. 421 pp. 280-290.
Fuhlendorff, J. U. et al. Proc. Natl. Acad. Sci. U.S.A. 1990 vol. 8 pp. 182-186.
Gehlert, D. et al.Curr. Pharm. Des. 1995 vol. 1(3) pp. 295-304.
Gerald, C. et al. Nature 1996 vol. 382 pp. 168-171.
Grouzmann, E. et al. J. Biol. Chem. 1997 vol. 272 pp. 7699-7706.
Grundemar, L. et al. J. Pharmacol. Exp. Ther. 1991 vol. 258 pp. 633-638.
Heilig, M. et al. Eur. J. Pharmacol. 1988, vol. 147 pp. 465-467.
Heilig, M. et al. Psychopharmacology 1989 vol. 98(4) pp. 524-529.
Heilig, M. et al. Regul. Pept. 1992 vol. 41 pp. 61-69.
Heilig, M. et al. Neuropsychopharmacology 1993 vol. 8(4) pp. 357-363.
Herzog, H. et al.Drug News & Perspectives 2002 vol. 15 pp. 506-510.
Kaga, T. et al. Peptides 2001 vol. 22 pp. 501-506.
Kalra, S.P. and W.R. Crowley. Front. Neuroendrocrinol. 1992 vol. 13(1) pp. 1-46.
Laburthe, M. et al. Endocrinology 1986 vol. 118(5) pp. 1910-1917.
Larhammar, D. et al. J. Biol. Chem. 1992 vol. 267 pp. 10935-10938.
Larsen et al. "Design and Application of Prodrugs, Drug Design, and Development" Krogsgaard-Larsen et al. Eds., Harwood Academic Publishers 1991.
Levine, A. S. et al. Peptides 1984 vol. 5 pp. 1025-1029.
Lundberg, J. M. et al. Trends Pharmacol. Sci. 1996, vol. 17 pp. 301-304.
Morris, M. J. et. al. J. Auton. Nerv. Syst. 1986 vol. 17(2) pp. 143-149.
NIH "Clinical Guidelines on Identification and Evaluation and Treatment of Overweight and Obesity in Adults" 1998.
Robinson et al., J. Med. Chem, 1996, vol. 39 pp. 10.
Saudek, V. et al Biochemistry 1990 vol. 29(19) pp. 4509-4519.
Shan et al., J Pharm Sci 1997 vol. 86(7) pp. 765-767.
Stahl Vermuth Eds. "Handbook of Pharmaceutical Salts Properties Selections and Use" Wiley-VCH and VHCA Zurich 2002.
Stanley, B. G. et al. Proc. Nat. Acad. Sci. U.S.A. 1985 vol. 82 pp. 3940-3943.
Stanley, B. G. et al. Life Sci. 1984 vol. 35(26) pp. 2635-2642.
Sweeney, J.B. et al. Tetrahedron 2002 vol. 58 pp. 10113-10126.
Tatemoto, K. et al. Nature 1982 vol. 296 pp. 659-660.
Thiele et al. Nature 1998 vol. 396 pp. 366-369.
Thiele, T.E. et al. Neuropeptides 2004 vol. 38(4) pp. 235-243.
Thiele, T.E. et al. Peptides 2004 vol. 25(6) pp. 975-983.
Thorsell, A. et al. Neurosci. Lett. 2002 vol. 332(1) pp. 1-4.
Wahlestedt, C. et al. Regul. Pept. 1986 vol. 13(3-4) pp. 307-318.
Weinberg, D. H. et al. J. Biol. Chem. 1996 vol. 271 pp. 16435-16438.
Widdowson, P.S. et al. J. Neurochem. 1992 vol. 59(1) pp. 73-80.
PCT Search Report for PCT/US2006/041940, dated Feb. 26, 2007.

* cited by examiner

SUBSTITUTED PIPERAZINES AND PIPERIDINES AS MODULATORS OF THE NEUROPEPTIDE Y2 RECEPTOR

CROSS REFERENCE TO RELATED APPLICATIONS

This application claims the benefit of U.S. Provisional Application 60/731,773 filed on Oct. 31, 2005, which is incorporated by reference herein in its entirety.

FIELD OF THE INVENTION

The invention provides novel non-peptidic NPY Y2 receptor inhibitors useful in treating or preventing: anxiolytic disorders and depression; injured mammalian nerve tissue; a condition responsive to treatment through administration of a neurotrophic factor; a neurological disorder; bone loss; substance related disorders; sleep/wake disorders; cardiovascular disease; obesity; or an obesity-related disorder. Compounds of the invention are also useful in modulating endocrine functions; particularly endocrine functions controlled by the pituitary and hypothalamic glands, and may be used to treat inovulation and infertility.

BACKGROUND OF THE INVENTION

Regulation and function of the mammalian central nervous system is governed by a series of interdependent receptors, neurons, neurotransmitters, and proteins. The neurons play a vital role in this system, for when externally or internally stimulated, they react by releasing neurotransmitters that bind to specific proteins. Common examples of endogenous small molecule neurotransmitters such as acetylcholine, adrenaline, norepinephrine, dopamine, serotonin, glutamate, and gamma-aminobutyric acid are well known, as are the specific receptors that recognize these compounds as ligands ("The Biochemical Basis of Neuropharmacology", Sixth Edition, Cooper, J. R.; Bloom, F. E.; Roth, R. H. Eds., Oxford University Press, New York, N.Y. 1991).

In addition to the endogenous small molecule neurotransmitters, there is increasing evidence that neuropeptides play an integral role in neuronal operations. Neuropeptides are now believed to be co-localized with perhaps more than one-half of the 100 billion neurons of the human central nervous system. In addition to being found in humans, neuropeptides have been discovered in a number of animal species. In some instances, the composition of these peptides is remarkably homogenous among species. This finding suggests that the function of neuropeptides is vital and has been impervious to evolutionary changes. Furthermore, neuropeptides, unlike small molecule neurotransmitters, are typically synthesized by the neuronal ribosome. In some cases, the active neuropeptides are produced as part of a larger protein that is enzymatically processed to yield the active substance. Based upon these differences, compared to small molecule neurotransmitters, neuropeptide-based strategies may offer novel therapies for the treatment of CNS diseases and disorders. Specifically, agents that affect the binding of neuropeptides to their respective receptors or that ameliorate responses that are mediated by neuropeptides are potential therapies for diseases associated with neuropeptides.

There are a number of afflictions that are associated with the complex interdependent system of receptors and ligands within the central nervous system; these include neurodegenerative diseases, affective disorders such as anxiety, depression, pain and schizophrenia, and affective conditions that include a metabolic component, namely obesity. Such conditions, disorders, and diseases have been treated with small molecules and peptides that modulate neuronal responses to endogenous neurotransmitters.

One example of this class of neuropeptides is neuropeptide Y (NPY). NPY was first isolated from porcine brain (Tatemoto, K. et al. Nature 1982, 296, 659) and was shown to be structurally similar to other members of the pancreatic polypeptide (PP) family such as peptide YY (PYY), which is primarily synthesized by endocrine cells in the gut, and pancreatic polypeptide, which is synthesized by the pancreas. NPY is a single peptide protein that consists of thirty-six amino acids containing an amidated C-terminus. Like other members of the pancreatic polypeptide family, NPY has a distinctive conformation that consists of an N-terminal polyproline helical region and an amphiphilic alpha-helix joined by a characteristic PP-fold (Vladimir, S. et al. Biochemistry 1990, 20, 4509). Furthermore, NPY sequences from a number of animal species have been elucidated and all show a high degree of amino acid homology to the human protein (more than 94% in rat, dog, rabbit, pig, cow, sheep) (see Larhammar, D. in "The Biology of Neuropeptide Y and Related Peptides", Colmers, W. F. and Wahlestedt, C. Eds., Humana Press, Totowa, N.J. 1993).

Endogenous receptor proteins that bind NPY and related peptides as ligands have been identified and distinguished, and several such proteins have been cloned and expressed. Five different receptor subtypes [Y1, Y2, Y4 (PP), Y5, Y6 (a pseudogene in human)] are recognized based upon binding profile, pharmacology, and cDNA sequence (Kaga, T. et al. Peptides 2001, 22, 501-506; Wahlestedt, C. et al. Ann. N.Y. Acad. Sci. 1990, 611, 7; Larhammar, D. et al. J. Biol. Chem. 1992, 267, 10935; Wahlestedt, C. et al. Regul. Pept. 1986, 13, 307; Fuhlendorff, J. U. et al. Proc. Natl. Acad. Sci. U.S.A. 1990, 87, 182; Grundemar, L. et al. J. Pharmacol. Exp. Ther. 1991, 258, 633; Laburthe, M. et al. Endocrinology 1986, 118, 1910; Castan, I. et al. Endocrinology 1992, 131, 1970; Gerald, C. et al. Nature 1996, 382, 168; Weinberg, D. H. et al. J. Biol. Chem. 1996, 271, 16435; Gehlert, D. et al. Curr. Pharm. Des. 1995, 1, 295; Lundberg, J. M. et al. Trends Pharmacol. Sci. 1996, 17, 301). All NPY receptor proteins belong to the family of so-called G-protein coupled receptors (GPCRs).

NPY itself is the archetypal substrate for the NPY receptors and its binding can elicit a variety of pharmacological and biological effects in vitro and in vivo. When administered to the brain of live animals (intracerebroventricularly (icv) or into the amygdala), NPY produced anxiolytic effects in established animal models of anxiety such as the elevated plus-maze, Vogel punished drinking, and Geller-Seifter's bar-pressing conflict paradigms (Heilig, M. et al. Psychopharmacology 1989, 98, 524; Heilig, M. et al. Regul. Pept. 1992, 41, 61; Heilig, M. et al. Neuropsychopharmacology 1993, 8, 357). Thus, compounds that mimic NPY are postulated to be useful for the treatment of anxiolytic disorders.

The immunoreactivity of NPY is notably decreased in the cerebrospinal fluid of patients with major depression and those of suicide victims (Widdowson, P. S. et al. J. Neurochem. 1992, 59, 73), and rats treated with tricyclic antidepressants displayed significant increases of NPY relative to a control group (Heilig, M. et al. Eur. J. Pharmacol. 1988, 147, 465). These findings suggest that an inadequate NPY response may play a role in some depressive illnesses, and that compounds that regulate the NPY-ergic system may be useful for the treatment of depression.

It is known that the anxiolytic properties of NPY are mediated through postsynaptic Y1 receptors, whereas presynaptic Y2 receptors negatively control the release of NPY and other cotransmitters (e.g. GABA). Consequently, antagonism of the Y2 receptor may lead to enhanced GABAergic and NPY-ergic effects and Y2 receptor antagonists should prove useful in the treatment of depression and anxiety.

NPY improved memory and performance scores in animal models of learning (Flood, J. F. et al. Brain Res. 1987, 421, 280) and therefore may serve as a cognition enhancer for the treatment of neurodegenerative diseases such as Alzheimer's Disease (AD) as well as AIDS-related and senile dementia.

Elevated plasma levels of NPY were present in animals and humans experiencing episodes of high sympathetic nerve activity such as surgery, newborn delivery, and hemorrhage (Morris, M. J. et. al. J. Auton. Nerv. Syst. 1986, 17, 143). Thus, chemical substances that alter the NPY-ergic system may be useful for alleviating migraine, pain, and the condition of stress.

NPY also mediates endocrine functions such as the release of luteinizing hormone (LH) in rodents (Kalra, S. P. et. al. Front. Neuroendrocrinol. 1992, 13, 1). Since LH is vital for mammalian ovulation, a compound that mimics the action of NPY could be useful for the treatment of infertility, particularly in women with so-called luteal phase defects.

NPY is a powerful stimulant of food intake; as little as one-billionth of a gram, when injected directly into the CNS, caused satiated rats to overeat (Clark, J. T. et al. Endocrinology 1984, 115, 427; Levine, A. S. et al. Peptides 1984, 5, 1025; Stanley, B. G. et al. Life Sci. 1984, 35, 2635; Stanley, B. G. et al. Proc. Nat. Acad. Sci. U.S.A. 1985, 82, 3940). Thus NPY is orexigenic in rodents but not anxiogenic when given intracerebroventricularly and so antagonism of neuropeptide receptors may be useful for the treatment of diabetes and eating disorders such as obesity, anorexia nervosa, and bulimia nervosa.

Recently, a key role of presynaptic hypothalamic Y2 receptor was suggested in central coordination of energy homeostasis and bone mass regulation (Herzog, H. et al. Drug News & Perspectives 2002, 15, 506-510). Studies analyzing Y2 receptor knockout mice have started to unravel some of the individual functions of this receptor subtype. Y2 receptor knockout mice showed a reduced body weight despite an increase in food intake, possibly due to the lack of the feedback inhibition of the postprandially released $PYY_{3-36}$ (Batterham, R. L. et al. Nature 2002, 418, 650-654). The Y2 receptor knockout mice also showed a significant increase in bone formation (Baldock, P. A. J. Clin. Invest. 2002, 109, 915-921). Specific deletion of the Y2 receptor in the hypothalamus in adult conditional Y2 receptor knockout mice also caused an increase in bone formation.

A direct link between NPY signaling and regulation of ethanol consumption was suggested by the demonstration that NPY over-expression in mice reduced ethanol self-administration, whereas the knockout of NPY expression increased ethanol self-administration (Thiele et al. Nature 1998, 396, 366-369). Studies have also indicates that NPY Y2 is involved in the neurobiological responses to ethanol and other drugs of abuse. Thiele and coworkers (Neuropeptides, 2004, 38(4), 235-243; Peptides 2004, 25(6), 975-983) described the low ethanol consumption of Y2 receptor knockout mice, as well as their increased voluntary water consumption. Recently, it has been demonstrated that icv administration of BIIE0246, a selective NPY Y2 antagonist, dose dependently reduced ethanol self-administration in rats (Thorsell et al. Neurosci. Lett. 2002, 332, 1-4). Therefore, modulators of NPY Y2 may allow for the treatment of alcohol and drug abuse.

Additionally, NPY Y2 antagonists have been suggested for the prevention of cardiovascular disease, for example, sudden death due to cardiac arrhythmias, post-myocardial infarction, or heart failure (See: Intl. Pat. Appl. Publ. WO 02/083137, Oct. 24, 2002).

Grouzmann and coworkers described a peptide-based ligand, T4-[NPY 33-36], which showed considerable affinity ($IC_{50}$=67 nM) for the NPY Y2 receptor (Grouzmann, E., et al. J. Biol. Chem. 1997, 272, 7699-7706). BIIE0246 also bound to the NPY Y2 receptor with significant affinity ($IC_{50}$=3.3 nM) (Doods, H., et al. Eur. J. Pharmacol. 1999, 384, R3-R5). However, the therapeutic potential for these compounds is limited due to their peptide-like composition and elevated molecular weight.

Thus, there remains a need for potent NPY Y2 modulators with desirable pharmaceutical properties.

SUMMARY OF THE INVENTION

Certain substituted piperazine and piperidine derivatives have now been found to have NPY Y2-modulating activity.

Thus, in one general aspect, the invention relates to compounds of the following Formula (I):

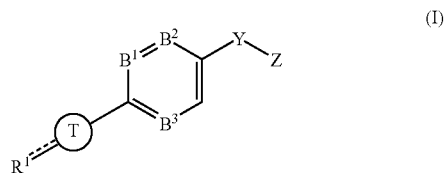

wherein $B^1$, $B^2$, and $B^3$ are each independently CH, $CR^2$, or N, with the proviso that $B^2$ and $B^3$ are not both N;

where each $R^2$ is independently —$C_{1-4}$alkyl, -ethynyl, —$C_{3-8}$cycloalkyl, —$OC_{1-4}$ alkyl, halo, —$CF_3$, or —CN;

Ring T is a heterocycloalkyl ring selected from the group consisting of:

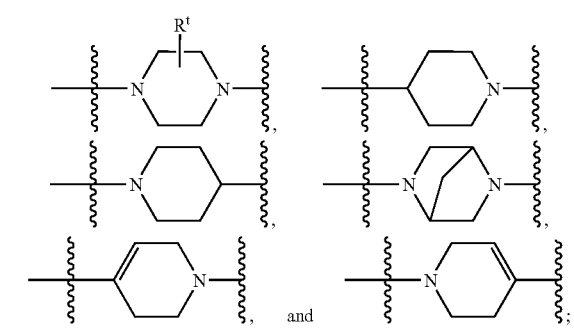

where $R^t$ is —H, —$C_{1-4}$alkyl, or —$CO_2C_{1-4}$alkyl;

$R^1$ is

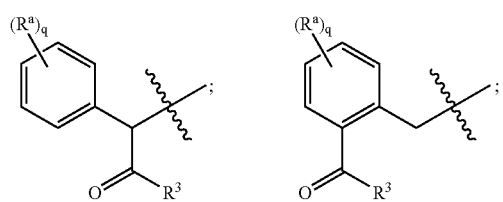

-continued

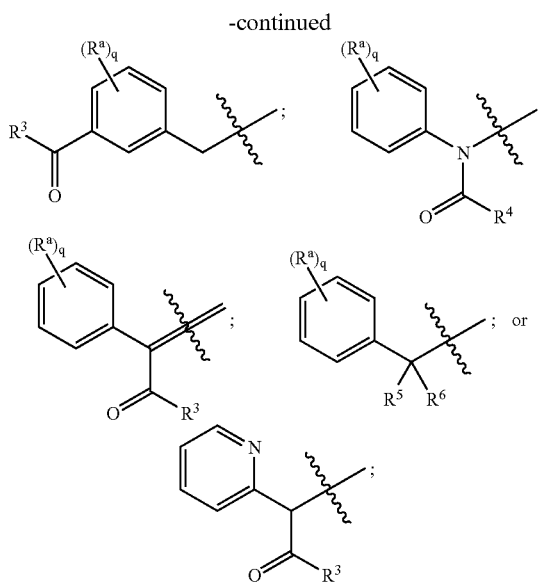

where q is 0, 1, 2, or 3;
each $R^a$ is independently —$C_{1-4}$alkyl, —$C_{3-8}$cycloalkyl, —$OC_{1-4}$alkyl, —OH, halo, —$NO_2$, —$N(R^u)R^v$, —$CF_3$, —$OCF_3$, —C(O)—$C_{1-4}$alkyl, —$C(O)OC_{1-4}$alkyl, —CN, —$S(O)_{1-2}$—$C_{1-6}$alkyl, —$N(R^u)$—$S(O)_{1-2}$—$C_{1-6}$alkyl, —$S(O)_{1-2}$—$N(R^u)R^v$, or a 4- to 7-membered monocyclic heterocycloalkyl, or two adjacent $R^a$ substituents taken together form —$O(CH_2)_{1-2}$—O—;
where $R^u$ and $R^v$ are each independently —H or —$C_{1-4}$alkyl;
$R^3$ is selected from the group consisting of:
  i) —$OC_{1-4}$alkyl, —$OC_{3-4}$alkenyl, —O-benzyl, —O-phenyl, —$NHNH_2$, phenyl;
  ii) —$NR^bR^c$, where $R^b$ is —H or —$C_{1-4}$alkyl and $R^c$ is a —$C_{1-4}$alkyl, —$C_{3-4}$alkenyl, monocyclic cycloalkyl optionally fused to phenyl, or monocyclic heterocycloalkyl group, each optionally substituted with $R^d$;
    where $R^d$ is —$C_{1-4}$alkyl, —$OC_{1-4}$alkyl, —OH, —$CF_3$, —$OCF_3$, halo, —$NO_2$, —$N(R^e)R^f$, —C(O)—$C_{1-4}$alkyl, —C(O)phenyl, —$C(O)OC_{1-4}$alkyl, —CN, —$S(O)_{1-2}$—$C_{1-6}$alkyl, —$N(R^e)$—$S(O)_{1-2}$—$C_{1-6}$alkyl, or —$S(O)_{1-2}$—$N(R^e)R^f$, or a 4- to 7-membered monocyclic heterocycloalkyl group optionally substituted with —$C_{1-4}$alkyl, fluoro, or —$CF_3$;
    where $R^e$ is —H or —$C_{1-4}$alkyl and $R^f$ is —$C_{1-4}$alkyl;
  iii) —$NR^gR^h$ where $R^g$ is —H or —$C_{1-4}$alkyl and $R^h$ is —$(CH_2)_{0-2}$-phenyl or —$(CH_2)_{0-2}$-(monocyclic heteroaryl);
    where each phenyl or heteroaryl is optionally substituted with $R^i$;
    $R^i$ is —$C_{1-4}$alkyl, —$OC_{1-4}$alkyl, —OH, —$CF_3$, —$OCF_3$, halo, —CN, or —$NR^jR^k$;
      where $R^j$ and $R^k$ are independently —H or —$C_{1-4}$alkyl, or $R^j$ and $R^k$ taken together with their nitrogen of attachment form a 4- to 7-membered monocyclic heterocycloalkyl; and
  iv) a nitrogen-linked 4- to 7-membered monocyclic heterocycloalkyl, optionally substituted with —$C_{1-4}$alkyl, —$OC_{1-4}$alkyl, —OH, —$CF_3$, —$OCF_3$, halo, —CN, —C(O)—$C_{1-4}$alkyl, —$C(O)OC_{1-4}$alkyl, or —$NR^jR^k$;

$R^4$ is —$C_{1-8}$alkyl, phenyl, or monocyclic heteroaryl, where each phenyl or heteroaryl is optionally substituted with —$C_{1-4}$alkyl, —$C_{3-8}$cycloalkyl, —$OC_{1-4}$alkyl, —OH, halo, —$NO_2$, —$N(R^w)R^x$, —$CF_3$, —$C(O)OC_{1-4}$alkyl, or —CN;
  where $R^w$ and $R^x$ are each independently —H or —$C_{1-4}$alkyl;
$R^5$ is —H or —$C_{1-4}$alkyl; and
$R^6$ is —H, —OH, —CN, or —$CH_2OH$;
Y is selected from the group consisting of —CH(OH)—, —C(O)—, —$CH_2C(O)$—, —C(=N—OH)—, —$CO_2$—, —$C(O)N(R^L)$—, —$CH_2C(O)N(R^L)$—, —$N(R^L)$—, —$N(R^L)C(O)$—, —$N(R^y)C(O)$—, —$CH_2N(R^L)C(O)$—, —$N(R^L)C(O)N(R^L)$—, —$N(R^L)SO_2$—, —$N(SO_2C_{1-4}$alkyl)$SO_2$—, —$N(R^L)SO_2N(R^L)$—, —$N(R^z)SO_2NH$—, and —$N(R^L)SO_2N(R^L)CO_2$—;
  where each $R^L$ is —H, —$C_{1-4}$alkyl, or phenyl; or, alternatively, two $R^L$ groups taken together form —$CH_2CH_2$—;
  $R^y$ and Z together form —$(CH_2)_3$— or —$(CH_2)_4$—, optionally substituted with —$C_{1-4}$alkyl; and
  $R^z$ and Z together form —$(CH_2)_2$— or —$(CH_2)_3$—, each optionally substituted with —$C_{1-4}$alkyl;
Z is selected from the group consisting of:
  a) RingA, where RingA is phenyl, optionally mono-, di-, or tri-substituted with $R^m$;
    where each $R^m$ is independently selected from the group consisting of —$C_{1-6}$alkyl, —$C_{1-6}$alkyl-OH, —$CF_3$, —$C_{2-6}$alkenyl, —$C_{2-6}$alkynyl, —$C_{3-8}$cycloalkyl, —CN, —$NO_2$, —$N(R^n)R^o$, —$C(O)C_{1-6}$alkyl, —C(O)OH, —$C(O)OC_{1-6}$alkyl, —$C(O)N(R^n)R^o$, —S—$C_{1-6}$alkyl, —$S(O)_{1-2}$—$C_{1-6}$alkyl, —$SCF_3$, halo, —OH, —$OC_{1-6}$alkyl, —$OCF_3$, —$OC_{3-6}$alkenyl, and —$OC_{3-6}$alkynyl;
    where $R^n$ and $R^o$ are each independently —H or —$C_{1-6}$alkyl;
  b) RingB, where RingB is monocyclic or fused bicyclic heteroaryl, optionally mono-, di-, or tri-substituted with $R^m$;
  c) RingC, where RingC is heterocycloalkyl, optionally mono- or di-substituted with —$C_{1-4}$alkyl, —$C_{3-8}$cycloalkyl, halo, phenyl, or pyridyl;
  d) RingD, where RingD is monocyclic cycloalkyl, optionally substituted with —OH, halo, or —$C_{1-4}$alkyl, and optionally fused to phenyl;
  e) —$C(R^q)_2$-RingA, —$C(R^q)_2$-RingB, —$CH_2$-RingC, —$CH_2$-RingD;
    where each $R^q$ is —H or —$C_{1-4}$alkyl, or two $R^q$ substituents taken together form a $C_{3-6}$cycloalkyl;
  f) —$C_{1-8}$alkyl, optionally substituted with —OH, halo, or —$CF_3$;
  g) -ethyl substituted with RingA, RingB, monocyclic heterocycloalkyl, or —$N(R^r)R^s$, and optionally further substituted with —OH or —$CF_3$;
    where $R^r$ and $R^s$ are each independently —H or —$C_{1-4}$alkyl;
  h) —CH=CH-RingA, —CH=CH-RingB; and
  i) bicyclo[2.2.1]heptan-2-yl;
or a pharmaceutically acceptable salt, pharmaceutically acceptable prodrug, or pharmaceutically active metabolite of such compound.

In another general aspect, the invention relates to compounds of the following Formula (II):

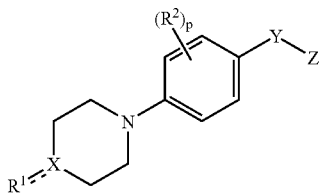

(II)

wherein
1) X is N or CH and $R^1$ is

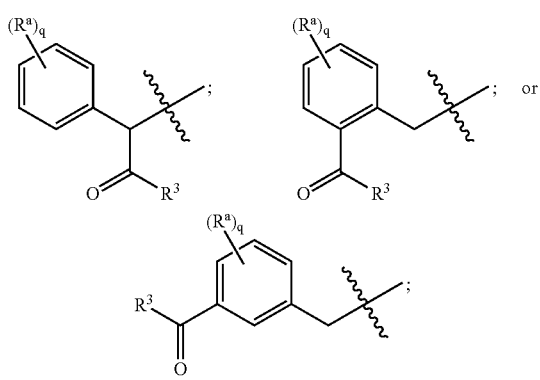

2) X is CH and $R^1$ is

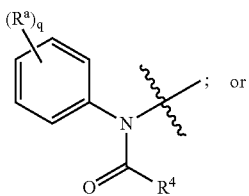

3) X is C and $R^1$ is

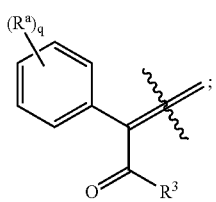

where for each of 1)-3),
q is 0, 1, 2, or 3;
each $R^a$ is independently —$C_{1-4}$alkyl, —$C_{3-8}$cycloalkyl, —$OC_{1-4}$alkyl, —OH, halo, —$NO_2$, —N(R$^u$)R$^v$, —$CF_3$, —C(O)—$C_{1-4}$alkyl, —C(O)O$C_{1-4}$alkyl, —CN, —S(O)$_{1-2}$—$C_{1-6}$alkyl, —N(R$^u$)—S(O)$_{1-2}$—$C_{1-6}$alkyl, —S(O)$_{1-2}$—N(R$^u$)R$^v$, or a 4- to 7-membered monocyclic heterocycloalkyl, or two adjacent $R^a$ substituents taken together form —O(CH$_2$)$_{1-2}$—O—;
where $R^u$ and $R^v$ are each independently —H or —$C_{1-4}$alkyl;
$R^3$ is selected from the group consisting of:
i) —$OC_{1-4}$alkyl, —$OC_{3-4}$alkenyl, —O-benzyl, —O-phenyl;
ii) —NR$^b$R$^c$, where $R^b$ is —H or —$C_{1-4}$alkyl and $R^c$ is a —$C_{1-4}$alkyl, —$C_{3-4}$alkenyl, monocyclic cycloalkyl optionally fused to phenyl, or monocyclic heterocycloalkyl group, each optionally substituted with $R^d$;
where $R^d$ is —$C_{1-4}$alkyl, —$OC_{1-4}$alkyl, —OH, —$CF_3$, —$OCF_3$, halo, —$NO_2$, —N(R$^e$)R$^f$, —C(O)—$C_{1-4}$alkyl, —C(O)phenyl, —C(O)O$C_{1-4}$alkyl, —CN, —S(O)$_{1-2}$—$C_{1-6}$alkyl, —N(R$^e$)—S(O)$_{1-2}$—$C_{1-6}$alkyl, or —S(O)$_{1-2}$—N(R$^e$)R$^f$, or a 4- to 7-membered monocyclic heterocycloalkyl group optionally substituted with —$C_{1-4}$alkyl, fluoro, or —$CF_3$;
where $R^e$ is —H or —$C_{1-4}$alkyl and $R^f$ is —$C_{1-4}$alkyl;
iii) —NR$^g$R$^h$, where $R^g$ is —H or —$C_{1-4}$alkyl and $R^h$ is —(CH$_2$)$_{0-2}$-phenyl or —(CH$_2$)$_{0-2}$-(monocyclic heteroaryl);
where each phenyl or heteroaryl is optionally substituted with $R^i$;
$R^i$ is —$C_{1-4}$alkyl, —$OC_{1-4}$alkyl, —OH, —$CF_3$, —$OCF_3$, halo, —CN, or —NR$^j$R$^k$;
where $R^j$ and $R^k$ are independently —H or —$C_{1-4}$alkyl, or $R^j$ and $R^k$ taken together with their nitrogen of attachment form a 4- to 7-membered monocyclic heterocycloalkyl; and
iv) a nitrogen-linked 4- to 7-membered monocyclic heterocycloalkyl, optionally substituted with —$C_{1-4}$alkyl, —$OC_{1-4}$alkyl, —OH, —$CF_3$, —$OCF_3$, halo, —CN, —C(O)—$C_{1-4}$alkyl, —C(O)O$C_{1-4}$alkyl, or —NR$^j$R$^k$;
$R^4$ is —$C_{1-8}$alkyl, phenyl, or monocyclic heteroaryl, where each phenyl or heteroaryl is optionally substituted with —$C_{1-4}$alkyl, —$C_{3-8}$cycloalkyl, —$OC_{1-4}$alkyl, —OH, halo, —$NO_2$, —N(R$^w$)R$^x$, —$CF_3$, —C(O)O$C_{1-4}$alkyl, or —CN;
where $R^w$ and $R^x$ are each independently —H or —$C_{1-4}$alkyl;
p is 0, 1, or 2;
each $R^2$ is independently —$C_{1-4}$alkyl, —$C_{3-8}$cycloalkyl, —$OC_{1-4}$alkyl, halo, —$CF_3$, or —CN;
Y is selected from the group consisting of —N(R$^L$)C(O)—, —C(O)N(R$^L$)—, and —N(R$^L$)C(O)N(R$^L$)—;
where each $R^L$ is —H, —$C_{1-4}$alkyl, or phenyl;
Z is selected from the group consisting of:
a) RingA, where RingA is phenyl, optionally mono-, di-, or tri-substituted with $R^m$;
where each $R^m$ is independently selected from the group consisting of —$C_{1-6}$alkyl, —$C_{1-6}$alkyl-OH, —$CF_3$, —$C_{2-6}$alkenyl, —$C_{2-6}$alkynyl, —$C_{3-8}$cycloalkyl, —CN, —$NO_2$, —N(R$^n$)R$^o$, —C(O)$C_{1-6}$alkyl, —C(O)OH, —C(O)O$C_{1-6}$alkyl, —C(O)N(R$^n$)R$^o$, —S—$C_{1-6}$alkyl, —S(O)$_{1-2}$—$C_{1-6}$alkyl, —$SCF_3$, halo, —OH, —$OC_{1-6}$alkyl, —$OCF_3$, —$OC_{3-6}$alkenyl, and —$OC_{3-6}$alkynyl;
where $R^n$ and $R^o$ are each independently —H or —$C_{1-6}$alkyl;
b) RingB, where RingB is monocyclic or fused bicyclic heteroaryl, optionally mono-, di-, or tri-substituted with $R^m$;
c) RingC, where RingC is heterocycloalkyl, optionally substituted with —$C_{1-4}$alkyl, —$C_{3-8}$cycloalkyl, or halo;
d) RingD, where RingD is monocyclic cycloalkyl, optionally substituted with —OH, halo, or —$C_{1-4}$alkyl, and optionally fused to phenyl;
e) —C(R$^q$)$_2$-RingA, —C(R$^q$)$_2$-RingB, —$CH_2$-RingC, —$CH_2$-RingD;

where each $R^q$ is —H or —$C_{1-4}$alkyl, or two $R^q$ substituents taken together form a $C_{3-6}$cycloalkyl;

f) —$C_{1-8}$alkyl, optionally substituted with —OH, halo, or —$CF_3$;

g) -ethyl substituted with RingA, RingB, monocyclic heterocycloalkyl, or —$N(R^r)R^s$, and optionally further substituted with —OH or —$CF_3$;
  where $R^r$ and $R^s$ are each independently —H or —$C_{1-4}$alkyl;

h) —CH=CH-RingA, and —CH=CH-RingB;

or a pharmaceutically acceptable salt, pharmaceutically acceptable prodrug, or pharmaceutically active metabolite of such compound.

In a further general aspect, the invention relates to pharmaceutical compositions each comprising: (a) an effective amount of an agent selected from compounds of Formula (I) or (II) and pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition mediated by NPY Y2 activity, comprising administering to the subject an effective amount of a compound of Formula (I) or (II) or a pharmaceutically acceptable salt, pharmaceutically acceptable prodrug, or pharmaceutically active metabolite of such compound.

In certain preferred embodiments of the method, the disease, disorder, or medical condition is selected from: anxiolytic disorders and depression; a condition requiring treatment of injured mammalian nerve tissue; a condition amenable to treatment through administration of a neurotrophic factor; a neurological disorder; bone loss; substance related disorders; sleep/wake disorders; cardiovascular disease such as cardiac arrhythmia, post-myocardial infarction, or heart failure; obesity; an obesity-related disorder; and a condition related to an endocrine function including inovulation and infertility.

Additional embodiments, features, and advantages of the invention will be apparent from the appended claims, which are incorporated into this summary by reference, as well as from the following detailed description.

DETAILED DESCRIPTION OF THE INVENTION

The invention may be more fully appreciated by reference to the following description, including the following glossary of terms and the concluding examples. For the sake of brevity, the disclosures of the publications cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Exemplary alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and the like.

The term "alkenyl" refers to a straight- or branched-chain alkenyl group having from 2 to 12 carbon atoms in the chain. (The double bond of the alkenyl group is formed by two $sp^2$ hybridized carbon atoms.) Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain. (The triple bond of the alkynyl group is formed by two sp hybridized carbon atoms.) Illustrative alkynyl groups include ethynyl, prop-2-ynyl, but-2-ynyl, but-3-ynyl, 2-methylbut-2-ynyl, hex-2-ynyl, and the like.

The term "heteroaryl" refers to a monocyclic, fused bicyclic, or fused polycyclic, aromatic heterocycle (ring structure having ring atoms selected from carbon atoms as well as nitrogen, oxygen, and sulfur heteroatoms) having from 3 to 12 ring atoms per heterocycle. Illustrative examples of heteroaryl groups include the following moieties:

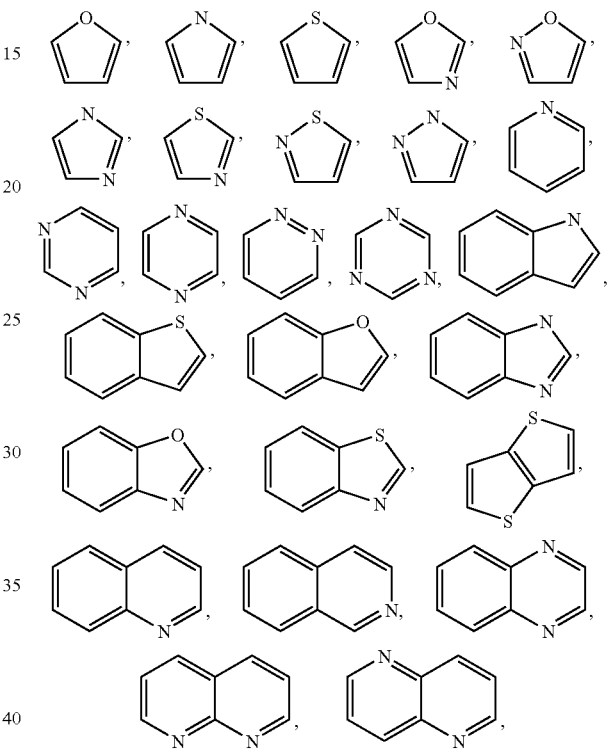

and the like.

The term "cycloalkyl" refers to a saturated or partially saturated, monocyclic, fused polycyclic, or spiro polycyclic, carbocycle having from 3 to 12 ring atoms per carbocycle. Illustrative examples of cycloalkyl groups include the following moieties:

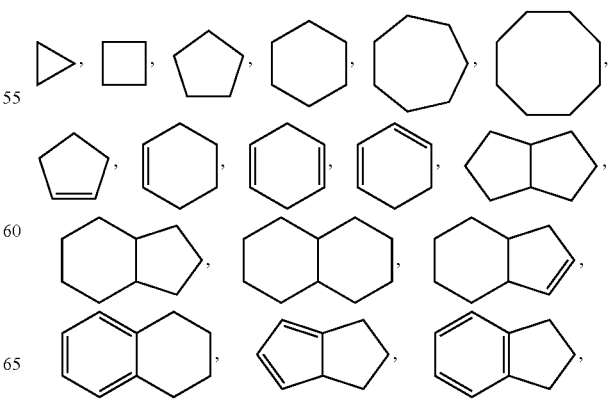

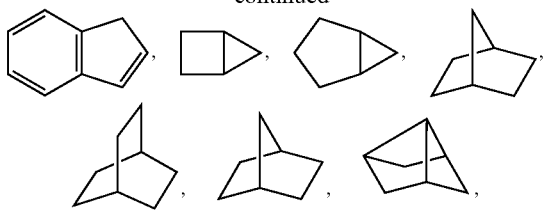

and the like.

A "heterocycloalkyl" refers to a monocyclic, fused polycyclic, or spiro polycyclic, ring structure that is saturated or partially saturated and has from 3 to 12 ring atoms per ring structure selected from carbon atoms as well as nitrogen, oxygen, and sulfur heteroatoms. Illustrative examples of heterocycloalkyl groups include:

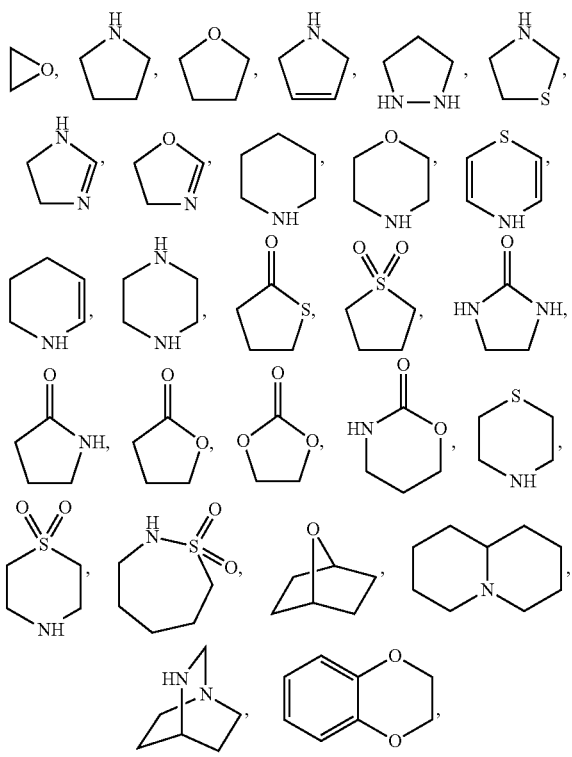

and the like.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Preferably, "optionally substituted" means that the specified group is unsubstituted or substituted by one, two, or three substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any given formula given herein is intended to represent a racemate, one or more enantiomeric forms, one or more diastereomeric forms, one or more atropisomeric forms, and mixtures thereof.

Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Various isotopically labeled compounds of the present invention, for example those into which radioactive isotopes such as $^3H$, $^{11}C$, and $^{14}C$ are incorporated. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

With respect to Formula (I), in preferred embodiments, $B^1$ is N and $B^2$ and $B^3$ are CH. In further preferred embodiments, $B^1$ and $B^3$ are N. In still further preferred embodiments, $B^1$ and $B^2$ are N.

In preferred embodiments, Ring T is

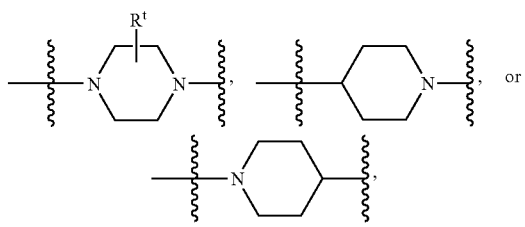

wherein $R^t$ is —H or —CH$_3$. In further preferred embodiments, Ring T is

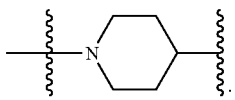

In preferred embodiments, $R^1$ is

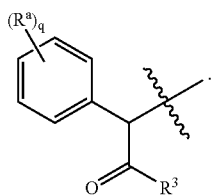

In further preferred embodiments, $R^1$ is

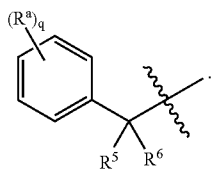

In preferred embodiments, Y is —N(H)C(O)— or —C(O)N(H)—. In further preferred embodiments, Y is —C(O)—.

In preferred embodiments, Z is piperidin-1-yl or pyrrolidin-1-yl, optionally substituted with methyl, ethyl, phenyl, or pyridinyl. In further preferred embodiments, Z is selected from the group consisting of isopropyl, 1-methylpropyl, isopentyl, cyclopropyl, cyclobutyl, cyclopentyl, and cyclohexyl.

With respect to Formula (II), in preferred embodiments of the invention, X is N and $R^1$ is

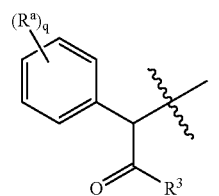

or X is CH and $R^1$ is

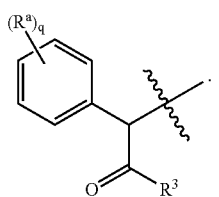

Preferably, q is 0. More preferably, q is 1 or 2.

Preferably, $R^a$ is methyl, ethyl, propyl, isopropyl, tert-butyl, cyclopropyl, cyclobutyl, cyclopentyl, cyclohexyl, methoxy, ethoxy, isopropoxy, sec-butyloxy, hydroxy, fluoro, bromo, chloro, iodo, nitro, amino, methylamino, dimethylamino, ethylamino, ethylmethylamino, diethylamino, dipropylamino, trifluoromethyl, acetyl, propionyl, methoxycarbonyl, ethoxycarbonyl, cyano, methylsulfonyl, methanesulfonylamino, methylsulfamoyl, pyrrolidinyl, piperidinyl, morpholinyl, or thiomorpholinyl. Preferably, two $R^a$ substituents form methylenedioxy. More preferably, $(R^a)_q$ is methyl, methoxy, fluoro, chloro, bromo, difluoro, dichloro, methoxy, trifluoromethyl, nitro, or cyano. Specific $(R^a)_q$-substituted phenyl groups are selected from the group consisting of phenyl, 4-methylphenyl, 3-methoxyphenyl, 4-methoxyphenyl, 2-fluorophenyl, 3-fluorophenyl, 4-fluorophenyl, 3-chlorophenyl, 4-chlorophenyl, 4-bromophenyl, 2,3-difluorophenyl, 2-fluoro-5-bromophenyl, 3,5-difluorophenyl, 3,4-dichlorophenyl, 2-chloro-4-fluorophenyl, 4-trifluoromethylphenyl, 4-nitrophenyl, 4-cyanophenyl, and benzo[1,3]dioxolanyl.

Preferably, $R^3$ is selected from the group consisting of:
i) methoxy, ethoxy, propoxy, isopropoxy, butoxy, allyloxy, benzyloxy, or phenyloxy;
ii) —NR$^b$R$^c$, where R$^b$ is —H, methyl, ethyl, propyl, isopropyl, or butyl; and R$^c$ is methyl, ethyl, propyl, isopropyl, butyl, tert-butyl, allyl, cyclopropyl, cyclobutyl, cyclopentyl, cyclohexyl, indanyl, azetidinyl, pyrrolidinyl, piperidinyl, homopiperidinyl, tetrahydrofuranyl, tetrahydropyranyl, piperazinyl, morpholinyl, thiomorpholinyl, dioxothiomorpholinyl, or thiazolidinyl;
iii) —NR$^g$R$^h$, where R$^g$ is —H, methyl, ethyl, propyl, isopropyl, or butyl; and R$^h$ is phenyl, pyridyl, pyrimidinyl, pyrazinyl, indolyl, furanyl, thiophenyl, pyrazolyl, imidazolyl, oxazolyl, isoxazolyl, thiazolyl, benzyl, pyridylmethyl, pyrimidinylmethyl, pyrazinylmethyl, indolylmethyl, furanylmethyl, thiophenylmethyl, pyrazolylmethyl, imidazolylmethyl, oxazolylmethyl, isoxazolylmethyl, thiazolylmethyl, phenethyl, or pyridylethyl; and
iv) azetidinyl, pyrrolidinyl, piperidinyl, homopiperidinyl, morpholinyl, thiomorpholinyl, tetrahydrofuranyl, tetrahydropyranyl, or thiazolidinyl;
where each of i)-iv) is optionally substituted as described above.

More preferably, $R^3$ is selected from the group consisting of methoxy, ethoxy, phenoxy, benzyloxy, hydroxy, ethylamino, diethylamino, propylamino, methylamino, dipropylamino, ethyl-methylamino, allylamino, cyclopropylamino, indanylamino, piperidinylamino, tetrahydropyranylamino, morpholinylamino, thiazolidinylamino, phenylamino, pyridylamino, isoxazolylamino, thiazolylamino, benzyl, thiophenylmethyl, furanylmethyl, pyridylmethyl, phenethyl, pyridylethyl, pyrrolidinyl, piperidinyl, piperazinyl, and morpholinyl, each optionally substituted as described above.

Even more preferably, $R^3$ is selected from the group consisting of:
i) methoxy;
ii) ethylamino, diethylamino, ethyl-methylamino, dipropylamino, 3-methoxypropylamino, 2,2,2-trifluoroethylamino, 2-fluoroethylamino, 2-ethoxyethylamino, 2-diethylaminoethylamino, methoxycarbonylmethylamino, —NHCH$_2$C(O)phenyl, allylamino, indan-1-ylamino, 2-pyrrolidin-1-yl-ethylamino, 2-morpholin-4-ylethylamino, tetrahydropyran-4-ylamino, 4,5-dihydro-thiazol-2-ylamino, 1-methyl-piperidin-4-ylamino, 1-isopropyl-piperidin-4-ylamino, morpholin-4-ylamino;
iii) phenylamino, 3-methoxyphenylamino, 4-morpholin-4-yl-phenylamino, 4-methylthiazol-2-ylamino, 5-methylthiazol-2-ylamino, isoxazol-3-ylamino, 6-methoxy-pyridin-3-ylamino, 4,6-dimethyl-pyridin-2-ylamino, benzylamino, 3-fluorobenzylamino, 4-methoxybenzylamino, pyridin-2-ylmethylamino, thiophen-2-ylmethylamino, furan-2-ylmethylamino, phenethylamino, 2-pyridin-4-yl-ethylamino; and iv) pyrrolidinyl, 3,3-difluoropyrrolidinyl, piperidinyl, 4-methyl-piperidin-1-yl, 4,4-difluoropiperidin-1-yl, piperazinyl, 4-methyl-piperazin-1-yl, 4-isopropyl-piperazin-1-yl, 4-(2-morpholin-4-yl-2-oxo-ethyl)-piperazin-1-yl, and morpholin-4-yl.

In further preferred embodiments, $R^3$ is 4-fluoro-piperidin-1-yl, 3,3-difluoro-azetidin-1-yl, azetidin-1-yl, or phenyl.

Preferably, $R^4$ is methyl, ethyl, propyl, isopropyl, butyl, isopentyl, isoheptyl, phenyl, pyridyl, pyrimidinyl, pyrazinyl, indolyl, furanyl, thiophenyl, pyrazolyl, imidazolyl, oxazolyl, isoxazolyl, or thiazolyl. More preferably, $R^4$ is isopentyl or methyl.

Preferably, each $R^2$ is independently methyl, ethyl, propyl, isopropyl, butyl, cyclopropyl, cyclobutyl, cyclopentyl, cyclohexyl, methoxy, ethoxy, propoxy, isopropoxy, butyloxy, fluoro, bromo, chloro, iodo, trifluoromethyl, or cyano. More preferably, each $R^2$ is independently methyl, fluoro, chloro, bromo, trifluoromethyl, or cyano. Even more preferably, $R^2$ is ethynyl or methoxy.

Preferably, each $R^L$ is independently —H, methyl, ethyl, propyl, isopropyl, butyl, tert-butyl, or phenyl.

Preferably, Y is —N(H)C(O)—, —N(phenyl)C(O)—, —C(O)N(H)—, —N(H)C(O)N(H)—, or —N(ethyl)C(O)N(ethyl)-. More preferably, Y is —N(H)C(O)—.

Preferably, Z is selected from the group consisting of:
a) RingA, where RingA is phenyl, indanyl, or tetrahydronaphthalenyl;
b) RingB, where RingB is pyridyl, pyrimidinyl, pyrazinyl, indolyl, furanyl, thiophenyl, pyrazolyl, imidazolyl, oxazolyl, isoxazolyl, thiazolyl, indolyl, benzofuranyl, benzothiophenyl, benzimidazolyl, benzoxazolyl, benzothiazolyl, pyrrolopyridinyl, imidazopyridinyl, quinolinyl, isoquinolinyl, or naphthyridinyl;
c) RingC, where RingC is azetidinyl, pyrrolidinyl, piperidinyl, homopiperidinyl, tetrahydrofuranyl, tetrahydropyranyl, piperazinyl, morpholinyl, thiomorpholinyl, dioxothiomorpholinyl, thiazolidinyl, or dihydroindolyl;
d) RingD, where RingD is cyclopropyl, cyclobutyl, cyclopentyl, cyclohexyl, cycloheptyl, cyclooctyl, indanyl, bicyclo[4.2.0]octa-1,3,5-triene, or tetrahydronaphthyl;
e) —CH$_2$-RingA, —CH$_2$-RingB, —CH$_2$-RingC, —CH$_2$-RingD, —CH(CH$_3$)-RingA, —CH(CH$_3$)-RingB, —C(CH$_3$)$_2$-RingA, —C(CH$_3$)$_2$-RingB,

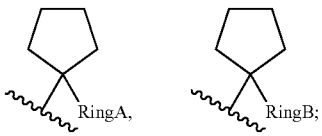

f) methyl, ethyl, propyl, isopropyl, butyl, sec-butyl, tert-butyl, pentyl, isopentyl, hexyl, heptyl, octyl;
g) -ethyl-RingA, -ethyl-RingB, -ethyl-(monocyclic heterocycloalkyl), —CH(RingA)CH$_3$, —CH(RingB)CH$_3$, —CH(monocyclic heterocycloalkyl)CH$_3$, -ethyl-N(R$^r$)R$^s$, —CH[N(R$^r$)R$^s$]CH$_3$; and
h) —CH=CH-RingA, and —CH=CH-RingB;

where each of a)-h) is optionally substituted as described above.

More preferably, Z is selected from the group consisting of:
a) phenyl, 2-methylphenyl, 3-methylphenyl, 4-methylphenyl, 2-ethylphenyl, 3-ethylphenyl, 4-ethylphenyl, 2-isopropylphenyl, 3-isopropylphenyl, 4-tert-butylphenyl, 2,5-dimethylphenyl, 2,6-dimethylphenyl, 4-hydroxymethylphenyl, 3-vinylphenyl, 4-vinylphenyl, 2-cyclohexylphenyl, 2-methoxyphenyl, 3-methoxyphenyl, 4-methoxyphenyl, 2-fluorophenyl, 3-fluorophenyl, 4-fluorophenyl, 2-chlorophenyl, 3-chlorophenyl, 4-chlorophenyl, 2-bromophenyl, 4-bromophenyl, 2-iodophenyl, 2,3-difluorophenyl, 2-fluoro-5-bromophenyl, 3,5-difluorophenyl, 3,4-dichlorophenyl, 2-chloro-4-fluorophenyl, 2-trifluoromethylphenyl, 4-trifluoromethylphenyl, 4-nitrophenyl, 2-aminophenyl, 2-methylaminophenyl, 2-cyanophenyl, 4-cyanophenyl;

b) 2-pyrrolyl, 2-furanyl, 3-furanyl, 2-thiophenyl, 3-thiophenyl, triazol-5-yl, 1H-methyl-pyrrol-2-yl, 2-ethylpyrazol-3-yl, 2-tert-butyl-pyrazol-3-yl, 2-methyl-thiophen-3-yl, 5-methyl-isoxazol-4-yl, 3,5-dimethyl-isoxazol-3-yl, 2-pyridyl, 3-pyridyl, 4-pyridyl, pyrimidin-5-yl, 2-bromo-pyridin-3-yl, 2-methyl-pyridin-3-yl, 2-methylsulfanyl-pyridin-3-yl;

c) tetrahydrofuran-3-yl, 1-cyclohexyl-azetidin-2-yl;

d) cyclopropyl, cyclobutyl, cyclopentyl, cyclohexyl, 2-methyl-2,2,3,3-tetramethylcyclopropyl, 1-methylcyclohexyl, bicyclo[4.2.0]octa-1,3,5-triene;

e) benzyl, 4-fluorobenzyl, 2,5-dimethylbenzyl, 2,6-difluorobenzyl, 2-methoxybenzyl, 1-(4-chloro-phenyl)-1-methylethyl, 1-(4-fluoro-phenyl)-ethyl, 1-phenylethyl, 1-phenylcyclopentyl, 4-methyl-thiophen-3-yl, 3,5-dimethyl-isoxazol-4-ylmethyl, 4-pyridylmethyl, cyclopropylmethyl, cyclohexylmethyl, 4-isopropyl-piperazin-1-ylmethyl;

f) methyl, ethyl, propyl, isopropyl, butyl, 1-methylpropyl, 2-methylpropyl, isopentyl, pentyl, 1-methylbutyl, 3-methylbutyl, 1-ethylpentyl, 1-propylbutyl;

g) phenethyl, 2-diethylaminoethyl, 2,2,2-trifluoro-1-pyrrolidin-2-ylmethyl-ethyl, 2,2,2-trifluoro-1-piperidin-2-ylmethyl-ethyl; and h) styryl, and 2-(2-methoxy-phenyl)-vinyl.

Even more preferably, Z is selected from the group consisting of isopropyl, 1-methylpropyl, isopentyl, cyclopropyl, cyclobutyl, cyclopentyl, and cyclohexyl. In further preferred embodiments, Z is piperidin-1-yl or pyrrolidin-1-yl, optionally substituted with methyl, ethyl, phenyl, or pyridinyl.

Preferred embodiments additionally include combinations of any of the above. In addition, the preferred embodiments described above apply to Formula (I) and Formula (II).

The present invention includes compounds of Formula (I) or (II), with the proviso that said compound is not a compound of formula:

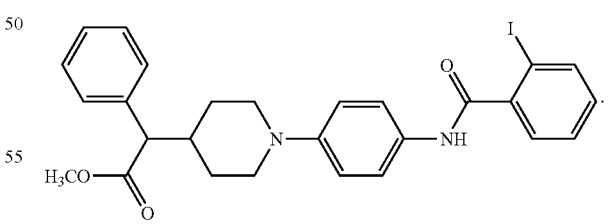

Preferably, the present invention includes compounds of Formula (I) or (II), with the proviso that when Z is phenyl, naphthalenyl, pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, or thienyl, and Y is —N(H)C(O)—, then one of R$^m$ is not 2-iodo or 2-bromo.

In preferred embodiments, compounds of the present invention are selected from the group consisting of:

| Ex. | Compound Name |
|---|---|
| 1 | 2-Ethyl-N-{3-fluoro-4-[4-(2-oxo-1-phenyl-2-pyrrolidin-1-yl-ethyl)-piperazin-1-yl]-phenyl}-butyramide; |
| 2 | 2-{4-[4-(2-Ethyl-butyrylamino)-2-fluoro-phenyl]-piperazin-1-ylmethyl}-benzoic acid methyl ester; |
| 3 | 2-Ethyl-N-(3-fluoro-4-{4-[3-(morpholine-4-carbonyl)-benzyl]-piperazin-1-yl}-phenyl)-butyramide; |
| 4 | N,N-Diethyl-2-{4-[4-(2-ethyl-butyrylamino)-2-fluoro-phenyl]-piperazin-1-ylmethyl}-benzamide; |
| 5 | 2-Ethyl-N-(3-fluoro-4-{4-[2-(morpholine-4-carbonyl)-benzyl]-piperazin-1-yl}-phenyl)-butyramide; |
| 6 | N-{4-[4-(Diethylcarbamoyl-phenyl-methyl)-piperazin-1-yl]-3-fluoro-phenyl}-2-ethyl-butyramide; |
| 7 | 2-Ethyl-N-{4-[4-(ethylcarbamoyl-phenyl-methyl)-piperazin-1-yl]-3-fluoro-phenyl}-butyramide; |
| 8 | 2-(1-{4-[3-(3,5-Dimethyl-isoxazol-4-yl)-ureido]-2-fluoro-phenyl}-piperidin-4-yl)-N,N-diethyl-2-phenyl-acetamide; |
| 9 | 2-(1-{4-[2-(3,5-Dimethyl-isoxazol-4-yl)-acetylamino]-2-fluoro-phenyl}-piperidin-4-yl)-N,N-diethyl-2-phenyl-acetamide; |
| 10 | 2-(1-{4-[3-(3,5-Dimethyl-isoxazol-4-yl)-ureido]-2-fluoro-phenyl}-piperidin-4-yl)-N-ethyl-2-phenyl-acetamide; |
| 11 | N-{4-[4-(Diethylcarbamoyl-phenyl-methyl)-piperidin-1-yl]-3-fluoro-phenyl}-2-ethyl-butyramide; |
| 12 | 3,5-Dimethyl-isoxazole-4-carboxylic acid {4-[4-(diethylcarbamoyl-phenyl-methyl)-piperidin-1-yl]-3-fluoro-phenyl}-amide; |
| 13 | 2-(1-{4-[2-(3,5-Dimethyl-isoxazol-4-yl)-acetylamino]-2-fluoro-phenyl}-piperidin-4-yl)-N-ethyl-2-phenyl-acetamide; |
| 14 | 2-Ethyl-N-{4-[4-(ethylcarbamoyl-phenyl-methyl)-piperidin-1-yl]-3-fluoro-phenyl}-butyramide; |
| 15 | 2-(1-{4-[3-(2,6-Dimethyl-phenyl)-ureido]-2-fluoro-phenyl}-piperidin-4-yl)-N-ethyl-2-phenyl-acetamide; |
| 16 | 2-Propyl-pentanoic acid {4-[4-(ethylcarbamoyl-phenyl-methyl)-piperidin-1-yl]-3-fluoro-phenyl}-amide; |
| 17 | N-Ethyl-2-(1-{2-fluoro-4-[3-(4-fluoro-benzyl)-ureido]-phenyl}-piperidin-4-yl)-2-phenyl-acetamide; |
| 18 | N-{4-[4-(Ethylcarbamoyl-phenyl-methyl)-piperidin-1-yl]-phenyl}-isobutyramide; |
| 19 | 2-{1-[4-(2-Cyclohexyl-acetylamino)-2-fluoro-phenyl]-piperidin-4-yl}-N-ethyl-2-phenyl-acetamide; |
| 20 | 2-(4-{4-[3-(3,5-Dimethyl-isoxazol-4-yl)-ureido]-2-fluoro-phenyl}-piperazin-1-yl)-N,N-diethyl-2-phenyl-acetamide; |
| 21 | 2-(4-{4-[2-(3,5-Dimethyl-isoxazol-4-yl)-acetylamino]-2-fluoro-phenyl}-piperazin-1-yl)-N,N-diethyl-2-phenyl-acetamide; |
| 22 | 3,5-Dimethyl-isoxazole-4-carboxylic acid {4-[4-(diethylcarbamoyl-phenyl-methyl)-piperazin-1-yl]-3-fluoro-phenyl}-amide; |
| 23 | 2-(4-{4-[3-(3,5-Dimethyl-isoxazol-4-yl)-ureido]-2-fluoro-phenyl}-piperazin-1-yl)-N-ethyl-2-phenyl-acetamide; |
| 24 | 2-(4-{4-[2-(3,5-Dimethyl-isoxazol-4-yl)-acetylamino]-2-fluoro-phenyl}-piperazin-1-yl)-N-ethyl-2-phenyl-acetamide; |
| 25 | 2-(4-{4-[3-(2,5-Dimethyl-phenyl)-ureido]-2-fluoro-phenyl}-piperazin-1-yl)-N-ethyl-2-phenyl-acetamide; |
| 26 | N-Ethyl-2-(4-{2-fluoro-4-[3-(4-fluoro-benzyl)-ureido]-phenyl}-piperazin-1-yl)-2-phenyl-acetamide; |
| 27 | Phenyl-{4-[4-(3-phenyl-acryloylamino)-phenyl]-piperazin-1-yl}-acetic acid methyl ester; |
| 28 | N-Ethyl-2-[4-(2-fluoro-4-{3-[(S)-1-(4-fluoro-phenyl)-ethyl]-ureido}-phenyl)-piperazin-1-yl]-2-phenyl-acetamide; |
| 29 | (S)-Tetrahydro-furan-3-carboxylic acid {4-[4-(diethylcarbamoyl-phenyl-methyl)-piperazin-1-yl]-3-fluoro-phenyl}-amide; |
| 30 | 2-(4-{4-[3-(3,5-Dimethyl-isoxazol-4-yl)-1,3-diethyl-ureido]-2-fluoro-phenyl}-piperazin-1-yl)-N,N-diethyl-2-phenyl-acetamide; |
| 31 | 4-[4-(Diethylcarbamoyl-phenyl-methyl)-piperazin-1-yl]-N-(3,5-dimethyl-isoxazol-4-ylmethyl)-3-fluoro-benzamide; |
| 32 | N-(1-{4-[3-(3,5-Dimethyl-isoxazol-4-yl)-ureido]-2-fluoro-phenyl}-piperidin-4-yl)-2-ethyl-N-phenyl-butyramide; |
| 33 | 2-Ethyl-N-{1-[4-(2-ethyl-butyrylamino)-2-fluoro-phenyl]-piperidin-4-yl}-N-phenyl-butyramide; |
| 34 | {4-[4-(2-Ethyl-butyrylamino)-2-fluoro-phenyl]-piperazin-1-yl}-(3-fluoro-phenyl)-acetic acid methyl ester; |
| 35 | N-(4-{4-[Diethylcarbamoyl-(3-fluoro-phenyl)-methyl]-piperazin-1-yl}-3-fluoro-phenyl)-2-ethyl-butyramide; |
| 36 | (4-Cyano-phenyl)-{4-[4-(2-ethyl-butyrylamino)-2-fluoro-phenyl]-piperazin-1-yl}-acetic acid methyl ester; |
| 37 | (3-Chloro-phenyl)-{4-[4-(2-ethyl-butyrylamino)-2-fluoro-phenyl]-piperazin-1-yl}-acetic acid methyl ester; |
| 38 | (2,3-Difluoro-phenyl)-{4-[4-(2-ethyl-butyrylamino)-2-fluoro-phenyl]-piperazin-1-yl}-acetic acid methyl ester; |
| 39 | {4-[2-Chloro-4-(2-methyl-benzoylamino)-phenyl]-piperazin-1-yl}-phenyl-acetic acid methyl ester; |

| Ex. | Compound Name |
|---|---|
| 40 | {4-[4-(2-Ethyl-butyrylamino)-2,6-difluoro-phenyl]-piperazin-1-yl}-phenyl-acetic acid methyl ester; |
| 41 | {4-[2,6-Dichloro-4-(2-ethyl-butyrylamino)-phenyl]-piperazin-1-yl}-phenyl-acetic acid methyl ester; |
| 42 | 2-Ethyl-N-{4-[4-(ethylcarbamoyl-phenyl-methyl)-piperazin-1-yl]-2-fluoro-phenyl}-butyramide; |
| 43 | N-{3-Cyano-4-[4-(ethylcarbamoyl-phenyl-methyl)-piperidin-1-yl]-phenyl}-2-ethyl-butyramide; |
| 44 | {4-[4-(2-Ethyl-butyrylamino)-2-fluoro-phenyl]-piperazin-1-yl}-phenyl-acetic acid methyl ester; |
| 45 | (4-{4-[(Bicyclo[4.2.0]octa-1(6),2,4-triene-7-carbonyl)-amino]-phenyl}-piperazin-1-yl)-phenyl-acetic acid methyl ester; |
| 46 | {4-[4-(2-Iodo-benzoylamino)-phenyl]-piperazin-1-yl}-phenyl-acetic acid methyl ester; |
| 47 | [4-(4-Benzoylamino-phenyl)-piperazin-1-yl]-phenyl-acetic acid methyl ester; |
| 48 | {4-[4-(Cyclohexanecarbonyl-amino)-phenyl]-piperazin-1-yl}-phenyl-acetic acid methyl ester; |
| 49 | {4-[4-(2-Cyclohexyl-benzoylamino)-phenyl]-piperazin-1-yl}-phenyl-acetic acid methyl ester; |
| 50 | {4-[4-(2-Methyl-benzoylamino)-phenyl]-piperazin-1-yl}-phenyl-acetic acid methyl ester; |
| 51 | {4-[4-(2-Ethyl-benzoylamino)-phenyl]-piperazin-1-yl}-phenyl-acetic acid methyl ester; |
| 52 | {4-[4-(2-Isopropyl-benzoylamino)-phenyl]-piperazin-1-yl}-phenyl-acetic acid methyl ester; |
| 53 | {4-[4-(2-Chloro-benzoylamino)-phenyl]-piperazin-1-yl}-phenyl-acetic acid methyl ester; |
| 54 | {4-[4-(2-Cyano-benzoylamino)-phenyl]-piperazin-1-yl}-phenyl-acetic acid methyl ester; |
| 55 | {4-[4-(2-Fluoro-benzoylamino)-phenyl]-piperazin-1-yl}-phenyl-acetic acid methyl ester; |
| 56 | {4-[4-(2-Methoxy-benzoylamino)-phenyl]-piperazin-1-yl}-phenyl-acetic acid methyl ester; |
| 57 | Phenyl-{4-[4-(2-trifluoromethyl-benzoylamino)-phenyl]-piperazin-1-yl}-acetic acid methyl ester; |
| 58 | {4-[4-(2-Methylamino-benzoylamino)-phenyl]-piperazin-1-yl}-phenyl-acetic acid methyl ester; |
| 59 | {4-[4-(Cyclopentanecarbonyl-amino)-phenyl]-piperazin-1-yl}-phenyl-acetic acid methyl ester; |
| 60 | {4-[4-(2-Ethyl-butyrylamino)-phenyl]-piperazin-1-yl}-phenyl-acetic acid methyl ester; |
| 61 | [4-(4-Benzoylamino-2-fluoro-phenyl)-piperazin-1-yl]-phenyl-acetic acid methyl ester; |
| 62 | {4-[2-Fluoro-4-(2-methyl-benzoylamino)-phenyl]-piperazin-1-yl}-phenyl-acetic acid methyl ester; |
| 63 | {4-[4-(2-Ethyl-benzoylamino)-2-fluoro-phenyl]-piperazin-1-yl}-phenyl-acetic acid methyl ester; |
| 64 | {4-[2-Fluoro-4-(2-isopropyl-benzoylamino)-phenyl]-piperazin-1-yl}-phenyl-acetic acid methyl ester; |
| 65 | {4-[2-Fluoro-4-(2-methoxy-benzoylamino)-phenyl]-piperazin-1-yl}-phenyl-acetic acid methyl ester; |
| 66 | [4-(4-Acetylamino-phenyl)-piperazin-1-yl]-phenyl-acetic acid methyl ester; |
| 67 | [4-(4-Acetylamino-2-fluoro-phenyl)-piperazin-1-yl]-phenyl-acetic acid methyl ester; |
| 68 | {4-[2-Fluoro-4-(2-methylamino-benzoylamino)-phenyl]-piperazin-1-yl}-phenyl-acetic acid methyl ester; |
| 69 | {4-[4-(3-Ethyl-benzoylamino)-phenyl]-piperazin-1-yl}-phenyl-acetic acid methyl ester; |
| 70 | {4-[4-(4-Ethyl-benzoylamino)-phenyl]-piperazin-1-yl}-phenyl-acetic acid methyl ester; |
| 71 | {4-[4-(4-Isopropyl-benzoylamino)-phenyl]-piperazin-1-yl}-phenyl-acetic acid methyl ester; |
| 72 | {4-[4-(3-Methyl-benzoylamino)-phenyl]-piperazin-1-yl}-phenyl-acetic acid methyl ester; |
| 73 | {4-[4-(4-Methyl-benzoylamino)-phenyl]-piperazin-1-yl}-phenyl-acetic acid methyl ester; |
| 74 | Phenyl-(4-{4-[(thiophene-2-carbonyl)-amino]-phenyl}-piperazin-1-yl)-acetic acid methyl ester; |
| 75 | {4-[4-(4-Hydroxymethyl-benzoylamino)-phenyl]-piperazin-1-yl}-phenyl-acetic acid methyl ester; |
| 76 | Phenyl-{4-[4-(3-vinyl-benzoylamino)-phenyl]-piperazin-1-yl}-acetic acid methyl ester; |
| 77 | Phenyl-{4-[4-(4-vinyl-benzoylamino)-phenyl]-piperazin-1-yl}-acetic acid methyl ester; |
| 78 | {4-[2-Fluoro-4-(4-methyl-pentanoylamino)-phenyl]-piperazin-1-yl}-phenyl-acetic acid methyl ester; |

-continued

| Ex. | Compound Name |
|---|---|
| 79 | {4-[4-(2-Ethyl-hexanoylamino)-2-fluoro-phenyl]-piperazin-1-yl}-phenyl-acetic acid methyl ester; |
| 80 | {4-[4-(4-tert-Butyl-benzoylamino)-phenyl]-piperazin-1-yl}-phenyl-acetic acid methyl ester; |
| 81 | [4-(4-Butyrylamino-phenyl)-piperazin-1-yl]-phenyl-acetic acid methyl ester; |
| 82 | {4-[4-(2-Ethyl-hexanoylamino)-phenyl]-piperazin-1-yl}-phenyl-acetic acid methyl ester; |
| 83 | [4-(4-Hexanoylamino-phenyl)-piperazin-1-yl]-phenyl-acetic acid methyl ester; |
| 84 | Phenyl-{4-[4-(3-phenyl-propionylamino)-phenyl]-piperazin-1-yl}-acetic acid methyl ester; |
| 85 | {4-[4-(2-Methyl-pentanoylamino)-phenyl]-piperazin-1-yl}-phenyl-acetic acid methyl ester; |
| 86 | [4-(4-Pentanoylamino-phenyl)-piperazin-1-yl]-phenyl-acetic acid methyl ester; |
| 87 | {4-[4-(4-Methyl-pentanoylamino)-phenyl]-piperazin-1-yl}-phenyl-acetic acid methyl ester; |
| 88 | 4-Methyl-pentanoic acid {4-[4-(ethylcarbamoyl-phenyl-methyl)-piperazin-1-yl]-3-fluoro-phenyl}-amide; |
| 89 | 2-Ethyl-hexanoic acid {4-[4-(ethylcarbamoyl-phenyl-methyl)-piperazin-1-yl]-3-fluoro-phenyl}-amide; |
| 90 | N-{4-[4-(Ethylcarbamoyl-phenyl-methyl)-piperazin-1-yl]-3-fluoro-phenyl}-3-phenyl-propionamide; |
| 91 | 3-Diethylamino-N-{4-[4-(ethylcarbamoyl-phenyl-methyl)-piperazin-1-yl]-3-fluoro-phenyl}-propionamide; |
| 92 | N-Ethyl-2-{4-[2-fluoro-4-(2-pyridin-4-yl-acetylamino)-phenyl]-piperazin-1-yl}-2-phenyl-acetamide; |
| 93 | N-{4-[4-(Ethylcarbamoyl-phenyl-methyl)-piperazin-1-yl]-3-fluoro-phenyl}-3,3,3-trifluoro-2-pyrrolidin-2-ylmethyl-propionamide; |
| 94 | N-{4-[4-(Ethylcarbamoyl-phenyl-methyl)-piperazin-1-yl]-3-fluoro-phenyl}-3,3,3-trifluoro-2-piperidin-2-ylmethyl-propionamide; |
| 95 | N-Ethyl-2-(4-{2-fluoro-4-[2-(4-isopropyl-piperazin-1-yl)-acetylamino]-phenyl}-piperazin-1-yl)-2-phenyl-acetamide; |
| 96 | 1-Cyclohexyl-azetidine-2-carboxylic acid {4-[4-(ethylcarbamoyl-phenyl-methyl)-piperazin-1-yl]-3-fluoro-phenyl}-amide; |
| 97 | (Z)-N-{4-[4-(Ethylcarbamoyl-phenyl-methyl)-piperazin-1-yl]-3-fluoro-phenyl}-3-(2-methoxy-phenyl)-acryl amide; |
| 98 | Phenyl-(4-{4-[(pyridine-3-carbonyl)-amino]-phenyl}-piperazin-1-yl)-acetic acid methyl ester; |
| 99 | {4-[2-Fluoro-4-(2-iodo-benzoylamino)-phenyl]-piperazin-1-yl}-phenyl-acetic acid methyl ester; |
| 100 | 2-Bromo-N-{4-[4-(ethylcarbamoyl-phenyl-methyl)-piperazin-1-yl]-3-fluoro-phenyl}-nicotinamide; |
| 101 | (4-{4-[(Furan-2-carbonyl)-amino]-phenyl}-piperazin-1-yl)-phenyl-acetic acid methyl ester; |
| 102 | (4-{4-[(Furan-3-carbonyl)-amino]-phenyl}-piperazin-1-yl)-phenyl-acetic acid methyl ester; |
| 103 | Phenyl-(4-{4-[(thiophene-3-carbonyl)-amino]-phenyl}-piperazin-1-yl)-acetic acid methyl ester; |
| 104 | Phenyl-(4-{4-[(1H-pyrrole-2-carbonyl)-amino]-phenyl}-piperazin-1-yl)-acetic acid methyl ester; |
| 105 | Phenyl-(4-{4-[(pyridine-4-carbonyl)-amino]-phenyl}-piperazin-1-yl)-acetic acid methyl ester; |
| 106 | Phenyl-(4-{4-[(pyridine-2-carbonyl)-amino]-phenyl}-piperazin-1-yl)-acetic acid methyl ester; |
| 107 | Phenyl-(4-{4-[(1H-pyrazole-4-carbonyl)-amino]-phenyl}-piperazin-1-yl)-acetic acid methyl ester; |
| 108 | Phenyl-(4-{4-[(pyrimidine-5-carbonyl)-amino]-phenyl}-piperazin-1-yl)-acetic acid methyl ester; |
| 109 | {4-[4-(3-Methyl-butyrylamino)-phenyl]-piperazin-1-yl}-phenyl-acetic acid methyl ester; |
| 110 | {4-[4-(2-Bromo-benzoylamino)-phenyl]-piperazin-1-yl}-phenyl-acetic acid methyl ester; |
| 111 | 2-Bromo-N-{4-[4-(diethylcarbamoyl-phenyl-methyl)-piperazin-1-yl]-3-fluoro-phenyl}-benzamide; |
| 112 | N-{4-[4-(Diethylcarbamoyl-phenyl-methyl)-piperazin-1-yl]-3-fluoro-phenyl}-2-ethyl-N-methyl-butyramide; |
| 113 | 4-[4-(Ethylcarbamoyl-phenyl-methyl)-piperazin-1-yl]-N-(1-ethyl-propyl)-3-fluoro-benzamide; |
| 114 | Phenyl-[4-(4-phenylcarbamoyl-phenyl)-piperazin-1-yl]-acetic acid methyl ester; |
| 115 | {4-[4-(1-Ethyl-propylcarbamoyl)-2-fluoro-phenyl]-piperazin-1-yl}-phenyl-acetic acid methyl ester; |
| 116 | {4-[4-(1-Ethyl-propylcarbamoyl)-phenyl]-piperazin-1-yl}-phenyl-acetic acid methyl ester; |
| 117 | 4-[4-(Ethylcarbamoyl-phenyl-methyl)-piperidin-1-yl]-N-(1-ethyl-propyl)-3-fluoro-benzamide; |

| Ex. | Compound Name |
|---|---|
| 118 | 2-{4-[4-(Acetyl-phenyl-amino)-phenyl]-piperazin-1-yl}-N-indan-5-yl-2-phenyl-acetamide; |
| 119 | 2-{4-[4-(3-Ethyl-1-phenyl-ureido)-phenyl]-piperazin-1-yl}-N-indan-5-yl-2-phenyl-acetamide; |
| 120 | {1-[4-(2-Methyl-butyrylamino)-phenyl]-piperidin-4-yl}-phenyl-acetic acid methyl ester; |
| 121 | Phenyl-{1-[4-(2-phenyl-propionylamino)-phenyl]-piperidin-4-yl}-acetic acid methyl ester; |
| 122 | (S)-Tetrahydro-furan-3-carboxylic acid {3-cyano-4-[4-(diethylcarbamoyl-phenyl-methyl)-piperazin-1-yl]-phenyl}-amide; |
| 123 | (R)-Tetrahydro-furan-3-carboxylic acid {3-cyano-4-[4-(diethylcarbamoyl-phenyl-methyl)-piperazin-1-yl]-phenyl}-amide; |
| 124 | N-(4-{4-[(5-Bromo-2-fluoro-phenyl)-diethylcarbamoyl-methyl]-piperazin-1-yl}-3-fluoro-phenyl)-2-ethyl-butyramide; |
| 125 | 1-Phenyl-cyclopentanecarboxylic acid {4-[4-(diethylcarbamoyl-phenyl-methyl)-piperazin-1-yl]-3-fluoro-phenyl}-amide; |
| 126 | (S)-Tetrahydro-furan-3-carboxylic acid {4-[4-(diethylcarbamoyl-phenyl-methyl)-piperidin-1-yl]-3-fluoro-phenyl}-amide; |
| 127 | {4-[4-(2-Ethyl-butyrylamino)-2-fluoro-phenyl]-piperazin-1-yl}-phenyl-acetic acid ethyl ester; |
| 128 | 2-Ethyl-2H-pyrazole-3-carboxylic acid {4-[4-(diethylcarbamoyl-phenyl-methyl)-piperazin-1-yl]-3-fluoro-phenyl}-amide; |
| 129 | N-(4-{4-[Diethylcarbamoyl-(3-methoxy-phenyl)-methyl]-piperazin-1-yl}-3-fluoro-phenyl)-2-ethyl-butyramide; |
| 130 | Cyclopentanecarboxylic acid {3-cyano-4-[4-(ethylcarbamoyl-phenyl-methyl)-piperidin-1-yl]-phenyl}-amide; |
| 131 | N-{4-[4-(Diethylcarbamoyl-phenyl-methyl)-piperidin-1-yl]-3-fluoro-phenyl}-2-methyl-nicotinamide; |
| 132 | (R)-Tetrahydro-furan-3-carboxylic acid {4-[4-(diethylcarbamoyl-phenyl-methyl)-piperidin-1-yl]-3-fluoro-phenyl}-amide; |
| 133 | (S)-Tetrahydro-furan-3-carboxylic acid {3-cyano-4-[4-(ethylcarbamoyl-phenyl-methyl)-piperidin-1-yl]-phenyl}-amide; |
| 134 | N,N-Diethyl-2-(1-{2-fluoro-4-[2-(4-methyl-thiophen-3-yl)-acetylamino]-phenyl}-piperidin-4-yl)-2-phenyl-acetamide; |
| 135 | Cyclobutanecarboxylic acid {4-[4-(diethylcarbamoyl-phenyl-methyl)-piperazin-1-yl]-3-fluoro-phenyl}-amide; |
| 136 | 1-Methyl-cyclohexanecarboxylic acid {4-[4-(diethylcarbamoyl-phenyl-methyl)-piperazin-1-yl]-3-fluoro-phenyl}-amide; |
| 137 | (S)-N-{4-[4-(Diethylcarbamoyl-phenyl-methyl)-piperazin-1-yl]-3-fluoro-phenyl}-2-methyl-butyramide; |
| 138 | N-(4-{4-[Diethylcarbamoyl-(3-fluoro-phenyl)-methylene]-piperidin-1-yl}-3-fluoro-phenyl)-2-ethyl-butyramide; |
| 139 | 2-(4-Chloro-phenyl)-N-{4-[4-(diethylcarbamoyl-phenyl-methyl)-piperazin-1-yl]-3-fluoro-phenyl}-isobutyramide; |
| 140 | N-{4-[4-(Diethylcarbamoyl-phenyl-methyl)-piperidin-1-yl]-3-fluoro-phenyl}-isobutyramide; |
| 141 | N-{4-[4-(Diethylcarbamoyl-phenyl-methyl)-piperidin-1-yl]-3-fluoro-phenyl}-2-methylsulfanyl-nicotinamide; |
| 142 | 2-Ethyl-N-{4-[4-(ethylcarbamoyl-phenyl-methyl)-piperidin-1-yl]-3,5-difluoro-phenyl}-butyramide; |
| 143 | Cyclopentanecarboxylic acid {4-[4-(diethylcarbamoyl-phenyl-methyl)-piperazin-1-yl]-3-fluoro-phenyl}-amide; |
| 144 | 2-Methyl-thiophene-3-carboxylic acid {4-[4-(diethylcarbamoyl-phenyl-methyl)-piperidin-1-yl]-3-fluoro-phenyl}-amide; |
| 145 | 1-Methyl-1H-pyrrole-2-carboxylic acid {4-[4-(diethylcarbamoyl-phenyl-methyl)-piperidin-1-yl]-3-fluoro-phenyl}-amide; |
| 146 | (3,5-Difluoro-phenyl)-{4-[4-(2-ethyl-butyrylamino)-2-fluoro-phenyl]-piperazin-1-yl}-acetic acid methyl ester; |
| 147 | 1-Methyl-cyclohexanecarboxylic acid {3-cyano-4-[4-(ethylcarbamoyl-phenyl-methyl)-piperidin-1-yl]-phenyl}-amide |
| 148 | (R)-Tetrahydro-furan-3-carboxylic acid {3-cyano-4-[4-(ethylcarbamoyl-phenyl-methyl)-piperidin-1-yl]-phenyl}-amide; |
| 149 | N-{4-[4-(Diethylcarbamoyl-phenyl-methyl)-piperidin-1-yl]-3-fluoro-phenyl}-2-methylsulfanyl-benzamide; |
| 150 | 2-Methyl-cyclopropanecarboxylic acid {4-[4-(diethylcarbamoyl-phenyl-methyl)-piperazin-1-yl]-3-fluoro-phenyl}-amide; |
| 151 | (S)-Tetrahydro-furan-3-carboxylic acid (4-{4-[2-(3,3-difluoro-pyrrolidin-1-yl)-2-oxo-1-phenyl-ethyl]-piperazin-1-yl}-3-fluoro-phenyl)-amide; |
| 152 | 2,2,3,3-Tetramethyl-cyclopropanecarboxylic acid {4-[4-(diethylcarbamoyl-phenyl-methyl)-piperazin-1-yl]-3-fluoro-phenyl}-amide; |
| 153 | N-(4-{4-[(2-Bromo-5-fluoro-phenyl)-diethylcarbamoyl-methyl]-piperazin-1-yl}-3-fluoro-phenyl)-2-ethyl-butyramide; |
| 154 | 2-(1-{4-[2-(2,5-Dimethyl-phenyl)-acetylamino]-2-fluoro-phenyl}-piperidin-4-yl)-N,N-diethyl-2-phenyl-acetamide; |
| 155 | N-(4-{4-[Diethylcarbamoyl-(4-fluoro-phenyl)-methyl]-piperazin-1-yl}-3-fluoro-phenyl)-2-ethyl-butyramide; |

| Ex. | Compound Name |
|---|---|
| 156 | 2-(1-{4-[2-(2,6-Difluoro-phenyl)-acetylamino]-2-fluoro-phenyl}-piperidin-4-yl)-N,N-diethyl-2-phenyl-acetamide; |
| 157 | N-{4-[4-(Diethylcarbamoyl-phenyl-methyl)-piperidin-1-yl]-3-fluoro-phenyl}-2,5-dimethyl-benzamide; |
| 158 | N-(4-{4-[2-(4,4-Difluoro-piperidin-1-yl)-1-(4-fluoro-phenyl)-2-oxo-ethyl]-piperazin-1-yl}-3-fluoro-phenyl)-2-ethyl-butyramide; |
| 159 | 2-Ethyl-N-(4-{4-[ethylcarbamoyl-(3-fluoro-phenyl)-methyl]-piperazin-1-yl}-3-fluoro-phenyl)-butyramide; |
| 160 | 2-Amino-N-{4-[4-(diethylcarbamoyl-phenyl-methyl)-piperidin-1-yl]-3-fluoro-phenyl}-benzamide; |
| 161 | 2-{4-[4-(2-Cyclopropyl-acetylamino)-2-fluoro-phenyl]-piperazin-1-yl}-N,N-diethyl-2-phenyl-acetamide; |
| 162 | N,N-Diethyl-2-(4-{2-fluoro-4-[2-(2-methoxy-phenyl)-acetylamino]-phenyl}-piperazin-1-yl)-2-phenyl-acetamide; |
| 163 | 5-Methyl-isoxazole-4-carboxylic acid {4-[4-(diethylcarbamoyl-phenyl-methyl)-piperidin-1-yl]-3-fluoro-phenyl}-amide; and |
| 164 | 2-tert-Butyl-5-methyl-2H-pyrazole-3-carboxylic acid {4-[4-(diethylcarbamoyl-phenyl-methyl)-piperazin-1-yl]-3-fluoro-phenyl}-amide; | and pharmaceutically acceptable salts thereof.

In further preferred embodiments, compounds of the present invention are selected from the group consisting of:

| Ex. | Compound Name |
|---|---|
| 165 | N,N-Diethyl-2-{4-[2-fluoro-4-(propane-1-sulfonylamino)-phenyl]-piperazin-1-yl}-2-phenyl-acetamide; |
| 166 | N-{4-[4-(Diethylcarbamoyl-phenyl-methyl)-piperazin-1-yl]-3-fluoro-phenyl}-N-dipropanesulfonanilide; |
| 167 | 2-[4-(4-Cyclopentanecarbonyl-2-fluoro-phenyl)-piperazin-1-yl]-N,N-diethyl-2-phenyl-acetamide; |
| 168 | 2-{4-[4-(Cyclopentyl-hydroxyimino-methyl)-2-fluoro-phenyl]-piperazin-1-yl}-N,N-diethyl-2-phenyl-acetamide; |
| 169 | N,N-Diethyl-2-{4-[2-fluoro-4-(2-methyl-butyryl)-phenyl]-piperazin-1-yl}-2-phenyl-acetamide; |
| 170 | N-{4-[4-(Diethylcarbamoyl-phenyl-methyl)-piperazin-1-yl]-3-fluoro-benzyl}-2-ethyl-butyramide; |
| 171 | {4-[2-Fluoro-4-(5-(3-pentyl)-1,2,5-thiadiazolidine-2-yl, 1,1-dioxide)-phenyl]-piperazin-1-yl}-phenyl-acetic acid ethyl ester; |
| 172 | 2-{4-[4-(1,3-Dipropyl-sulfamoyl)-2-fluoro-phenyl]-piperazin-1-yl}-N,N-diethyl-2-phenyl-acetamide; |
| 173 | 3-{4-[4-(Diethylcarbamoyl-phenyl-methyl)-piperazin-1-yl]-3-fluoro-phenyl}-1,2,5-thiadiazolidine, 1,1-dioxide-2-carboxylic acid methyl ester; |
| 174 | N,N-Diethyl-2-{4-[2-fluoro-4-(1,2,5-thiadiazolidine-2-yl, 1,1-dioxide)-phenyl]-piperazin-1-yl}-2-phenyl-acetamide; |
| 175 | 3-{4-[4-(Ethoxycarbonyl-phenyl-methyl)-piperazin-1-yl]-3-fluoro-phenyl}-1,2,5-thiadiazolidine, 1,1-dioxide-2-carboxylic acid methyl ester; |
| 176 | {4-[2-Fluoro-4-(1,2,5-thiadiazolidine-2-yl, 1,1-dioxide)-phenyl]-piperazin-1-yl}-phenyl-acetic acid ethyl ester; |
| 177 | {4-[2-Fluoro-4-(5-(1-Ethyl-pyrrolidin-3-yl)-1,2,5-thiadiazolidine-2-yl, 1,1-dioxide)-phenyl]-piperazin-1-yl}-phenyl-acetic acid ethyl ester; |
| 178 | {4-[2-Fluoro-4-(5-(tetrahydro-furan-3-yl)-1,2,5-thiadiazolidine-2-yl, 1,1-dioxide)-phenyl]-piperazin-1-yl}-phenyl-acetic acid ethyl ester; |
| 179 | {4-[2-Fluoro-4-(5-propyl-1,2,5-thiadiazolidine-2-yl, 1,1-dioxide)-phenyl]-piperazin-1-yl}-phenyl-acetic acid ethyl ester; |
| 180 | {4-[2-Fluoro-4-(5-cyclopentyl-1,2,5-thiadiazolidine-2-yl, 1,1-dioxide)-phenyl]-piperazin-1-yl}-phenyl-acetic acid ethyl ester; |
| 181 | 4-[1-(Diethylcarbamoyl-phenyl-methyl)-1,2,3,6-tetrahydro-pyridin-4-yl]-3-fluoro-benzoic acid methyl ester; |
| 182 | N-{2-[4-(Diethylcarbamoyl-phenyl-methyl)-piperazin-1-yl]-pyrimidin-5-yl}-2-ethyl-butyramide; |
| 183 | N-{6-[4-(Diethylcarbamoyl-phenyl-methyl)-piperazin-1-yl]-pyridazin-3-yl}-2-ethyl-butyramide; |
| 184 | 2-Ethyl-N-{3-fluoro-4-[4-(hydrazinocarbonyl-phenyl-methyl)-piperazin-1-yl]-phenyl}-butyramide; |
| 185 | 4-[4-(Diethylcarbamoyl-phenyl-methyl)-piperazin-1-yl]-3-fluoro-benzoic acid methyl ester; |
| 186 | 2-Ethyl-2H-pyrazole-3-carboxylic acid {4-[4-(diethylcarbamoyl-phenyl-methyl)-piperidin-1-yl]-3-fluoro-phenyl}-amide; |

-continued

| Ex. | Compound Name |
|---|---|
| 187 | 1-Ethyl-1H-pyrrole-2-carboxylic acid {4-[4-(diethylcarbamoyl-phenyl-methyl)-piperidin-1-yl]-3-fluoro-phenyl}-amide; |
| 188 | 2-Ethyl-N-{3-fluoro-4-[4-(1-hydroxy-1-phenyl-pentyl)-piperidin-1-yl]-phenyl}-butyramide; |
| 189 | 2-Ethyl-N-{3-fluoro-4-[4-(1-phenyl-pentyl)-piperidin-1-yl]-phenyl}-butyramide; |
| 190 | 4-[4-(Diethylcarbamoyl-phenyl-methyl)-piperazin-1-yl]-N-(1-ethyl-propyl)-3-fluoro-benzamide; |
| 191 | N,N-Diethyl-2-{4-[2-fluoro-4-(pyridin-2-ylamino)-phenyl]-piperazin-1-yl}-2-phenyl-acetamide; |
| 192 | N,N-Diethyl-2-{4-[2-fluoro-4-(3-methyl-pyridin-2-ylamino)-phenyl]-piperazin-1-yl}-2-phenyl-acetamide; |
| 193 | N-{4-[1-(Diethylcarbamoyl-phenyl-methyl)-1,2,3,6-tetrahydro-pyridin-4-yl]-3-fluoro-phenyl}-2-ethyl-butyramide; |
| 194 | N-{4-[1-(Diethylcarbamoyl-phenyl-methyl)-piperidin-4-yl]-3-fluoro-phenyl}-2-ethyl-butyramide; |
| 195 | N-(4-{4-[(3-Chloro-phenyl)-diethylcarbamoyl-methyl]-piperazin-1-yl}-3-fluoro-phenyl)-2-ethyl-butyramide; |
| 196 | N-(4-{4-[2-(4,4-Difluoro-piperidin-1-yl)-1-(3-fluoro-phenyl)-2-oxo-ethyl]-piperazin-1-yl}-3-fluoro-phenyl)-2-ethyl-butyramide; |
| 197 | N-(4-{4-[Diethylcarbamoyl-(2,4-difluoro-phenyl)-methyl]-piperazin-1-yl}-3-fluoro-phenyl)-2-ethyl-butyramide; |
| 198 | N-(4-{4-[2-(3,3-Difluoro-pyrrolidin-1-yl)-1-(4-fluoro-phenyl)-2-oxo-ethyl]-piperazin-1-yl}-3-fluoro-phenyl)-2-ethyl-butyramide; |
| 199 | N-(4-{4-[2-(3,3-Difluoro-pyrrolidin-1-yl)-1-(3-fluoro-phenyl)-2-oxo-ethyl]-piperazin-1-yl}-3-fluoro-phenyl)-2-ethyl-butyramide; |
| 200 | N-(4-{4-[(5-Bromo-2-fluoro-phenyl)-diethylcarbamoyl-methyl]-piperazin-1-yl}-3-fluoro-phenyl)-2-ethyl-butyramide; |
| 201 | N-(4-{4-[Diethylcarbamoyl-(3,4-difluoro-phenyl)-methyl]-piperazin-1-yl}-3-fluoro-phenyl)-2-ethyl-butyramide; |
| 202 | Cyclopentanecarboxylic acid {6-[4-(diethylcarbamoyl-phenyl-methyl)-piperazin-1-yl]-pyridin-3-yl}-amide; |
| 203 | N-{6-[4-(Diethylcarbamoyl-phenyl-methyl)-piperazin-1-yl]-pyridin-3-yl}-2-ethyl-butyramide; |
| 204 | Cyclopentanecarboxylic acid [4-(diethylcarbamoyl-phenyl-methyl)-3,4,5,6-tetrahydro-2H-[1,2']bipyridinyl-5'-yl]-amide; |
| 205 | N-[4-(Diethylcarbamoyl-phenyl-methyl)-3,4,5,6-tetrahydro-2H-[1,2']bipyridinyl-5'-yl]-2-ethyl-butyramide; |
| 206 | 2-Ethyl-N-(3-fluoro-4-{4-[2-(4-fluoro-piperidin-1-yl)-2-oxo-1-phenyl-ethyl]-piperidin-1-yl}-phenyl)-butyramide; |
| 207 | N-(4-{4-[2-(3,3-Difluoro-azetidin-1-yl)-2-oxo-1-phenyl-ethyl]-piperidin-1-yl}-3-fluoro-phenyl)-2-ethyl-butyramide; |
| 208 | N-(4-{4-[2-(4,4-Difluoro-piperidin-1-yl)-2-oxo-1-phenyl-ethyl]-piperidin-1-yl}-3-fluoro-phenyl)-2-ethyl-butyramide; |
| 209 | N-{4-[4-(2-Azetidin-1-yl-2-oxo-1-phenyl-ethyl)-piperidin-1-yl]-3-fluoro-phenyl}-2-ethyl-butyramide; |
| 210 | N-(4-{4-[2-(3,3-Difluoro-pyrrolidin-1-yl)-2-oxo-1-phenyl-ethyl]-piperidin-1-yl}-3-fluoro-phenyl)-2-ethyl-butyramide; |
| 211 | 2-Ethyl-N-{3-fluoro-4-[4-(2-oxo-1-phenyl-2-pyrrolidin-1-yl-ethyl)-piperidin-1-yl]-phenyl}-butyramide; |
| 212 | N-{4-[4-(Cyclopropylcarbamoyl-phenyl-methyl)-piperidin-1-yl]-3-fluoro-phenyl}-2-ethyl-butyramide; |
| 213 | 2-Ethyl-N-(3-fluoro-4-{4-[(4-methyl-thiazol-2-ylcarbamoyl)-phenyl-methyl]-piperidin-1-yl}-phenyl)-butyramide; |
| 214 | {1-[4-(2-Ethyl-butyrylamino)-2-fluoro-phenyl]-piperidin-4-yl}-phenyl-acetic acid methyl ester; |
| 215 | 2-Ethyl-N-{3-fluoro-4-[4-(2-oxo-1-phenyl-2-piperidin-1-yl-ethyl)-piperidin-1-yl]-phenyl}-butyramide; |
| 216 | 2-Ethyl-N-(3-fluoro-4-{4-[2-(4-methyl-piperazin-1-yl)-2-oxo-1-phenyl-ethyl]-piperidin-1-yl}-phenyl)-butyramide; |
| 217 | N-{3-Cyano-4-[4-(diethylcarbamoyl-phenyl-methyl)-piperidin-1-yl]-phenyl}-2-ethyl-butyramide; |
| 218 | N-{3-Cyano-4-[4-(diethylcarbamoyl-phenyl-methyl)-piperidin-1-yl]-phenyl}-2-methyl-butyramide; |
| 219 | N-{3-Bromo-4-[4-(diethylcarbamoyl-phenyl-methyl)-piperidin-1-yl]-phenyl}-2-ethyl-butyramide; |
| 220 | Cyclopentanecarboxylic acid {4-[4-(diethylcarbamoyl-phenyl-methyl)-piperidin-1-yl]-3-fluoro-phenyl}-amide; |
| 221 | Cyclopentanecarboxylic acid {3-cyano-4-[4-(diethylcarbamoyl-phenyl-methyl)-piperazin-1-yl]-phenyl}-amide; |
| 222 | Cyclobutanecarboxylic acid {4-[4-(diethylcarbamoyl-phenyl-methyl)-piperidin-1-yl]-3-fluoro-phenyl}-amide; |
| 223 | N-{3-Bromo-4-[4-(diethylcarbamoyl-phenyl-methyl)-piperazin-1-yl]-phenyl}-2-ethyl-butyramide; |
| 224 | Cyclopentanecarboxylic acid {3-cyano-4-[4-(diethylcarbamoyl-phenyl-methyl)-piperazin-1-yl]-2-fluoro-phenyl}-amide; |
| 225 | N-{4-[4-(Diethylcarbamoyl-phenyl-methyl)-piperazin-1-yl]-2,5-difluoro-phenyl}-2-ethyl-butyramide; |

| Ex. | Compound Name |
|---|---|
| 226 | N-{4-[4-(Diethylcarbamoyl-phenyl-methyl)-piperazin-1-yl]-3,5-difluoro-phenyl}-2-ethyl-butyramide; |
| 227 | N-{3-Cyano-4-[4-(diethylcarbamoyl-phenyl-methyl)-piperazin-1-yl]-2-fluoro-phenyl}-2-ethyl-butyramide; |
| 228 | Bicyclo[2.2.1]heptane-2-carboxylic acid {4-[4-(diethylcarbamoyl-phenyl-methyl)-piperazin-1-yl]-3-fluoro-phenyl}-amide; |
| 229 | Cyclopropanecarboxylic acid {4-[4-(diethylcarbamoyl-phenyl-methyl)-piperidin-1-yl]-3-fluoro-phenyl}-amide; |
| 230 | Cyclopentanecarboxylic acid {4-[4-(diethylcarbamoyl-phenyl-methyl)-piperazin-1-yl]-3,5-difluoro-phenyl}-amide; |
| 231 | Cyclopentanecarboxylic acid {4-[4-(diethylcarbamoyl-phenyl-methyl)-piperazin-1-yl]-3-methyl-phenyl}-amide; |
| 232 | N-{4-[4-(Diethylcarbamoyl-phenyl-methyl)-piperazin-1-yl]-3-methyl-phenyl}-2-ethyl-butyramide; |
| 233 | N-{4-[4-(Diethylcarbamoyl-phenyl-methyl)-piperazin-1-yl]-2,3-difluoro-phenyl}-2-ethyl-butyramide; |
| 234 | N-{4-[4-(Cyano-phenyl-methyl)-piperidin-1-yl]-3-fluoro-phenyl}-2-ethyl-butyramide; |
| 235 | N-{4-[4-(Diethylcarbamoyl-phenyl-methyl)-piperazin-1-yl]-3-methoxy-phenyl}-2-ethyl-butyramide; |
| 236 | (R)-Tetrahydro-furan-3-carboxylic acid {4-[4-(ethylcarbamoyl-phenyl-methyl)-piperazin-1-yl]-3,5-difluoro-phenyl}-amide; |
| 237 | N-{2-Cyano-4-[4-(diethylcarbamoyl-phenyl-methyl)-piperazin-1-yl]-phenyl}-2-ethyl-butyramide; |
| 238 | Cyclopentanecarboxylic acid {4-[4-(diethylcarbamoyl-phenyl-methyl)-piperazin-1-yl]-3-methoxy-phenyl}-amide; |
| 239 | Cyclopentanecarboxylic acid {4-[4-(ethylcarbamoyl-phenyl-methyl)-piperazin-1-yl]-3,5-difluoro-phenyl}-amide; |
| 240 | N-{4-[4-(Diethylcarbamoyl-phenyl-methyl)-piperazin-1-yl]-3-ethynyl-phenyl}-2-ethyl-butyramide; |
| 241 | 2-{4-[4-(2-Cyclopropyl-acetylamino)-2-fluoro-phenyl]-piperazin-1-yl}-N,N-diethyl-2-phenyl-acetamide; |
| 242 | 2-{4-[4-(2-Cyclopentyl-acetylamino)-2-fluoro-phenyl]-piperazin-1-yl}-N,N-diethyl-2-phenyl-acetamide; |
| 243 | 2-Methyl-cyclopropanecarboxylic acid {4-[4-(diethylcarbamoyl-phenyl-methyl)-piperazin-1-yl]-3-fluoro-phenyl}-amide; |
| 244 | Cyclopentanecarboxylic acid {4-[4-(diethylcarbamoyl-phenyl-methyl)-piperazin-1-yl]-3-fluoro-phenyl}-amide; |
| 245 | 4-[4-(Diethylcarbamoyl-phenyl-methyl)-piperazin-1-yl]-N-(1-ethyl-propyl)-3-fluoro-benzamide; |
| 246 | N-{4-[4-(Diethylcarbamoyl-phenyl-methyl)-piperazin-1-yl]-3-fluoro-benzyl}-4,4,4-trifluoro-2-methyl-butyramide; |
| 247 | (S)-Tetrahydro-furan-3-carboxylic acid 4-[4-(diethylcarbamoyl-phenyl-methyl)-piperazin-1-yl]-3-fluoro-benzylamide; |
| 248 | (R)-(−)-N-{4-[4-(Diethylcarbamoyl-phenyl-methyl)-piperidin-1-yl]-3-fluoro-phenyl}-2-ethyl-butyramide; |
| 249 | (S)-(+)-N-{4-[4-(Diethylcarbamoyl-phenyl-methyl)-piperidin-1-yl]-3-fluoro-phenyl}-2-ethyl-butyramide; |
| 250 | N-(3-Cyano-4-{4-[diethylcarbamoyl-(4-methoxy-phenyl)-methyl]-piperazin-1-yl}-phenyl)-2-ethyl-butyramide; |
| 251 | N-(4-{4-[Diethylcarbamoyl-(4-methoxy-phenyl)-methyl]-piperazin-1-yl}-3-fluoro-phenyl)-2-ethyl-butyramide; |
| 252 | N-(4-{4-[Diethylcarbamoyl-(4-hydroxy-phenyl)-methyl]-piperazin-1-yl}-3-fluoro-phenyl)-2-ethyl-butyramide; |
| 253 | N-(4-{4-[(4-Chloro-phenyl)-diethylcarbamoyl-methyl]-piperazin-1-yl}-3-fluoro-phenyl)-2-ethyl-butyramide; |
| 254 | N-(4-{4-[(4-Cyano-phenyl)-diethylcarbamoyl-methyl]-piperazin-1-yl}-3-fluoro-phenyl)-2-ethyl-butyramide; |
| 255 | N-(4-{4-[Diethylcarbamoyl-(4-ethoxy-phenyl)-methyl]-piperazin-1-yl}-3-fluoro-phenyl)-2-ethyl-butyramide; |
| 256 | N-(4-{4-[Diethylcarbamoyl-(4-trifluoromethoxy-phenyl)-methyl]-piperazin-1-yl}-3-fluoro-phenyl)-2-ethyl-butyramide; |
| 257 | N-{4-[4-(Diethylcarbamoyl-phenyl-methyl)-3-methyl-piperazin-1-yl]-3-fluoro-phenyl}-2-ethyl-butyramide; |
| 258 | N-{4-[4-(Diethylcarbamoyl-pyridin-2-yl-methyl)-2-methyl-piperazin-1-yl]-3-fluoro-phenyl}-2-ethyl-butyramide; |
| 259 | 2-Ethyl-N-{3-fluoro-4-[4-(2-oxo-1,2-diphenyl-ethyl)-piperazin-1-yl]-phenyl}-butyramide; |
| 260 | N-{4-[4-(Diethylcarbamoyl-pyridin-2-yl-methyl)-piperazin-1-yl]-3-fluoro-phenyl}-2-ethyl-butyramide; |
| 261 | N-(4-{4-[2-(3,3-Difluoro-pyrrolidin-1-yl)-2-oxo-1-pyridin-2-yl-ethyl]-piperazin-1-yl}-3-fluoro-phenyl)-2-ethyl-butyramide; |
| 262 | {4-[4-(2-Ethyl-butyrylamino)-2-fluoro-phenyl]-piperazin-1-yl}-(4-hydroxy-phenyl)-acetic acid methyl ester; |
| 263 | {4-[4-(2-Ethyl-butyrylamino)-2-fluoro-phenyl]-piperazin-1-yl}-(4-methoxy-phenyl)-acetic acid methyl ester; |
| 264 | {4-[4-(2-Ethyl-butyrylamino)-2-fluoro-phenyl]-piperazin-1-yl}-pyridin-2-yl-acetic acid methyl ester; |

| Ex. | Compound Name |
|---|---|
| 265 | 4-[4-(2-Ethyl-butyrylamino)-2-fluoro-phenyl]-1-(methoxycarbonyl-phenyl-methyl)-piperazine-2-carboxylic acid methyl ester (diastereomer 2); |
| 266 | 2-Ethyl-N-{3-fluoro-4-[4-(2-hydroxy-1-phenyl-ethyl)-piperazin-1-yl]-phenyl}-butyramide; |
| 267 | 2-Ethyl-N-{3-fluoro-4-[4-(1-phenyl-ethyl)-piperazin-1-yl]-phenyl}-butyramide; |
| 268 | N-[4-(4-Benzyl-piperazin-1-yl)-3-fluoro-phenyl]-2-ethyl-butyramide; |
| 269 | 4-[4-(2-Ethyl-butyrylamino)-2-fluoro-phenyl]-1-(methoxycarbonyl-phenyl-methyl)-piperazine-2-carboxylic acid methyl ester (diastereomer 1); |
| 270 | 1-Benzo[1,3]dioxol-5-ylmethyl-4-[4-(2-ethyl-butyrylamino)-2-fluoro-phenyl]-piperazine-2-carboxylic acid methyl ester; |
| 271 | 1-Benzyl-4-[4-(2-ethyl-butyrylamino)-2-fluoro-phenyl]-piperazine-2-carboxylic acid methyl ester; |
| 272 | N-{4-[5-(Diethylcarbamoyl-phenyl-methyl)-2,5-diaza-bicyclo[2.2.1]heptyl]-3-fluoro-phenyl}-2-ethyl-butyramide; |
| 273 | 1-(3,5-Difluoro-benzyl)-4-[4-(2-ethyl-butyrylamino)-2-fluoro-phenyl]-piperazine-2-carboxylic acid methyl ester; |
| 274 | N,N-Diethyl-2-{4-[2-fluoro-4-(2-oxo-pyrrolidin-1-yl)-phenyl]-piperazin-1-yl}-2-phenyl-acetamide; |
| 275 | N,N-Diethyl-2-(4-{2-fluoro-4-[2-oxo-2-(2-phenyl-piperidin-1-yl)-ethyl]-phenyl}-piperazin-1-yl)-2-phenyl-acetamide; |
| 276 | N,N-Diethyl-2-(4-{2-fluoro-4-[2-oxo-2-(2-phenyl-pyrroldin-1-yl)-ethyl]-phenyl}-piperazin-1-yl)-2-phenyl-acetamide; |
| 277 | N,N-Diethyl-2-(4-{4-[2-(2-ethyl-piperidin-1-yl)-2-oxo-ethyl]-2-fluoro-phenyl}-piperazin-1-yl)-2-phenyl-acetamide; |
| 278 | N,N-Diethyl-2-(4-{2-fluoro-4-[(furan-2-ylmethyl-methyl-carbamoyl)-methyl]-phenyl}-piperazin-1-yl)-2-phenyl-acetamide; |
| 279 | 2-(4-{4-[2-(2,5-Dimethyl-pyrrolidin-1-yl)-2-oxo-ethyl]-2-fluoro-phenyl}-piperazin-1-yl)-N,N-diethyl-2-phenyl-acetamide; |
| 280 | N,N-Diethyl-2-(4-{2-fluoro-4-[2-oxo-2-(3,4,5,6-tetrahydro-2H-[2,3']bipyridinyl-1-yl)-ethyl]-phenyl}-piperazin-1-yl)-2-phenyl-acetamide; |
| 281 | N,N-Diethyl-2-(4-{4-[(1-ethyl-propylcarbamoyl)-methyl]-2-fluoro-phenyl}-piperazin-1-yl)-2-phenyl-acetamide; |
| 282 | N,N-Diethyl-2-(4-{2-fluoro-4-[2-(2-methyl-pyrrolidin-1-yl)-2-oxo-ethyl]-phenyl}-piperazin-1-yl)-2-phenyl-acetamide; |
| 283 | N,N-Diethyl-2-{4-[2-fluoro-4-(2-oxo-2-pyrrolidin-1-yl-ethyl)-phenyl]-piperazin-1-yl}-2-phenyl-acetamide; |
| 284 | N,N-Diethyl-2-{4-[4-(3-ethyl-2-oxo-1-phenyl-pentyl)-piperazin-1-yl]-3-fluoro-phenyl}-acetamide; |
| 285 | N-Benzyl-2-{4-[4-(3-ethyl-2-oxo-1-phenyl-pentyl)-piperazin-1-yl]-3-fluoro-phenyl}-acetamide; |
| 286 | N-Benzyl-2-{4-[4-(3-ethyl-2-oxo-1-phenyl-pentyl)-piperazin-1-yl]-3-fluoro-phenyl}-N-methyl-acetamide; |
| 287 | N-Benzyl-N-ethyl-2-{4-[4-(3-ethyl-2-oxo-1-phenyl-pentyl)-piperazin-1-yl]-3-fluoro-phenyl}-acetamide; |
| 288 | 2-(4-{4-[2-(3,3-Difluoro-pyrrolidin-1-yl)-2-oxo-1-phenyl-ethyl]-piperazin-1-yl}-3-fluoro-phenyl)-N-(1-ethyl-propyl)-acetamide; |
| 289 | 2-(4-{4-[2-(3,3-Difluoro-pyrrolidin-1-yl)-2-oxo-1-phenyl-ethyl]-piperazin-1-yl}-3-fluoro-phenyl)-N,N-diethyl-acetamide; |
| 290 | N,N-Diethyl-2-[4-(4-ethylcarbamoylmethyl-2-fluoro-phenyl)-piperazin-1-yl]-2-phenyl-acetamide; |
| 291 | 2-[4-(4-Cyclopentylcarbamoylmethyl-2-fluoro-phenyl)-piperazin-1-yl]-N,N-diethyl-2-phenyl-acetamide; |
| 292 | N-{4-[4-(Dimethylcarbamoyl-phenyl-methyl)-piperazin-1-yl]-3-fluoro-phenyl}-2-ethyl-butyramide; |
| 293 | N-{4-[4-(Diethylcarbamoyl-phenyl-methyl)-piperazin-1-yl]-3-trifluoromethyl-phenyl}-2-ethyl-butyramide; |
| 294 | N-{4-[4-(Diethylcarbamoyl-phenyl-methyl)-piperazin-1-yl]-2-trifluoromethyl-phenyl}-2-ethyl-butyramide; |
| 295 | N-{4-[4-(Diethylcarbamoyl-phenyl-methyl)-piperazin-1-yl]-2-methyl-phenyl}-2-ethyl-butyramide; and |
| 296 | N-{4-[4-(Diethylcarbamoyl-phenyl-methyl)-piperazin-1-yl]-2-fluoro-phenyl}-2-ethyl-butyramide; | and pharmaceutically acceptable salts thereof.

The invention includes also pharmaceutically acceptable salts of the compounds represented by Formula (I) or (II). Pharmaceutically acceptable salts of the above-described specific compounds are especially preferred. See, e.g., S. M. Berge, et al., "Pharmaceutical Salts", J. Pharm. Sci., 1977, 66:1-19, and *Handbook of Pharmaceutical Salts, Proportions, Selection, and Use*; Stahl, P. H. Wermuth, C. G., Eds.; Wiley-VCH and VHCA: Zurich, 2002. However, salts of acids and bases that are non-pharmaceutically acceptable may also find use, for example, in the preparation or purification of a pharmaceutically acceptable compound. All salts, whether pharmaceutically acceptable or not are included within the ambit of the present invention.

A "pharmaceutically acceptable salt" is intended to mean a salt of a free acid or base of a compound represented by Formula (I) or (II) that is not toxic, biologically intolerable, or otherwise biologically undesirable. Preferred pharmaceutically acceptable salts are those that are pharmacologically effective and suitable for contact with the tissues of patients without undue toxicity, irritation, or allergic response. A compound of Formula (I) or (II) may possess a sufficiently acidic group, a sufficiently basic group, or both types of functional groups, and accordingly react with a number of inorganic or organic bases, and inorganic and organic acids, to form a pharmaceutically acceptable salt. Exemplary pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) or (II) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or the like.

If the compound of Formula (I) or (II) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to treatment methods employing pharmaceutically acceptable prodrugs of the compounds of Formula (I) or (II). The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) or (II)). A "pharmaceutically acceptable prodrug" is a prodrug that is not toxic, biologically intolerable, or otherwise biologically unsuitable for administration to the subject. Conventional procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I) or (II). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) or (II) as amides or alkyl esters. Exemplary amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Preferred amides are derived from ammonia, $C_{1-3}$alkyl primary amines, and di($C_{1-2}$alkyl) amines. Exemplary esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

Pharmaceutically active metabolites may also be used in the methods of the invention. A "pharmaceutically active metabolite" means a pharmacologically active product of metabolism in the body of a compound of Formula (I) or (II) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formula (I) or (II) and their pharmaceutically acceptable salts, pharmaceutically acceptable prodrugs, and pharmaceutically active metabolites (collectively, "agents") of the present invention are useful as NPY Y2 inhibitors in the methods of the invention. The agents may be used in the inventive methods for the treatment or prevention of medical conditions, diseases, or disorders mediated through inhibition or modulation of NPY Y2, such as those described herein.

Compounds of the invention are potent, non-peptidic, low molecular weight, selective NPY Y2 inhibitors and are useful in treating or preventing: anxiolytic disorders and depression; injured mammalian nerve tissue; conditions responsive to treatment through administration of a neurotrophic factor; neurological disorders; bone loss; substance related disorders; sleep/wake disorders; cardiovascular disease; and metabolic disorders such as obesity or an obesity-related disorder. Compounds of the invention modulate endocrine functions; particularly those controlled by the pituitary and hypothalamic glands, and therefore may be used to treat inovulation and infertility that may be due to insufficient release of luteinizing hormone (LH) or luteal phase defect. Compounds of the invention are also useful in the treatment of chronic heart failure.

The compounds compete with the endogenous ligands NPY and possibly non-endogenous ligands, and bind to the NPY Y2 receptor. In addition, the compounds demonstrate antagonist activity by antagonizing the action of NPY upon binding to the Y2 receptor. The compounds described herein are ligands of the NPY Y2 receptor, but are not necessarily limited solely in their pharmacological or biological action due to binding to this or any neuropeptide, neurotransmitter or G-protein coupled receptor. For example, the described compounds may also undergo binding to dopamine or serotonin receptors.

Symptoms or disease states are intended to be included within the scope of "medical conditions, disorders, or diseases."

For example, "anxiolytic disorders" include affective disorders such as all types of depression, bipolar disorder, cyclothymia, and dysthymia, anxiety disorders such as generalized anxiety disorder, panic, phobias, and obsessive-compulsive disorder, stress disorders including post-traumatic stress disorder, hemorrhagic stress, stress-induced psychotic episodes, psychosocial dwarfism, stress headaches, stress-induced immune systems disorders such as stress-induced fever, and stress-related sleep disorders, and can include eating disorders such as anorexia nervosa, bulimia nervosa, and obesity, and drug addiction.

"Depression" refers to major depressive disorders, dysthymia, bipolar or manic disorders, and the like.

"Nerve tissue" as used herein refers to any vertebrate nerve tissue, particularly including mammalian cells of the central nervous system (CNS) and peripheral nervous system (PNS). More particularly, nerve tissue includes spinal cord neuronal structures, peripheral nervous system nerves, and even nerve cells of the brain.

"Nerve tissue injury", "injured mammalian nerve tissue", or "CNS or PNS nerve tissue injury" include any damage to relevant nerve tissue irrespective of cause, e.g., injuries attributable to trauma including but not limited to nerve tissue lesions, traumatically-induced compression, tumors, hemorrhage, infectious processes, spinal stenosis, or impaired blood supply.

"Treating injured mammalian nerve tissue" includes, but is not limited, to the in vivo administration of compounds, compositions, and methods of the instant invention to restore action potential or nerve impulse conduction through a nerve tissue lesion. The term may also include such administration in an effort to reduce the damaging effects of any injury to mammalian nerve tissue, whether through restoration of action potential or nerve impulse conduction, by stimulating growth or proliferation of nervous tissue, by ameliorating unwanted conditions in the extracellular microenvironment near an injury, or otherwise.

"Neurotrophic factor", as used herein, refers to compounds that are capable of stimulating growth or proliferation of nervous tissue, including compounds of the instant invention and known neurotrophic factors described previously herein.

"Neurological disorders" include CNS disorders such as tinitus, spasticity, and neuropathic pain, supranuclear palsy, AIDS related dementias, multiinfarct dementia, neurodegenerative disorders such as Alzheimer's disease, Parkinson's disease, and Huntington's disease, head trauma, spinal cord trauma, ischemic neuronal damage, amyotrophic lateral sclerosis, and disorders of pain perception such as fibromyalgia and epilepsy.

"Bone loss" refers to enhancement of bone growth or prevention of bone loss caused by conditions such as osteoporosis, osteomalacia, Paget's disease, disorders of bone homeostasis, and the like.

"Substance related disorders" refer to misuse, addiction, or dependence disorders related to the consumption of alcohol, amphetamines (such as, for example, 3,4-methylene-dioxy-N-methylamphetamine, also known as "MDMA" or "ecstacy"), cannabis, hallucinogens (such as, for example, cocaine), inhalants, nicotine, opioids, phencyclidine, narcotics, or sedatives, or combinations thereof.

"Sleep/wake disorders" include narcolepsy; sleep apnea disorders such as central sleep apnea, obstructive sleep apnea, and mixed sleep apnea; hypersomnia, including excessive daytime sleepiness (EDS), and, in particular, hypersomnia associated with narcolepsy or sleep apnea disorder; sleep/wake disturbances associated with attention deficit hyperactive disorder (ADHD); circadian rhythm abnormalities such as delayed sleep phase syndrome, advance sleep phase syndrome, non-24 hour sleep/wake disorder, jet lag, or shiftwork disorder; parasomnia disorders such as somnambulism, pavor nocturnus, REM sleep behavior disorder, sleep bruxism, or sleep enuresis; sleep-related movement disorders such as sleep bruxism, restless legs syndrome, or periodic limb movement; insomnia, including extrinsic insomnia, psychophysiologic insomnia, drug-dependent insomnia, or alcohol-dependent insomnia; sleep/wake disturbances associated with mental disorders such as depression, anxiety, schizophrenia, or other psychotic disorders; sleep/wake disturbances associated with neurological disorders such as migraine, epilepsy, Parkinson's disease, or Alzheimer's disease; and sleep/wake disturbances associated with fibromyalgia, headaches, gastroesophageal reflux disease, coronary artery ischemia, cardiac arrhythmias, abnormal swallowing, choking, or laryngospasm.

"Obesity" refers to a condition in which a subject has a body mass index of greater than or equal to 30. "Over-weight" refers to a condition in which a subject has a body mass index of greater or equal to 25.0. The body mass index and other definitions are according to the "NIH Clinical Guidelines on the Identification and Evaluation, and Treatment of Overweight and Obesity in Adults" (1998).

"Obesity-related disorder" includes anorexia nervosa, wasting, AIDS-related weight loss, bulimia, cachexia, lipid disorders including hyperlipidemia and hyperuricemia, insulin resistance, noninsulin dependent diabetes mellitus (NIDDM, or Type II diabetes), insulin dependent diabetes mellitus (IDDM or Type I diabetes), diabetes-related complications including microangiopathic lesions, ocular lesions, retinopathy, neuropathy, and renal lesions, cardiovascular disease including cardiac insufficiency, coronary insufficiency, and high blood pressure, atherosclerosis, atheromatous disease, stroke, hypertension, Syndrome X, gallbladder disease, osteoarthritis, sleep apnea, forms of cancer such as uterine, breast, colorectal, kidney, and gallbladder, high cholesterol levels, complications of pregnancy, menstrual irregularities, hirsutism, muscular dystrophy, infertility, and increased surgical risk.

"Cardiovascular disease" includes, for example, cardiac arrhythmia, post-myocardial infarction, and heart failure.

Thus, the pharmaceutical agents may be used to treat subjects diagnosed with or suffering from a disease, disorder, or condition mediated through NPY Y2 activity. The term "treat" or "treating" as used herein is intended to refer to administration of at least one agent of the invention or a composition of the invention to a subject for the purpose of effecting a therapeutic or prophylactic benefit through modulation of NPY Y2 activity. Treating includes reversing, ameliorating, alleviating, inhibiting the progress of, lessening the severity of, or preventing a disease, disorder or condition, or one or more symptoms of such disease, disorder or condition mediated through modulation of NPY Y2 activity. The term "subject" refers to a mammalian patient in need of such treatment, such as a human. "Modulators" include both inhibitors and activators, where "inhibitors" refer to compounds that decrease, prevent, inactivate, desensitize or down-regulate NPY Y2 expression or activity, and "activators" are compounds that increase, activate, facilitate, sensitize, or up-regulate NPY Y2 expression or activity.

Accordingly, the invention relates to methods of using the pharmaceutical agents described herein to treat subjects diagnosed with or suffering from a disease, disorder, or condition mediated through NPY Y2 activity, such as: anxiolytic disorders and depression; injured mammalian nerve tissue; conditions responsive to treatment through administration of a neurotrophic factor; neurological disorders; bone loss; substance related disorders; metabolic disorders such as obesity or an obesity-related disorder; inovulation and infertility that may be due to insufficient release of luteinizing hormone (LH) or luteal phase defect; and cardiovascular disease, cardiac arrhythmia, post-myocardial infarction, or chronic heart failure. In particular, the invention relates to methods of using the pharmaceutical agents described herein to treat subjects diagnosed with or suffering from a disease, disorder, or condition mediated through NPY Y2 activity, such as anxiety and alcoholism.

In a treatment method according to the invention, an effective amount of at least one pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment.

Effective amounts or doses of the agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of agent per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active compounds in the treatment of the above conditions. The additional compounds may be coadministered separately with an agent of Formula (I) or (II) or included with such an agent as an additional active ingredient in a pharmaceutical composition according to the invention. In an exemplary embodiment, additional active compounds are those that are known or discovered to be effective in the treatment of conditions, disorders, or diseases mediated by NPY Y2 activity, such as another NPY Y2 modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention. In one illustrative embodiment, a composition according to the invention may contain one or more additional active ingredients selected from anxiolytics, antidepressants, and hypnotics.

The agents of the invention are used, alone or in combination with one or more other active ingredients, to formulate pharmaceutical compositions of the invention. A pharmaceutical composition of the invention comprises: (a) an effective amount of at least one pharmaceutical agent in accordance with the invention; and (b) a pharmaceutically acceptable excipient.

A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the pharmaceutical agents may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient mixed with pharmaceutically acceptable excipients such as inert diluents, disintegrating agents, binding agents, lubricating agents, sweetening agents, flavoring agents, coloring agents, and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The agents of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Exemplary agents useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I) or (II). One skilled in the art will recognize that methods shown for Formula (II) in the following Schemes are applicable to the preparation of compounds of Formula (I) as well.

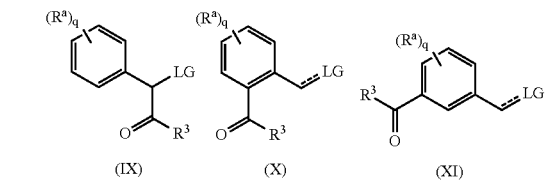

The compounds of Formula (I) or (II) of the invention may be produced by any number of reaction schemes. Referring to Scheme A, piperazines (V) may be coupled with nitrobenzenes (VI) in the presence of a suitable base such as $K_2CO_3$, $Na_2CO_3$, or KOH, neat or in a solvent such as THF, DMF, or NMP, to form compounds (VII). Piperazines (V) are optionally protected with a suitable protecting group (PG), such as with a Boc or benzyl group. Preferably, reactions are performed in the presence of K₂CO₃ in DMF at elevated temperatures of about 50° C. to about 80° C. Reduction of the nitro group to an amino group may be accomplished with SnCl₂ or SnCl₂.2H₂O in a solvent such as EtOH or EtOAc, or mixtures thereof, at temperatures of about room temperature to about reflux temperature. Alternatively, reduction may be accomplished by hydrogenation over a palladium catalyst such as Pd/C, in a solvent such as EtOH. The free amine may then be converted to an amide of formula (VIII) by: 1) reaction with Z—C(O)-LG1, where LG1 is a chloride or fluoride, in the presence of an amine base such as TEA or iPr₂NEt, in a solvent such as THF, DCM, or DCE; or 2) reaction with Z—C(O)-LG1, where LG1 is OH, under amide coupling conditions; or may be converted to a urea of formula (VIII) by reaction with an isocyanate, in a solvent such as DCM or DCE, with or without a tertiary amine base. Amide coupling conditions may include a coupling agent, such as EDC, DCC, HATU, PyBoP, PyBroP, polymer-supported carbodiimide, and the like, with an optional additives, such as HOBt or a tertiary amine base (such as TEA, iPr₂NEt, NMM, and the like), in a solvent such as DCM, DCE, THF, or DMF. Deprotection of compounds of formula (VIII) may be accomplished using standard methods to give amines (VIIIa). Where PG is a Boc group, conditions may include HCl in Et₂O or MeOH, or TFA.

Reaction of amines (VIIIa) with alkylating agents (IX), (X), or (XI), where LG is a leaving group such as a iodide, bromide, chloride, tosylate, mesylate, or the like, to produce compounds of Formula (I) or (II), may be accomplished under basic conditions. Suitable bases include K₂CO₃, Na₂CO₃, or NaH, in a solvent such as THF or DMF, at a temperature between room temperature and reflux temperature. Preferred conditions employ K₂CO₃ in DMF at room temperature.

Where LG is an aldehyde group, coupling of amines (VIIIa) with aldehydes (X) or (XI) is accomplished under reductive amination conditions, such as NaBH(OAc)₃ or NaBH₃CN in a solvent such as DCM, DCE, MeOH, or EtOH.

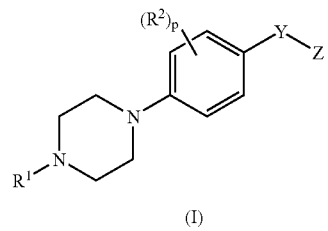

(I)

Referring to Scheme B, nitrobenzenes of formula (VII) may be converted to amines (XII) through deprotection and alkylation or reductive amination protocols as described in Scheme A. Reduction of the nitro group and coupling as described in Scheme A gives rise to amides and ureas of Formula (I) or (II).

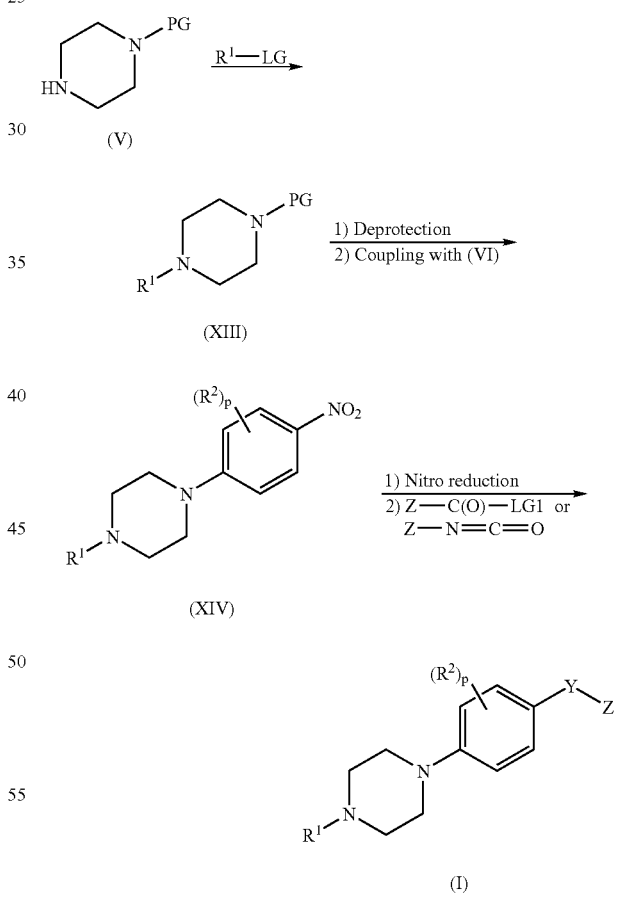

Scheme B

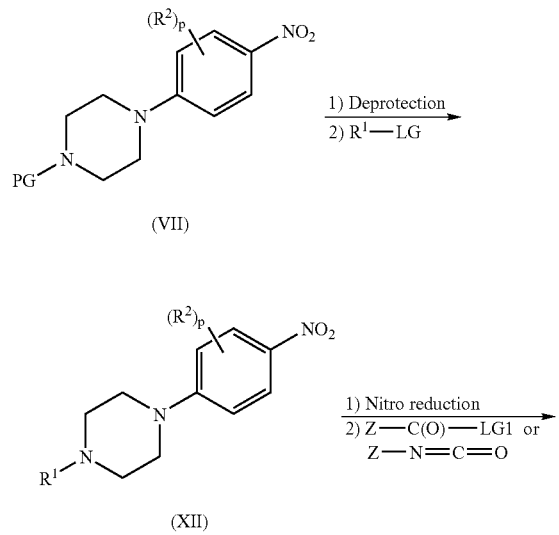

Referring to Scheme C, protected piperazines (V) are reacted with R1-LG as described in Scheme A to give amines (XIII). Removal of the PG Protecting group and coupling with (VI) are performed as in Scheme A to give nitrobenzenes (XIV). Nitro reduction and coupling as in Scheme A give amides and ureas of Formula (I) or (II).

Scheme D

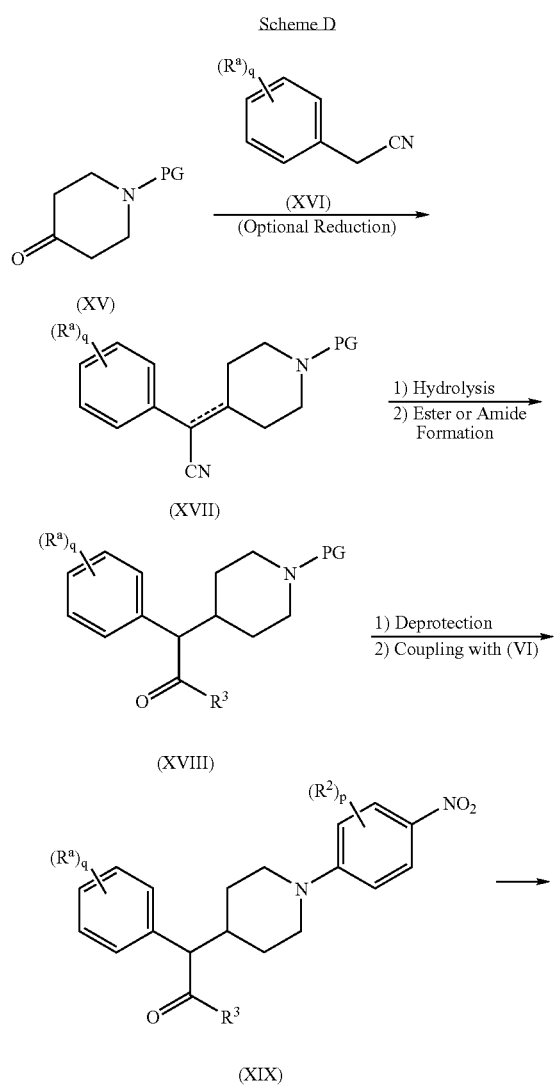

Referring to Scheme D, piperidones (XV) are coupled with phenyl acetonitriles (XVI) in the presence of a suitable base, such as NaOEt in EtOH, or sodium bis(trimethylsilyl)amide (NaHMDS) in THF, to give piperidin-4-ylidenes (XVII). Optional reduction of the double bond gives saturated piperidines (XVII). The reduction may alternatively be performed at a later stage in the sequence. Also, particular embodiments of piperidin-4-ylidenes and saturated piperidines (XVII) are commercially available. Hydrolysis of the cyano group to acids (XVIIa) may be performed with 48% HBr at elevated temperatures The acid may be converted to an ester group by treatment with a suitable acid, such as HCl, in MeOH or EtOH, or to an amide group via a peptide coupling, or by activation to an acid chloride and reaction with a suitable amine. Compounds of formula (XVIII) are then deprotected and coupled with fluoro-nitrobenzenes (VI) according to methods described in Scheme A to provide nitrobenzenes (XIX), which are ultimately converted to compounds of Formula (I) or (II) as described in the preceding Schemes. In an alternative embodiment, where PG is benzyl, where the reduction is a hydrogenation, this step may remove PG. If so, the PG may be replaced with the same or a different compatible protecting group, and the process continued as shown above. Or, the free piperidine may be coupled with (VI) directly and taken through steps analogous to Scheme C. Then, hydrolysis of the cyano group to an ester or to an acid followed by amide formation would give rise to compounds of Formula (I) or (II). One skilled in the art will recognize that the order of steps in the sequence may be altered, e.g. 1) coupling with (XVI); 2) deprotection of PG; 3) coupling with (VI); 4) hydrolysis of the nitrile to form an acid; 5) conversion of the acid to an ester or amide; 6) optional double bond reduction; and 7) insertion of —Y—Z as in the preceding schemes.

Scheme E

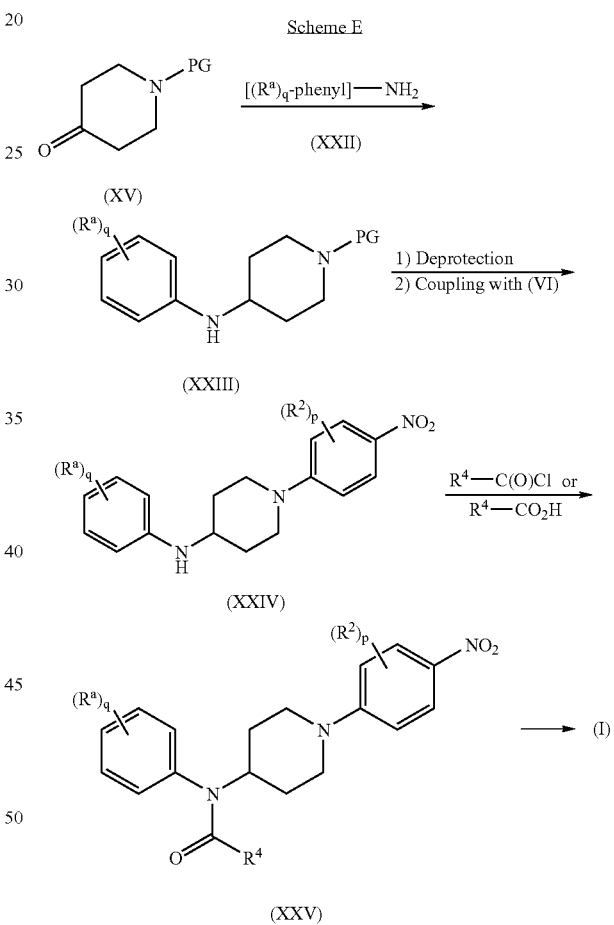

Referring to Scheme E, piperidones (XV) may be coupled with anilines (XXII) under reductive amination conditions as previously described, to form amines (XXIII). Deprotection and coupling with (VI) may be accomplished as in the preceding Schemes to give nitrobenzenes (XXIV). The free amine group reacted with a suitable $R^4$-containing acid or acid chloride as described in Scheme A, to provide compounds of formula (XXV). Further transformations, including nitro reduction and coupling as described in the preceding Schemes, give rise to compounds of Formula (I) or (II).

Scheme F

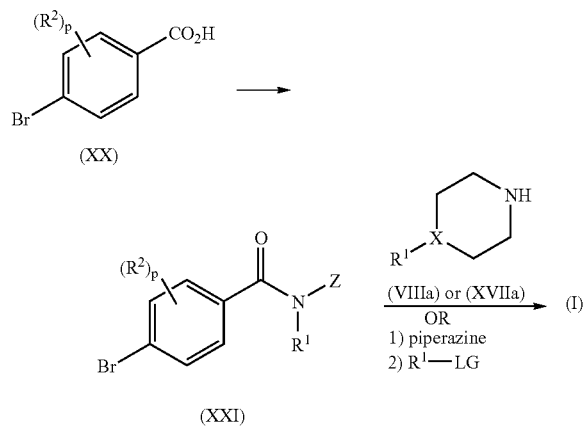

Compounds of Formula (I) or (II) where Y is —C(O)—N(R¹)— may be prepared according to Scheme F. Commercially available bromobenzoic acids (XX) are converted to amides (XXI) under amide coupling conditions or by 1) activation as an acid chloride using oxalyl chloride, and 2) reaction with a suitable amine Z—N(R¹)H. Piperidines or piperazines of formula (VIIIa) or (XVIIa), or optionally protected piperazine, may be coupled with bromides (XXI) under palladium(0)-catalyzed conditions. Preferred conditions include tris(dibenzylidineacetone)-palladium(0) [Pd$_2$(dba)$_3$], Pd(PPh$_3$)$_4$, or PdCl$_2$dppf, in the presence of a base such as K$_3$PO$_4$, Na$_2$CO$_3$, Cs$_2$CO$_3$, or NaOtBu, and optional phosphine-based additives such as Ph$_3$P, BINAP, (dicyclohexylphosphino)-biphenyl, X-Phos, or the like, in a solvent such as toluene, at room temperatures, or elevated temperatures up to about 100° C., and optionally using a microwave reactor.

One skilled in the art will recognize that the methodology depicted in Scheme F is applicable to the preparation of compounds of Formula (I) or (II) where —C(O)N(R¹)—Z is any —Y—Z group as defined therein.

SCHEME G

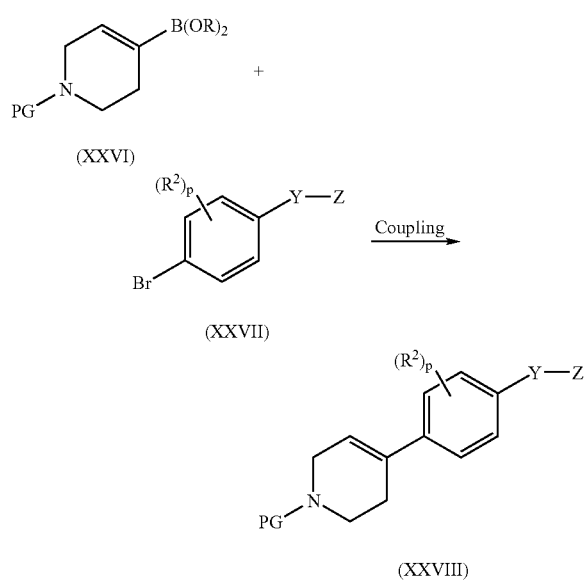

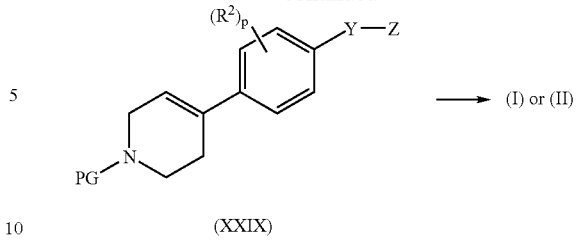

Compounds of Formula (I) or (II) may also be prepared according to Scheme G. Suzuki coupling of dihydropyridine reagents (XXVI), where —B(OR)$_2$ is a boronic acid or boronic ester, with bromides (XXVII) is accomplished under palladium(0)-catalyzed conditions as described in Scheme F. Compounds (XXIX) may be converted into compounds of Formula (I) or (II) according to the previous Schemes. Additionally, hydrogenation of the double bond in the presence of a suitable catalyst such as Pd/C, provides piperidine analogs (not shown), that may be converted to further embodiments of Formula (I) and (II).

Additional methods are useful in the preparation of compounds of Formula (I) or (II). Such methods include reaction of ureas where R¹ is —H with an alkylating agent to form ureas where R¹ is —C$_{1-4}$alkyl. Preferably, alkylations are performed in the presence of a suitable base such as NaH, in a polar solvent such as THF or DMF. Suitable alkylating agents include alkyl halides such as alkyl bromides.

Compounds of Formula (I) or (II) where —C(O)—R³ is an ester group may be converted to compounds of Formula (I) or (II) where —C(O)—R³ is an amide group using methods known to one skilled in the art. This transformation may be accomplished at any stage of the synthetic sequence shown above. In a preferred embodiment, esters are hydrolyzed to their corresponding acids, for example, with LiOH in mixtures of THF, MeOH, and water. Amides are then prepared from the acids using the methods described in the preceding schemes.

The following specific examples are provided to further illustrate the invention and various preferred embodiments.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention. Unless otherwise noted, the materials used in the examples were obtained from readily available commercial sources or synthesized by standard methods known to those skilled in the art.

Purification and Analytical Methods

Mass spectra were obtained on an Agilent series 1100 MSD using electrospray ionization (ESI) in positive mode unless otherwise indicated. Calculated mass corresponds to the exact mass.

Thin-layer chromatography was performed using Merck silica gel 60 F$_{254}$ 2.5 cm×7.5 cm 250 μm or 5.0 cm×10.0 cm 250 μm pre-coated silica gel plates. Preparative thin-layer chromatography was performed using EM Science silica gel 60 F$_{254}$ 20 cm×20 cm 0.5 mm or Analtech silica gel GF 2000 um pre-coated plates with a 20 cm×4 cm concentrating zone.

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Normal phase flash column chromatography (FCC) was typically performed with RediSep® silica gel columns using 2 M ammonia in methanol/dichloromethane as eluent.

Chiral chromatography was performed using supercritical fluid chromatography (SFC)HPLC on a Chiralpak AD-H column (Chiral Technologies), eluting with isocratic 20% TEA/MeOH/CO$_2$ under 100 bar pressure at 25° C. Analytical: 4.6×250 mm column, 2 mL/min flow rate. Preparative: 21×250 mm column, 37.5 mL/min flow rate.

Preparative Reversed-Phase HPLC was performed on a Gilson® instrument under the following conditions: Column: YMC-Pack ODS-A, 5 µm, 75×30 mm; Flow rate: 25 mL/min; Detection: λ=220 & 254 nm; Gradient (acetonitrile/water, 0.05% trifluoroacetic acid): 15% acetonitrile/85% water to 99% acetonitrile/1% water ramp over 20 min; or on an Agilent® 1100 Series instrument under the following conditions: Column: Phenomenex Gemini, 5 µm, 100×30 mm; Flow rate: 30 mL/min; Detection: λ=220 & 254 nm; Gradient (acetonitrile/water, 20 mM NH$_4$OH): 5% acetonitrile/95% water to 99% acetonitrile/1% water ramp over 20 min.

Synthetic Methods

Unless otherwise stated, reaction solutions were stirred at room temperature (rt).

Bromo phenylacetic acid esters were used to prepare compounds of the invention, and were prepared according to methods known in the literature. For example, bromo-thiophen-2-yl-acetic acid methyl ester (See: J. Med. Chem. 1981, 24, 481-490; Tetrahedron 2002, 58, 10113-10126) and bromo-thiophen-3-yl-acetic acid methyl ester (See: PCT Intl. Appl. Publ. WO93/14077) were synthesized from thiophen-2-yl-acetic acid methyl ester and thiophen-3-yl-acetic acid methyl ester respectively.

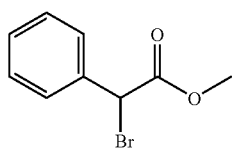

Intermediate A; Bromo phenyl acetic acid methyl ester (Method A).

Step A. Phenyl acetic acid methyl ester. Concentrated H$_2$SO$_4$ (1.00 mL) was added to a stirred solution of substituted phenyl acetic acid (6.50 mmol) in MeOH (10.0 mL) and the solution was heated at reflux for 3 h. The mixture was concentrated and the residue was partitioned between DCM (50.0 mL) and satd. aq. NaHCO$_3$ (50 mL). The organic layer was washed with water (2×30 mL), dried (MgSO$_4$), and concentrated to yield the title compound.

Step B. Azo-bis-isobutyronitrile (AIBN, 0.25 mmol) was added to a stirred solution of phenyl-acetic acid methyl ester (5.00 mmol) and N-bromosuccinimide (NBS, 5.50 mmol) in CCl$_4$ (30 mL) under nitrogen. The reaction mixture was heated at reflux for 24 h. The mixture was cooled and diluted with hexanes (60 mL). The mixture was filtered, and the filtrate was concentrated to give the title compound, which was used without any purification in the next step.

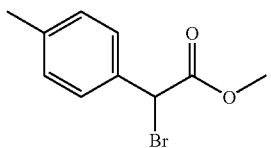

Intermediate B; Bromo-p-tolyl-acetic acid methyl ester (Method B).

A mixture of p-tolyl-acetic acid (5.00 g, 33.3 mmol) in thionyl chloride (10.0 mL) was stirred at rt for 2 h, then was heated at 65° C. for 1 h. The mixture was cooled to rt and treated with NBS (11.9 g, 66.7 mmol) and 48% aq. HBr (10 drops). The mixture was heated at 90° C. for 1 h, slowly treated with thionyl chloride (5.00 mL), and heated at reflux for an additional 45 min. The reaction mixture was cooled and concentrated and the residue was poured into MeOH (30 mL). The black tar residue was diluted with DCM and washed with water (2×30 mL). The combined organic layers were dried (MgSO$_4$) and concentrated to give a dark black oil (7.50 g), which was distilled under vacuum using a Kugelrohr apparatus to yield the title compound as a colorless oil (4.50 g, 56%).

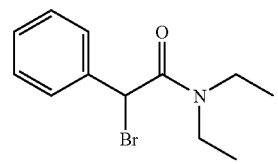

Intermediate C; 2-Bromo-N,N-diethyl-2-phenyl-acetamide.

To a solution of α-bromophenylacetic acid (0.40 g, 1.8 mmol) and diethylamine (0.21 mL, 2.0 mmol) in DCM (20 mL) was added EDC (0.42 g, 2.2 mmol). After 18 h, the mixture was diluted with 1 N NaOH (15 mL) and extracted with DCM (3×25 mL). The organic layers were combined, dried (Na$_2$SO$_4$), and concentrated. Chromatography of the resulting residue (SiO$_2$; 2 M NH$_3$ in MeOH/DCM) gave the title compound (0.24 g, 48%). MS (ESI): mass calcd. for C$_{12}$H$_{16}$BrNO, 269.04. m/z found, 270.1 [M+H]$^+$. $^1$H NMR (CDCl$_3$): 7.14-7.07 (m, 5H), 3.26-3.23 (m, 4H), 1.22-1.18 (m, 6H).

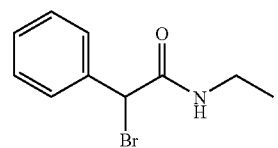

Intermediate D; 2-Bromo-N-ethyl-2-phenyl-acetamide.

This compound was prepared as described in Intermediate C.

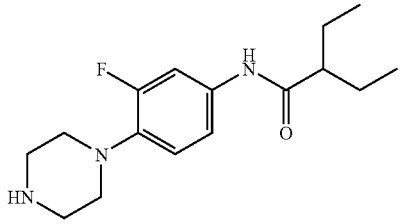

Intermediate E; 2-Ethyl-N-(3-fluoro-4-piperazin-1-yl-phenyl)-butyramide.

Step A. 4-(2-Fluoro-4-nitro-phenyl)-piperazine-1-carboxylic acid tert-butyl ester. To a solution of 1-(2-fluoro-4-nitro-phenyl)-piperazine (6.33 g, 28.1 mmol) and iPr$_2$NEt (3.83 g, 29.6 mmol) in DCM (50.0 mL) was added a solution of di-tert-butyl dicarbonate (6.44 g, 29.6 mmol) in DCM (50 mL). After 16 h, the mixture was diluted with DCM (100 mL) and washed with water. The organic layer was dried (MgSO$_4$) and concentrated to give a yellow solid (9.39 g). MS: mass calcd. for $C_{15}H_{20}FN_3O_4$, 325.14. m/z found, 326.2 [M+H]$^+$.

Step B. 4-(4-Amino-2-fluoro-phenyl)-piperazine-1-carboxylic acid tert-butyl ester. A solution of 4-(2-fluoro-4-nitro-phenyl)-piperazine-1-carboxylic acid tert-butyl ester (9.30 g, 28.6 mmol) in EtOH (80 mL) was hydrogenated (H$_2$, 50 psi) in the presence of 10% Pd/C (0.50 g). After 2.5 h, the mixture was filtered and the filtrate was concentrated to yield the title compound (7.17 g, 85%). MS: mass calcd. for $C_{15}H_{22}FN_3O_2$, 295.17. m/z found, 296.2 [M+H]$^+$. $^1$H NMR (CDCl$_3$): 6.80-6.78 (m, 1H), 6.44-6.36 (m, 2H), 3.66-3.50 (m, 6H), 2.93-2.85 (m, 4H), 1.47 (s, 9H).

Step C. 2-Ethyl-N-(3-fluoro-4-piperazin-1-yl-phenyl)-butyramide. To a solution of 4-(4-amino-2-fluoro-phenyl)-piperazine-1-carboxylic acid tert-butyl ester (2.0 g, 8.9 mmol) and Et$_3$N (1.4 mL, 10.0 mmol) in DCM (60 mL) was added 1-ethylbutyryl chloride (1.4 mL, 10.0 mol). The mixture was stirred for 18 h, quenched with 1 N NaHCO$_3$ (50 mL), and extracted with DCM (3×50 mL). The organic layers were combined, dried (Na$_2$SO$_4$), and concentrated. Chromatography of the residue (SiO$_2$; EtOAc/hexanes) gave 4-[4-(2-ethyl-butyrylamino)-2-fluoro-phenyl]-piperazine-1-carboxylic acid tert-butyl ester. A mixture of this intermediate in MeOH (25 mL) and 2 N HCl in Et$_2$O (10 mL) was stirred for 18 h. The solution was concentrated to give 2-ethyl-N-(3-fluoro-4-piperazin-1-yl-phenyl)-butyramide hydrochloride. This salt was treated with 1 N NaOH (10 mL) and extracted with EtOAc (40 mL). The organic layer was dried and concentrated to give the title compound as the free base (1.5 g, 58%). MS (ESI): mass calcd. for $C_{16}H_{24}FN_3O$, 293.19. m/z found, 294.4 [M+H]$^+$. $^1$H NMR (CDCl$_3$): 7.25-7.23 (m, 1H), 7.17 (s, 1H), 6.58-6.55 (m, 1H), 3.08-3.00 (m, 8H), 2.02-1.99 (m, 1H), 1.80-1.50 (m, 4H), 1.00-0.95 (m, 6H).

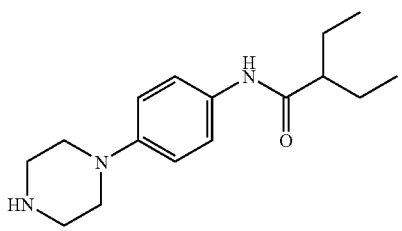

Intermediate F; 2-Ethyl-N-(4-piperazin-1-yl-phenyl)-butyramide.

The title compound may be prepared according to the procedures described for Intermediate E, with the appropriate substituent changes.

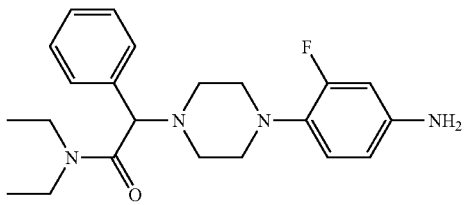

Intermediate G; 2-[4-(4-Amino-2-fluoro-phenyl)-piperazin-1-yl]-N,N-diethyl-2-phenyl-acetamide.

Step A. 2-Chloro-N,N-diethyl-2-phenyl-acetamide. To a mixture of 2-chloro-2-phenylacetyl chloride (1.6 mL, 10 mmol) and TEA (2.8 mL, 20 mmol) in DCE (50 mL) was added Et$_2$NH (1.1 mL, 10 mmol). The reaction mixture was stirred at rt for 4 h, then was washed with H$_2$O (50 mL). The organic layer was concentrated to give the crude title compound.

Step B. 2-[4-(4-Amino-2-fluoro-phenyl)-piperazin-1-yl]-N,N-diethyl-2-phenyl-acetamide. To a mixture of 2-chloro-N,N-diethyl-2-phenyl-acetamide (10 mmol) and K$_2$CO$_3$ (20 mmol) in DMF (30 mL) was added 1-(2-fluoro-4-nitrophenyl)-piperazine (2.3 g, 10 mmol). The reaction mixture was stirred at 50° C. for 3 h, then was diluted with H$_2$O (500 mL). The solution was decanted, leaving a semi-solid, which was collected. The semi-solid was diluted with 1:1 EtOH/EtOAc (100 mL), treated with SnCl$_2$.2H$_2$O (10 g), and heated at 100° C. for 16 h. The mixture was cooled to rt, diluted with ice water (100 mL), basified to pH=9 with NaHCO$_3$, and extracted with EtOAc (3×200 mL). The organic layers were combined, dried (Na$_2$SO$_4$), and concentrated to give the crude title compound.

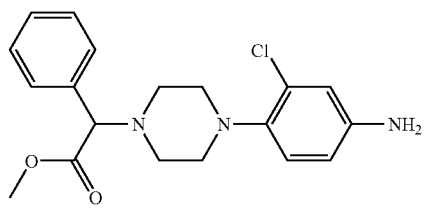

Intermediate H; [4-(4-Amino-2-chloro-phenyl)-piperazin-1-yl]-phenyl-acetic acid methyl ester.

Step A. [4-(2-Chloro-4-nitro-phenyl)-piperazin-1-yl]-phenyl-acetic acid methyl ester. To a mixture of 3-chloro-4-fluoronitrobenzene (160 mg, 0.94 mmol) and phenyl-piperazin-1-yl-acetic acid methyl ester (210 mg, 0.85 mmol) in DMF (3 mL) was added K$_2$CO$_3$ (350 mg, 2.5 mmol). The reaction mixture was stirred at 80° C. for 16 h. After cooling to rt, the mixture was diluted with water (15 mL) and extracted with EtOAc/hexanes (3:1, 75 mL). The organic layer was washed with water (3×), dried (Na$_2$SO$_4$), and concentrated to provide the title compound (153 mg, 46%) as a yellow powder, which was used without further purification. MS (ESI): mass calcd. for $C_{19}H_{20}ClN_3O_4$, 389.83; m/z found, 390.4 [M+H]$^+$.

Step B. To a mixture of 4-(2-chloro-4-nitro-phenyl)-piperazin-1-yl]-phenyl-acetic acid methyl ester (150 mg, 0.39 mmol) in EtOH (25 mL) was added SnCl$_2$.H$_2$O (530 mg, 2.4 mmol). The mixture was heated at reflux for 1.5 h. After cooling to rt, the mixture was concentrated. The resulting solid was suspended in water and treated with 1 N NaOH until pH ~14. This aqueous solution was extracted with DCM (2×). The organic extracts were combined, dried (Na$_2$SO$_4$), and concentrated to provide the title compound (49 mg, 36%), which was used without further purification. MS (ESI): mass calcd. for C$_{19}$H$_{22}$ClN$_3$O$_2$, 359.85. m/z found, 360.4 [M+H]$^+$. $^1$H NMR (CDCl$_3$): 7.43-7.37 (m, 1H), 7.32-7.24 (m, 8H), 6.81 (d, J=8.5, 1H), 6.65 (d, J=2.7, 1H), 6.47 (dd, J=8.5, 2.7, 1H), 4.00 (s, 1H), 3.03-2.87 (m, 4H), 2.66-2.49 (m, 4H).

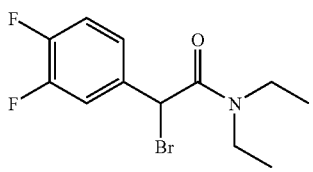

Intermediate I; 2-Bromo-2-(3,4-difluoro-phenyl)-N,N-diethyl-acetamide.

Step A. (3,4-Difluoro-phenyl)-acetyl chloride. To a mixture of 3,4-difluorophenyl acetic acid (5.00 g, 29 mmol) in tetrachloromethane (70 mL) was added thionyl chloride (8.5 mL, 116 mmol). After 18 h at reflux, the solution was concentrated to give the title compound (5.5 g, 100%). $^1$H NMR (CDCl$_3$): 7.22-7.08 (m, 2H), 7.40-6.96 (m, 1H), 4.11 (s, 2H). The crude product was carried forward to the next step.

Step B. Bromo-(3,4-difluoro-phenyl)-acetyl chloride. A solution of (3,4-difluoro-phenyl)-acetyl chloride (5.5 g, 29 mmol), N-bromosuccinamide (5.575 g, 31.30 mmol) and AIBN (200 mg) in tetrachloromethane was heated at reflux for 18 h. The mixture was cooled and filtered, and the filtrate was concentrated. The resulting oily residue (6.7 g) was distilled under vacuum using Kugelrohr apparatus to yield the title compound as yellowish oily liquid (4.44 g, 57%). $^1$H NMR (CDCl$_3$): 7.23-7.17 (m, 1H), 7.08-7.01 (m, 2H), 5.86 (s, 1H).

Step C. 2-Bromo-2-(3,4-difluoro-phenyl)-N,N-diethyl-acetamide. A solution of bromo-(3,4-difluoro-phenyl)-acetyl chloride (1.15 g, 4.27 mmol) in DCM (30 mL) was treated with diethylamine (625 mg, 8.54 mmol) slowly. After 10 h, the solution was diluted with DCM (60 mL), washed with water, dried (Na$_2$SO$_4$), and concentrated to yield the crude title compound (950 mg). $^1$H NMR gave satisfactory results.

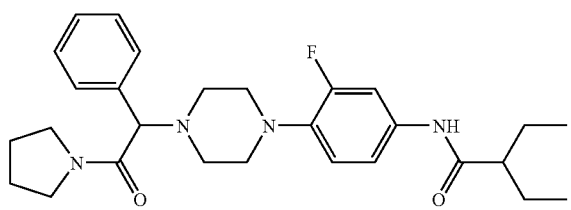

Example 1

2-Ethyl-N-{3-fluoro-4-[4-(2-oxo-1-phenyl-2-pyrrolidin-1-yl-ethyl)-piperazin-1-yl]-phenyl}-butyramide To a solution of 2-ethyl-N-(3-fluoro-4-piperazin-1-yl-phenyl)-butyramide (0.08 g, 0.27 mmol) and Na$_2$CO$_3$ (0.03 g, 0.30 mmol) in DMF (2 mL) was added 2-bromo-2-phenyl-1-pyrrolidin-1-yl-ethanone (0.09 g, 0.30 mmol). After 18 h of stirring the mixture was diluted with EtOAc (30 mL) and washed with water (3×30 mL). The organic layer was dried (MgSO$_4$) and concentrated. Chromatography of the resulting residue (SiO$_2$; 2 M NH$_3$ in MeOH/DCM) gave the title compound (0.08 mg, 51%). MS (ESI): mass calcd. for C$_{28}$H$_{37}$FN$_4$O$_2$, 480.29. m/z found, 481.4 [M+H]$^+$. $^1$H NMR (DMSO): 7.52-7.47 (m, 3H), 7.36-7.29 (m, 3H), 7.07-7.05 (m, 1H), 6.87-6.83 (m, 1H), 3.42-3.38 (m, 1H), 3.09 (br s, 4H), 2.69 (s, 4H), 2.10-1.45 (m, 12H), 0.96-0.94 (m, 6H).

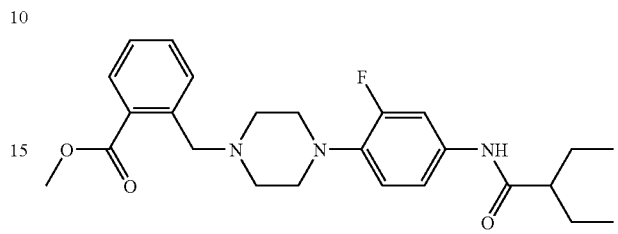

Example 2

2-{4-[4-(2-Ethyl-butyrylamino)-2-fluoro-phenyl]-piperazin-1-ylmethyl}-benzoic acid methyl ester To a solution of 2-ethyl-N-(3-fluoro-4-piperazin-1-yl-phenyl)-butyramide (0.05 mg, 0.17 mmol) and methyl-2-formyl benzoate (0.03 mg, 0.19 mmol) in DCM (10 mL) was added NaBH(OAc)$_3$ (0.03 mg, 0.13 mmol). After 18 h, the mixture was diluted with 1 N NaOH (15 mL) and extracted with DCM (3×25 mL). The organic layers were combined, dried (Na$_2$SO$_4$), and concentrated. Chromatography of the resulting residue (SiO$_2$; 2 M NH$_3$ in MeOH/DCM) gave the title compound (0.70 g, 93%). MS (ESI) mass calcd. for C$_{25}$H$_{32}$FN$_3$O$_3$, 441.24. m/z found, 442.4 [M+H]$^+$. $^1$H NMR (CDCl$_3$): 7.70 (d, J=7.3, 1H), 7.48-7.43 (m, 2H), 7.34-7.30 (m, 1H), 7.14-7.08 (m, 2H), 6.88-6.84 (m, 1H), 3.90 (s, 3H), 3.00 (s, 4H), 2.61-2.58 (m, 4H), 2.00-1.97 (m, 1H), 1.74-1.47 (m, 4H), 0.96-0.93 (m, 6H).

Examples 3-5 were prepared using methods similar to those described in Example 2, with the appropriate substituent changes.

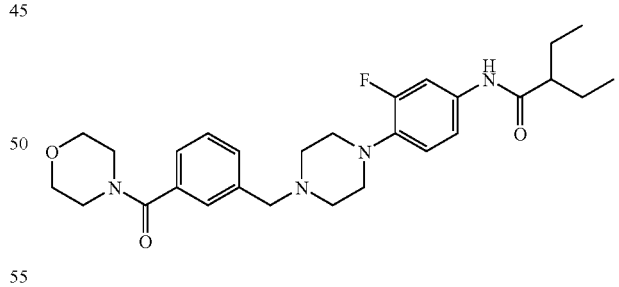

Example 3

2-Ethyl-N-(3-fluoro-4-{4-[3-(morpholine-4-carbonyl)-benzyl]-piperazin-1-yl}-phenyl)-butyramide MS (ESI) mass calcd. for C$_{28}$H$_{37}$FN$_4$O$_3$, 496.28. m/z found, 497.4 [M+H]$^+$. $^1$H NMR (CDCl$_3$): 7.48-7.38 (m, 3H), 7.32-7.29 (m, 1H), 7.25 (m, 1H), 7.12-7.08 (m, 1H), 6.90-6.85 (m, 1H), 3.80-3.52 (m, 8H), 3.07 (s, 4H), 2.64 (s, 4H), 2.03-2.01 (m, 1H), 1.75-1.70 (m, 2H), 1.59-1.54 (m, 2H), 0.95-0.92 (m, 6H).

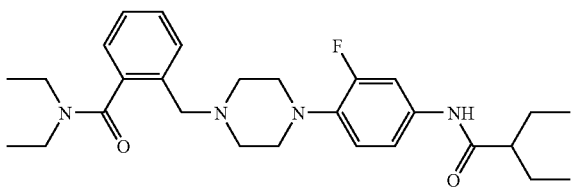

Example 4

N,N-Diethyl-2-{4-[4-(2-ethyl-butyrylamino)-2-fluoro-phenyl]-piperazin-1-ylmethyl}-benzamide

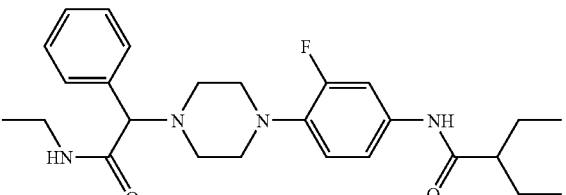

Example 7

2-Ethyl-N-{4-[4-(ethylcarbamoyl-phenyl-methyl)-piperazin-1-yl]-3-fluoro-phenyl}-butyramide The title compound was prepared according to the methods described in Example 1, with the appropriate substituent changes.

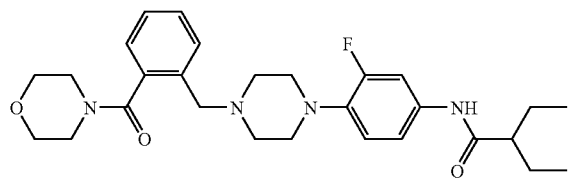

Example 5

2-Ethyl-N-(3-fluoro-4-{4-[2-(morpholine-4-carbonyl)-benzyl]-piperazin-1-yl}-phenyl)-butyramide

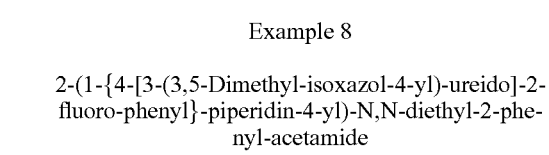

Example 8

2-(1-{4-[3-(3,5-Dimethyl-isoxazol-4-yl)-ureido]-2-fluoro-phenyl}-piperidin-4-yl)-N,N-diethyl-2-phenyl-acetamide Step A. [1-(2-Fluoro-4-nitro-phenyl)-piperidin-4-yl]-phenyl-acetonitrile. To a mixture of phenyl-piperidin-4-yl-acetonitrile hydrochloride (2.4 g, 10 mmol) and K₂CO₃ (20 mmol) in DMF (30 mL) was added 1,2-difluoro-4-nitro-benzene (1.6 g, 10 mmol). The reaction mixture was stirred at 50° C. for 3 h. The mixture was diluted with H₂O (500 mL), which was decanted off. The resulting semi-solid was collected, dried, and used directly in the next step.

Step B. N,N-Diethyl-2-[1-(2-fluoro-4-nitro-phenyl)-piperidin-4-yl]-2-phenyl-acetamide. A mixture of [1-(2-fluoro-4-nitro-phenyl)-piperidin-4-yl]-phenyl-acetonitrile in 48% HBr (75 mL) was stirred at 100° C. for 8 h, then was cooled to rt and diluted with H₂O (500 mL). The resulting yellow solid was collected by filtration and dried under vacuum. A solution of this yellow solid in DMF (0.50 mL) in DCE (100 mL) was treated with (COCl)₂ (100 mmol), dropwise, and was stirred at rt for 30 min. The mixture was concentrated and dried under vacuum. The residue was dissolved in DCE (100 mL) and treated with TEA (2.8 mL, 20 mmol) and Et₂NH (1.1 mL, 10 mmol). The reaction mixture was stirred at rt for 4 h and was washed with H₂O (100 mL). The organic layer was concentrated, and the resulting crude material was carried on directly to the next step.

Step C. 2-[1-(4-Amino-2-fluoro-phenyl)-piperidin-4-yl]-N,N-diethyl-2-phenyl-acetamide. A solution of N,N-diethyl-2-[1-(2-fluoro-4-nitro-phenyl)-piperidin-4-yl]-2-phenyl-acetamide and SnCl₂.2H₂O (10 g) in 1:1 EtOH/EtOAc (100 mL) was heated at 100° C. for 16 h. The mixture was cooled to rt, diluted with ice water (100 mL), basified to pH=9 with NaHCO₃, and extracted with EtOAc (3×200 mL). The

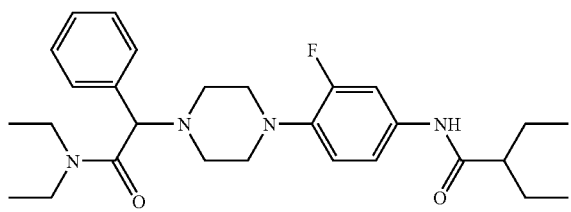

Example 6

N-{4-[4-(Diethylcarbamoyl-phenyl-methyl)-piperazin-1-yl]-3-fluoro-phenyl}-2-ethyl-butyramide A solution of 2-ethyl-N-(3-fluoro-4-piperazin-1-yl-phenyl)-butyramide (0.030 g, 0.084 mmol), 2-bromo-N,N-diethyl-2-phenyl-acetamide (0.025 g, 0.094 mmol), and Na₂CO₃ (0.013 g, 0.12 mmol) in DMF (2 mL) was stirred at rt for 18 h. The reaction mixture was diluted with EtOAc (25 mL) and washed with H₂O (3×15 mL). The organic layer was dried (Na₂SO₄) and concentrated. Chromatography of the resulting residue (SiO₂; 2 M NH₃ in MeOH/DCM) gave the title compound (0.018 g, 38%). MS (ESI): mass calcd. for C₂₈H₃₉FN₄O₂, 482.31. m/z found, 483.5 [M+H]⁺. ¹H NMR (CDCl₃): 7.53-7.45 (m, 3H), 7.38-7.31 (m, 3H), 7.10-7.07 (m, 1H), 6.89-6.84 (m, 1H), 3.50-3.37 (m, 2H), 3.30-3.15 (m, 2H), 3.08 (s, 4H), 2.70 (br s, 4H), 2.05-2.01 (m, 1H), 1.75-1.68 (m, 1H), 1.60-1.52 (m, 2H), 1.09-1.02 (m, 6H), 0.97-0.91 (m, 6H).

organic layers were combined, dried (Na$_2$SO$_4$), and concentrated to give the crude title compound.

Step D. A mixture of 2-[1-(4-amino-2-fluoro-phenyl)-piperidin-4-yl]-N,N-diethyl-2-phenyl-acetamide (0.30 mmol) and 4-isocyanato-3,5-dimethyl-isoxazole (1.0 mmol) in DCE (10 mL) was stirred at rt for 16 h. The precipitate that had formed was collected by filtration and dried under vacuum to give the title compound (78 mg, 50%). MS (ESI): mass calcd. for C$_{29}$H$_{36}$FN$_5$O$_3$, 521.28; m/z found, 522.4 [M+H]$^+$. $^1$H NMR (CDCl$_3$): 7.95-7.75 (br s, 1H), 7.40-7.20 (m, 5H), 7.30-6.90 (br s, 1H), 6.80-6.70 (m, 2H), 3.60-3.10 (m, 7H), 2.45-2.35 (m, 2H), 2.28 (s, 3H), 2.20-2.10 (m, 4H), 2.00-1.90 (m, 1H), 1.52-1.40 (m, 1H), 1.35-1.20 (m, 2H), 1.18-1.03 (m, 6H).

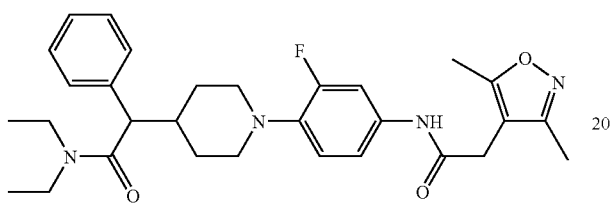

Example 9

2-(1-{4-[2-(3,5-Dimethyl-isoxazol-4-yl)-acetylamino]-2-fluoro-phenyl}-piperidin-4-yl)-N,N-diethyl-2-phenyl-acetamide A mixture of (3,5-dimethyl-isoxazol-4-yl)-acetic acid (1.0 mmol) and DMF (0.050 mL) in DCE (10 mL) was treated with (COCl)$_2$ (10 mmol), dropwise. The mixture was stirred at rt for 1 h and was concentrated. The residue was diluted with DCE (10 mL) and treated with 2-[1-(4-amino-2-fluoro-phenyl)-piperidin-4-yl]-N,N-diethyl-2-phenyl-acetamide (0.30 mmol) and TEA (2.0 mmol). After 16 h, the mixture was diluted with H$_2$O (10 mL) and extracted. The organic layer was concentrated and the residue was purified by PTLC to provide the title compound (87 mg, 56%). MS (ESI): mass calcd. for C$_{30}$H$_{37}$FN$_4$O$_3$, 520.28; m/z found, 521.4 [M+H]$^+$. $^1$H NMR (CDCl$_3$): 7.40-7.20 (m, 6H), 6.96 (dd, J=8.6, 1.6, 1H), 6.83 (t, J=9.0, 1H), 3.50-3.10 (m, 9H), 2.70-2.60 (m, 1H), 2.52-2.42 (m, 1H), 2.38 (s, 3H), 2.30-2.20 (m, 4H), 2.08-1.98 (m, 1H), 1.50-1.15 (m, 3H), 1.15-1.03 (m, 6H).

Examples 10 to 19 were prepared using methods similar to those described in Example 8 or 9, with the appropriate substituent changes.

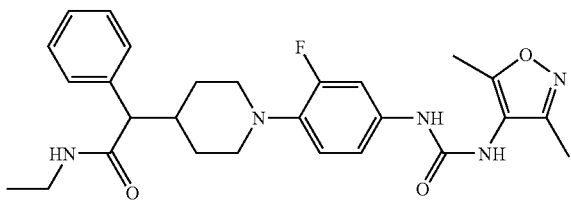

Example 10

2-(1-{4-[3-(3,5-Dimethyl-isoxazol-4-yl)-ureido]-2-fluoro-phenyl}-piperidin-4-yl)-N-ethyl-2-phenyl-acetamide MS (ESI): mass calcd. for C$_{27}$H$_{32}$FN$_5$O$_3$, 493.25. m/z found, 494.5 [M+H]$^+$. $^1$H NMR (CDCl$_3$): 7.40-7.20 (m, 6H), 7.06-6.92 (m, 2H), 3.40-3.05 (m, 5H), 2.72-2.64 (m, 1H), 2.58-2.47 (m, 1H), 2.31 (s, 3H), 2.20-2.10 (m, 4H), 1.92-1.85 (m, 1H), 1.57-1.43 (m, 1H), 1.36-1.20 (m, 2H), 1.10-1.05 (m, 3H).

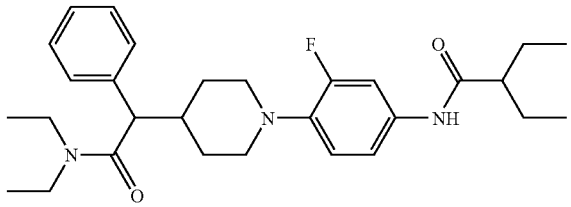

Example 11

N-{4-[4-(Diethylcarbamoyl-phenyl-methyl)-piperidin-1-yl]-3-fluoro-phenyl}-2-ethyl-butyramide MS (ESI): mass calcd. for C$_{28}$H$_{39}$FN$_4$O$_2$, 481.31. m/z found, 482.4 [M+H]$^+$. $^1$H NMR (CDCl$_3$): 7.64 (s, 1H), 7.55-7.46 (m, 1H), 7.45-7.21 (m, 5H), 7.27-7.08 (m, 1H), 6.94-6.80 (m, 1H), 3.55-3.15 (m, 7H), 2.72-2.62 (m, 1H), 2.53-2.43 (m, 1H), 2.32-2.22 (m, 1H), 2.10-2.00 (m, 2H), 1.80-1.65 (m, 2H), 1.60-1.43 (m, 3H), 1.40-1.20 (m, 2H), 1.20-1.05 (m, 6H), 1.00-0.90 (m, 6H).

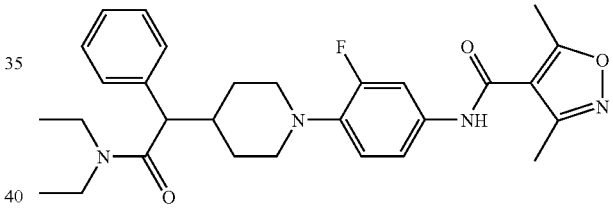

Example 12

3,5-Dimethyl-isoxazole-4-carboxylic acid {4-[4-(diethylcarbamoyl-phenyl-methyl)-piperidin-1-yl]-3-fluoro-phenyl}-amide MS (ESI): mass calcd. for C$_{29}$H$_{35}$FN$_4$O$_3$, 506.27. m/z found, 507.4 [M+H]$^+$. $^1$H NMR (CDCl$_3$): 7.75 (s, 1H), 7.53-7.12 (m, 7H), 6.90 (t, J=9.0, 1H), 3.50-3.10 (m, 7H), 2.70-2.60 (m, 4H), 2.55-2.45 (m, 4H), 2.30-2.20 (m, 1H), 2.08-2.00 (m, 1H), 1.52-1.42 (m, 1H), 1.38-1.20 (m, 2H), 1.15 (t, J=7.2, 3H), 1.07 (t, J=7.2, 3H).

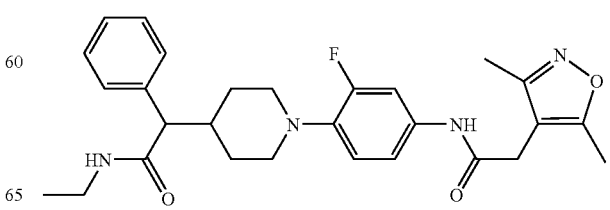

Example 13

2-(1-{4-[2-(3,5-Dimethyl-isoxazol-4-yl)-acetylamino]-2-fluoro-phenyl}-piperidin-4-yl)-N-ethyl-2-phenyl-acetamide MS (ESI): mass calcd. for $C_{28}H_{33}FN_4O_3$, 492.25. m/z found, 493.4 [M+H]$^+$. $^1$H NMR (CDCl$_3$): 7.40-7.15 (m, 6H), 7.17 (s, 1H), 6.99-6.91 (m, 1H), 6.83 (t, J=9.0, 1H), 5.59-5.91 (m, 1H), 3.47-3.10 (m, 6H), 2.95-2.87 (m, 1H), 2.73-2.65 (m, 1H), 2.58-2.46 (m, 1H), 2.40 (s, 3H), 2.28-2.20 (m, 4H), 2.07-1.93 (m, 1H), 1.54-1.42 (m, 1H), 1.39-1.20 (m, 2H), 1.10 (t, J=7.2, 3H).

Example 14

2-Ethyl-N-{4-[4-(ethylcarbamoyl-phenyl-methyl)-piperidin-1-yl]-3-fluoro-phenyl}-butyramide MS (ESI): mass calcd. for $C_{27}H_{36}FN_3O_2$, 453.28. m/z found, 454.5 [M+H]$^+$. $^1$H NMR (CDCl$_3$): 7.50-7.20 (m, 6H), 7.08-7.03 (m, 1H), 6.87-6.76 (m, 1H), 5.98-5.72 (m, 1H), 3.40-3.10 (m, 4H), 2.98-2.90 (m, 1H), 2.70-2.61 (m, 1H), 2.53-2.43 (m, 1H), 2.28-2.13 (m, 1H), 2.08-1.92 (m, 2H), 1.74-1.62 (m, 2H), 1.60-1.43 (m, 3H), 1.40-1.21 (m, 2H), 1.08 (t, J=7.3, 3H), 0.93 (t, J=7.3, 6H).

Example 15

2-(1-{4-[3-(2,6-Dimethyl-phenyl)-ureido]-2-fluoro-phenyl}-piperidin-4-yl)-N-ethyl-2-phenyl-acetamide MS (ESI): mass calcd. for $C_{30}H_{35}FN_4O_2$, 502.27. m/z found, 503.5 [M+H]$^+$. $^1$H NMR (MeOD): 7.50-6.90 (m, 11H), 3.38-3.07 (m, 5H), 2.73-2.67 (m, 1H), 2.58-2.47 (m, 1H), 2.31 (s, 3H), 2.27 (s, 3H), 2.20-2.13 (m, 1H), 1.94-1.86 (m, 1H), 1.54-1.47 (m, 1H), 1.38-1.20 (m, 2H), 1.08 (t, J=7.2, 3H).

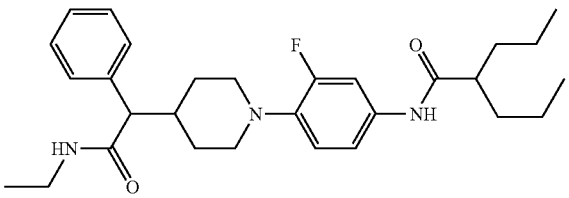

Example 16

2-Propyl-pentanoic acid {4-[4-(ethylcarbamoyl-phenyl-methyl)-piperidin-1-yl]-3-fluoro-phenyl}-amide MS (ESI): mass calcd. for $C_{29}H_{40}FN_3O_2$, 481.31. m/z found, 482.5 [M+H]$^+$. $^1$H NMR (MeOD): 7.50-6.94 (m, 8H), 3.40-3.05 (m, 5H), 2.74-2.64 (m, 1H), 2.60-2.51 (m, 1H), 2.40-2.32 (m, 1H), 2.24-2.10 (m, 1H), 1.95-1.85 (m, 1H), 1.68-1.18 (m, 11H), 1.08 (t, J=7.3, 3H), 0.93 (t, J=7.3, 6H).

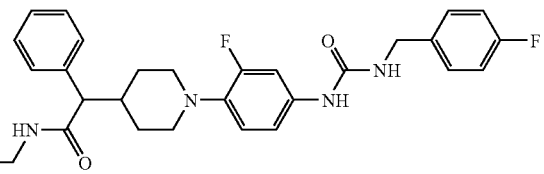

Example 17

N-Ethyl-2-(1-{2-fluoro-4-[3-(4-fluoro-benzyl)-ureido]-phenyl}-piperidin-4-yl)-2-phenyl-acetamide MS (ESI): mass calcd. for $C_{29}H_{32}F_2N_4O_2$, 506.25. m/z found, 507.2 [M+H]$^+$. $^1$H NMR (MeOD): 7.40-7.20 (m, 8H), 7.10-6.90 (m, 4H), 3.40-3.10 (m, 7H), 2.74-2.64 (m, 1H), 2.60-2.51 (m, 1H), 2.40-2.32 (m, 1H), 1.95-1.85 (m, 1H), 1.60-1.50 (m, 1H), 1.40-1.20 (m, 2H), 1.08 (t, J=7.3, 3H).

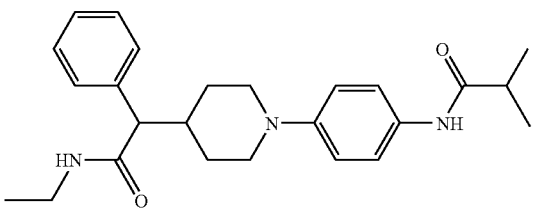

Example 18

N-{4-[4-(Ethylcarbamoyl-phenyl-methyl)-piperidin-1-yl]-phenyl}-isobutyramide

MS (ESI): mass calcd. for $C_{25}H_{33}N_3O_2$, 407.26. m/z found, 408.5 [M+H]$^+$. $^1$H NMR (CDCl$_3$): 7.40-7.25 (m, 6H), 7.14 (s, 1H), 6.88-6.82 (m, 2H), 5.64 (t, J=5.4, 1H), 3.70-3.10

(m, 4H), 2.90-2.86 (m, 1H), 2.78-2.68 (m, 1H), 2.60-2.52 (m, 1H), 2.51-2.45 (m, 1H), 2.30-2.20 (m, 1H), 2.07-1.95 (m, 1H), 1.48-1.30 (m, 2H), 1.30-1.10 (m, 7H), 0.98 (t, J=7.2, 3H).

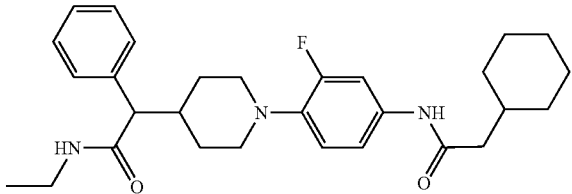

Example 19

2-{1-[4-(2-Cyclohexyl-acetylamino)-2-fluoro-phenyl]-piperidin-4-yl}-N-ethyl-2-phenyl-acetamide MS (ESI): mass calcd. for $C_{29}H_{38}FN_3O_2$, 479.30. m/z found, 480.5 [M+H]+. $^1$H NMR (CDCl$_3$): 7.50-6.80 (m, 8H), 5.55 (s, 1H), 3.40-3.12 (m, 4H), 2.94-2.90 (m, 1H), 2.77-2.63 (m, 1H), 2.60-2.48 (m, 1H), 2.35-2.15 (m, 3H), 2.09-1.97 (m, 1H), 1.95-1.60 (m, 6H), 1.58-1.43 (m, 1H), 1.40-0.95 (m, 10H).

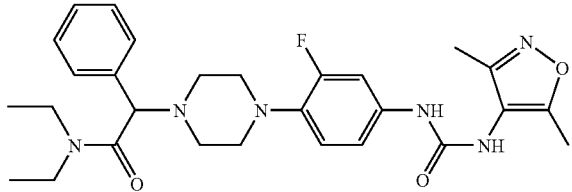

Example 20

2-(4-{4-[3-(3,5-Dimethyl-isoxazol-4-yl)-ureido]-2-fluoro-phenyl}-piperazin-1-yl)-N,N-diethyl-2-phenyl-acetamide A mixture of 2-[4-(4-amino-2-fluoro-phenyl)-piperazin-1-yl]-N,N-diethyl-2-phenyl-acetamide (0.30 mmol) and 4-isocyanato-3,5-dimethyl-isoxazole (1.0 mmol) in DCE (10 mL) was stirred at rt for 16 h. The solid that had formed was collected by filtration and dried under vacuum to give the title compound (100 mg, 64%). MS (ESI): mass calcd. for $C_{28}H_{35}FN_6O_3$, 522.28. m/z found, 523.4 [M+H]+. $^1$H NMR (CDCl$_3$): 8.60-8.40 (br s, 1H), 7.60-7.25 (m, 6H), 6.78-6.71 (m, 1H), 6.68-6.57 (m, 1H), 4.21 (s, 1H), 3.60-3.40 (m, 2H), 3.39-3.15 (m, 2H), 2.95-2.45 (m, 8H), 2.24 (s, 3H), 2.13 (s, 3H), 1.11 (t, J=7.1, 3H), 1.05 (t, J=7.1, 3H).

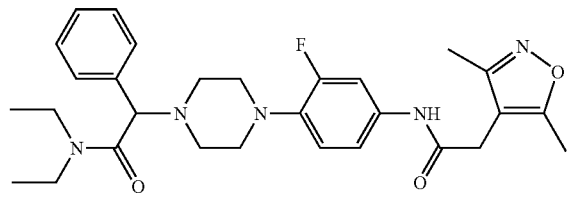

Example 21

2-(4-{4-[2-(3,5-Dimethyl-isoxazol-4-yl)-acetylamino]-2-fluoro-phenyl}-piperazin-1-yl)-N,N-diethyl-2-phenyl-acetamide A mixture of (3,5-dimethyl-isoxazol-4-yl)-acetic acid (1.0 mmol) and DMF (0.050 mL) in DCE (10 mL) was treated with (COCl)$_2$ (10 mmol) dropwise, and was stirred at rt for 1 h. The mixture was concentrated and dried under vacuum. The residue was diluted with DCE (10 mL) and 2-[4-(4-amino-2-fluoro-phenyl)-piperazin-1-yl]-N,N-diethyl-2-phenyl-acetamide (0.30 mmol) and TEA (2.0 mmol) were added. The mixture was stirred at rt for 16 h, then was washed with H$_2$O (10 mL). The organic layer was concentrated, and the residue was purified by PTLC to provide the title compound (78 mg, 45%). MS (ESI): mass calcd. for $C_{29}H_{36}FN_5O_3$, 521.28. m/z found, 522.4 [M+H]+. $^1$H NMR (CDCl$_3$): 7.59-7.25 (m, 6H), 7.09-6.98 (m, 1H), 6.68-6.57 (m, 1H), 4.21 (s, 1H), 3.50-3.36 (m, 4H), 3.35-3.15 (m, 2H), 3.13-3.00 (m, 4H), 2.73-2.60 (m, 4H), 2.37 (s, 3H), 2.23 (s, 3H), 1.16-1.06 (m, 6H).

Examples 22 to 28 were prepared using methods similar to those described in Example 20 or 21, with the appropriate substituent changes.

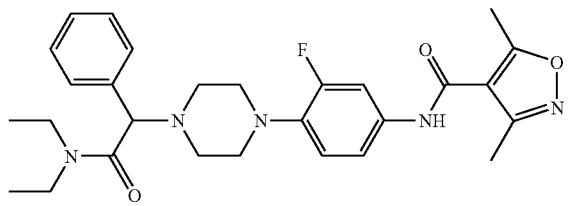

Example 22

3,5-Dimethyl-isoxazole-4-carboxylic acid {4-[4-(diethylcarbamoyl-phenyl-methyl)-piperazin-1-yl]-3-fluoro-phenyl}-amide MS (ESI): mass calcd. for $C_{28}H_{34}FN_5O_3$, 507.27. m/z found, 508.3 [M+H]+. $^1$H NMR (CDCl$_3$): 7.59-7.08 (m, 8H), 6.81 (t, J=9.0, 1H), 4.23 (s, 1H), 3.50-3.36 (m, 2H), 3.35-3.15 (m, 2H), 3.15-3.00 (m, 4H), 2.75-2.60 (m, 7H), 2.47 (s, 3H), 1.16-1.02 (m, 6H).

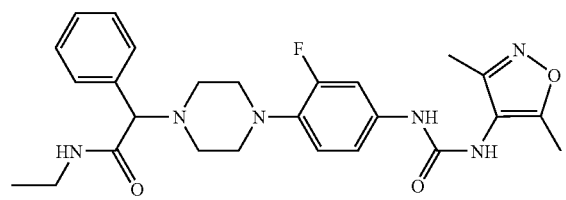

Example 23

2-(4-{4-[3-(3,5-Dimethyl-isoxazol-4-yl)-ureido]-2-fluoro-phenyl}-piperazin-1-yl)-N-ethyl-2-phenyl-acetamide MS (ESI): mass calcd. for $C_{26}H_{31}FN_6O_3$, 494.24. m/z found, 495.2 [M+H]+. $^1$H NMR (CDCl$_3$): 7.33-7.26 (m, 5H), 7.22 (t, J=5.8, 1H), 7.16 (dd, J=13.8, 2.4, 1H), 6.93 (dd, J=8.6, 2.0, 1H), 6.81 (t, J=9.0, 1H), 3.88 (s, 1H), 3.40-3.32 (m, 2H), 3.10-3.00 (m, 4H), 2.62-2.57 (m, 4H), 2.34 (s, 3H), 2.20 (s, 3H), 1.17 (t, J=7.2, 3H).

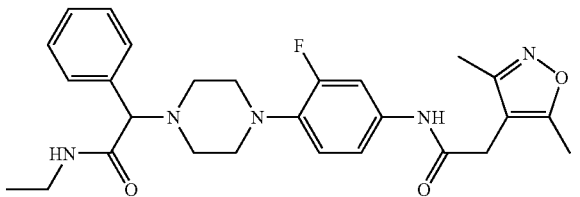

Example 24

2-(4-{4-[2-(3,5-Dimethyl-isoxazol-4-yl)-acetylamino]-2-fluoro-phenyl}-piperazin-1-yl)-N-ethyl-2-phenyl-acetamide MS (ESI): mass calcd. for $C_{27}H_{32}FN_5O_3$, 493.25. m/z found, 494.4 [M+H]$^+$. $^1$H NMR (CDCl$_3$): 8.10 (s, 1H), 7.38-7.28 (m, 5H), 7.20 (t, J=5.8, 1H), 7.10 (dd, J=8.7, 1.6, 1H), 6.82 (t, J=9.0, 1H), 3.88 (s, 1H), 3.40-3.30 (m, 4H), 3.15-3.00 (m, 4H), 2.65-2.42 (m, 4H), 2.33 (s, 3H), 2.20 (s, 3H), 1.16 (t, J=7.2, 3H).

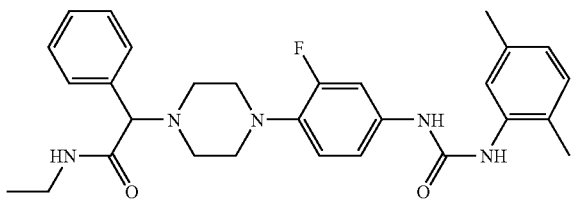

Example 25

2-(4-{4-[3-(2,5-Dimethyl-phenyl)-ureido]-2-fluoro-phenyl}-piperazin-1-yl)-N-ethyl-2-phenyl-acetamide MS (ESI): mass calcd. for $C_{29}H_{34}FN_5O_2$, 503.27. m/z found, 504.2 [M+H]$^+$. $^1$H NMR (MeOD): 7.55-7.25 (m, 7H), 7.10-6.95 (m, 3H), 6.88-6.82 (m, 1H), 3.80 (s, 1H), 3.30-3.15 (m, 2H), 3.15-3.00 (m, 4H), 2.60-2.50 (m, 4H), 2.28 (s, 3H), 2.22 (s, 3H), 1.10 (t, J=7.2, 3H).

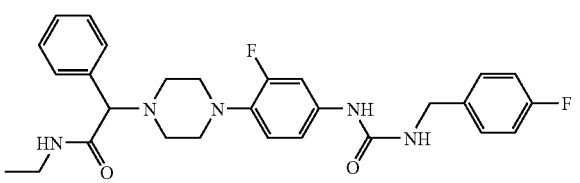

Example 26

N-Ethyl-2-(4-{2-fluoro-4-[3-(4-fluoro-benzyl)-ureido]-phenyl}-piperazin-1-yl)-2-phenyl-acetamide MS (ESI): mass calcd. for $C_{28}H_{31}F_2N_5O_2$, 507.24. m/z found, 508.2 [M+H]$^+$. $^1$H NMR (MeOD): 7.55-7.18 (m, 12H), 3.76 (s, 1H), 3.34 (s, 2H), 3.25-3.15 (m, 4H), 2.60-2.42 (m, 4H), 1.11-1.05 (m, 3H).

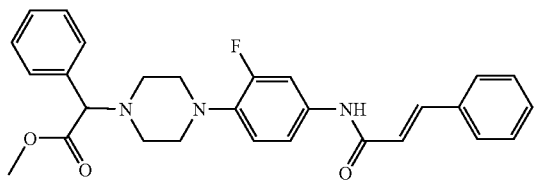

Example 27

Phenyl-{4-[4-(3-phenyl-acryloylamino)-phenyl]-piperazin-1-yl}-acetic acid methyl ester MS (ESI): mass calcd. for $C_{28}H_{29}N_3O_3$, 455.22. m/z found, 456.5 [M+H]$^+$. $^1$H NMR (CDCl$_3$): 7.80-7.28 (m, 15H), 6.87 (d, J=9.0, 2H), 6.55 (d, J=7.2, 1H), 4.06 (s, 1H), 3.71 (s, 3H), 3.25-3.10 (m, 4H), 2.70-2.55 (m, 4H).

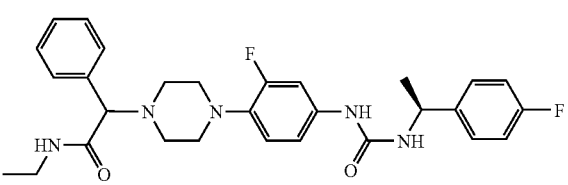

Example 28

N-Ethyl-2-[4-(2-fluoro-4-{3-[(S)-1-(4-fluoro-phenyl)-ethyl]-ureido}-phenyl)-piperazin-1-yl]-2-phenyl-acetamide MS (ESI): mass calcd. for $C_{29}H_{33}F_2N_5O_2$, 521.26. m/z found, 522.4 [M+H]$^+$. $^1$H NMR (MeOD): 7.70-7.42 (m, 6H), 7.40-7.27 (m, 3H), 7.10-6.92 (m, 4H), 3.36-3.20 (m, 12H), 1.44 (d, J=6.9, 3H), 1.06 (t, J=7.3, 3H).

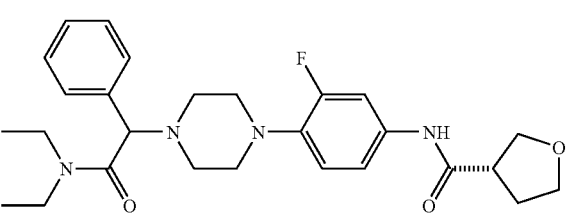

Example 29

(S)-Tetrahydro-furan-3-carboxylic acid {4-[4-(diethylcarbamoyl-phenyl-methyl)-piperazin-1-yl]-3-fluoro-phenyl}-amide A mixture of 2-[4-(4-amino-2-fluoro-phenyl)-piperazin-1-yl]-N,N-diethyl-2-phenyl-acetamide (0.30 mmol) and DCC (1.0 mmol) in DCE (10 mL) was stirred at rt for 1 h, then was treated with (S)-tetrahydro-furan-3-carboxylic acid (1.0 mmol), and was stirred at rt for 16 h. The mixture was concentrated, and the residue was purified by PTLC to provide the title compound (74 mg, 51%). MS (ESI): mass calcd. for $C_{27}H_{35}FN_4O_3$, 482.27. m/z found, 483.4 [M+H]$^+$. $^1$H NMR (CDCl$_3$): 7.75-7.60 (m, 1H), 7.55-7.26 (m, 5H), 7.10-7.00

(m, 1H), 6.84 (t, J=9.0, 1H), 4.21 (s, 1H), 4.05-3.72 (m, 4H), 3.50-3.10 (m, 4H), 3.10-2.95 (m, 5H), 2.73-2.60 (m, 4H), 2.28-2.18 (m, 2H), 1.14-1.02 (m, 6H).

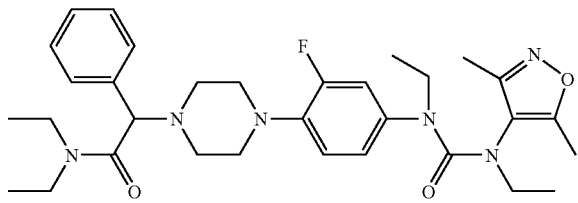

Example 30

2-(4-{4-[3-(3,5-Dimethyl-isoxazol-4-yl)-1,3-diethyl-ureido]-2-fluoro-phenyl}-piperazin-1-yl)-N,N-diethyl-2-phenyl-acetamide To a mixture of 2-(4-{4-[3-(3,5-dimethyl-isoxazol-4-yl)-ureido]-2-fluoro-phenyl}-piperazin-1-yl)-N-ethyl-2-phenyl-acetamide (43.0 mg) in DMF (2 mL) was added NaH (60% in mineral oil, 115 mg). After 30 min, EtBr (100 μL) was added and the mixture was stirred at rt for 1 h. MeOH (1 mL) was added and the mixture was concentrated. PTLC of the residue provided the title compound (31.0 mg, 44%). MS (ESI): mass calcd. for $C_{32}H_{43}FN_6O_3$, 578.34; m/z found, 579.5 [M+H]$^+$. $^1$H NMR (CDCl$_3$): 7.50-7.10 (m, 5H), 6.70 (t, J=8.7, 1H), 6.50-6.43 (m, 2H), 4.23 (s, 1H), 3.60-3.15 (m, 8H), 3.15-3.00 (m, 4H), 2.75-2.60 (m, 4H), 1.91 (s, 3H), 1.90 (s, 3H), 1.12-1.00 (m, 12H).

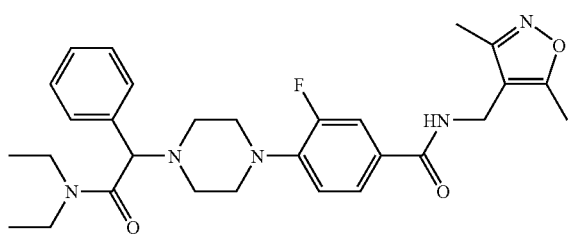

Example 31

4-[4-(Diethylcarbamoyl-phenyl-methyl)-piperazin-1-yl]-N-(3,5-dimethyl-isoxazol-4-ylmethyl)-3-fluoro-benzamide Step A. 4-Bromo-N-(3,5-dimethyl-isoxazol-4-ylmethyl)-3-fluoro-benzamide. To a mixture of 4-bromo-3-fluoro-benzoic acid (3.0 mmol) and DMF (0.10 mL) in DCE (10 mL) was added (COCl)$_2$ (4.0 mL) dropwise. After 30 min, the mixture was concentrated and dried under vacuum. The residue was dissolved in DCE (20 mL), treated with C-(3,5-dimethyl-isoxazol-4-yl)-methylamine (3.0 mmol) and TEA (8.0 mmol), and stirred at rt for 16 h. The mixture was treated with H$_2$O (10 mL). The resulting precipitate was collected by filtration to give the title compound (650 mg, 69%).

Step B. N,N-Diethyl-2-phenyl-2-piperazin-1-yl-acetamide. To a mixture of 2-chloro-N,N-diethyl-2-phenyl-acetamide (10 mmol) and K$_2$CO$_3$ (20 mmol) in DMF (30 mL) was added piperazine-1-carboxylic acid tert-butyl ester (10 mmol). The reaction mixture was stirred at 50° C. for 3 h, then was diluted with H$_2$O (500 mL) and extracted with EtOAc (3×200 mL). The organic layers were combined and concentrated. The residue was dissolved in DCE (50 mL) and treated with HCl (1 M in Et$_2$O, 35 mL). After 16 h, the mixture was concentrated to give the title compound.

Step C. A mixture of 4-bromo-N-(3,5-dimethyl-isoxazol-4-ylmethyl)-3-fluoro-benzamide (0.31 mmol), N,N-diethyl-2-phenyl-2-piperazin-1-yl-acetamide (0.20 mmol), Cs$_2$CO$_3$ (1.2 mmol), Pd$_2$(dba)$_3$ (0.0030 mmol), and BINAP (0.0120 mmol) in toluene (2.0 mL) was stirred at 100° C. for 16 h. The mixture was cooled to rt and purified by PTLC to provide the title compound (60 mg, 58%). MS (ESI): mass calcd. for $C_{29}H_{36}FN_5O_3$, 521.28. m/z found, 522.4 [M+H]$^+$. $^1$H NMR (CDCl$_3$): 7.50-7.25 (m, 7H), 6.82 (t, J=8.5, 1H), 6.51 (t, J=5.2, 1H), 4.31 (d, J=5.3, 2H), 4.22 (s, 1H), 3.48-3.36 (m, 2H), 3.30-3.10 (m, 6H), 2.73-2.60 (m, 4H), 2.36 (s, 3H), 2.21 (s, 3H), 1.12-1.02 (m, 6H).

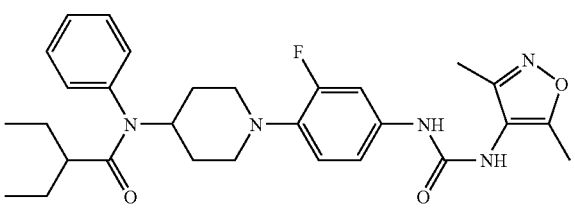

Example 32

N-(1-{4-[3-(3,5-Dimethyl-isoxazol-4-yl)-ureido]-2-fluoro-phenyl}-piperidin-4-yl)-2-ethyl-N-phenyl-butyramide Step A. 4-Phenylamino-piperidine-1-carboxylic acid tert-butyl ester. To a mixture of aniline (10 mmol) and 4-oxo-piperidine-1-carboxylic acid tert-butyl ester (10 mmol) in DCE (100 mL) was added NaBH$_3$CN (1 M in THF, 40 mmol). The mixture was stirred at rt for 16 h, washed with satd. aq. NaHCO$_3$, and concentrated to give the title compound, which was used for the next step.

Step B. 2-Ethyl-N-phenyl-N-piperidin-4-yl-butyramide. To a mixture of 2-ethyl-butyryl chloride (10 mmol) and TEA (20 mmol) in DCE (100 mL) was added 4-phenylamino-piperidine-1-carboxylic acid tert-butyl ester (10 mmol). The reaction mixture was stirred at rt for 4 h, then was washed with H$_2$O (10 mL). The organic layer was concentrated. The residue was dissolved in DCE (50 mL) and treated with HCl (1 M in Et$_2$O, 35 mL). The mixture was stirred at rt for 16 h and concentrated to give the crude title compound.

Step C. N-[1-(4-amino-2-fluoro-phenyl)-piperidin-4-yl]-2-ethyl-N-phenyl-butyramide. To a mixture of 2-ethyl-N-phenyl-N-piperidin-4-yl-butyramide (10 mmol) and K$_2$CO$_3$ (40 mmol) in DMF (30 mL) was added 1,2-difluoro-4-nitro-benzene (1.6 g, 10 mmol). The reaction mixture was stirred at 50° C. for 3 h, then was diluted with H$_2$O (500 mL). The solution was decanted, leaving a semi-solid, which was collected and re-dissolved into 1:1 EtOH/EtOAc (100 mL). The mixture was treated with SnCl$_2$.2H$_2$O (10 g) and was heated at 100° C. for 16 h. The mixture was cooled to rt, diluted with ice water (100 mL), basified to pH=9 with NaHCO$_3$, and extracted with EtOAc (3×200 mL). The organic layers were combined, dried (Na$_2$SO$_4$), and concentrated to give the crude title compound.

Step D. A mixture of N-[1-(4-amino-2-fluoro-phenyl)-piperidin-4-yl]-2-ethyl-N-phenyl-butyramide (0.30 mmol) and 4-isocyanato-3,5-dimethyl-isoxazole (1.0 mmol) in DCE (10 mL) was stirred at rt for 16 h. The mixture was concentrated and the residue was purified by PTLC to give the title compound (56 mg, 36%). MS (ESI): mass calcd. for $C_{29}H_{36}FN_5O_3$, 521.28. m/z found, 522.4 [M+H]$^+$. $^1$H NMR (CDCl$_3$): 8.00-7.82 (br s, NH), 7.55-7.41 (m, 4H), 7.20-7.11 (m, 2H), 7.10-6.95 (br s, NH), 6.94-6.75 (m, 2H), 4.90-4.72 (m, 1H), 3.40-3.22 (m, 2H), 2.66-2.57 (m, 2H), 2.33 (s, 3H), 2.24 (s, 3H), 2.09-2.00 (m, 1H), 1.94-1.85 (m, 2H).1.70-1.58 (m, 2H), 1.57-1.45 (m, 2H), 1.42-1.30 (m, 2H), 0.85 (t, J=7.2, 6H).

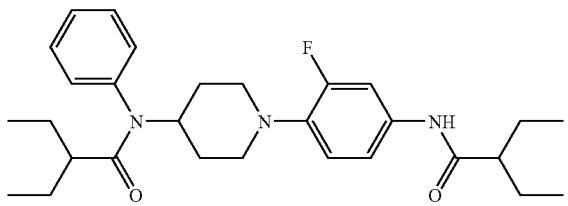

Example 33

2-Ethyl-N-{1-[4-(2-ethyl-butyrylamino)-2-fluoro-phenyl]-piperidin-4-yl}-N-phenyl-butyramide To a mixture of N-[1-(4-amino-2-fluoro-phenyl)-piperidin-4-yl]-2-ethyl-N-phenyl-butyramide (0.30 mmol) and TEA (2.0 mmol) in DCM (10 mL) was added 2-ethyl-butyryl chloride (1.0 mmol). After 16 h, the mixture was washed with H$_2$O (10 mL). The organic layer was concentrated and the residue was purified by PTLC to provide the title compound (45 mg, 31%). MS (ESI): mass calcd. for $C_{29}H_{40}FN_3O_2$, 481.31. m/z found, 482.4 [M+H]$^+$. $^1$H NMR (CDCl$_3$): 7.50-7.35 (m, 5H), 7.15-7.03 (m, 2H), 6.86 (t, J=8.8, 1H), 4.90-4.72 (m, 1H), 3.44-3.30 (m, 2H), 2.80-2.67 (m, 2H), 2.30-1.30 (m, 14H), 0.95 (t, J=7.3, 6H), 0.80 (t, J=7.2, 6H).

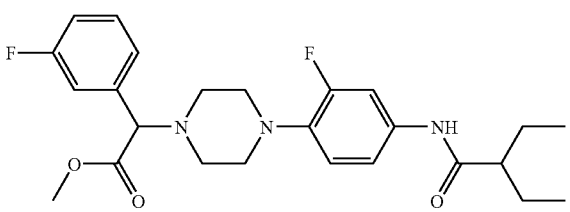

Example 34

{4-[4-(2-Ethyl-butyrylamino)-2-fluoro-phenyl]-piperazin-1-yl}-(3-fluoro-phenyl)-acetic acid methyl ester Step A. 4-[4-(2-Ethyl-butyrylamino)-2-fluoro-phenyl]-piperazine-1-carboxylic acid tert-butyl ester. To a solution of 4-(4-amino-2-fluoro-phenyl)-piperazine-1-carboxylic acid tert-butyl ester (2.96 g, 10.0 mmol) and TEA (1.52 g, 15.0 mmol) in DCM (60 mL) was added 2-ethyl butyryl chloride (2.08 g, 15.0 mmol). After 18 h, the mixture was diluted with DCM (50 mL) and washed with satd. aq. NaHCO$_3$ (1×30 mL) and water (2×30 mL). The organic layer was dried (Na$_2$SO$_4$) and concentrated. The residue was purified (SiO$_2$; acetone/DCM and EtOAc/DCM) to yield the title compound (2.00 g, 51%). $^1$H NMR (CDCl$_3$): 7.55-7.45 (m, 1H), 7.15 (br s, 1H), 7.14-7.08 (m, 1H), 6.86 (t, J=9.0, 1H), 3.62-3.54 (m, 4H), 3.01-2.93 (m, 4H), 2.04-1.96 (m, 1H), 1.76-1.65 (m, 2H), 1.60-1.50 (m, 2H), 1.48 (s, 9H), 0.94 (t, J=7.4, 6H).

Step B. 2-Ethyl-N-(3-fluoro-4-piperazin-1-yl-phenyl)-butyramide dihydro-chloride. A solution of 4-[4-(2-ethyl-butyrylamino)-2-fluoro-phenyl]-piperazine-1-carboxylic acid tert-butyl ester (2.00 g) in MeOH (60 mL) was treated with 4 M HCl in dioxane (20 mL). After 5 h, the mixture was concentrated to yield the title compound (1.60 g). MS: mass calcd. for $C_{16}H_{24}FN_3O_3$, 293.19. m/z found, 294.2 [M+H]$^+$. $^1$H NMR (DMSO): 8.44-8.41 (m, 1H), 7.89-7.80 (m, 2H), 7.56-7.31 (m, 9H), 7.07-7.01 (m, 1H), 6.81 (s, 1H), 6.75 (t, J=9.0, 1H), 6.60 (dd, J=8.6, 1.9, 1H), 4.24-4.13 (m, 2H), 4.08 (s, 1H), 3.06-3.01 (m, 4H), 2.67-2.56 (m, 4H), 1.24 (t, J=7.1, 3H).

Step C. A mixture of 2-ethyl-N-(3-fluoro-4-piperazin-1-yl-phenyl)-butyramide dihydrochloride (0.26 g, 0.70 mmol), bromo-(3-fluoro-phenyl)-acetic acid methyl ester (0.23 g, 0.91 mmol), and anhydrous K$_2$CO$_3$ (0.34 g, 2.45 mmol) in DMF (10 mL) was stirred for 20 h. The mixture was diluted with water (100 mL) and extracted with DCM (2×30 mL). The combined organic layers were washed with water, dried (Na$_2$SO$_4$), and concentrated. The residue was purified (SiO$_2$; acetone/DCM) to give the title compound (0.25 g, 78%). MS: mass calcd. for $C_{25}H_{31}F_2N_3O_3$, 459.23. m/z found, 460.3 [M+H]$^+$. $^1$H NMR (CDCl$_3$): 7.48-7.43 (m, 1H), 7.35-7.28 (m, 1H), 7.25-7.20 (m, 2H), 7.17 (br s, 1H), 7.12-7.07 (m, 1H), 7.05-6.99 (m, 1H), 6.86 (t, J=9.0, 1H), 4.07 (s, 1H), 3.71 (s, 3H), 3.11-3.04 (m, 4H), 2.70-2.59 (m, 4H), 2.03-1.95 (m, 1H), 1.75-1.66 (m, 2H), 1.59-1.49 (m, 2H), 0.93 (t, J=7.4, 6H).

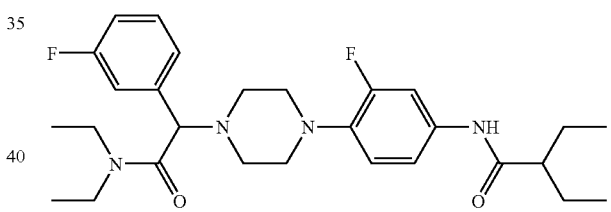

Example 35

N-(4-{4-[Diethylcarbamoyl-(3-fluoro-phenyl)-methyl]-piperazin-1-yl}-3-fluoro-phenyl)-2-ethyl-butyramide Step A. {4-[4-(2-Ethyl-butyrylamino)-2-fluoro-phenyl]-piperazin-1-yl}-(3-fluoro-phenyl)-acetic acid. A mixture of {4-[4-(2-ethyl-butyrylamino)-2-fluoro-phenyl]-piperazin-1-yl}-(3-fluoro-phenyl)-acetic acid methyl ester (0.22 g, 0.47 mmol) in water/MeOH (1:4, 5 mL) was treated with KOH (0.095 g, 1.70 mmol) and the resulting mixture was heated at reflux for 24 h. The mixture was cooled to rt and acidified to pH 6.5 with AcOH. The mixture was diluted with water and extracted with DCM. The organic layer was dried (Na$_2$SO$_4$) and concentrated to yield the title compound (0.24 g), which was carried forward to the next step.

Step B. N-(4-{4-[Diethylcarbamoyl-(3-fluoro-phenyl)-methyl]-piperazin-1-yl}-3-fluoro-phenyl)-2-ethyl-butyramide. A mixture of {4-[4-(2-ethyl-butyrylamino)-2-fluoro-phenyl]-piperazin-1-yl}-(3-fluoro-phenyl)-acetic acid (0.47 mmol), PyBOP (1.41 mmol), iPr$_2$NEt (1.41 mmol), and Et$_2$NH (1.41 mmol) in DMF (5 mL) was heated at 50° C. for 18 h. The mixture was cooled to rt, diluted with water (100 mL), and extracted with DCM. The organic layer was concentrated, and the residue was purified (SiO$_2$; 2 M NH$_3$ in MeOH/DCM) to give the title compound (74%). MS: mass calcd. for C$_{28}$H$_{38}$F$_2$N$_4$O$_2$, 500.3; m/z found, 500.4 [M+H]$^+$. $^1$H NMR (CDCl$_3$): 7.52-7.46 (m, 1H), 7.34-7.28 (m, 3H), 7.10-7.05 (m, 1H), 7.14-6.97 (m, 1H), 6.85 (t, J=9.0, 1H), 4.24 (s, 1H), 3.48.3.39 (m, 2H), 3.35-3.21 (m, 2H), 3.12-3.00 (m, 4H), 2.74-2.60 (m, 4H), 2.05-1.95 (m, 1H), 1.76-1.64 (m, 2H), 1.59-1.48 (m, 2H), 1.12-1.06 (m, 6H), 0.93 (t, J=7.4, 6H).

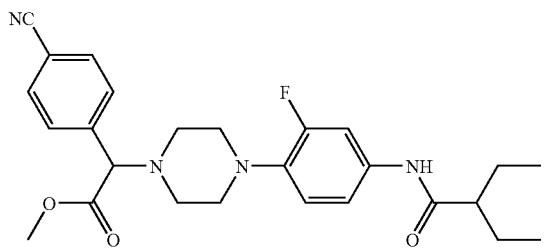

Example 36

(4-Cyano-phenyl)-{4-[4-(2-ethyl-butyrylamino)-2-fluoro-phenyl]-piperazin-1-yl}-acetic acid methyl ester Step A. 4-[4-(2-Ethyl-butyrylamino)-2-fluoro-phenyl]-piperazine-1-carboxylic acid tert-butyl ester. To a solution of 4-(4-amino-2-fluorophenyl)piperazine-1-carboxylic acid-tert-butyl ester (3.11 g, 10.5 mmol) and TEA (1.60 g, 15.8 mmol) in DCM (50 mL) was added 2-ethylbutyryl chloride (2.17 mL, 15.8 mmol) slowly. After 18 h, the mixture was washed with water, dried (Na$_2$SO$_4$), and concentrated. The residue was purified twice [SiO$_2$; 1) acetone/DCM, 2) EtOAc/hexanes] to give the title compound. (2.07 g, 50%).

Step B. 2-Ethyl-N-(3-fluoro-4-piperazin-1-yl-phenyl)-butyramide dihydrochloride. A solution of 4-[4-(2-ethyl-butyrylamino)-2-fluoro-phenyl]-piperazine-carboxylic-acid-tert-butyl ester (1.96 g) in MeOH (50 mL) was treated slowly with HCl (4 M in dioxane, 15 mL), and the resulting mixture was stirred at rt for 6 h. The mixture was concentrated to give the title compound (1.60 g). MS: mass calcd. for C$_{16}$H$_{24}$FN$_3$O, 293.19. m/z found, 294.2 [M+H]$^+$. $^1$H NMR (CDCl$_3$): 10.03 (s, 1H), 9.17 (br s, 2H), 7.66-7.60 (m, 1H), 7.29 (dd, J=8.6, 1.90, 1H), 7.04 (t, J=9.4, 1H), 3.27-3.12 (m, 8H), 2.24-2.15 (m, 1H), 1.53-1.48 (m, 2H), 1.47-1.38 (m, 2H), 0.83 (t, J=7.4, 6H).

Step C. A mixture of 2-ethyl-N-(3-fluoro-4-piperazin-1-yl-phenyl)-butyramide dihydrochloride (0.06 g, 0.16 mmol), bromo-(4-cyano-phenyl)-acetic acid methyl ester (0.05 g, 0.20 mmol), and anhydrous K$_2$CO$_3$ (0.08 g, 0.55 mmol) in DMF (5 mL) was stirred at rt for 20 h. The mixture was diluted with water (100 mL) and extracted with DCM (2×30 mL). The combined organic phases were washed with water, dried (Na$_2$SO$_4$), and concentrated. The residue was purified (SiO$_2$; acetone/DCM) to give the title compound (0.06 g, 79%). MS: mass calcd. for C$_{26}$H$_{31}$FN$_4$O$_3$, 466.24. m/z found, 467.4 [M+H]$^+$. $^1$H NMR (CDCl$_3$): 7.68-7.60 (m, 4H), 7.45 (dd, J=14.0, 2.4, 1H), 7.27 (br s, 1H), 7.13-7.08 (m, 1H), 6.85 (t, J=9.0, 1H), 4.14 (s, 1H), 3.72 (s, 3H), 3.10-3.03 (m, 4H), 2.69-2.56 (m, 4H), 2.04-1.95 (m, 1H), 1.74-1.62 (m, 2H), 1.59-1.48 (m, 2H), 0.92 (t, J=7.4, 6H).

Examples 37 and 38 were prepared using the methods described in Example 36 with the appropriate substituent changes.

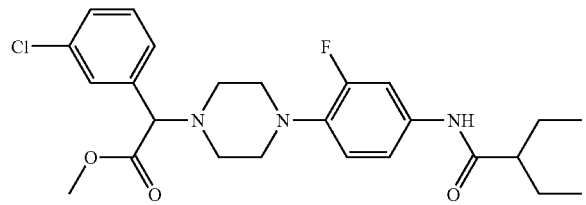

Example 37

(3-Chloro-phenyl)-{4-[4-(2-ethyl-butyrylamino)-2-fluoro-phenyl]-piperazin-1-yl}-acetic acid methyl ester

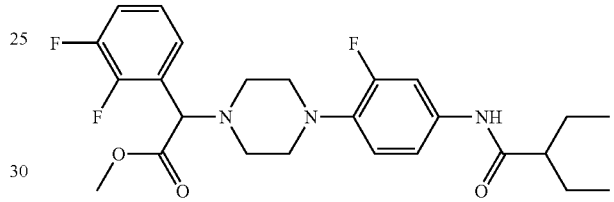

Example 38

(2,3-Difluoro-phenyl)-{4-[4-(2-ethyl-butyrylamino)-2-fluoro-phenyl]-piperazin-1-yl}-acetic acid methyl ester

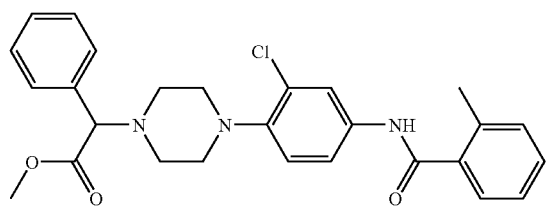

Example 39

{4-[2-Chloro-4-(2-methyl-benzoylamino)-phenyl]-piperazin-1-yl}-phenyl-acetic acid methyl ester To a mixture of [4-(4-amino-2-chloro-phenyl)-piperazin-1-yl]-phenyl-acetic acid methyl ester (25 mg, 0.07 mmol), 2-methyl-benzoic acid (19 mg, 0.14 mmol), EDC (27 mg, 0.14 mmol), and HOBt (19 mg, 0.14 mmol) in DCM (5 mL) was added N-methylmorpholine (77 μL, 0.70 mmol). After 16 h, the mixture was diluted with satd. aq. NaHCO$_3$ (10 mL) and extracted with DCM (75 mL). The organic fraction was washed with brine, dried (Na$_2$SO$_4$), and concentrated. The residue was purified by SiO$_2$ column chromatography to provide the title compound (16 mg, 46%). MS (ESI): mass calcd. for C$_{27}$H$_{28}$ClN$_3$O$_3$, 477.18. m/z found, 478.4 [M+H]$^+$. $^1$H NMR (CDCl$_3$): 7.76-7.60 (m, 1H), 7.51-7.23 (m, 8H), 7.22-7.15 (m, 2H), 6.97 (d, J=8.7, 1H), 3.66 (s, 3H), 3.15-2.93 (m, 5H), 2.85-2.49 (m, 4H), 2.42 (s, 3H).

Examples 40 and 41 were prepared using methods similar to those described in Example 39, with the appropriate substituent changes.

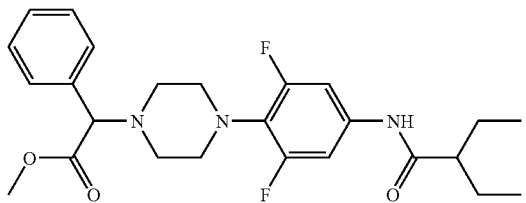

Example 40

{4-[4-(2-Ethyl-butyrylamino)-2,6-difluoro-phenyl]-piperazin-1-yl}-phenyl-acetic acid methyl ester MS (ESI): mass calcd. for C$_{25}$H$_{31}$F$_2$N$_3$O$_3$, 459.23. m/z found, 460.2 [M+H]$^+$. $^1$H NMR (CDCl$_3$): 7.53-7.43 (m, 5H), 7.24 (d, J=11.3, 2H), 5.09 (s, 1H), 3.78 (s, 3H), 3.42-3.32 (m, 5H), 3.21-3.12 (m, 3H), 2.16-2.01 (m, 1H), 1.66-1.54 (m, 2H), 1.52-1.41 (m, 2H), 0.87 (t, J=7.4, 6H).

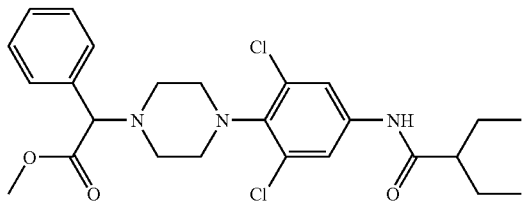

Example 41

{4-[2,6-Dichloro-4-(2-ethyl-butyrylamino)-phenyl]-piperazin-1-yl}-phenyl-acetic acid methyl ester MS (ESI): mass calcd. for C$_{25}$H$_{31}$Cl$_2$N$_3$O$_3$, 491.17. m/z found, 492.3/494.3 [M+H]$^+$. $^1$H NMR (CDCl$_3$): 7.51 (s, 1H), 7.47 (dd, J=8.3, 1.7, 2H), 7.38-7.28 (m, 3H), 7.17 (br s, 1H), 4.05 (s, 1H), 3.69 (s, 3H), 3.22-3.15 (m, 4H), 2.57-2.52 (m, 4H), 2.04-1.94 (m, 1H), 1.76-1.60 (m, 2H), 1.59-1.45 (m, 2H), 0.92 (t, J=7.4, 3H).

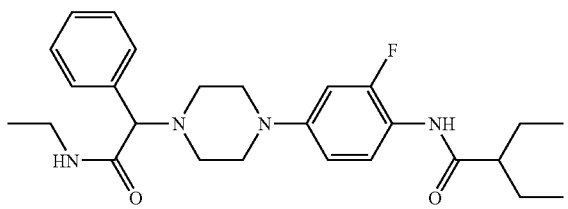

Example 42

2-Ethyl-N-{4-[4-(ethylcarbamoyl-phenyl-methyl)-piperazin-1-yl]-2-fluoro-phenyl}-butyramide Step A. N-(4-Bromo-2-fluoro-phenyl)-2-ethyl-butyramide. To a solution of 4-bromo-2-fluoro-phenylamine (1.0 g, 5.2 mmol) and TEA (4.0 mL, 36 mmol) in DCM (20 mL) was added 2-ethyl-butyryl chloride (3.6 mL, 26 mmol). After 16 h, the mixture was diluted with satd. aq. NaHCO$_3$ and extracted with DCM. The organic portion was washed twice with satd. aq. NaHCO$_3$ and brine, dried (Na$_2$SO$_4$), and concentrated. The crude residue was purified by SiO$_2$ column chromatography to provide the title compound (390 mg, 26%). MS (ESI): mass calcd. for C$_{12}$H$_{15}$BrFNO, 288.16. m/z found, 290.2 [M+H]$^+$.

Step B. To a solution of N-(4-bromo-2-fluoro-phenyl)-2-ethyl-butyramide (20 mg, 0.07 mmol), N-ethyl-2-phenyl-2-piperazin-1-yl-acetamide (18 mg, 0.07 mmol), Pd$_2$(dba)$_3$ (10 mg), and 2-(dicyclohexylphosphino)biphenyl (1 mg) in toluene was added sodium tert-butoxide (20 mg). The mixture was heated in a focused microwave at 110° C. for 1.5 h. The crude reaction mixture was purified by reverse phase HPLC (Agilent method) to provide the title compound (4 mg, 13%). MS (ESI): mass calcd. for C$_{26}$H$_{35}$FN$_4$O$_2$, 454.27. m/z found, 455.4 [M+H]$^+$. $^1$H NMR (CDCl$_3$): 8.10 (dd, J=9.6, 8.9, 1H), 7.38-7.30 (m, 3H), 7.14-6.99 (m, 2H), 6.68-6.59 (m, 2H), 3.88 (s, 1H), 3.43-3.29 (m, 2H), 3.21-3.10 (m, 4H), 2.66-2.55 (m, 4H), 2.12-2.00 (m, 1H), 1.79-1.67 (m, 2H), 1.66-1.47 (m, 2H), 1.18 (t, J=7.2, 3H), 0.98 (t, J=7.4, 6H).

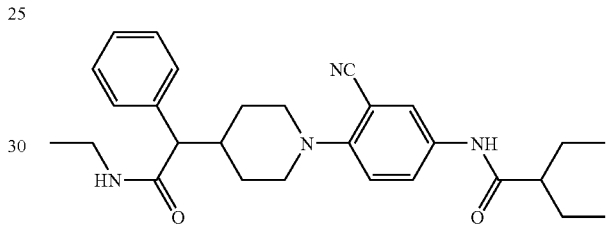

Example 43

N-{3-Cyano-4-[4-(ethylcarbamoyl-phenyl-methyl)-piperidin-1-yl]-phenyl}-2-ethyl-butyramide Step A. (1-Benzyl-piperidin-4-yl)-phenyl-acetic acid. A mixture of (1-benzyl-piperidin-4-yl)-phenyl-acetonitrile (11 g, 39 mmol) and 48% HBr/HOAc (50 mL) was heated at reflux for 16 h. After cooling to rt, the reaction mixture was poured into ice (400 g). The resulting solid was isolated by filtration and dried to provide the title compound as a tan powder (13.1 g, 100%). MS (ESI): mass calcd. for C$_{20}$H$_{23}$NO$_2$, 309.40. m/z found, 310.3 [M+H]$^+$.

Step B. 2-(1-Benzyl-piperidin-4-yl)-N-ethyl-2-phenyl-acetamide. To a suspension of (1-benzyl-piperidin-4-yl)-phenyl-acetic acid (7.1 g, 21 mmol) in DCM (150 mL) was added (COCl)$_2$ (2 M in DCM; 40 mL) and DMF (100 μL). After stirring for 2 h, the reaction mixture was concentrated. The powdery residue was dissolved in DCM (50 mL) and EtNH$_2$ (2.0 M in THF; 30 mL) was added. After 2 h, the mixture was diluted with 1 N NaOH (30 mL) and extracted with DCM (50 mL). The organic portion was washed with 1 N NaOH and brine, dried (Na$_2$SO$_4$), and concentrated. The residue was purified by SiO$_2$ column chromatography to provide the title compound (4.0 g, 57%). MS (ESI): mass calcd. for C$_{22}$H$_{28}$N$_2$O, 336.47. m/z found, 337.4 [M+H]$^+$.

Step C. N-Ethyl-2-phenyl-2-piperidin-4-yl-acetamide. To a solution of 2-(1-benzyl-piperidin-4-yl)-N-ethyl-2-phenyl-acetamide (4.0 g, 12 mmol) in EtOH, was added Pd/C (10%, 250 mg). The reaction mixture was then subjected to H$_2$ on a Parr shaker apparatus at 65 Psi. After 16 h, the reaction mixture was filtered through a pad of diatomaceous earth, and the filtrate was concentrated to provide the title compound as a white powder (2.9 g, 100%). MS (ESI): mass calcd. for $C_{15}H_{22}N_2O$, 246.35. m/z found, 247.4 [M+H]+.

Step D. 2-[1-(2-Cyano-4-nitro-phenyl)-piperidin-4-yl]-N-ethyl-2-phenyl-acetamide. To a solution of N-ethyl-2-phenyl-2-piperidin-4-yl-acetamide (500 mg, 2 mmol) and 2-fluoro-5-nitro-benzonitrile (337 mg, 2.03 mmol) in DMF was added $K_2CO_3$ (840 mg, 6.1 mmol). The solution was heated to 80° C. for 16 h. After cooling to rt, $H_2O$ and 3:1 EtOAc/hexanes were added. The organic portion was washed three times with $H_2O$ and once with brine, dried ($Na_2SO_4$) and concentrated to provide the title compound (yellow powder, 686 mg, 86%).

Step E. 2-[1-(4-Amino-2-cyano-phenyl)-piperidin-4-yl]-N-ethyl-2-phenyl-acetamide. 2-[1-(2-Cyano-4-nitro-phenyl)-piperidin-4-yl]-N-ethyl-2-phenyl-acetamide was subjected to reaction conditions similar to those described in Step C to provide the title compound as a yellow powder (600 mg, 95%). MS (ESI): mass calcd. for $C_{22}H_{26}N_4O$, 362.47. m/z found, 363.2 [M+H]+.

Step F. 2-[1-(4-Amino-2-cyano-phenyl)-piperidin-4-yl]-N-ethyl-2-phenyl-acetamide was subjected to the conditions described in Example 42, Step A, to provide the title compound (7.4 mg, 22%). MS (ESI): mass calcd. for $C_{28}H_{36}N_4O_2$, 460.28. m/z found, 461.4 [M+H]+. 1H NMR (CDCl3): 7.75 (d, J=2.6, 1H), 7.60 (dd, J=8.9, 2.6, 1H), 7.37-7.26 (m, 4H), 7.19 (br s, 1H), 6.92 (d, J=8.9, 1H), 5.56 (t, J=5.4, 1H). 3.50 (br d, J=10.8, 1H), 3.41-3.25 (m, 2H), 3.22-3.09 (m, 1H), 2.90 (d, J=10.4, 1H), 2.79 (dt, J=2.3, 11.9, 1H), 2.64 (dt, J=3.2, 11.3, 1H), 2.30-2.15 (m, 1H), 2.09-1.89 (m, 2H), 1.86-1.42 (m, 6H), 1.38-1.22 (m, 1H), 1.09 (t, J=7.2, 3H), 0.94 (t, J=7.4, 6H).

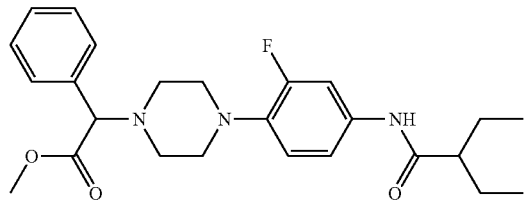

Example 44

{4-[4-(2-Ethyl-butyrylamino)-2-fluoro-phenyl]-piperazin-1-yl}-phenyl-acetic acid methyl ester Step A. [4-(2-Fluoro-4-nitro-phenyl)-piperazin-1-yl]-phenyl-acetic acid methyl ester. A mixture of 1-(2-fluoro-4-nitrophenyl)-piperazine (4.0 g, 18 mmol), methyl α-bromophenyl acetate (2.9 mL, 18 mmol) and $K_2CO_3$ (3.0 g, 21 mmol) in DMF (40 mL) was stirred at rt for 18 h. The reaction mixture was poured into $H_2O$ (150 mL) and extracted with EtOAc (2×). The combined organic layers were washed with 0.5 N HCl and brine, dried ($Na_2SO_4$), and concentrated to give an orange solid (6.5 g, 98%). MS (ESI): mass calcd. for $C_{19}H_{20}FN_3O_4$, 373.38. m/z found, 374.4 [M+H]+. 1H NMR (CDCl3): 7.98-7.95 (m, 1H), 7.89-7.86 (dd, J=13.1, 2.6, 1H), 7.45-7.43 (m, 2H), 7.39-7.34 (m, 3H), 6.87 (t, J=8.8, 1H), 4.09 (s, 1H), 3.71 (s, 3H), 3.33-3.31 (m, 4H), 2.66-2.64 (m, 4H).

Step B. [4-(4-Amino-2-fluoro-phenyl)-piperazin-1-yl]-phenyl-acetic acid methyl ester. To a solution of 4-(2-fluoro-4-nitro-phenyl)-piperazin-1-yl]-phenyl-acetic acid methyl ester (1.0 g, 2.7 mmol) in EtOH (25 mL) was added 10% Pd/C (125 mg). The mixture was stirred for 6 h under $H_2$ (balloon). The mixture was filtered through a plug of diatomaceous earth and the filtrate was concentrated to give a light brown solid (910 mg, 99%). MS (ESI): mass calcd. for $C_{19}H_{22}FN_3O_2$, 343.40. m/z found, 344.4 [M+H]+. 1H NMR (CDCl3): 7.46-7.44 (m, 2H), 7.37-7.31 (m, 3H), 6.82-6.76 (m, 1H), 6.44-6.36 (m, 2H), 4.05 (s, 1H), 3.70 (s, 3H), 3.52 (br s, 2H), 3.03-3.00 (m, 4H), 2.62-2.61 (m, 4H).

Step C. A mixture of 2-ethylbutyric acid (32 µL, 0.22 mmol), polymer-supported carbodiimide (240 mg, 0.29 mmol), and HOBt (33 mg, 0.25 mmol) in DCM (5 mL) was stirred at rt for 15 min. A solution of [4-(4-amino-2-fluoro-phenyl)-piperazin-1-yl]-phenyl-acetic acid methyl ester (50 mg, 0.15 mmol) in DCM (1 mL) was added and the mixture was stirred for 16 h. Polymer-bound tetraalkylammonium carbonate (PB-carbonate; 250 mg, 0.77 mmol) was added and the mixture was stirred for 2 h. The resins were removed by filtration and the filtrate was concentrated to give an oil, which was purified by PTLC to give a peach solid (37 mg, 57%). MS (ESI): mass calcd. for $C_{25}H_{32}FN_3O_3$, 441.54; m/z found, 442.5 [M+H]+. 1H NMR (CDCl3): 7.46-7.44 (m, 3H), 7.36-7.33 (m, 3H), 7.19-7.12 (m, 1H), 7.00 (br s, 1H), 6.87 (t, J=9.0, 1H), 4.06 (s, 1H), 3.70 (s, 3H), 3.09-3.08 (m, 4H), 2.64-2.62 (m, 4H), 2.02-1.95 (m, 1H), 1.70-1.67 (m, 2H), 1.56-1.53 (m, 2H), 0.94 (t, J=7.4, 6H).

Examples 45 to 77 were prepared using methods similar to those described in Example 44, with the appropriate substituent changes.

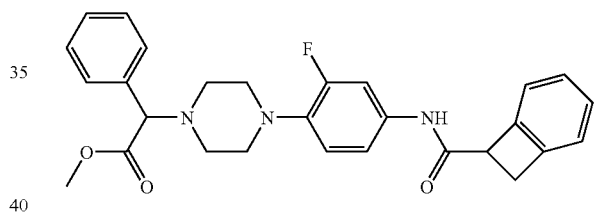

Example 45

(4-{4-[(Bicyclo[4.2.0]octa-1 (6),2,4-triene-7-carbonyl)-amino]-phenyl}-piperazin-1-yl)-phenyl-acetic acid methyl ester MS (ESI): mass calcd. for $C_{28}H_{29}N_3O_3$, 455.55. m/z found, 456.5 [M+H]+. 1H NMR (CDCl3): 7.46-7.45 (m, 2H), 7.44-7.30 (m, 7H), 7.24-7.22 (m, 2H), 7.19-7.18 (m, 1H), 6.84-6.62 (m, 2H), 4.33-4.32 (m, 1H), 4.04 (s, 1H), 3.69 (s, 3H), 3.64-3.63 (m, 1H), 3.42-3.41 (m, 1H), 3.16-3.14 (m, 4H), 2.61-2.59 (m, 4H).

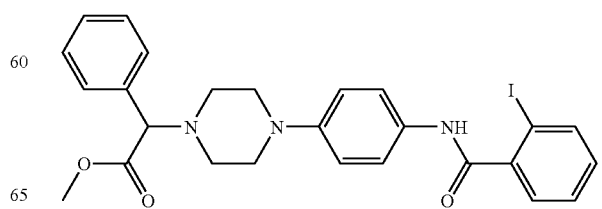

Example 46

{4-[4-(2-Iodo-benzoylamino)-phenyl]-piperazin-1-yl}-phenyl-acetic acid methyl ester

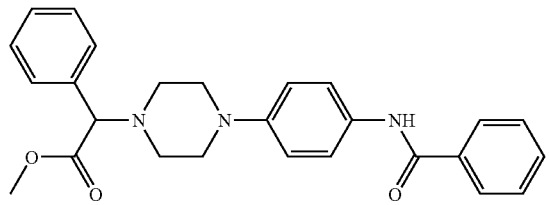

Example 47

[4-(4-Benzoylamino-phenyl)-piperazin-1-yl]-phenyl-acetic acid methyl ester

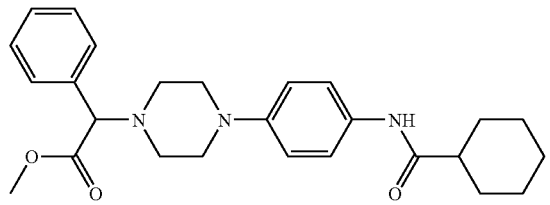

Example 48

{4-[4-(Cyclohexanecarbonyl-amino)-phenyl]-piperazin-1-yl}-phenyl-acetic acid methyl ester

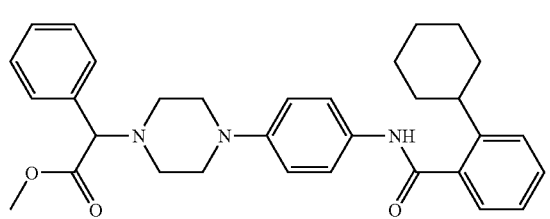

Example 49

{4-[4-(2-Cyclohexyl-benzoylamino)-phenyl]-piperazin-1-yl}-phenyl-acetic acid methyl ester

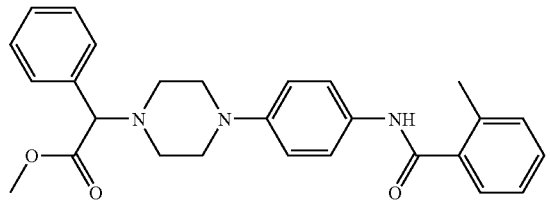

Example 50

{4-[4-(2-Methyl-benzoylamino)-phenyl]-piperazin-1-yl}-phenyl-acetic acid methyl ester

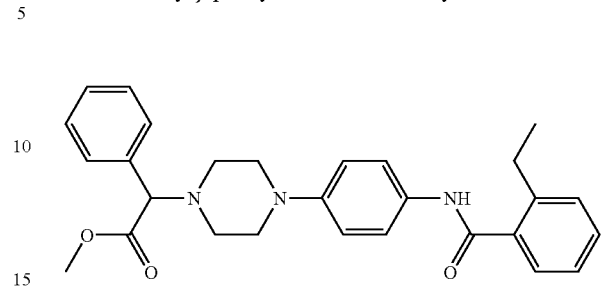

Example 51

{4-[4-(2-Ethyl-benzoylamino)-phenyl]-piperazin-1-yl}-phenyl-acetic acid methyl ester

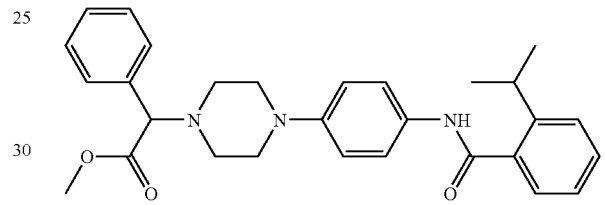

Example 52

{4-[4-(2-Isopropyl-benzoylamino)-phenyl]-piperazin-1-yl}-phenyl-acetic acid methyl ester

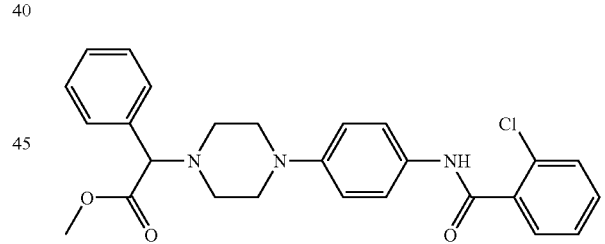

Example 53

{4-[4-(2-Chloro-benzoylamino)-phenyl]-piperazin-1-yl}-phenyl-acetic acid methyl ester

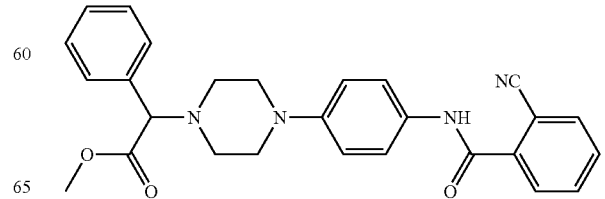

Example 54

{4-[4-(2-Cyano-benzoylamino)-phenyl]-piperazin-1-yl}-phenyl-acetic acid methyl ester

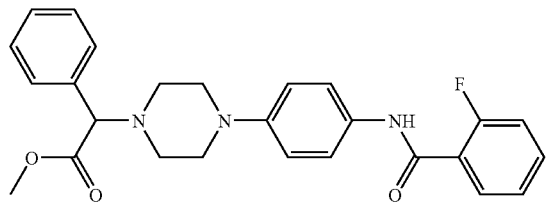

Example 55

{4-[4-(2-Fluoro-benzoylamino)-phenyl]-piperazin-1-yl}-phenyl-acetic acid methyl ester

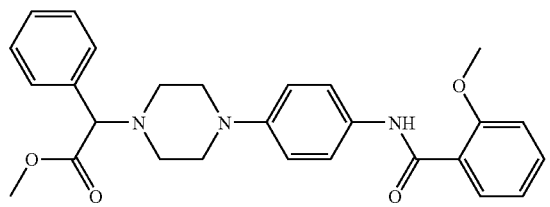

Example 56

{4-[4-(2-Methoxy-benzoylamino)-phenyl]-piperazin-1-yl}-phenyl-acetic acid methyl ester

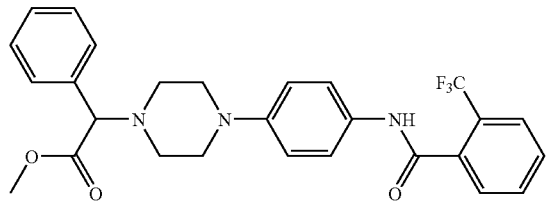

Example 57

Phenyl-{4-[4-(2-trifluoromethyl-benzoylamino)-phenyl]-piperazin-1-yl}-acetic acid methyl ester

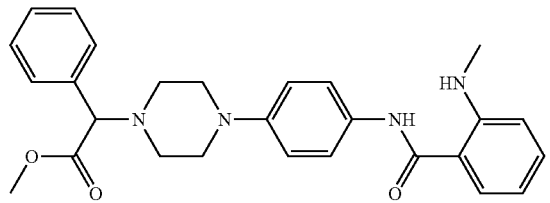

Example 58

{4-[4-(2-Methylamino-benzoylamino)-phenyl]-piperazin-1-yl}-phenyl-acetic acid methyl ester

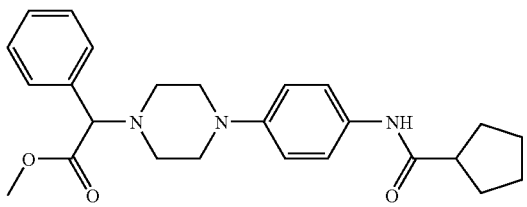

Example 59

{4-[4-(Cyclopentanecarbonyl-amino)-phenyl]-piperazin-1-yl}-phenyl-acetic acid methyl ester

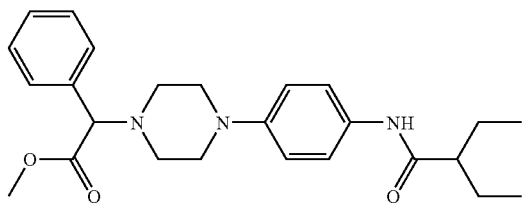

Example 60

{4-[4-(2-Ethyl-butyrylamino)-phenyl]-piperazin-1-yl}-phenyl-acetic acid methyl ester

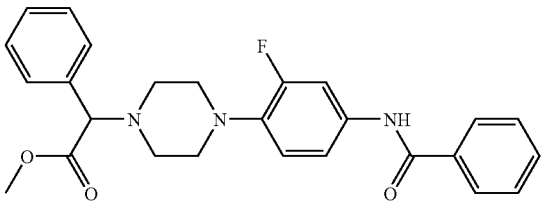

Example 61

[4-(4-Benzoylamino-2-fluoro-phenyl)-piperazin-1-yl]-phenyl-acetic acid methyl ester

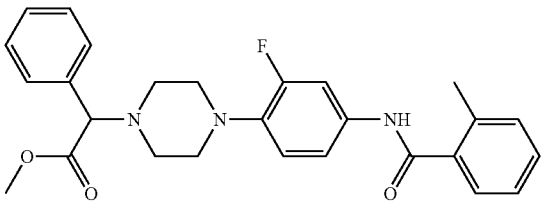

Example 62

{4-[2-Fluoro-4-(2-methyl-benzoylamino)-phenyl]-piperazin-1-yl}-phenyl-acetic acid methyl ester

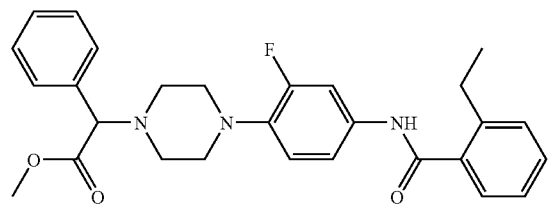

Example 63

{4-[4-(2-Ethyl-benzoylamino)-2-fluoro-phenyl]-piperazin-1-yl}-phenyl-acetic acid methyl ester

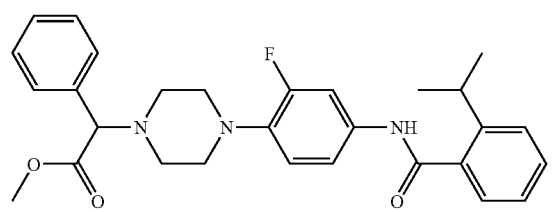

Example 64

{4-[2-Fluoro-4-(2-isopropyl-benzoylamino)-phenyl]-piperazin-1-yl}-phenyl-acetic acid methyl ester

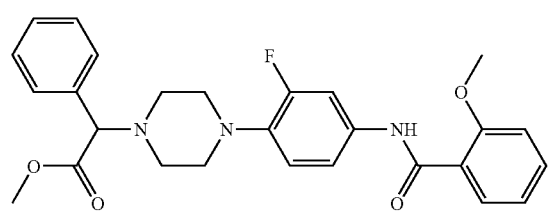

Example 65

{4-[2-Fluoro-4-(2-methoxy-benzoylamino)-phenyl]-piperazin-1-yl}-phenyl-acetic acid methyl ester

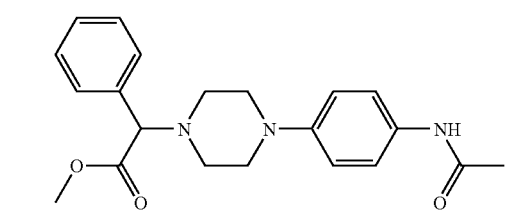

Example 66

[4-(4-Acetylamino-phenyl)-piperazin-1-yl]-phenyl-acetic acid methyl ester

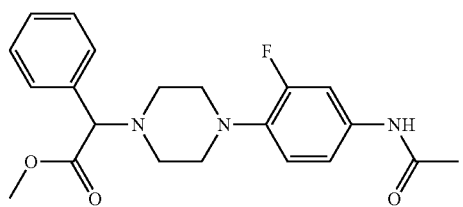

Example 67

[4-(4-Acetylamino-2-fluoro-phenyl)-piperazin-1-yl]-phenyl-acetic acid methyl ester

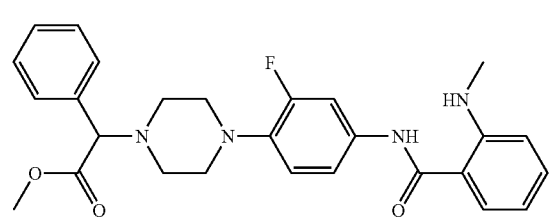

Example 68

{4-[2-Fluoro-4-(2-methylamino-benzoylamino)-phenyl]-piperazin-1-yl}-phenyl-acetic acid methyl ester

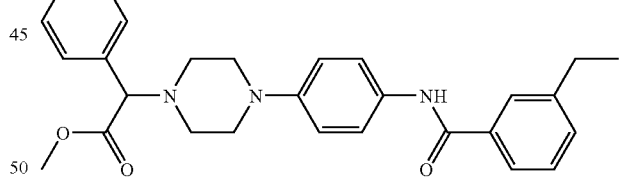

Example 69

{4-[4-(3-Ethyl-benzoylamino)-phenyl]-piperazin-1-yl}-phenyl-acetic acid methyl ester

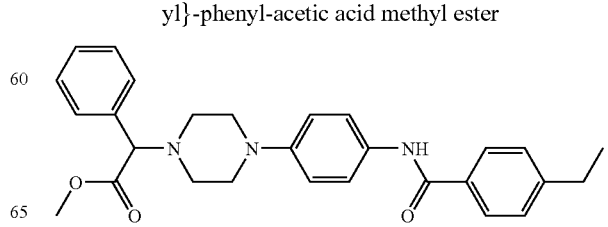

Example 70

{4-[4-(4-Ethyl-benzoylamino)-phenyl]-piperazin-1-yl}-phenyl-acetic acid methyl ester

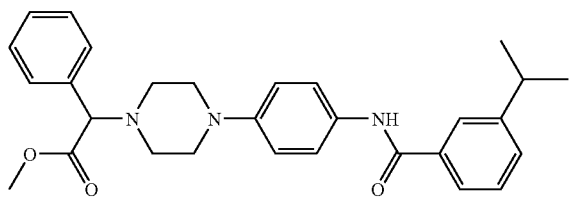

Example 71

{4-[4-(4-Isopropyl-benzoylamino)-phenyl]-piperazin-1-yl}-phenyl-acetic acid methyl ester

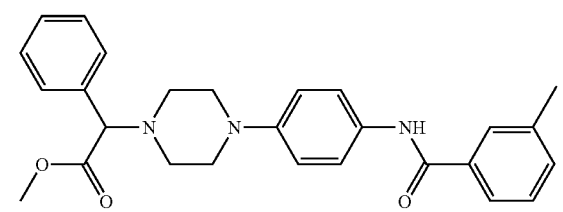

Example 72

{4-[4-(3-Methyl-benzoylamino)-phenyl]-piperazin-1-yl}-phenyl-acetic acid methyl ester

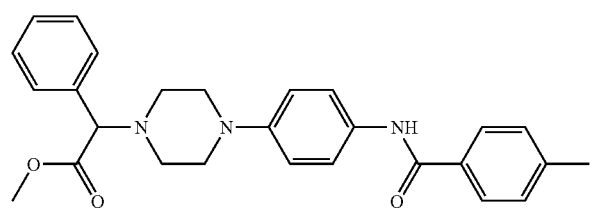

Example 73

{4-[4-(4-Methyl-benzoylamino)-phenyl]-piperazin-1-yl}-phenyl-acetic acid methyl ester

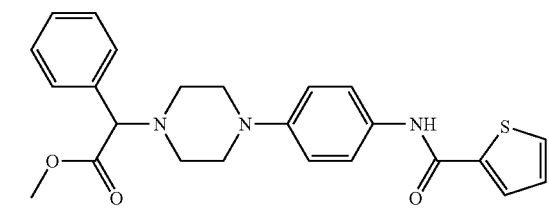

Example 74

Phenyl-(4-{4-[(thiophene-2-carbonyl)-amino]-phenyl}-piperazin-1-yl)-acetic acid methyl ester

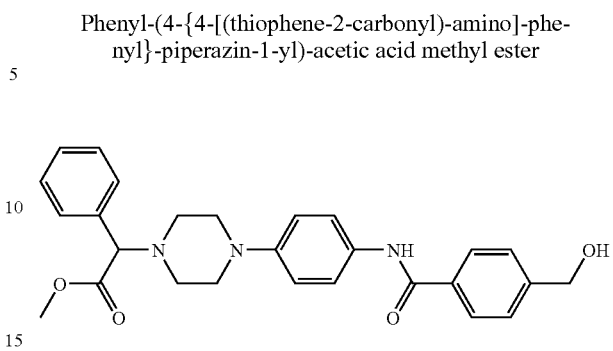

Example 75

{4-[4-(4-Hydroxymethyl-benzoylamino)-phenyl]-piperazin-1-yl}-phenyl-acetic acid methyl ester

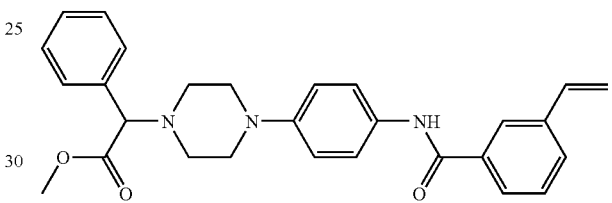

Example 76

Phenyl-{4-[4-(3-vinyl-benzoylamino)-phenyl]-piperazin-1-yl}-acetic acid methyl ester

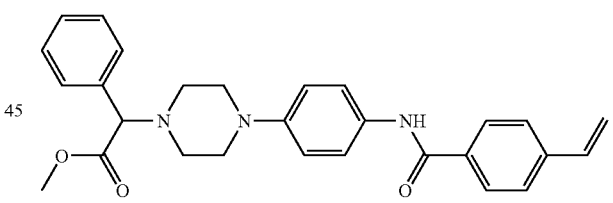

Example 77

Phenyl-{4-[4-(4-vinyl-benzoylamino)-phenyl]-piperazin-1-yl}-acetic acid methyl ester

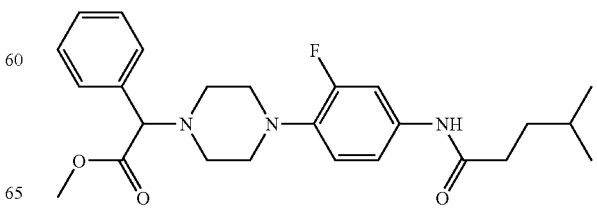

Example 78

{4-[2-Fluoro-4-(4-methyl-pentanoylamino)-phenyl]-piperazin-1-yl}-phenyl-acetic acid methyl ester A solution of [4-(4-amino-2-fluoro-phenyl)-piperazin-1-yl]-phenyl-acetic acid methyl ester (35 mg, 0.10 mmol) in DCM (2 mL) was treated with 4-methylvaleroyl chloride (15 mg, 0.11 mmol) followed by TEA (16 μL, 0.11 mmol). After 16 h, the mixture was purified directly by PTLC to give a beige solid (33 mg, 73%). MS (ESI): mass calcd. for $C_{25}H_{32}FN_3O_3$, 441.55; m/z found, 442.5 [M+H]$^+$. $^1$H NMR (CDCl$_3$): 7.46-7.44 (m, 2H), 7.42-7.39 (m, 1H), 7.36-7.32 (m, 3H), 7.05-7.03 (m, 1H), 6.98 (br s, 1H), 6.88-6.84 (m, 1H), 4.06 (s, 1H), 3.70 (s, 3H), 3.10-3.06 (m, 4H), 2.34-2.31 (m, 4H), 2.35-2.31 (m, 2H), 1.62-1.60 (m, 3H), 0.92 (d, J=6.1, 6H).

Examples 79 to 87 were prepared using methods similar to those described in Example 78, with the appropriate substituent changes.

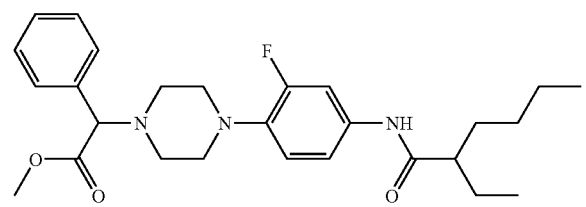

Example 79

{4-[4-(2-Ethyl-hexanoylamino)-2-fluoro-phenyl]-piperazin-1-yl}-phenyl-acetic acid methyl ester MS (ESI): mass calcd. for $C_{27}H_{38}FN_3O_3$, 469.59. m/z found, 470.5 [M+H]$^+$. $^1$H NMR (CDCl$_3$): 7.46-7.44 (m, 3H), 7.37-7.33 (m, 3H), 7.10-7.06 (m, 1H), 6.99 (br s, 1H), 6.86 (t, J=9.0, 1H), 4.06 (s, 1H), 3.70 (s, 3H), 3.09-3.08 (m, 4H), 3.02-2.98 (m, 1H), 2.64-2.62 (m, 4H), 2.03-1.98 (m, 2H), 1.68-1.66 (m, 2H), 1.50-1.47 (m, 1H), 1.32-1.25 (m, 4H), 0.95-0.92 (m, 3H), 0.89-0.86 (m, 4H).

Example 80

{4-[4-(4-tert-Butyl-benzoylamino)-phenyl]-piperazin-1-yl}-phenyl-acetic acid methyl ester

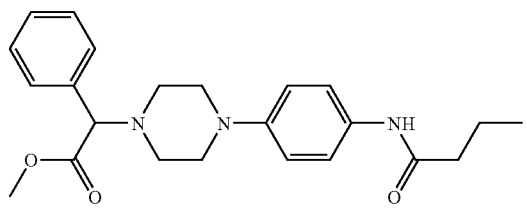

Example 81

[4-(4-Butyrylamino-phenyl)-piperazin-1-yl]-phenyl-acetic acid methyl ester

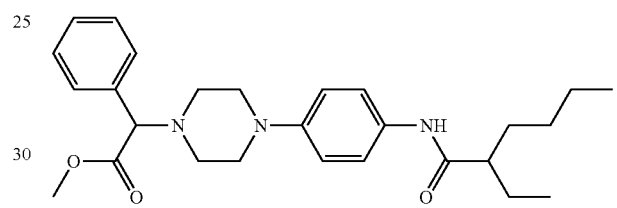

Example 82

{4-[4-(2-Ethyl-hexanoylamino)-phenyl]-piperazin-1-yl}-phenyl-acetic acid methyl ester

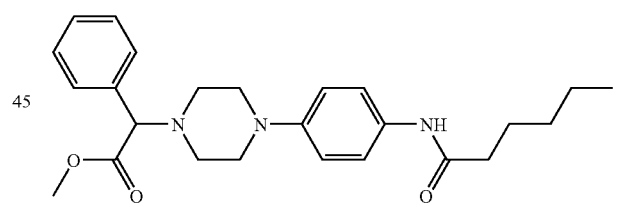

Example 83

[4-(4-Hexanoylamino-phenyl)-piperazin-1-yl]-phenyl-acetic acid methyl ester

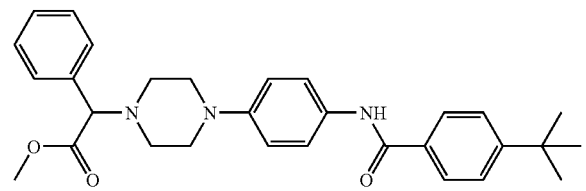

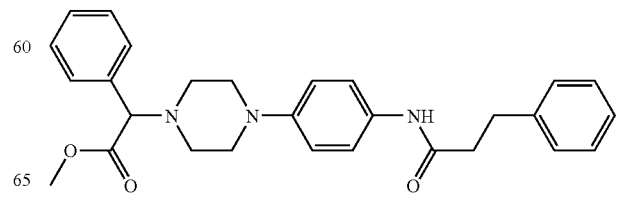

Example 84

Phenyl-{4-[4-(3-phenyl-propionylamino)-phenyl]-piperazin-1-yl}-acetic acid methyl ester

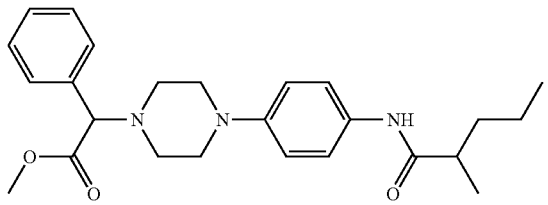

Example 85

{4-[4-(2-Methyl-pentanoylamino)-phenyl]-piperazin-1-yl}-phenyl-acetic acid methyl ester

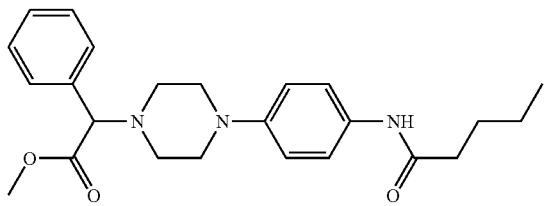

Example 86

[4-(4-Pentanoylamino-phenyl)-piperazin-1-yl]-phenyl-acetic acid methyl ester

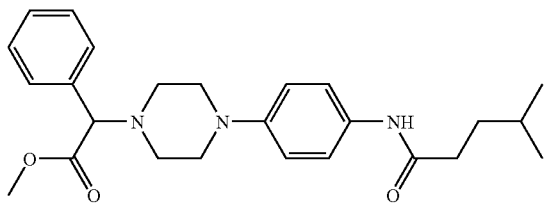

Example 87

{4-[4-(4-Methyl-pentanoylamino)-phenyl]-piperazin-1-yl}-phenyl-acetic acid methyl ester

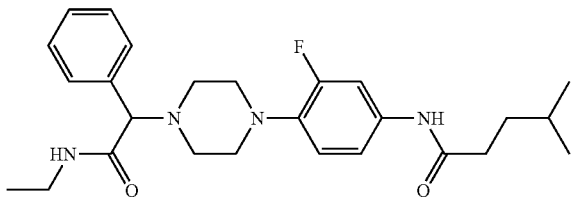

Example 88

4-Methyl-pentanoic acid {4-[4-(ethylcarbamoyl-phenyl-methyl)-piperazin-1-yl]-3-fluoro-phenyl}-amide Step A. [4-(2-Fluoro-4-nitro-phenyl)-piperazin-1-yl]-phenyl-acetic acid methyl ester. The title compound was prepared using methods similar to those described in Example 44, Step A.

Step B. [4-(2-Fluoro-4-nitro-phenyl)-piperazin-1-yl]-phenyl-acetic acid.

A mixture of [4-(2-fluoro-4-nitro-phenyl)-piperazin-1-yl]-phenyl-acetic acid methyl ester (600 mg, 1.6 mmol) and LiOH.H$_2$O (135 mg, 3.2 mmol) in THF (14 mL), H$_2$O (3 mL), and MeOH (3 mL) was stirred at rt for 18 h. The mixture was concentrated to half volume. The residual aqueous mixture was acidified to pH 5 with 1 N HCl and extracted with EtOAc (3×). The combined organic layers were dried (MgSO$_4$) and concentrated to give the crude material as an orange-yellow foam (614 mg, 100%).

Step C. N-Ethyl-2-[4-(2-fluoro-4-nitro-phenyl)-piperazin-1-yl]-2-phenyl-acetamide. A mixture of [4-(2-fluoro-4-nitro-phenyl)-piperazin-1-yl]-phenyl-acetic acid (600 mg, 1.7 mmol), Et$_2$NH (2.0 M in THF; 3.5 mL, 3.4 mmol), and HATU (760 mg, 2.0 mmol) in 10 mL DMF was treated with iPr$_2$NEt (350 µL, 2.0 mmol). After 18 h, the mixture was diluted with H$_2$O and extracted with 3:1 EtOAc/hexanes (2×). The combined organic layers were washed with satd. aq. NaHCO$_3$, satd aq. NH$_4$Cl, and brine, dried (Na$_2$SO$_4$), and concentrated to give an orange solid (645 mg, 100%). MS (ESI): mass calcd. for C$_{20}$H$_{23}$FN$_4$O$_3$, 386.42. m/z found, 387.4 [M+H]$^+$. $^1$H NMR (CDCl$_3$): 7.99-7.97 (m, 1H), 7.91-7.88 (m, 1H), 7.36-7.32 (m, 5H), 6.98-6.94 (m, 1H), 6.89 (t, J=8.8, 1H), 3.89 (s, 1H), 3.37-3.31 (m, 6H), 2.63-2.61 (m, 4H), 1.17 (t, J=7.3, 3H).

Step D. 2-[4-(4-Amino-2-fluoro-phenyl)-piperazin-1-yl]-N-ethyl-2-phenyl-acetamide. A mixture of N-ethyl-2-[4-(2-fluoro-4-nitro-phenyl)-piperazin-1-yl]-2-phenyl-acetamide (450 mg, 1.2 mmol) and SnCl$_2$.2H$_2$O (525 mg, 2.3 mmol) was heated at reflux in EtOH (50 mL) for 18 h. The mixture was concentrated, and the residue was diluted with 1 N NaOH and extracted with EtOAc (3×). The combined organic layers were washed with brine, dried (Na$_2$SO$_4$), and concentrated to give an oil, which was purified by PTLC to give an orange brown foam (200 mg, 48%). MS (ESI): mass calcd. for C$_{20}$H$_{25}$FN$_4$O$_2$, 356.44; m/z found, 357.5 [M+H]$^+$. $^1$H NMR (CDCl$_3$): 7.33-7.32 (m, 4H), 7.32-7.28 (m, 1H), 7.10 (br s, 1H), 6.80-6.76 (m, 1H), 6.42-6.37 (m, 2H), 3.98 (s, 1H), 3.54 (br s, 2H), 3.36-3.31 (m, 2H), 3.00-2.98 (m, 4H), 2.61-2.55 (m, 4H), 1.16 (t, J=7.3, 3H).

Step E. A solution of 2-[4-(4-amino-2-fluoro-phenyl)-piperazin-1-yl]-N-ethyl-2-phenyl-acetamide (44 mg, 0.12 mmol) in DCM (2 mL) was treated with 4-methylvaleroyl chloride (20 mg, 0.15 mmol) followed by TEA (21 µL, 0.15 mmol). After 16 h, the mixture was purified directly by PTLC to give a beige solid (53 mg, 94%). MS (ESI): mass calcd. for C$_{26}$H$_{35}$FN$_4$O$_2$, 454.59; m/z found, 455.5 [M+H]$^+$. $^1$H NMR (CDCl$_3$): 7.38-7.28 (m, 5H), 7.10-7.04 (m, 2H), δ 7.00 (br s, 1H), 6.86 (t, J=9.0, 1H), 3.88 (s, 1H), 3.40-3.31 (m, 3H), 3.07-3.06 (m, 4H), 2.61-2.57 (m, 4H), 2.34-2.31 (m, 3H), 1.62-1.59 (m, 2H), 1.16 (t, J=7.2, 3H), 0.93 (d, J=6.1, 6H).

Examples 89 and 90 were prepared using methods similar to those described in Example 88, with the appropriate substituent changes.

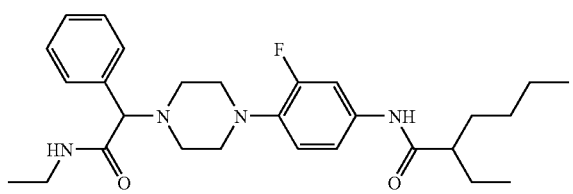

Example 89

2-Ethyl-hexanoic acid {4-[4-(ethylcarbamoyl-phenyl-methyl)-piperazin-1-yl]-3-fluoro-phenyl}-amide

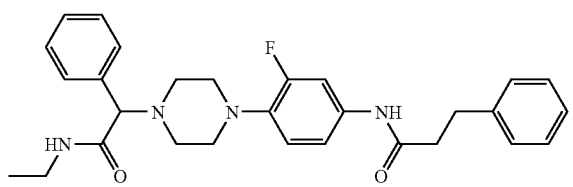

Example 90

N-{4-[4-(Ethylcarbamoyl-phenyl-methyl)-piperazin-1-yl]-3-fluoro-phenyl}-3-phenyl-propionamide

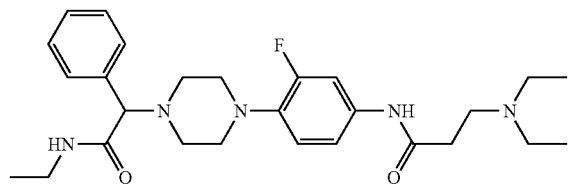

Example 91

3-Diethylamino-N-{4-[4-(ethylcarbamoyl-phenyl-methyl)-piperazin-1-yl]-3-fluoro-phenyl}-propionamide A mixture of 2-[4-(4-amino-2-fluoro-phenyl)-piperazin-1-yl]-N-ethyl-2-phenyl-acetamide (22 mg, 0.06 mmol), 3-diethylaminopropionic acid hydrochloride (13 mg, 0.07 mmol) and PyBroP (34 mg, 0.07 mmol) in DCM (2 mL) was treated with iPr$_2$NEt (0.032 mL, 0.19 mmol). After 18 h, the mixture was washed with satd. aq. NaHCO$_3$ and brine, dried (MgSO$_4$), and concentrated to give an oil, which was purified by PTLC to give a beige solid (17 mg, 56%). MS (ESI): mass calcd. for C$_{27}$H$_{38}$FN$_5$O$_2$, 483.62. m/z found, 484.4 [M+H]$^+$. $^1$H NMR (CDCl$_3$): 11.15 (s, 1H), 7.38-7.37 (m, 1H), 7.36-7.35 (m, 1H), 7.33-7.32 (m, 3H), 7.31-7.28 (m, 1H), 7.13-7.09 (m, 2H), 6.85 (t, J=9.0, 1H), 3.88 (s, 1H), 3.38-3.33 (m, 2H), 3.06-3.04 (m, 4H), 2.79-2.76 (m, 1H), 2.69-2.65 (m, 4H), 2.59-2.58 (m, 4H), 2.50-2.47 (m, 1H), 1.40-1.38 (m, 1H), 1.35-1.32 (t, J=7.3, 1H), 1.77-1.22 (m, 9H).

Examples 92-97 were prepared using methods similar to those described in Example 91, with the appropriate substituent changes.

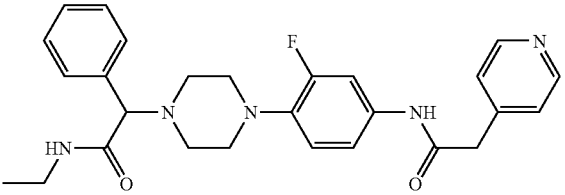

Example 92

N-Ethyl-2-{4-[2-fluoro-4-(2-pyridin-4-yl-acetylamino)-phenyl]-piperazin-1-yl}-2-phenyl-acetamide MS (ESI): mass calcd. for C$_{27}$H$_{30}$FN$_5$O$_2$, 475.56. m/z found, 476.2 [M+H]$^+$. $^1$H NMR (CDCl$_3$): 8.54-8.52 (m, 2H), 8.06 (s, 1H), 7.37 (dd, J=14.0, 2.3, 1H), 7.33-7.27 (m, 6H), 7.21-7.18 (m, 1H), 7.13-7.10 (m, 1H), 3.89 (s, 1H), 3.69-3.63 (m, 2H), 3.34-3.31 (m, 2H), 3.14-3.10 (m, 2H), 3.05-3.03 (m, 4H), 2.57-2.56 (m, 4H), 1.15 (t, J=7.2, 3H).

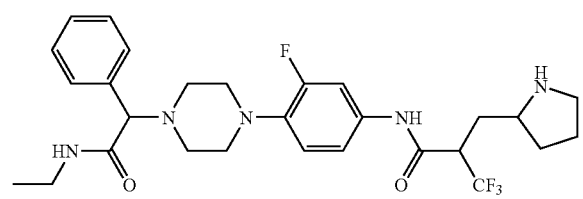

Example 93

N-{4-[4-(Ethylcarbamoyl-phenyl-methyl)-piperazin-1-yl]-3-fluoro-phenyl}-3,3,3-trifluoro-2-pyrrolidin-2-ylmethyl-propionamide MS (ESI): mass calcd. for C$_{28}$H$_{35}$F$_4$N$_5$O$_2$, 549.60. m/z found, 550.3 [M+H]$^+$. $^1$H NMR (CDCl$_3$): 11.02 (s, 1H), 7.34-7.25 (m, 5H), 7.11-7.05 (m, 2H), 6.87-6.84 (m, 1H), 3.88 (s, 1H), 3.59-3.51 (m, 2H), 3.36-3.31 (m, 2H), 3.24-3.20 (m, 2H), 3.07-3.05 (m, 3H), 2.82-2.78 (m, 1H), 2.69-2.67 (m, 1H), 2.59-2.58 (m, 4H), 2.00-1.96 (m, 1H), 1.92-1.89 (m, 4H), 1.78-1.75 (m, 2H), 1.16 (t, J=7.2, 3H).

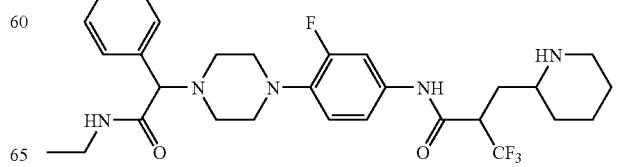

Example 94

N-{4-[4-(Ethylcarbamoyl-phenyl-methyl)-piperazin-1-yl]-3-fluoro-phenyl}-3,3,3-trifluoro-2-piperidin-2-ylmethyl-propionamide

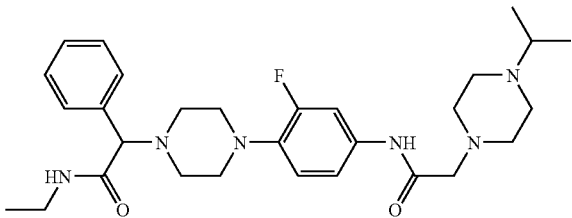

Example 95

N-Ethyl-2-(4-{2-fluoro-4-[2-(4-isopropyl-piperazin-1-yl)-acetylamino]-phenyl}-piperazin-1-yl)-2-phenyl-acetamide

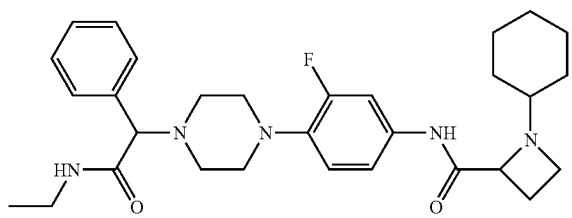

Example 96

1-Cyclohexyl-azetidine-2-carboxylic acid {4-[4-(ethylcarbamoyl-phenyl-methyl)-piperazin-1-yl]-3-fluoro-phenyl}-amide

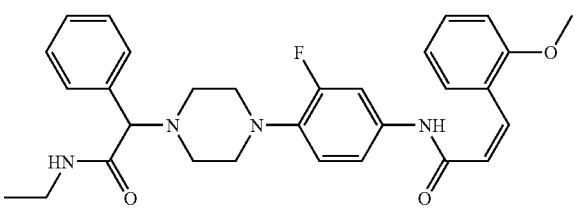

Example 97

(Z)—N-{4-[4-(Ethylcarbamoyl-phenyl-methyl)-piperazin-1-yl]-3-fluoro-phenyl}-3-(2-methoxy-phenyl)-acryl amide

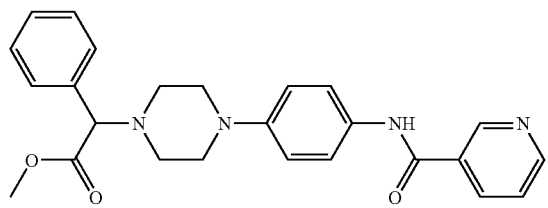

Example 98

Phenyl-(4-{4-[(pyridine-3-carbonyl)-amino]-phenyl}-piperazin-1-yl)-acetic acid methyl ester A mixture of [4-(4-amino-phenyl)-piperazin-1-yl]-phenyl-acetic acid methyl ester (50 mg, 0.15 mmol), nicotinic acid (23 mg, 0.18 mmol), and HATU (70 mg, 0.18 mmol) in DMF (2 mL) was treated with iPr$_2$NEt (32 µL, 0.18 mmol). After 16 h, the mixture was diluted with H$_2$O and extracted with DCM. The organic layer was washed with satd. aq. NaHCO$_3$ and brine, dried (MgSO$_4$), and concentrated to give an oil, which was purified by PTLC to give a tan solid (51 mg, 77%). MS (ESI): mass calcd. for C$_{25}$H$_{26}$N$_4$O$_3$, 430.50; m/z found, 431.4 [M+H]$^+$. $^1$H NMR (CDCl$_3$): 9.07-9.06 (m, 1H), 8.77-8.76 (m, 1H), 8.20-8.18 (m, 1H), 8.01 (s, 1H), 7.68 (br s, 1H), 7.51-7.42 (m, 4H), 7.38-7.32 (m, 3H), 6.92-6.90 (m, 2H), 4.06 (s, 1H), 3.71 (s, 3H), 3.22-3.20 (m, 4H), 2.64-2.62 (m, 4H).

Examples 99-111 were prepared using methods similar to those described in Example 98, with the appropriate substituent changes.

Example 99

{4-[2-Fluoro-4-(2-iodo-benzoylamino)-phenyl]-piperazin-1-yl}-phenyl-acetic acid methyl ester

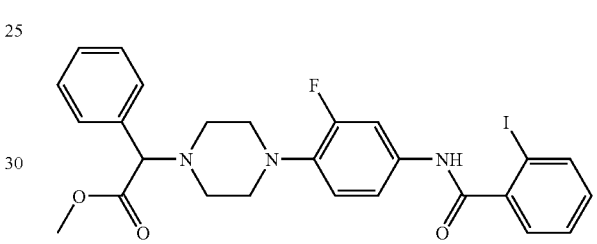

MS (ESI): mass calcd. for C$_{26}$H$_{25}$FIN$_3$O$_3$, 573.40. m/z found, 574.3 [M+H]$^+$. $^1$H NMR (CDCl$_3$): 8.01 (s, 1H), 7.91-7.89 (m, 1H), 7.56-7.55 (m, 1H), 7.53-7.52 (m, 1H), 7.51-7.50 (m, 1H), 7.47-7.41 (m, 2H), 7.38-7.33 (m, 3H), 7.18-7.14 (m, 2H), 6.92 (t, J=9.0, 1H), 4.07 (s, 1H), 3.71 (m, 3H), 3.12-3.11 (m, 4H), 2.65-2.64 (m, 4H).

Example 100

2-Bromo-N-{4-[4-(ethylcarbamoyl-phenyl-methyl)-piperazin-1-yl]-3-fluoro-phenyl}-nicotinamide

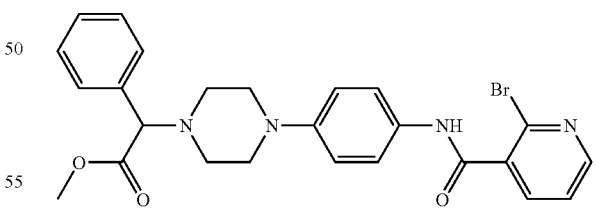

MS (ESI): mass calcd. for C$_{26}$H$_{27}$BrFN$_5$O$_2$, 540.44. m/z found, 540.2/542.1 [M+H]$^+$. $^1$H NMR (CDCl$_3$): 8.48-8.46 (m, 1H), 8.02-7.99 (m, 3H), 7.51 (dd, J=13.8, 2.4, 1H), 7.42-7.39 (m, 1H), 7.35-7.29 (m, 4H), 7.24-7.20 (m, 1H), 7.09-

7.06 (m, 1H), 6.93 (t, J=9.0, 1H), 3.91 (s, 1H), 3.37-3.32 (m, 2H), 3.12-3.10 (m, 4H), 2.65-2.61 (m, 4H), 1.17 (t, J=7.2, 3H).

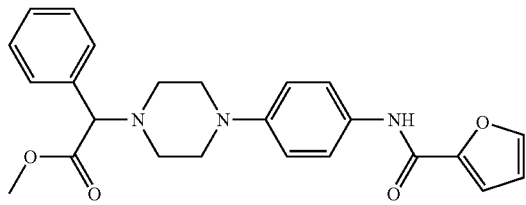

Example 101

(4-{4-[(Furan-2-carbonyl)-amino]-phenyl}-piperazin-1-yl)-phenyl-acetic acid methyl ester

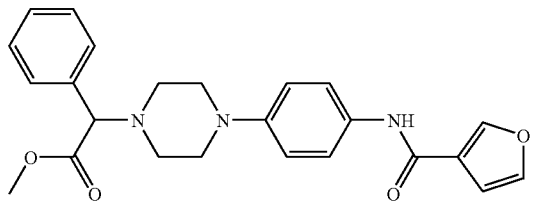

Example 102

(4-{4-[(Furan-3-carbonyl)-amino]-phenyl}-piperazin-1-yl)-phenyl-acetic acid methyl ester

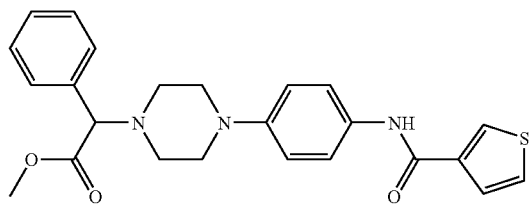

Example 103

Phenyl-(4-{4-[(thiophene-3-carbonyl)-amino]-phenyl}-piperazin-1-yl)-acetic acid methyl ester

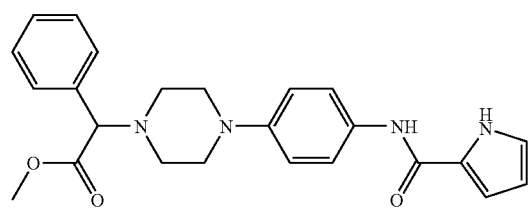

Example 104

Phenyl-(4-{4-[(1H-pyrrole-2-carbonyl)-amino]-phenyl}-piperazin-1-yl)-acetic acid methyl ester

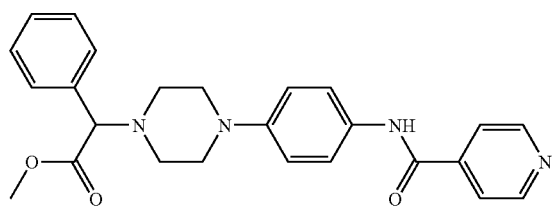

Example 105

Phenyl-(4-{4-[(pyridine-4-carbonyl)-amino]-phenyl}-piperazin-1-yl)-acetic acid methyl ester

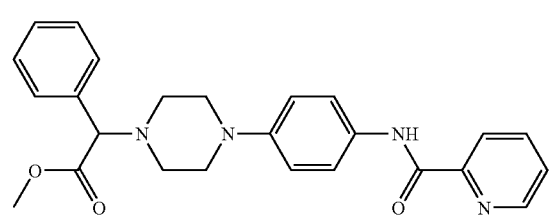

Example 106

Phenyl-(4-{4-[(pyridine-2-carbonyl)-amino]-phenyl}-piperazin-1-yl)-acetic acid methyl ester

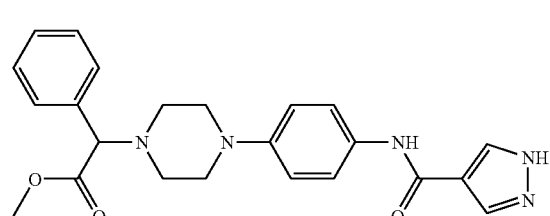

Example 107

Phenyl-(4-{4-[(1H-pyrazole-4-carbonyl)-amino]-phenyl}-piperazin-1-yl)-acetic acid methyl ester

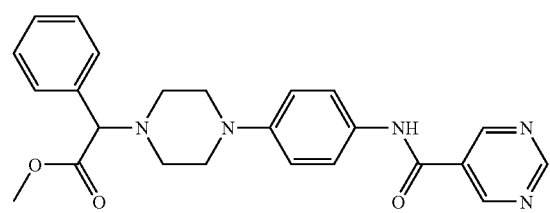

Example 108

Phenyl-(4-{4-[(pyrimidine-5-carbonyl)-amino]-phenyl}-piperazin-1-yl)-acetic acid methyl ester

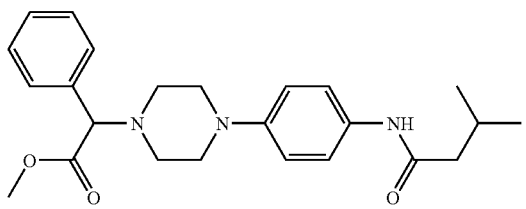

Example 109

{4-[4-(3-Methyl-butyrylamino)-phenyl]-piperazin-1-yl}-phenyl-acetic acid methyl ester

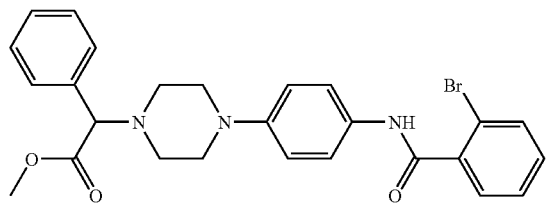

Example 110

{4-[4-(2-Bromo-benzoylamino)-phenyl]-piperazin-1-yl}-phenyl-acetic acid methyl ester

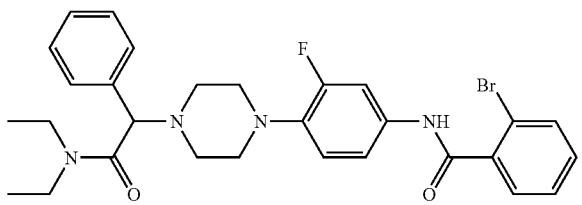

Example 111

2-Bromo-N-{4-[4-(diethylcarbamoyl-phenyl-methyl)-piperazin-1-yl]-3-fluoro-phenyl}-benzamide

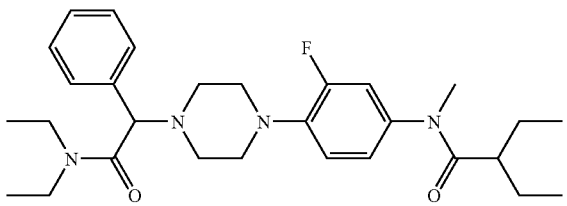

Example 112

N-{4-[4-(Diethylcarbamoyl-phenyl-methyl)-piperazin-1-yl]-3-fluoro-phenyl}-2-ethyl-N-methyl-butyramide A solution of N-{4-[4-(diethylcarbamoyl-phenyl-methyl)-piperazin-1-yl]-3-fluoro-phenyl}-2-ethyl-butyramide (48 mg, 0.10 mmol) in DMF (2 mL) was treated with NaH (60% in mineral oil; 5 mg, 0.12 mmol). After 10 min, MeI (7 µL, 0.12 mmol) was added. After 3 h, the mixture was diluted with water and extracted with DCM. The organic layer was concentrated to give an oil, which was purified by PTLC to give an off white solid (25 mg, 50%). MS (ESI): mass calcd. for $C_{29}H_{41}FN_4O_2$, 496.96. m/z found, 497.5 [M+H]+. $^1$H NMR (CDCl$_3$): 7.49-7.46 (m, 2H), 7.40-7.32 (m, 3H), 6.93-6.89 (m, 1H), 6.87-6.81 (m, 2H), 4.37 (s, 1H), 3.51-3.47 (m, 1H), 3.45-3.40 (m, 1H), 3.33-3.25 (m, 1H), 3.24 (s, 3H), 3.19-3.16 (m, 5H), 2.75-2.70 (m, 4H), 2.23-2.19 (m, 1H), 1.63-1.56 (m, 2H), 1.41-1.33 (m, 2H), 1.12-1.05 (m, 6H), 0.81 (t, J=7.4, 6H).

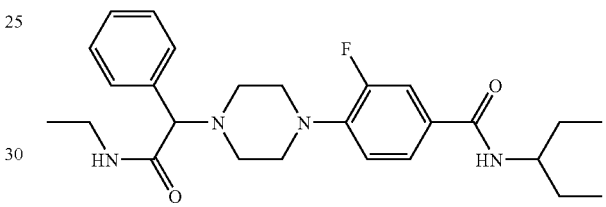

Example 113

4-[4-(Ethylcarbamoyl-phenyl-methyl)-piperazin-1-yl]-N-(1-ethyl-propyl)-3-fluoro-benzamide Step A. 4-Bromo-N-(1-ethyl-propyl)-3-fluoro-benzamide. A mixture of 4-bromo-3-fluorobenzoic acid (300 mg, 1.4 mmol), 1-ethylpropylamine (160 µL, 1.4 mmol), and HATU (570 mg, 1.5 mmol) in DMF (3 mL) was treated with iPr$_2$NEt (260 µL, 1.5 mmol). After 16 h, the mixture was diluted with H$_2$O and extracted with EtOAc. The organic layer was washed with satd. aq. NaHCO$_3$, satd. aq. NH$_4$Cl, and brine, dried (Na$_2$SO$_4$), and concentrated to give a beige solid (380 mg, 97%). MS (ESI): mass calcd. for $C_{12}H_{15}BrFNO$, 288.16; m/z found, 290.3 [M+H]+. $^1$H NMR (CDCl$_3$): 7.64-7.60 (m, 1H), 7.54 (dd, J=2.0, 9.0, 1H), 7.40 (dd, J=2.0, 8.3, 1H), 4.04-3.94 (m, 1H), 2.81 (s, 1H), 1.71-1.62 (m, 2H), 1.53-1.43 (m, 2H), 0.95 (t, J=7.4, 6H).

Step B. N-(1-Ethyl-propyl)-3-fluoro-4-piperazin-1-yl-benzamide. A mixture of piperazine (30 mg, 0.4 mmol), 4-bromo-N-(1-ethyl-propyl)-3-fluoro-benzamide (150 mg, 0.5 mmol), Pd$_2$(dba)$_3$ (6 mg, 0.007 mmol), 2-dicyclohexylphosphino-2',4',6'-triisopropyl-1,1'-biphenyl (X-Phos; 3 mg, 0.006 mmol), and NaOtBu (70 mg, 0.7 mmol) in toluene (3 mL) was heated at 100° C. for 30 min in a focused microwave reactor. The solids were removed by filtration and the filtrate was concentrated to give an oil, which was purified by PTLC to give a yellow solid (20 mg, 22%). MS (ESI): mass calcd. for $C_{16}H_{24}FN_3O$, 293.38. m/z found, 294.4 [M+H]+. $^1$H NMR (CDCl$_3$): 7.48-7.47 (m, 1H), 7.45-7.42 (m, 1H), 6.92 (t, J=8.4, 1H), 5.69-5.67 (m, 1H), 4.00-3.95 (m, 1H), 3.14-3.11 (m, 4H), 3.06-3.04 (m, 4H), 1.67-1.60 (m, 2H), 1.51-1.42 (m, 2H), 0.94 (t, J=7.4, 6H).

Step C. A mixture of N-(1-ethyl-propyl)-3-fluoro-4-piperazin-1-yl-benzamide (12 mg, 0.04 mmol), 2-bromo-N-ethyl-2-phenyl-acetamide (12 mg, 0.05 mmol), and $K_2CO_3$ (8 mg, 0.05 mmol) in DMF (2 mL) was stirred for 16 h. The mixture was poured into water and extracted with DCM. The organic layer was dried ($MgSO_4$) and purified by PTLC to give a white solid (6 mg, 34%). MS (ESI): mass calcd. for $C_{26}H_{35}FN_4O_2$, 454.58. m/z found, 455.5 $[M+H]^+$. $^1H$ NMR ($CDCl_3$): 7.47-7.42 (m, 2H), 7.34-7.30 (m, 5H), 7.05-7.02 (m, 1H), 6.90 (t, J=8.4, 1H), 5.67 (d, J=8.9, 1H), 3.99-3.94 (m, 1H), 3.89 (s, 1H), 3.37-3.31 (m, 2H), 3.19-3.17 (m, 4H), 2.64-2.55 (m, 4H), 1.66-1.59 (m, 5H), 1.49-1.42 (m, 2H), 1.16 (t, J=7.2, 3H), 0.93 (t, J=7.4, 6H).

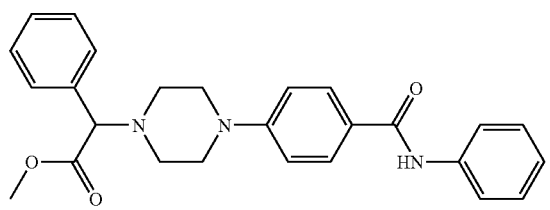

Example 114

Phenyl-[4-(4-phenylcarbamoyl-phenyl)-piperazin-1-yl]-acetic acid methyl ester

Step A. 4-(4-Phenylcarbamoyl-phenyl)-piperazine-1-carboxylic acid tert-butyl ester. A mixture of tert-butyl-1-piperazine-carboxylate (50 mg, 0.3 mmol), 4-bromo-N-phenyl-benzamide (110 mg, 0.4 mmol), tris(dibenzylideneacetone)-dipalladium(0) (5 mg, 0.005 mmol), X-Phos (2 mg, 0.004 mmol), and NaOtBu (80 mg, 0.8 mmol) in toluene (3 mL) was heated at 100° C. for 30 min in a focused microwave reactor. The solids were removed by filtration and the filtrate was concentrated to give an oil, which was purified by PTLC to give a beige solid (14 mg, 13%). MS (ESI): mass calcd. for $C_{22}H_{27}N_3O_3$, 381.47; m/z found, 382.5 $[M+H]^+$. $^1H$ NMR ($CDCl_3$): 7.80 (d, J=8.8, 2H), 7.70 (br s, 1H), 7.62 (d, J=7.7, 2H), 7.38-7.34 (m, 2H), 7.13 (t, J=7.3, 1H), 6.93 (d, J=8.9, 2H), 3.61-3.58 (m, 4H), 3.30-3.28 (m, 4H), 1.49 (s, 9H).

Step B. N-Phenyl-4-piperazin-1-yl-benzamide. To a solution of 4-(4-phenylcarbamoyl-phenyl)-piperazine-1-carboxylic acid tert-butyl ester (12 mg, 0.3 mmol) in DCM (1 mL) was added trifluoroacetic acid (5 mL). After stirring at rt for 90 min, the reaction mixture was concentrated and the resulting oil was purified by PTLC to give an off white solid (7 mg, 76%). MS (ESI): mass calcd. for $C_{17}H_{19}N_3O$, 281.35. m/z found, 282.4 $[M+H]^+$. $^1H$ NMR ($CDCl_3$): 7.79 (d, J=9.0, 2H), 7.71 (br s, 1H), 7.64-7.61 (m, 2H), 7.38-7.34 (m, 2H). 7.15-7.10 (m, 1H), 6.93 (d, J=9.0, 2H), 3.30-3.27 (m, 4H), 3.06-3.03 (m, 4H).

Step C. A mixture of N-phenyl-4-piperazin-1-yl-benzamide (4 mg, 0.02 mmol), methyl α-bromophenyl acetate (3 μL, 0.02 mmol), and $K_2CO_3$ (3 mg, 0.02 mmol) in DMF (1 mL) was stirred for 16 h. The mixture was diluted with $H_2O$ and extracted with methanolic DCM (2x). The combined organic layers were dried ($MgSO_4$) and concentrated to give an oil, which was purified by PTLC to give a white solid (3 mg, 44%). MS (ESI): mass calcd. for $C_{26}H_{27}N_3O_3$, 429.51.

m/z found, 430.4 $[M+H]^+$. $^1H$ NMR ($CDCl_3$): 7.71 (d, J=8.9, 2H), 7.69 (br s, 1H), 7.61 (d, J=7.6, 2H), 7.47-7.45 (m, 2H), 7.39-7.33 (m, 5H), 7.12 (t, J=7.4, 1H), 6.89 (d, J=8.9, 2H), 4.07 (s, 1H), 3.71 (s, 3H), 3.36-3.33 (m, 4H), 2.64-2.61 (m, 4H).

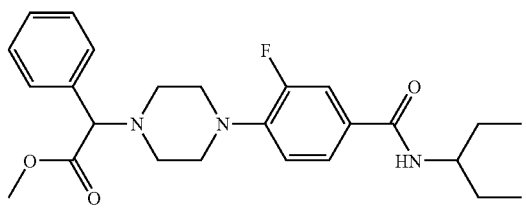

Example 115

{4-[4-(1-Ethyl-propylcarbamoyl)-2-fluoro-phenyl]-piperazin-1-yl}-phenyl-acetic acid methyl ester Step A. 4-(Methoxycarbonyl-phenyl-methyl)-piperazine-1-carboxylic acid tert-butyl ester. A mixture of tert-butyl-1-piperazine carboxylate (600 mg, 3.2 mmol), methyl α-bromophenyl acetate (510 μL, 3.2 mmol) and $K_2CO_3$ (540 mg, 3.9 mmol) in DMF (2 mL) was stirred at rt for 4 h. The reaction mixture was poured into $H_2O$ (20 mL) and extracted with 4:1 EtOAc/hexanes (3x). The combined organic layers were washed with brine, dried ($Na_2SO_4$), and concentrated to give an oil, which was purified by PTLC to give a colorless oil (1.1 g, 100%). MS (ESI): mass calcd. for $C_{18}H_{26}N_2O_4$, 334.41. m/z found, 335.4 $[M+H]^+$. $^1H$ NMR ($CDCl_3$): 7.42-7.40 (m, 2H), 7.35-7.32 (m, 3H), 4.02 (s, 1H), 3.69 (s, 3H), 3.45-3.42 (m, 4H), 2.41-2.39 (m, 4H), 1.43 (s, 9H).

Step B. Phenyl-piperazin-1-yl-acetic acid methyl ester. To a solution of 4-(methoxycarbonyl-phenyl-methyl)-piperazine-1-carboxylic acid tert-butyl ester (900 mg, 2.7 mmol) in DCM (10 mL) was added trifluoroacetic acid (5 mL). After 18 h, the reaction mixture was concentrated. The resulting oil was dissolved in DCM and washed with satd. aq. $NaHCO_3$ (3x). The organic layer was dried ($MgSO_4$) and concentrated to give an oil (230 mg, 36%). MS (ESI): mass calcd. for $C_{13}H_{18}N_2O_2$, 234.29. m/z found, 235.4 $[M+H]^+$. $^1H$ NMR ($CDCl_3$): 7.43-7.41 (m, 2H), 7.35 (m, 3H), 3.99 (s, 1H), 3.68 (m, 3H), 2.92-2.89 (m, 4H), 2.45-2.41 (m, 4H).

Step C. A mixture of phenyl-piperazin-1-yl-acetic acid methyl ester (80 mg, 0.4 mmol), 4-bromo-N-(1-ethyl-propyl)-3-fluoro-benzamide (prepared as described in Example 113, Step A; 150 mg, 0.5 mmol), $Pd_2(dba)_3$ (6 mg, 0.007 mmol), X-Phos (3 mg, 0.007 mmol), and NaOtBu (67 mg, 0.9 mmol) in toluene (5 mL) was heated at 100° C. for 18 h. The solids were removed by filtration and the filtrate was concentrated to give an oil, which was purified by PTLC to give a beige solid (9 mg, 6%). MS (ESI): mass calcd. for $C_{25}H_{32}FN_3O_3$, 441.54; m/z found, 442.5 $[M+H]^+$. $^1H$ NMR ($CDCl_3$): 7.46-7.43 (m, 4H), 7.38-7.33 (m, 3H), 6.90 (t, J=8.3, 1H), 5.66 (d, J=8.5, 1H), 4.07 (s, 1H), 3.70 (s, 3H), 3.20-3.18 (m, 4H), 2.65-2.63 (m, 4H), 1.68-1.55 (m, 3H), 1.49-1.42 (m, 2H), 0.93 (t, J=7.4, 6H).

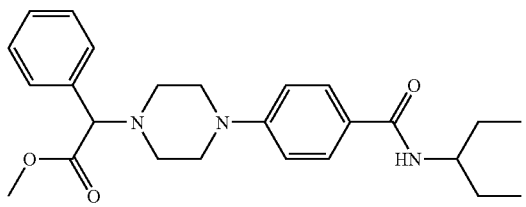

Example 116

{4-[4-(1-Ethyl-propylcarbamoyl)-phenyl]-piperazin-1-yl}-phenyl-acetic acid methyl ester The title compound was prepared according to the methods described in Example 115, with the appropriate substituent changes.

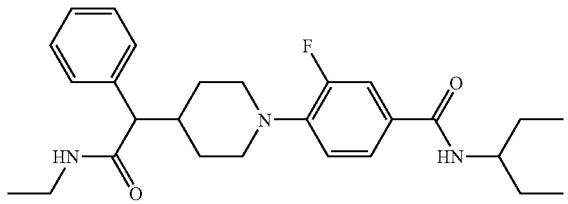

Example 117

4-[4-(Ethylcarbamoyl-phenyl-methyl)-piperidin-1-yl]-N-(1-ethyl-propyl)-3-fluoro-benzamide Step A. (1-Benzyl-piperidin-4-yl)-phenyl-acetic acid. A mixture of 1-benzyl-4-(α-cyanobenzyl)-piperidine (1.0 g, 3.4 mmol) and 48% HBr (15 mL) was heated at 105° C. for 20 h. After cooling to rt, the mixture was quenched with water. The precipitate was collected by vacuum filtration. The solids were dried under vacuum to give an off-white solid (1.1 g, 100%). MS (ESI): mass calcd. for $C_{20}H_{23}NO_2$, 309.40. m/z found, 310.4 [M+H]$^+$. $^1$H NMR (CDCl$_3$): 7.49-7.46 (m, 5H), 7.34-7.32 (m, 4H), 7.29-7.26 (m, 1H), 4.69-4.55 (m, 2H), 4.27 (s, 2H), 3.51-3.48 (m, 1H), 3.13-3.01 (m, 1H), 2.98-2.91 (m, 1H), 2.36-2.28 (m, 2H), 2.16-2.13 (m, 1H), 1.54-1.50 (m, 1H), 1.34-1.24 (m, 2H).

Step B. 2-(1-Benzyl-piperidin-4-yl)-N-ethyl-2-phenyl-acetamide. A mixture of (1-benzyl-piperidin-4-yl)-phenyl-acetic acid (600 mg, 1.9 mmol), HATU (890 mg, 2.3 mmol), and Et$_2$NH (2.0 M in THF; 2.5 mL, 5.0 mmol) in DMF (10 mL) was stirred at rt for 18 h. The mixture was diluted with water and extracted with 3:1 EtOAc/hexanes (3×). The combined organic layers were washed with satd. aq. NaHCO$_3$ and brine, dried (Na$_2$SO$_4$), and concentrated to give an oil, which solidified upon standing (490 mg, 76%). MS (ESI): mass calcd. for $C_{22}H_{28}N_2O$, 336.47. m/z found, 337.5 [M+H]$^+$. $^1$H NMR (CDCl$_3$): 7.32-7.29 (m, 3H), 7.28-7.26 (m, 5H), 7.24-7.22 (m, 2H), 5.45-5.43 (m, 1H), 3.46 (s, 2H), 3.32-3.25 (m, 1H), 3.17-3.12 (m, 1H), 2.89-2.86 (m, 2H), 2.79-2.76 (m, 1H), 2.10-2.08 (m, 1H), 2.04-1.98 (m, 1H), 1.89-1.83 (m, 2H), 1.35-1.19 (m, 3H), 1.06 (t, J=7.3, 3H).

Step C. N-Ethyl-2-phenyl-2-piperidin-4-yl-acetamide. To a solution of 2-(1-benzyl-piperidin-4-yl)-N-ethyl-2-phenyl-acetamide (485 mg, 1.4 mmol) in EtOH (10 mL) was added 10% Pd/C (70 mg). The mixture was stirred for 4 d under H$_2$ (balloon). The mixture was filtered through a plug of diatomaceous earth and the filtrate was concentrated to give a peach solid (360 mg, 100%). MS (ESI): mass calcd. for $C_{15}H_{22}N_2O$, 246.35. m/z found, 247.4 [M+H]$^+$. $^1$H NMR (CDCl$_3$): 7.31-7.30 (m, 3H), 7.27-7.23 (m, 2H), 5.60-5.57 (m, 1H), 3.33-3.27 (m, 2H), 3.19-3.12 (m, 2H), 2.95-2.91 (m, 1H), 2.78-2.74 (m, 2H), 2.30-2.26 (m, 2H), 1.52-1.49 (m, 1H), 1.31-1.25 (m, 3H), 1.06 (6, J=7.3, 3H).

Step D. A mixture of N-ethyl-2-phenyl-2-piperidin-4-yl-acetamide (90 mg, 0.3 mmol), 4-bromo-N-(1-ethyl-propyl)-3-fluoro-benzamide (prepared as in Example 113, Step A; 120 mg, 0.4 mmol), Pd$_2$(dba)$_3$ (6 mg, 0.007 mmol), X-Phos (3 mg, 0.006 mmol), and NaOtBu (70 mg, 0.7 mmol) in toluene (3 mL) was heated at 100° C. for 18 h. The solids were removed by filtration and the filtrate was concentrated to give an oil, which was purified by PTLC to give a white solid (2 mg, 1%). MS (ESI): mass calcd. for $C_{27}H_{36}FN_3O_2$, 453.59; m/z found, 454.5 [M+H]$^+$. $^1$H NMR (CDCl$_3$): 7.69-7.67 (m, 2H), 7.60-7.58 (m, 2H), 7.44-7.43 (m, 1H), 7.41 (s, 1H), 7.36-7.31 (m, 4H), 6.89 (t, J=8.5, 1H), 5.64-5.62 (m, 1H), 5.48-5.45 (m, 1H), 3.99-3.96 (m, 1H), 3.74-3.70 (m, 1H), 3.56-3.53 (m, 1H), 3.44-3.41 (m, 1H), 3.36-3.30 (m, 1H), 3.21-3.15 (m, 1H), 2.91-2.88 (m, 1H), 2.80-2.75 (m, 1H), 2.64-2.58 (m, 1H), 2.29-2.26 (m, 1H), 2.04-2.00 (m, 1H), 1.65-1.61 (m, 1H), 1.49-1.43 (m, 1H), 1.27-1.23 (m, 1H), 1.09 (t, J=7.3, 3H), 0.93 (t, J=7.4, 6H).

The compounds in Examples 118-137 were prepared according to the methods described in the preceding examples.

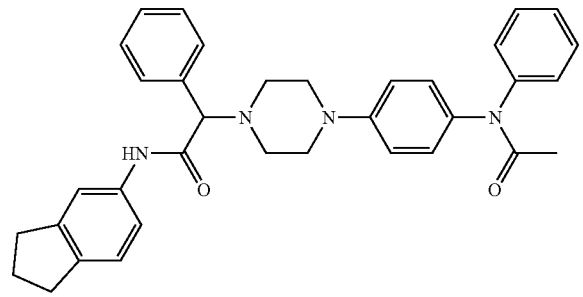

Example 118

2-{4-[4-(Acetyl-phenyl-amino)-phenyl]-piperazin-1-yl}-N-indan-5-yl-2-phenyl-acetamide

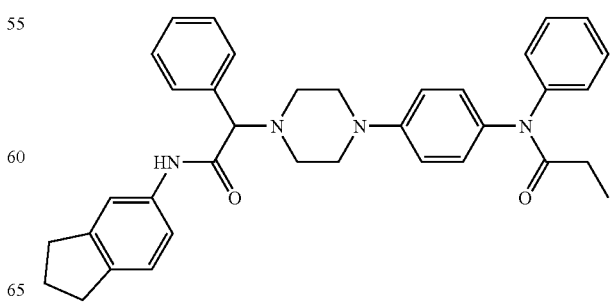

97

Example 119

2-{4-[4-(3-Ethyl-1-phenyl-ureido)-phenyl]-piperazin-1-yl}-N-indan-5-yl-2-phenyl-acetamide Example 120

{1-[4-(2-Methyl-butyrylamino)-phenyl]-piperidin-4-yl}-phenyl-acetic acid methyl ester Example 121

Phenyl-{1-[4-(2-phenyl-propionylamino)-phenyl]-piperidin-4-yl}-acetic acid methyl ester

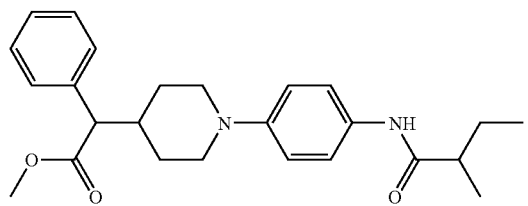

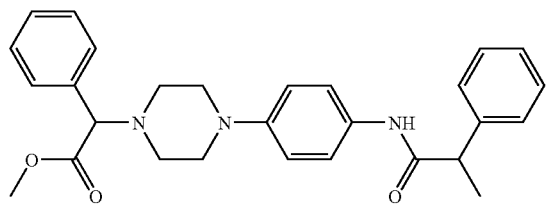

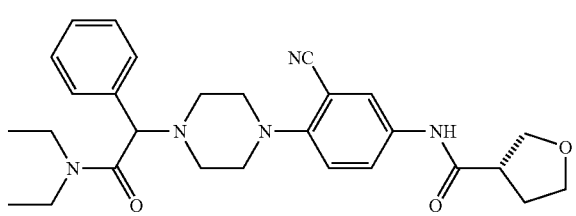

98

Example 122

(S)-Tetrahydro-furan-3-carboxylic acid {3-cyano-4-[4-(diethylcarbamoyl-phenyl-methyl)-piperazin-1-yl]-phenyl}-amide Example 123

(R)-Tetrahydro-furan-3-carboxylic acid {3-cyano-4-[4-(diethylcarbamoyl-phenyl-methyl)-piperazin-1-yl]-phenyl}-amide Example 124

N-(4-{4-[(5-Bromo-2-fluoro-phenyl)-diethylcarbamoyl-methyl]-piperazin-1-yl}-3-fluoro-phenyl)-2-ethyl-butyramide

Example 125

1-Phenyl-cyclopentanecarboxylic acid {4-[4-(diethylcarbamoyl-phenyl-methyl)-piperazin-1-yl]-3-fluoro-phenyl}-amide

Example 128

2-Ethyl-2H-pyrazole-3-carboxylic acid {4-[4-(diethylcarbamoyl-phenyl-methyl)-piperazin-1-yl]-3-fluoro-phenyl}-amide

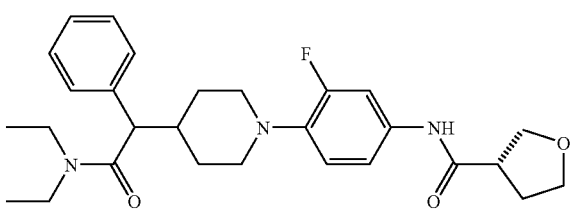

Example 126

(S)-Tetrahydro-furan-3-carboxylic acid {4-[4-(diethylcarbamoyl-phenyl-methyl)-piperidin-1-yl]-3-fluoro-phenyl}-amide

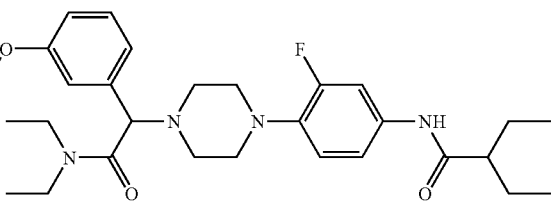

Example 129

N-(4-{4-[Diethylcarbamoyl-(3-methoxy-phenyl)-methyl]-piperazin-1-yl}-3-fluoro-phenyl)-2-ethyl-butyramide

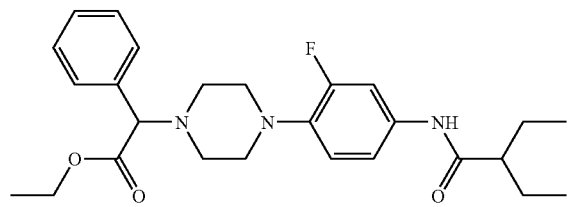

Example 127

{4-[4-(2-Ethyl-butyrylamino)-2-fluoro-phenyl]-piperazin-1-yl}-phenyl-acetic acid ethyl ester

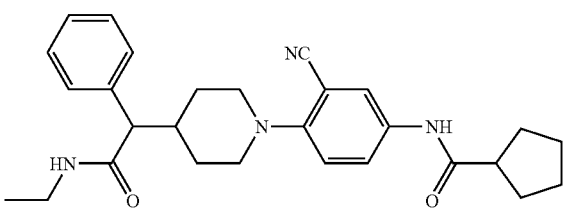

Example 130

Cyclopentanecarboxylic acid {3-cyano-4-[4-(ethylcarbamoyl-phenyl-methyl)-piperidin-1-yl]-phenyl}-amide

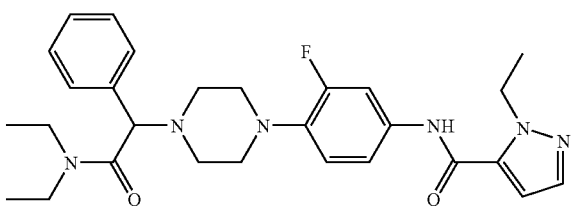

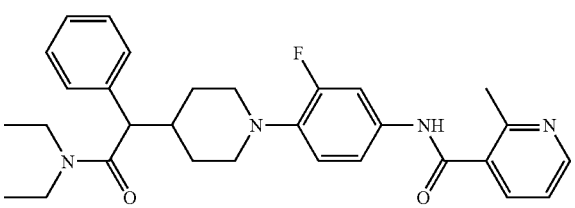

101

Example 131

N-{4-[4-(Diethylcarbamoyl-phenyl-methyl)-piperidin-1-yl]-3-fluoro-phenyl}-2-methyl-nicotinamide

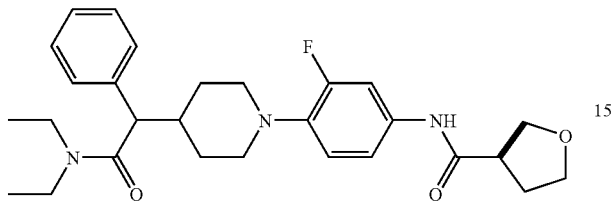

Example 132

(R)-Tetrahydro-furan-3-carboxylic acid {4-[4-(diethylcarbamoyl-phenyl-methyl)-piperidin-1-yl]-3-fluoro-phenyl}-amide

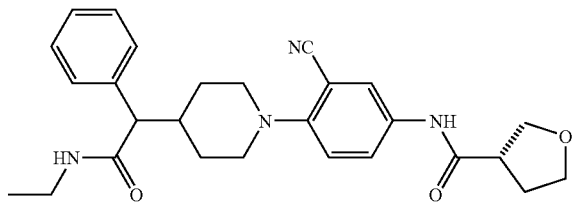

Example 133

(S)-Tetrahydro-furan-3-carboxylic acid {3-cyano-4-[4-(ethylcarbamoyl-phenyl-methyl)-piperidin-1-yl]-phenyl}-amide

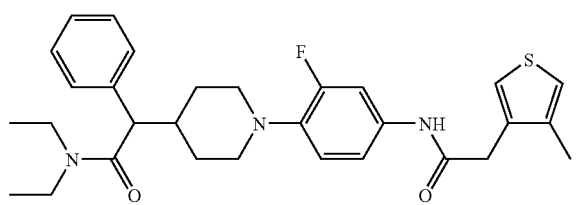

102

Example 134

N,N-Diethyl-2-(1-{2-fluoro-4-[2-(4-methyl-thiophen-3-yl)-acetylamino]-phenyl}-piperidin-4-yl)-2-phenyl-acetamide

Example 135

Cyclobutanecarboxylic acid {4-[4-(diethylcarbamoyl-phenyl-methyl)-piperazin-1-yl]-3-fluoro-phenyl}-amide

Example 136

1-Methyl-cyclohexanecarboxylic acid {4-[4-(diethylcarbamoyl-phenyl-methyl)-piperazin-1-yl]-3-fluoro-phenyl}-amide

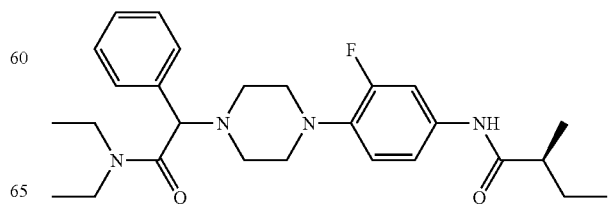

Example 137

(S)-N-{4-[4-(Diethylcarbamoyl-phenyl-methyl)-piperazin-1-yl]-3-fluoro-phenyl}-2-methyl-butyramide

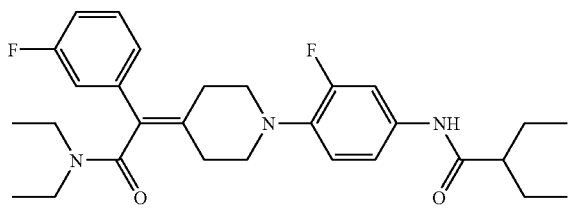

Example 138

N-(4-{4-[Diethylcarbamoyl-(3-fluoro-phenyl)-methylene]-piperidin-1-yl}-3-fluoro-phenyl)-2-ethyl-butyramide Step A. 3-Fluoro-phenyl-piperidin-4-ylidene-acetonitrile. To a mixture of 3-fluoro-phenyl-acetonitrile (3.2 g, 24 mmol) and 4-oxo-piperidine-1-carboxylic acid tert-butyl ester (4.0 g, 20 mmol) in THF (100 mL) was added NaHMDS (1.0 M in THF, 24 mL). The mixture was stirred at rt for 16 h, then was diluted with MeOH (16 mL) and concentrated. The residue was diluted with TFA (40 mL) and stirred at rt for 16 h. The mixture was concentrated and the residue was diluted with satd. aq. NaHCO$_3$ (160 mL) and extracted with EtOAc (3×80 mL). The combined organic layers were filtered and concentrated to provide the crude title compound.

Step B. [1-(2-Fluoro-4-nitro-phenyl)-piperidin-4-ylidene]-(3-fluoro-phenyl)-acetonitrile. To a mixture of 3-fluoro-phenyl-piperidin-4-ylidene-acetonitrile and K$_2$CO$_3$ (20 mmol) in DMF (30 mL) was added 1,2-difluoro-4-nitrobenzene (1.6 g, 10 mmol). The reaction mixture was stirred at 50° C. for 3 h, then was diluted with H$_2$O (500 mL). The solution was decanted, leaving a semi-solid, which was collected, dried, and used directly in the next step.

Step C. 2-[1-(4-Amino-2-fluoro-phenyl)-piperidin-4-ylidene]-N,N-diethyl-2-(3-fluoro-phenyl)-acetamide. A solution of [1-(2-fluoro-4-nitro-phenyl)-piperidin-4-ylidene]-(3-fluoro-phenyl)-acetonitrile in 48% HBr (75 mL) was stirred at 100° C. for 8 h. The mixture was cooled to rt and diluted with H$_2$O (500 mL). The resulting yellow solid was collected by filtration and dried under vacuum. A mixture of this yellow solid and DMF (0.50 mL) in DCE (100 mL) was treated with (COCl)$_2$ (100 mmol) dropwise and was stirred at rt for 30 min. The mixture was concentrated and dried under vacuum. The residue was diluted with DCE (100 mL) and treated with TEA (2.8 mL, 20 mmol) and Et$_2$NH (1.1 mL, 10 mmol). The reaction mixture was stirred at rt for 4 h, then was washed with H$_2$O (100 mL). The organic layer was separated and concentrated. The residue was dissolved in 1:1 EtOH/EtOAc (100 mL), treated with SnCl$_2$.2H$_2$O (10 g), and heated at 100° C. for 16 h. The mixture was cooled to rt, diluted with ice water (100 mL), basified to pH=9 with NaHCO$_3$, and extracted with EtOAc (3×200 mL). The organic layers were combined, dried (Na$_2$SO$_4$), and concentrated to give the crude title compound.

Step D. To a mixture of 2-[1-(4-amino-2-fluoro-phenyl)-piperidin-4-ylidene]-N,N-diethyl-2-(3-fluoro-phenyl)-acetamide (0.33 mmol) and TEA (2.0 mmol) in DCE (10 mL) was added 2-ethylbutyryl chloride (1 mmol) dropwise. The mixture was stirred at rt for 16 h, then was washed with H$_2$O (10 mL). The organic layer was concentrated and the residue was purified by PTLC to provide the title compound (54 mg, 33%). MS (ESI): mass calcd. for C$_{29}$H$_{37}$F$_2$N$_3$O$_2$, 497.29. m/z found, 498.4 [M+H]$^+$. $^1$H NMR (CDCl$_3$): 7.58-7.53 (m, 1H), 7.47 (NH, 1H), 7.37-7.32 (m, 1H), 7.18-7.06 (m, 3H), 7.04-6.97 (m, 1H), 6.92-6.85 (m, 1H), 3.50-3.00 (m, 6H), 2.62-2.52 (m, 4H), 2.10-2.02 (m, 1H), 1.79-1.67 (m, 4H), 1.62-1.52 (m, 2H), 1.16 (t, J=7.1, 3H), 1.00-0.87 (m, 9H).

The compounds in Examples 139-164 were prepared according to the methods described in the preceding examples.

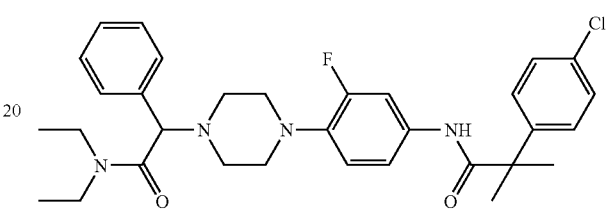

Example 139

2-(4-Chloro-phenyl)-N-{4-[4-(diethylcarbamoyl-phenyl-methyl)-piperazin-1-yl]-3-fluoro-phenyl}-isobutyramide

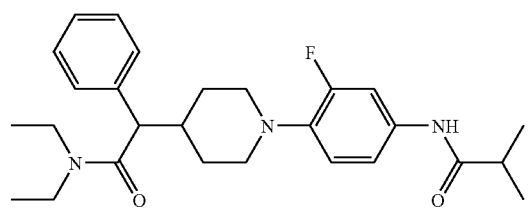

Example 140

N-{4-[4-(Diethylcarbamoyl-phenyl-methyl)-piperidin-1-yl]-3-fluoro-phenyl}-isobutyramide

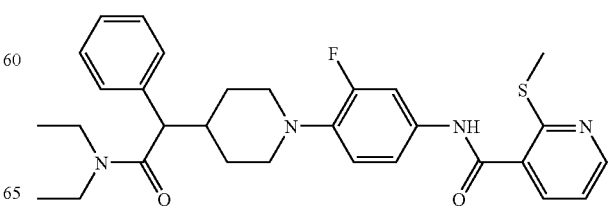

Example 141

N-{4-[4-(Diethylcarbamoyl-phenyl-methyl)-piperidin-1-yl]-3-fluoro-phenyl}-2-methylsulfanyl-nicotinamide

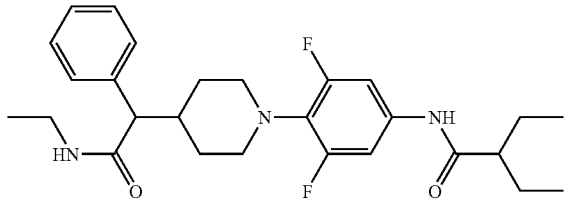

Example 142

2-Ethyl-N-{4-[4-(ethylcarbamoyl-phenyl-methyl)-piperidin-1-yl]-3,5-difluoro-phenyl}-butyramide

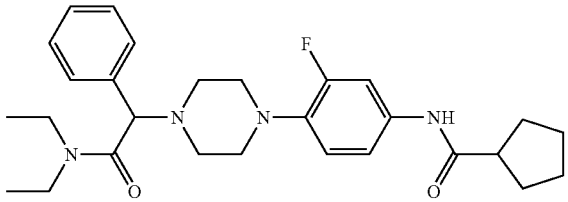

Example 143

Cyclopentanecarboxylic acid {4-[4-(diethylcarbamoyl-phenyl-methyl)-piperazin-1-yl]-3-fluoro-phenyl}-amide

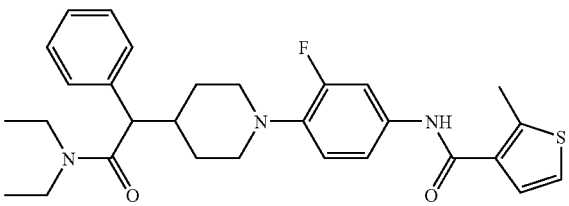

Example 144

2-Methyl-thiophene-3-carboxylic acid {4-[4-(diethylcarbamoyl-phenyl-methyl)-piperidin-1-yl]-3-fluoro-phenyl}-amide

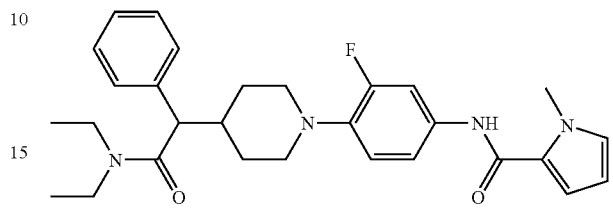

Example 145

1-Methyl-1H-pyrrole-2-carboxylic acid {4-[4-(diethylcarbamoyl-phenyl-methyl)-piperidin-1-yl]-3-fluoro-phenyl}-amide

Example 146

(3,5-Difluoro-phenyl)-{4-[4-(2-ethyl-butyrylamino)-2-fluoro-phenyl]-piperazin-1-yl}-acetic acid methyl ester

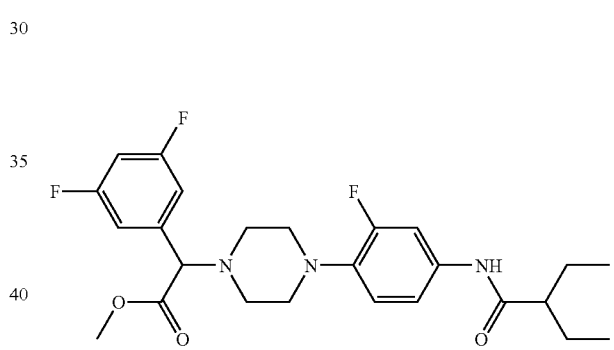

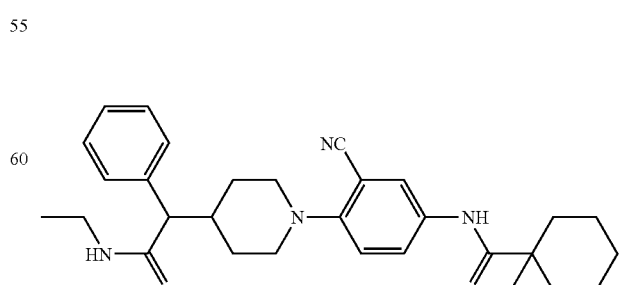

Example 147

1-Methyl-cyclohexanecarboxylic acid {3-cyano-4-[4-(ethylcarbamoyl-phenyl-methyl)-piperidin-1-yl]-phenyl}-amide Example 150

2-Methyl-cyclopropanecarboxylic acid {4-[4-(diethylcarbamoyl-phenyl-methyl)-piperazin-1-yl]-3-fluoro-phenyl}-amide

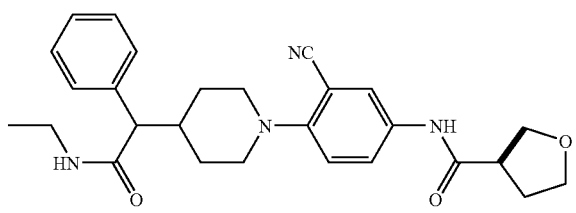

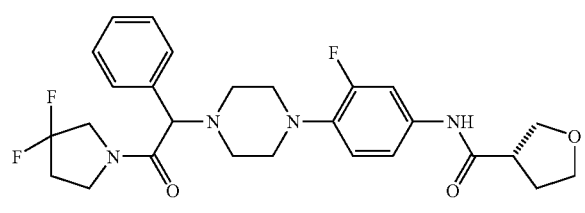

Example 148

(R)-Tetrahydro-furan-3-carboxylic acid {3-cyano-4-[4-(ethylcarbamoyl-phenyl-methyl)-piperidin-1-yl]-phenyl}-amide Example 151

(S)-Tetrahydro-furan-3-carboxylic acid (4-{4-[2-(3,3-difluoro-pyrrolidin-1-yl)-2-oxo-1-phenyl-ethyl]-piperazin-1-yl}-3-fluoro-phenyl)-amide

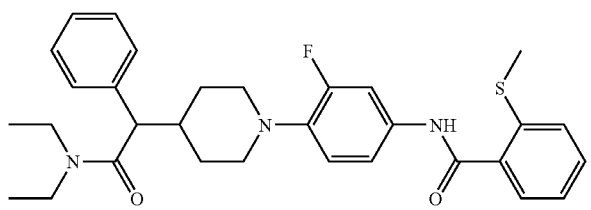

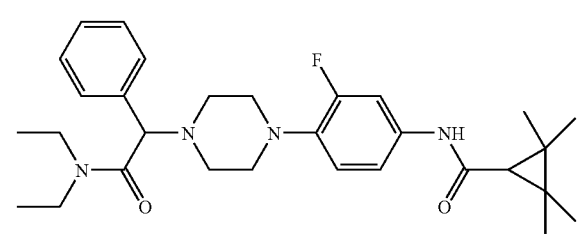

Example 149

N-{4-[4-(Diethylcarbamoyl-phenyl-methyl)-piperidin-1-yl]-3-fluoro-phenyl}-2-methylsulfanyl-benzamide Example 152

2,2,3,3-Tetramethyl-cyclopropanecarboxylic acid {4-[4-(diethylcarbamoyl-phenyl-methyl)-piperazin-1-yl]-3-fluoro-phenyl}-amide

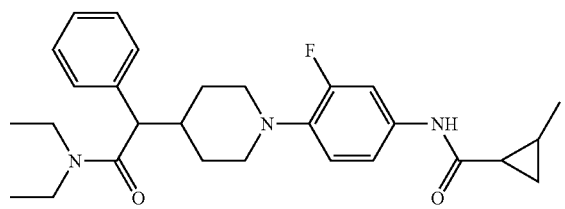

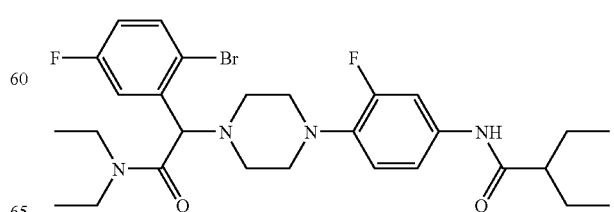

Example 153

N-(4-{4-[(2-Bromo-5-fluoro-phenyl)-diethylcarbamoyl-methyl]-piperazin-1-yl}-3-fluoro-phenyl)-2-ethyl-butyramide Example 156

2-(1-{4-[2-(2,6-Difluoro-phenyl)-acetylamino]-2-fluoro-phenyl}-piperidin-4-yl)-N,N-diethyl-2-phenyl-acetamide

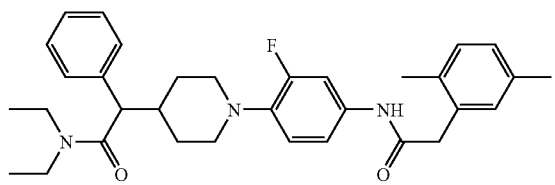

Example 154

2-(1-{4-[2-(2,5-Dimethyl-phenyl)-acetylamino]-2-fluoro-phenyl}-piperidin-4-yl)-N,N-diethyl-2-phenyl-acetamide

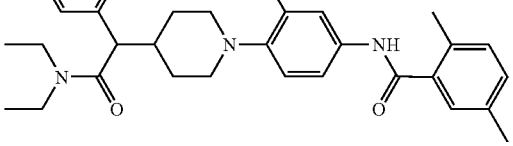

Example 157

N-{4-[4-(Diethylcarbamoyl-phenyl-methyl)-piperidin-1-yl]-3-fluoro-phenyl}-2,5-dimethyl-benzamide

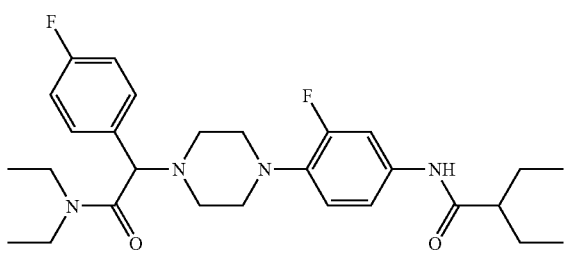

Example 155

N-(4-{4-[Diethylcarbamoyl-(4-fluoro-phenyl)-methyl]-piperazin-1-yl}-3-fluoro-phenyl)-2-ethyl-butyramide

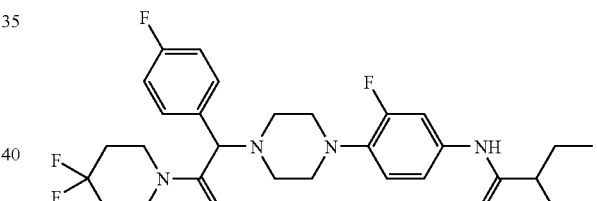

Example 158

N-(4-{4-[2-(4,4-Difluoro-piperidin-1-yl)-1-(4-fluoro-phenyl)-2-oxo-ethyl]-piperazin-1-yl}-3-fluoro-phenyl)-2-ethyl-butyramide

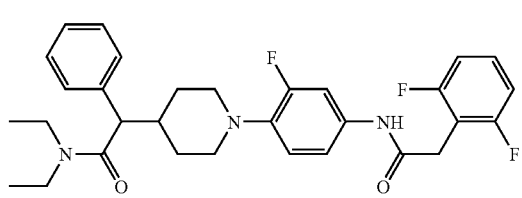

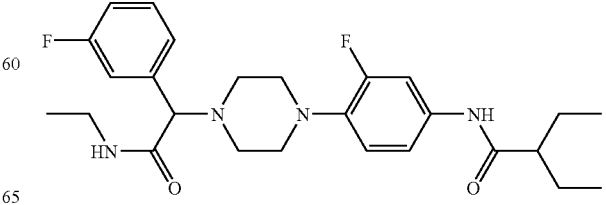

Example 159

2-Ethyl-N-(4-{4-[ethylcarbamoyl-(3-fluoro-phenyl)-methyl]-piperazin-1-yl}-3-fluoro-phenyl)-butyramide

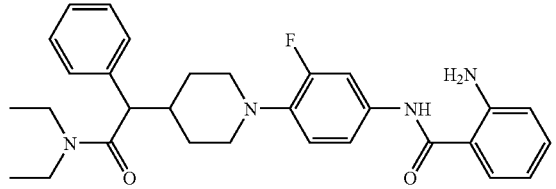

Example 160

2-Amino-N-{4-[4-(diethylcarbamoyl-phenyl-methyl)-piperidin-1-yl]-3-fluoro-phenyl}-benzamide

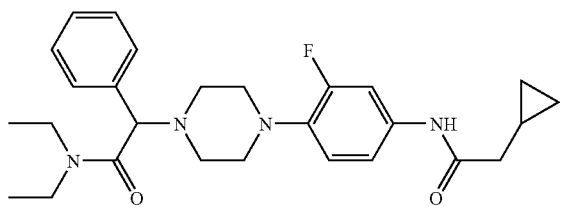

Example 161

2-{4-[4-(2-Cyclopropyl-acetylamino)-2-fluoro-phenyl]-piperazin-1-yl}-N,N-diethyl-2-phenyl-acetamide

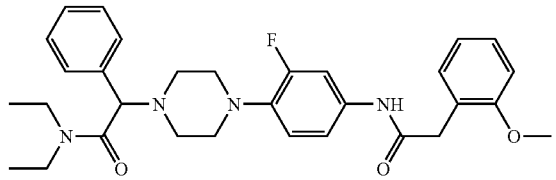

Example 162

N,N-Diethyl-2-(4-{2-fluoro-4-[2-(2-methoxy-phenyl)-acetylamino]-phenyl}-piperazin-1-yl)-2-phenyl-acetamide

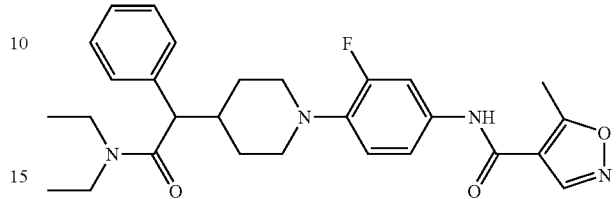

Example 163

5-Methyl-isoxazole-4-carboxylic acid {4-[4-(diethylcarbamoyl-phenyl-methyl)-piperidin-1-yl]-3-fluoro-phenyl}-amide

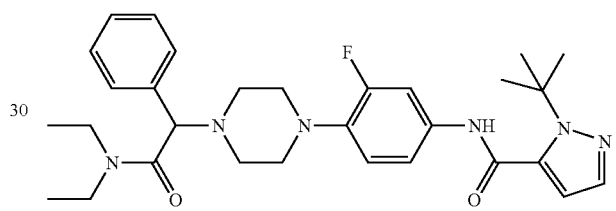

Example 164

2-tert-Butyl-5-methyl-2H-pyrazole-3-carboxylic acid {4-[4-(diethylcarbamoyl-phenyl-methyl)-piperazin-1-yl]-3-fluoro-phenyl}-amide The compounds in Examples 165-274 were prepared using the methods described in the preceding examples, with exceptions as noted.

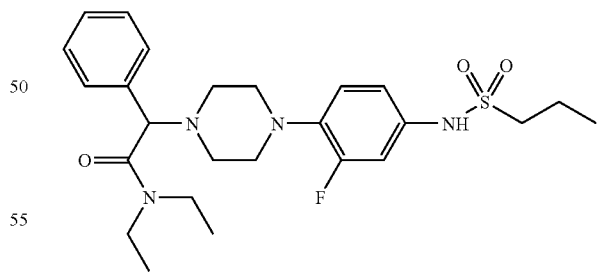

Example 165

N,N-Diethyl-2-{4-[2-fluoro-4-(propane-1-sulfonylamino)-phenyl]-piperazin-1-yl}-2-phenyl-acetamide MS: 491.5. $^1$H NMR (CDCl$_3$): 7.46-7.42 (m, 2H), 7.37-7.29 (m, 3H), 7.08 (br, 1H), 7.06-7.02 (m, 1H), 6.98-6.94 (m, 1H), 6.87-6.82 (m, 1H), 4.23 (s, 1H), 3.51-3.36 (m, 2H), 3.32-3.23 (m, 1H), 3.22-3.14 (m, 1H), 3.08-2.99 (m, 6H), 2.72-2.60 (m, 4H), 1.89-1.80 (m, 2H), 1.10-0.99 (m, 9H).

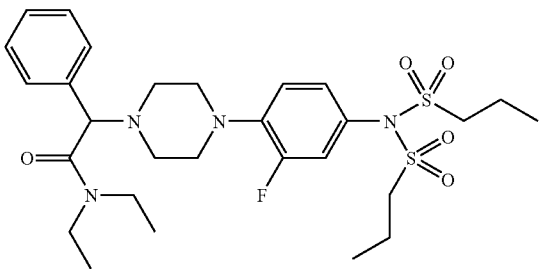

Example 166

N-{4-[4-(Diethylcarbamoyl-phenyl-methyl)-piperazin-1-yl]-3-fluoro-phenyl}-N-dipropanesulfonanilide

MS: 597.5.

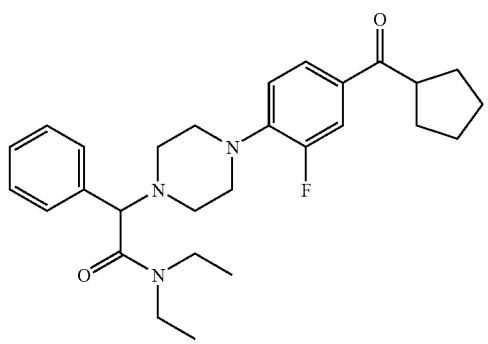

Example 167

2-[4-(4-Cyclopentanecarbonyl-2-fluoro-phenyl)-piperazin-1-yl]-N,N-diethyl-2-phenyl-acetamide Step A: 4-(4-Cyclopentanecarbonyl-2-fluoro-phenyl)-piperazine-1-carboxylic acid tert-butyl ester. A −78° C. solution of 4-(4-cyano-2-fluoro-phenyl)-piperazine-1-carboxylic acid tert-butyl ester (0.27 g, 0.87 mmol) in Et$_2$O (10 mL) was treated with cyclopentylmagnesium chloride (1.5 mL, 2 M). The mixture was allowed to slowly reach rt overnight. The reaction was then cooled to 0° C. and water added (10 mL). The pH of the mixture was adjusted to ~7 with 1 M HCl and was extracted with Et$_2$O and the solvent removed. Purification on SiO$_2$EtOAc/hexanes) provided 0.19 g of the title compound. MS (ESI): mass calcd. for C$_{21}$H$_{29}$FN$_2$O$_3$, 376.47. m/z found, 377.5 [M+H]$^+$.

Step B: 2-[4-(4-Cyclopentanecarbonyl-2-fluoro-phenyl)-piperazin-1-yl]-N,N-diethyl-2-phenyl-acetamide. A solution of 4-(4-cyclopentanecarbonyl-2-fluoro-phenyl)-piperazine-1-carboxylic acid tert-butyl ester (0.11 g, 0.29 mmol) in DCM (5 mL) was treated with trifluoroacetic acid (1.5 mL). After 3 h the solvent was removed and water (5 mL) and 1 M NaOH were added (~pH 10). The mixture was extracted with DCM and the solvent removed. The residue was then taken up in DMF (2 mL) and K$_2$CO$_3$ was added (0.13 g, 0.91 mmol). This mixture was then treated with 2-bromo-N,N-diethyl-2-phenyl-acetamide (0.11 g) as described in previous examples to provide 0.072 g of the title compound. MS: 466.6. $^1$H NMR (CDCl$_3$): 7.69-7.66 (m, 1H), 7.63-7.59 (m, 1H), 7.47-7.43 (m, 2H), 7.38-7.30 (m, 3H), 6.90-6.86 (m, 1H), 4.26 (s, 1H), 3.63-3.56 (m, 1H), 3.51-3.35 (m, 2H), 3.31-3.14 (m, 6H), 2.76-2.67 (m, 4H), 1.92-1.85 (m, 4H), 1.75-1.57 (m, 4H), 1.09 (t, J=7.1, 3H) 1.04 (t, J=7.1, 3H).

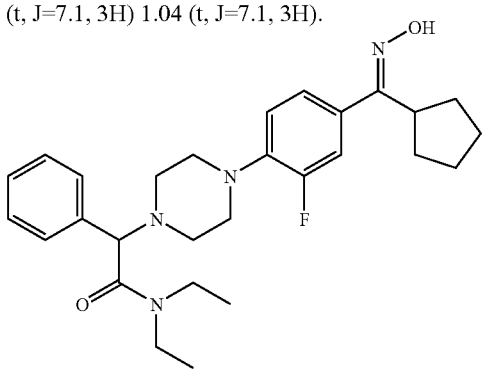

Example 168

2-{4-[4-(Cyclopentyl-hydroxyimino-methyl)-2-fluoro-phenyl]-piperazin-1-yl}-N,N-diethyl-2-phenyl-acetamide

MS: 481.6.

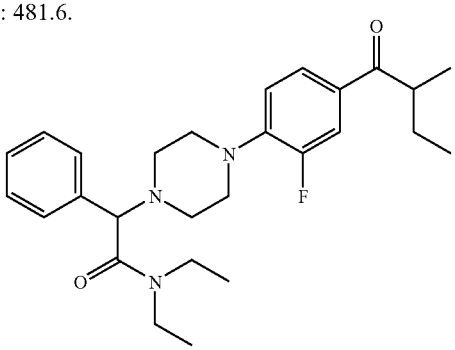

Example 169

N,N-Diethyl-2-{4-[2-fluoro-4-(2-methyl-butyryl)-phenyl]-piperazin-1-yl}-2-phenyl-acetamide

MS: 454.6.

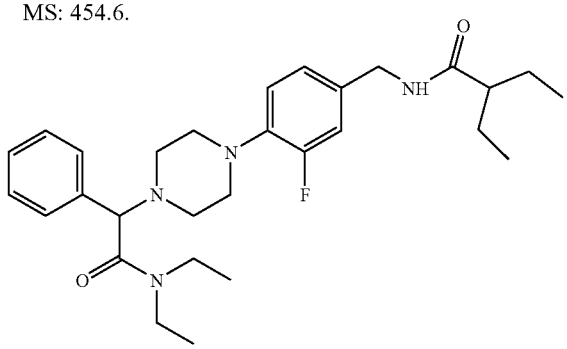

Example 170

N-{4-[4-(Diethylcarbamoyl-phenyl-methyl)-piperazin-1-yl]-3-fluoro-benzyl}-2-ethyl-butyramide Step A: N,N-Diethyl-2-[4-(2-fluoro-4-formyl-phenyl)-piperazin-1-yl]-2-phenyl-acetamide. 3-Fluoro-4-piperazin-1-yl-benzaldehyde (0.65 g, 3.1 mmol) was treated with 2-bromo-N,N-diethyl-2-phenyl-acetamide (0.95 g) as described in previous examples to provide 1.11 g of the title compound. MS (ESI): mass calcd. for $C_{21}H_{29}FN_2O_3$, 376.47. m/z found, 377.5 $[M+H]^+$.

Step B: N,N-Diethyl-2-[4-(2-fluoro-4-hydroxymethyl-phenyl)-piperazin-1-yl]-2-phenyl-acetamide. A solution of N,N-diethyl-2-[4-(2-fluoro-4-formyl-phenyl)-piperazin-1-yl]-2-phenyl-acetamide (0.76 g, 1.92 mmol) in ethanol (35 mL) was treated with $NaBH_4$ (0.11 g). After 3 d, the solvent was removed and water (5 mL) and 1 M NaOH were added (~pH 10). The mixture was extracted with DCM and the solvent removed. Purification on $SiO_2$EtOAc/hexanes) provided 0.73 g of the title compound. MS (ESI): mass calcd. for $C_{23}H_{30}FN_3O_2$, 399.5. m/z found, 400.5 $[M+H]^+$.

Step C: 2-{4-[4-(1,3-Dioxo-1,3-dihydro-isoindol-2-ylmethyl)-2-fluoro-phenyl]-piperazin-1-yl}-N,N-diethyl-2-phenyl-acetamide. A solution of N,N-diethyl-2-[4-(2-fluoro-4-hydroxymethyl-phenyl)-piperazin-1-yl]-2-phenyl-acetamide (0.14 g, 0.362 mmol) in THF (3 mL) was added triphenylphosphine (96.5 mg), phthalimide (76.9 mg), and diethyl azodicarboxylate (50 µL), and the mixture stirred at rt. After 16 h, the solvent was removed and the residue purified on $SiO_2$EtOAc/hexanes) to provide 115.5 mg of the title compound. MS (ESI): mass calcd. for $C_{31}H_{33}FN_4O_3$, 528.62. m/z found, 529.6 $[M+H]^+$.

Step D: N-{4-[4-(Diethylcarbamoyl-phenyl-methyl)-piperazin-1-yl]-3-fluoro-benzyl}-2-ethyl-butyramide. A solution of 2-{4-[4-(1,3-dioxo-1,3-dihydro-isoindol-2-ylmethyl)-2-fluoro-phenyl]-piperazin-1-yl}-N,N-diethyl-2-phenyl-acetamide (0.09 g, 0.16 mmol) in ethanol (3 mL) was added hydrazine (50 µL) and the mixture stirred at rt. After 6 h, the solvent was removed and the residue treated with 2-ethyl-butyryl chloride (30 µL) as described in previous examples to provide 0.04 g of the title compound. MS: 497.6. $^1$H NMR (CDCl$_3$): 7.47-7.43 (m, 2H), 7.37-7.29 (m, 3H), 6.96-6.91 (m, 2H), 6.88-6.84 (m, 1H), 5.72-5.67 (br, 1H), 4.37 (d, J=5.3, 2H), 4.23 (s, 1H), 3.49-3.36 (m, 2H), 3.31-3.15 (m, 2H), 3.14-3.05 (m, 4H), 2.74-2.63 (m, 4H), 1.89-1.82 (m, 1H), 1.68-1.58 (m, 2H), 1.53-1.43 (m, 2H), 1.10-1.01 (m, 6H), 0.91-0.86 (m, 6H).

tion of [4-(4-amino-2-fluoro-phenyl)-piperazin-1-yl]-phenyl-acetic acid ethyl ester (1.4 g, 4.0 mmol) in acetonitrile (40 mL) was treated with iodoethanol (0.9 mL) and $K_2CO_3$ (0.75 g, 5.4 mmol). After 24 h at 80° C., the mixture was cooled, diluted with water, extracted with $Et_2O$, and concentrated. Purification of the residue on $SiO_2$EtOAc/hexanes) provided the title compound (0.77 g). MS (ESI): mass calcd. for $C_{22}H_{28}FN_3O_3$, 401.47. m/z found, 402.2 $[M+H]^+$.

Step B: 3-{4-[4-(Ethoxycarbonyl-phenyl-methyl)-piperazin-1-yl]-3-fluoro-phenyl}-1,2,5-thiadiazolidine, 1,1-dioxide-2-carboxylic acid methyl ester. A solution of 3-{4-[2-fluoro-4-(2-hydroxy-ethylamino)-phenyl]-piperazin-1-yl}-phenyl-acetic acid ethyl ester (0.77 g, 1.9 mmol) in THF (30 mL) was treated with (methoxycarbonylsulfamoyl)triethylammonium hydroxide, inner salt (1.1 g) and the mixture was heated to reflux. After 6 h, the solvent was removed and the residue was purified on $SiO_2$ (EtOAc/hexanes) to provide the title compound (0.84 g). MS (ESI): mass calcd. for $C_{24}H_{29}FN_4O_6S$, 520.57; m/z found, 521.2 $[M+H]^+$.

Step C: 3-{4-[2-Fluoro-4-(1,2,5-thiadiazolidine-2-yl 1,1-dioxide)-phenyl]-piperazin-1-yl}-phenyl-acetic acid ethyl ester. A solution of 3-{4-[4-(ethoxycarbonyl-phenyl-methyl)-piperazin-1-yl]-3-fluoro-phenyl}-1,2,5-thiadiazolidine, 1,1-dioxide-2-carboxylic acid methyl ester (0.77 g, 1.48 mmol) in methanol (25 mL) was treated with 1 M NaOH (2 mL) and stirred at rt. After 8 h, the mixture was concentrated, diluted with satd. aq. $NH_4Cl$ and water, and extracted with DCM. The organic solution was concentrated and the residue purified on $SiO_2$ (EtOAc/hexanes) to give the title compound (0.49 g). MS (ESI): mass calcd. for $C_{22}H_{27}FN_4O_4S$, 462.54. m/z found, 463.1 $[M+H]^+$.

Step D: 3-{4-[2-Fluoro-4-(5-(3-pentyl)-1,2,5-thiadiazolidine-2-yl,1,1-dioxide)-phenyl]-piperazin-1-yl}-phenyl-acetic acid ethyl ester. To a solution of 3-{4-[2-fluoro-4-(1,2,5-thiadiazolidine-2-yl,1,1-dioxide)-phenyl]-piperazin-1-yl}-phenyl-acetic acid ethyl ester (0.08 g, 0.17 mmol) in THF (3 mL) was added triphenylphosphine (96.5 mg), 3-pentanol (50 µL) and diethyl azodicarboxylate (50 µL) and mixture was stirred at rt. After 16 h, the solvent was removed and the residue purified on $SiO_2$ (EtOAc/hexanes) to provide 0.043 g of the title compound. MS: 533.3. $^1$H NMR (CDCl$_3$): 7.48-7.45 (m, 2H), 7.38-7.30 (m, 3H), 7.06-6.99 (m, 2H), 6.95-6.90 (m, 1H), 4.24-4.10 (m, 2H), 4.04 (s, 1H), 3.74-3.71 (m, 2H), 3.45-3.41 (m, 2H), 3.40-3.34 (m, 1H), 3.12-3.08 (m, 4H), 2.66-2.62 (m, 4H), 1.65-1.59 (m, 4H), 1.24-1.20 (m, 3H), 1.02-0.98 (m, 3H).

The compounds in Examples 172-179 were prepared using methods analogous to those described in Example 171.

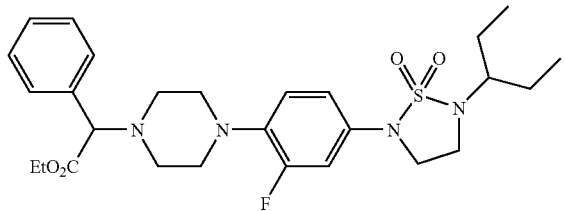

Example 171

{4-[2-Fluoro-4-(5-(3-pentyl)-1,2,5-thiadiazolidine-2-yl,1,1-dioxide)-phenyl]-piperazin-1-yl}-phenyl-acetic acid ethyl ester Step A: 3-{4-[2-Fluoro-4-(2-hydroxy-ethylamino)-phenyl]-piperazin-1-yl}-phenyl-acetic acid ethyl ester. A solu-

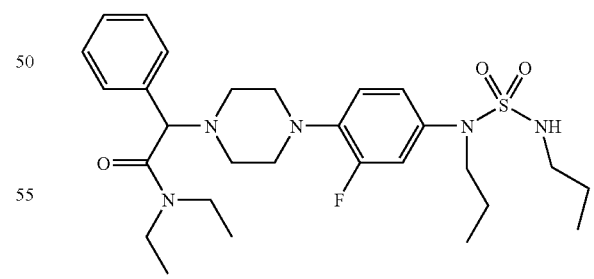

Example 172

2-{4-[4-(1,3-Dipropyl-sulfamoyl)-2-fluoro-phenyl]-piperazin-1-yl}-N,N-diethyl-2-phenyl-acetamide MS: 548.6. $^1$H NMR (CDCl$_3$): 7.47-7.44 (m, 2H), 7.38-7.30 (m, 3H), 7.07-7.01 (m, 2H), 6.89-6.84 (m, 1H), 4.24 (s, 1H), 4.07-4.03 (m, 1H), 3.54-3.49 (m, 2H), 3.49-3.36 (m, 2H), 3.31-3.09 (m, 6H), 3.01 (q, J=7.1, 2H), 2.74-2.63 (m, 4H), 1.57-1.42 (m, 4H), 1.09 (t, J=7.1, 3H), 1.04 (t, J=7.1, 3H), 0.91 (t, J=7.4, 3H), 0.88 (t, J=7.1, 3H).

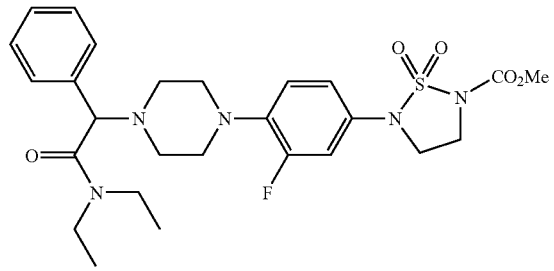

Example 173

3-{4-[4-(Diethylcarbamoyl-phenyl-methyl)-piper-azin-1-yl]-3-fluoro-phenyl}-1,2,5-thiadiazolidine, 1,1-dioxide-2-carboxylic acid methyl ester MS: 548.3. ¹H NMR (CDCl₃): 7.47-7.43 (m, 2H), 7.38-7.30 (m, 3H), 7.09-7.05 (m, 2H), 6.95-6.90 (m, 1H), 4.25 (s, 1H), 4.01-3.97 (m, 2H), 3.93 (s, 3H), 3.79-3.75 (m, 2H), 3.50-3.36 (m, 2H), 3.32-3.24 (m, 1H), 3.23-3.09 (m, 5H), 2.75-2.64 (m, 4H), 1.11-1.02 (m, 6H).

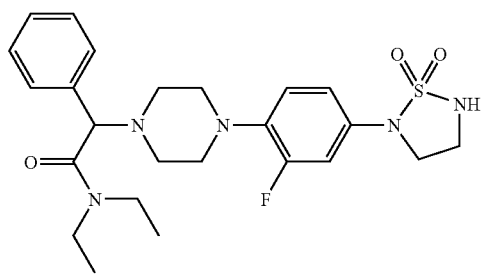

Example 174

N,N-Diethyl-2-{4-[2-fluoro-4-(1,2,5-thiadiazolidine-2-yl,1,1-dioxide)-phenyl]-piperazin-1-yl}-2-phenyl-acetamide

MS: 490.5.

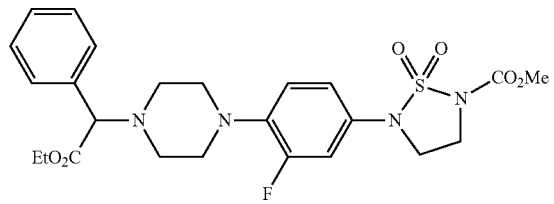

Example 175

3-{4-[4-(Ethoxycarbonyl-phenyl-methyl)-piperazin-1-yl]-3-fluoro-phenyl}-1,2,5-thiadiazolidine, 1,1-dioxide-2-carboxylic acid methyl ester

MS: 521.2.

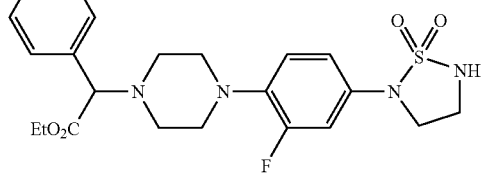

Example 176

{4-[2-Fluoro-4-(1,2,5-Thiadiazolidine-2-yl,1,1-dioxide)-phenyl]-piperazin-1-yl}-phenyl-acetic acid ethyl ester

MS: 463.1.

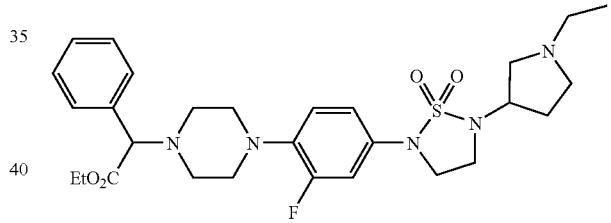

Example 177

{4-[2-Fluoro-4-(5-(1-Ethyl-pyrrolidin-3-yl)-1,2,5-thiadiazolidine-2-yl, 1,1-dioxide)-phenyl]-piperazin-1-yl}-phenyl-acetic acid ethyl ester

MS: 560.4.

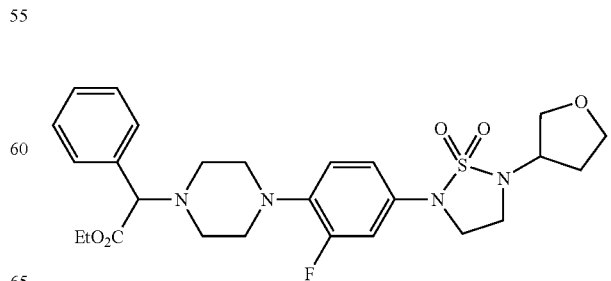

Example 178

{4-[2-Fluoro-4-(5-(tetrahydro-furan-3-yl)-1,2,5-thia-
diazolidine-2-yl, 1,1-dioxide)-phenyl]-piperazin-1-
yl}-phenyl-acetic acid ethyl ester

MS: 533.3.

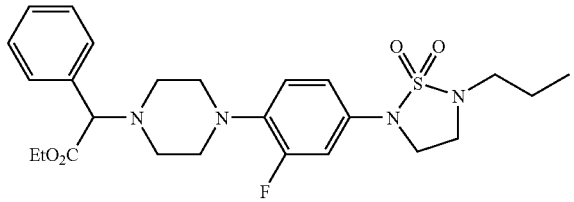

Example 179

{4-[2-Fluoro-4-(5-propyl-1,2,5-thiadiazolidine-2-yl,
1,1-dioxide)-phenyl]-piperazin-1-yl}-phenyl-acetic
acid ethyl ester MS: 505.4. $^1$H NMR (CDCl$_3$): 7.48-7.45 (m, 2H), 7.38-7.30 (m, 3H), 7.03-6.97 (m, 2H), 6.95-6.90 (m, 1H), 4.24-4.10 (m, 2H), 4.04 (s, 1H), 3.74 (t, J=6.3, 2H), 3.45 (t, J=6.3, 2H), 3.13-3.05 (m, 6H), 2.67-2.67 (m, 4H), 1.74-1.66 (m, 2H), 1.21 (t, J=7.1, 3H) 1.00 (t, J=7.4, 3H).

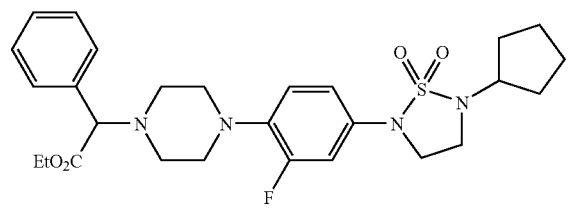

Example 180

{4-[2-Fluoro-4-(5-cyclopentyl-1,2,5-thiadiazolidine-
2-yl,1,1-dioxide)-phenyl]-piperazin-1-yl}-phenyl-
acetic acid ethyl ester

MS: 531.3.

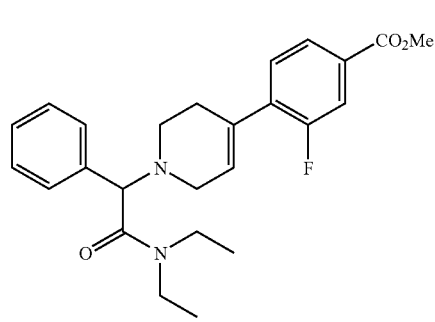

Example 181

4-[1-(Diethylcarbamoyl-phenyl-methyl)-1,2,3,6-
tetrahydro-pyridin-4-yl]-3-fluoro-benzoic acid
methyl ester

MS: 425.5.

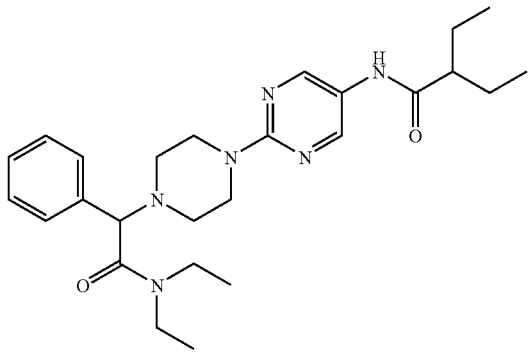

Example 182

N-{2-[4-(Diethylcarbamoyl-phenyl-methyl)-piper-
azin-1-yl]-pyrimidin-5-yl}-2-ethyl-butyramide

MS: 467.6.

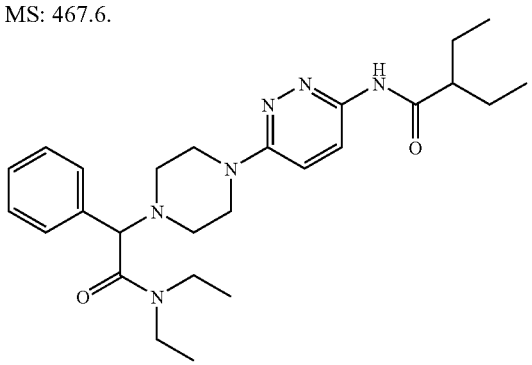

Example 183

N-{6-[4-(Diethylcarbamoyl-phenyl-methyl)-piper-
azin-1-yl]-pyridazin-3-yl}-2-ethyl-butyramide

MS: 467.5.

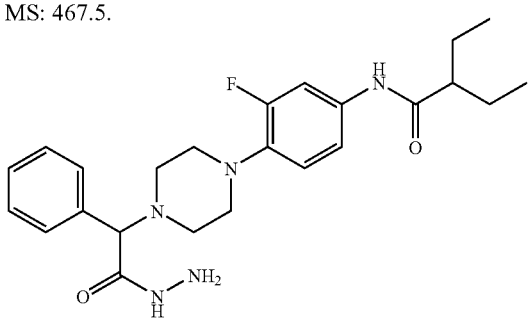

Example 184

2-Ethyl-N-{3-fluoro-4-[4-(hydrazinocarbonyl-phenyl-methyl)-piperazin-1-yl]-phenyl}-butyramide

MS: 442.6.

Example 185

4-[4-(Diethylcarbamoyl-phenyl-methyl)-piperazin-1-yl]-3-fluoro-benzoic acid methyl ester

MS: 428.3.

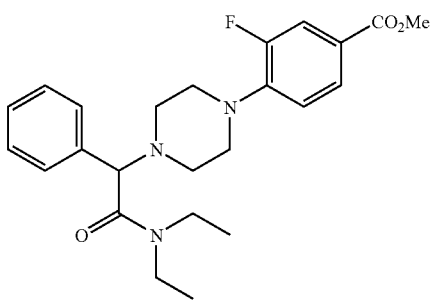

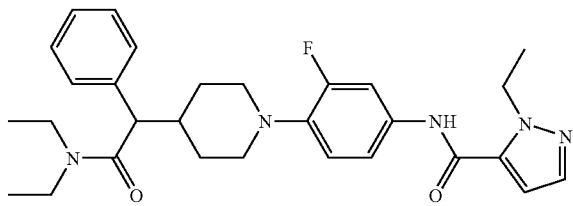

Example 186

2-Ethyl-2H-pyrazole-3-carboxylic acid {4-[4-(diethylcarbamoyl-phenyl-methyl)-piperidin-1-yl]-3-fluoro-phenyl}-amide MS: 506.4. $^1$H NMR (CDCl$_3$): 8.50 (s, 1H), 7.46-7.42 (m, 2H), 7.37-7.14 (m, 6H), 6.85 (t, J=9.1, 1H), 6.68 (d, J=2.1, 1H), 4.61 (q, J=7.1, 2H), 3.50-3.10 (m, 7H), 2.58-2.40 (m, 2H), 2.25-2.16 (m, 1H), 2.01-1.94 (m, 1H), 1.48-1.38 (m, 4H), 1.34-1.18 (m, 2H), 1.14-1.02 (m, 6H).

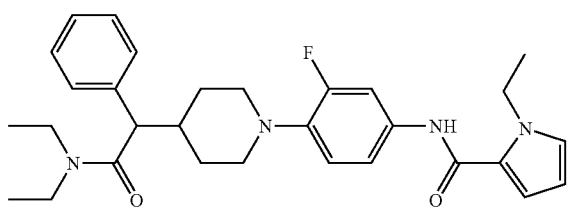

Example 187

1-Ethyl-1H-pyrrole-2-carboxylic acid {4-[4-(diethylcarbamoyl-phenyl-methyl)-piperidin-1-yl]-3-fluoro-phenyl}-amide To the solution of 1H-pyrrole-2-carboxylic acid {4-[4-(diethylcarbamoyl-phenyl-methyl)-piperidin-1-yl]-3-fluoro-phenyl}-amide (40 mg, 0.084 mmol) in THF (5 mL), NaOtBu (48 mg, 0.50 mmol) and ethyl bromide (54 mg, 0.50 mmol) was added. The mixture was stirred at 25° C. for 1 h and purified by PTLC to provide the title compound (27 mg, 42%). MS: 505.4. $^1$H NMR (CDCl$_3$): 7.65 (s, 1H), 7.46 (dd, J=4.0, 2.4, 1H), 7.28-7.21 (m, 5H), 7.10-7.16 (m, 1H), 6.90-6.82 (m, 2H), 6.69-6.67 (m, 1H), 6.12 (dd, J=3.9, 2.6, 1H), 4.49 (dd, J=14.3, 6.8, 2H), 3.50-3.12 (m, 7H), 2.71-2.63 (m, 1H), 2.53-2.46 (m, 1H), 2.31-2.21 (m, 1H), 2.08-2.00 (m, 1H), 1.50-1.21 (m, 6H), 1.15-1.04 (m, 6H).

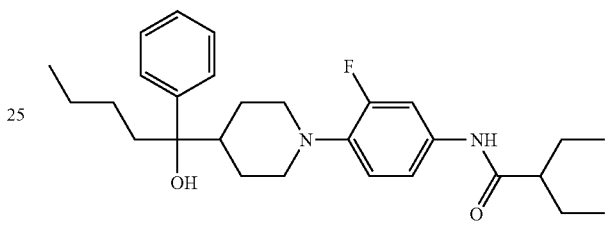

Example 188

2-Ethyl-N-{3-fluoro-4-[4-(1-hydroxy-1-phenyl-pentyl)-piperidin-1-yl]-phenyl}-butyramide To a solution of n-BuLi (1 mL, 2.5 M in hexanes) in THF (10 mL) at −78° C., N-[4-(4-benzoyl-piperidin-1-yl)-3-fluoro-phenyl]-2-ethyl-butyramide (200 mg, 0.50 mmol) in THF (10 mL) was added. After 10 min, the mixture was warmed to 25° C. and diluted with satd. aq. NaHCO$_3$ (10 mL). The mixture was extracted with EtOAc, and the organic layer was concentrated and purified by PTLC to provide the title compound (130 mg, 57%). MS: 455.4. $^1$H NMR (CDCl$_3$): 7.42-7.15 (m, 7H), 6.84 (t, J=9.1, 1H), 3.42 (d, J=11.7, 1H), 3.32 (d, J=11.7, 1H), 2.61-2.45 (m, 2H), 2.01-1.82 (m, 4H), 1.78-1.62 (m, 3H), 1.61-1.41 (m, 6H), 1.32-1.15 (m, 4H), 0.98-0.80 (m, 9H).

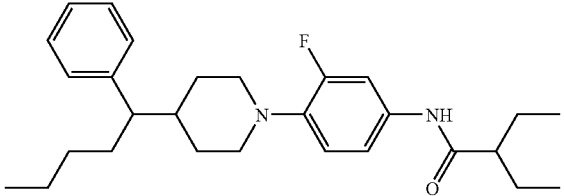

Example 189

2-Ethyl-N-{3-fluoro-4-[4-(1-phenyl-pentyl)-piperidin-1-yl]-phenyl}-butyramide

To a solution of 2-ethyl-N-{3-fluoro-4-[4-(1-hydroxy-1-phenyl-pentyl)-piperidin-1-yl]-phenyl}-butyramide (17 mg, 0.037 mmol) and Et₃SiH (0.025 mL) in DCM (0.15 mL) was added TFA (0.25 mL). The mixture was stirred at 25° C. for 0.5 h and purified by PTLC to provide the title compound (9 mg, 55%). MS: 439.4. ¹H NMR (CDCl₃): 7.40 (dd, J=14.0, 2.5, 1H), 7.32-7.25 (m, 2H), 7.22-7.17 (m, 1H), 7.14-7.06 (m, 3H), 7.02 (s, 1H), 7.06 (t, J=9.2, 1H), 3.47-3.22 (m, 2H), 2.65-2.55 (m, 1H), 2.52-2.43 (m, 1H), 2.38-2.30 (m, 1H), 2.03 (m, 2H), 1.88-1.15 (m, 12H), 1.10-0.98 (m, 2H), 0.92 (t, J=7.4, 6H), 0.81 (t, J=7.3, 3H).

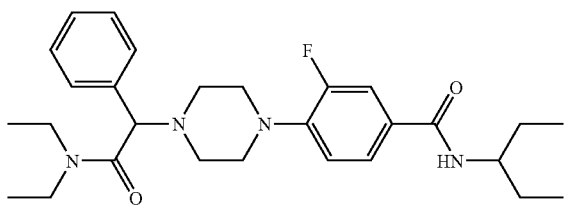

Example 190

4-[4-(Diethylcarbamoyl-phenyl-methyl)-piperazin-1-yl]-N-(1-ethyl-propyl)-3-fluoro-benzamide MS: 484.0. ¹H NMR (CDCl₃): 7.50-7.30 (m, 7H), 6.76 (t, J=8.9, 1H), 5.77 (d, J=9.0, 1H), 4.25 (s, 1H), 4.02-3.92 (m, 1H), 3.50-3.12 (m, 8H), 2.78-2.64 (m, 4H), 1.68-1.58 (m, 2H), 1.51-1.42 (m, 2H), 1.09 (t, J=7.1, 3H), 1.04 (t, J=7.1 3H), 0.93 (t, J=7.4, 6H).

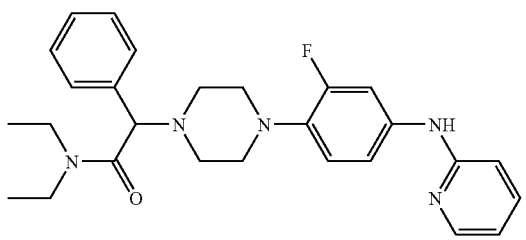

Example 191

N,N-Diethyl-2-{4-[2-fluoro-4-(pyridin-2-ylamino)-phenyl]-piperazin-1-yl}-2-phenyl-acetamide A mixture of 2-[4-(4-amino-2-fluoro-phenyl)-piperazin-1-yl]-N,N-diethyl-2-phenyl-acetamide (110 mg, 0.29 mmol) and 2-pyridine bromide (468 mg, 3.0 mmol) was stirred at 130° C. for 16 h. The resulting mixture was cooled and purified by PTLC to provide the title compound (65 mg, 49%). MS: 462.3. ¹H NMR (CDCl₃): 8.20-8.17 (m, 1H), 7.50-7.28 (m, 6H), 7.18-7.12 (m, 1H), 7.00-6.84 (m, 2H), 6.77-6.68 (m, 2H), 6.34 (s, 1H), 4.24 (s, 1H), 3.52-3.35 (m, 2H), 3.32-3.05 (m, 6H), 2.78-2.60 (m, 4H), 1.12-1.03 (m, 6H).

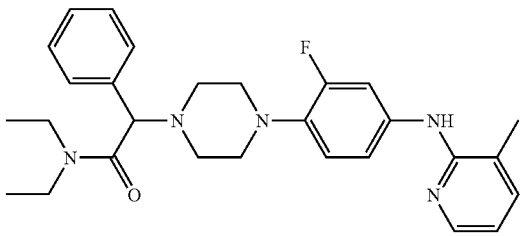

Example 192

N,N-Diethyl-2-{4-[2-fluoro-4-(3-methyl-pyridin-2-ylamino)-phenyl]-piperazin-1-yl}-2-phenyl-acetamide MS: 476.3. ¹H NMR (CDCl₃): 7.52-7.19 (m, 6H), 7.15 (dd, J=14.0, 2.5, 1H), 7.08-6.85 (m, 2H), 6.60 (t, J=7.9, 2H), 6.45 (s, 1H), 4.24 (s, 1H), 3.52-3.40 (m, 2H), 3.33-3.17 (m, 2H), 3.16-3.05 (m, 4H), 2.77-2.65 (m, 4H), 2.42 (s, 3H), 1.13-1.04 (m, 6H).

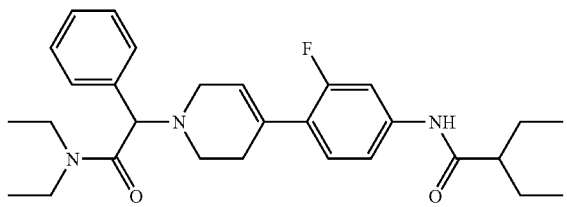

Example 193

N-{4-[1-(Diethylcarbamoyl-phenyl-methyl)-1,2,3,6-tetrahydro-pyridin-4-yl]-3-fluoro-phenyl}-2-ethyl-butyramide Step A. 4-[4-(2-Ethyl-butyrylamino)-2-fluoro-phenyl]-3,6-dihydro-2H-pyridine-1-carboxylic acid tert-butyl ester. A mixture of 3,6-dihydro-2H-pyridine-1-tert-butoxycarbonyl-4-boronic acid pinacol ester (300 mg, 0.97 mmol), N-(4-bromo-3-fluoro-phenyl)-2-ethyl-butyramide (190 mg, 0.66 mmol), PdCl₂ dppf (49 mg, 0.060 mmol), and Na₂CO₃ (1.5 mL, 2 M in EtOH) in toluene (5 mL) was stirred at 80° C. for 16 h. The resulting mixture was cooled and purified by PTLC to provide the title compound (98 mg, 38%).

Step B. To a solution of 4-[4-(2-ethyl-butyrylamino)-2-fluoro-phenyl]-3,6-dihydro-2H-pyridine-1-carboxylic acid tert-butyl ester (96 mg, 0.25 mmol) in MeOH (5 mL) was added HCl (2 mL, 1 M in Et₂O). After 16 h at 25° C., the mixture was concentrated and the residue re-dissolved in DMF (2 mL). The solution was treated with 2-chloro-N,N-diethyl-2-phenyl-acetamide (225 mg, 0.32 mmol) and K₂CO₃ (138 mg, 1.0 mmol), and was stirred at 25° C. for 16 h. The resulting mixture was purified by PTLC to provide the title compound (25 mg, 21%). MS: 480.4. ¹H NMR (CDCl₃): 7.57-7.45 (m, 3H), 7.40-7.27 (m, 4H), 7.20-7.06 (m, 2H), 5.90 (s, 1H), 4.43 (s, 1H), 3.55-3.15 (m, 6H), 2.92-2.83 (m, 1H), 2.74-2.64 (m, 1H), 2.53-2.44 (m, 2H), 2.07-1.98 (m, 1H), 1.76-1.47 (m, 4H), 1.17-0.90 (m, 12H).

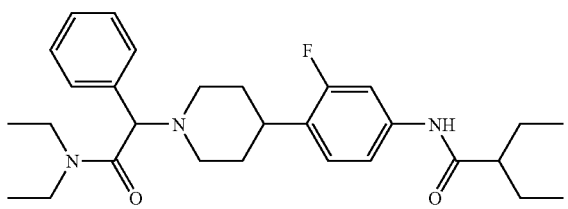

Example 194

N-{4-[1-(Diethylcarbamoyl-phenyl-methyl)-piperidin-4-yl]-3-fluoro-phenyl}-2-ethyl-butyramide To a solution of N-{4-[1-(diethylcarbamoyl-phenyl-methyl)-1,2,3,6-tetrahydro-pyridin-4-yl]-3-fluoro-phenyl}-2-ethyl-butyramide (10 mg, 0.021 mmol) in HOAc (1 mL), H$_2$O (0.1 mL) and 10% Pd/C (2 mg) were added. The mixture was stirred under H$_2$ (1 atm) at 25° C. for 16 h. The mixture was neutralized to pH ~7 with 1 M NaOH. The mixture was extracted with DCM (2×5 mL), and the organic layer was concentrated and purified by PTLC to provide the title compound (7 mg, 70%). MS: 482.4. $^1$H NMR (CDCl$_3$): 7.53-7.28 (m, 6H), 7.19-7.03 (m, 3H), 4.26 (s, 1H), 3.50-3.05 (m, 5H), 2.98-2.92 (m, 1H), 2.83-2.75 (m, 1H), 2.44-2.36 (m, 1H), 2.30-1.95 (m, 2H), 1.90-1.47 (m, 8H), 1.08 (t, J=7.0, 3H), 1.04 (t, J=7.1, 3H), 0.91 (m, 6H).

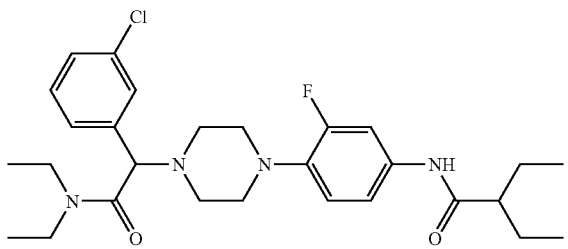

Example 195

N-(4-{4-[(3-Chloro-phenyl)-diethylcarbamoyl-methyl]-piperazin-1-yl}-3-fluoro-phenyl)-2-ethyl-butyramide MS: 517.2. $^1$H NMR (mixture of rotamers; CDCl$_3$): 7.54-7.46 (m, 1H), 7.42-7.20 (m, 4H), 7.12-7.04 (m, 1H), 6.90-6.80 (m, 1H), 4.68 (s, 0.4H), 4.21 (s, 0.6H), 3.52-3.00 (m, 7H), 2.81-2.52 (m, 4H), 2.06-1.94 (m, 1H), 1.80-1.62 (m, 4H), 1.60-1.48 (m, 1H), 1.16-1.05 (m, 6H), 1.00-0.88 (m, 6H).

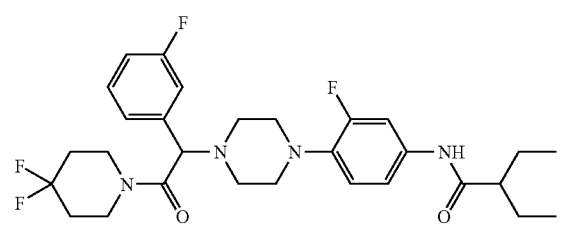

Example 196

N-(4-{4-[2-(4,4-Difluoro-piperidin-1-yl)-1-(3-fluoro-phenyl)-2-oxo-ethyl]-piperazin-1-yl}-3-fluoro-phenyl)-2-ethyl-butyramide MS: 549.4. $^1$H NMR (CDCl$_3$): 7.52-7.30 (m, 2H), 7.24-7.00 (m, 5H), 6.86 (m, 1H), 4.36 (s, 1H), 3.90-3.40 (m, 6H), 3.20-2.90 (m, 3H), 2.80-2.40 (m, 2H), 2.10-1.95 (m, 2H), 1.95-1.80 (m, 1H), 1.80-1.60 (m, 4H), 1.60-1.45 (m, 3H), 0.97-0.89 (m, 6H).

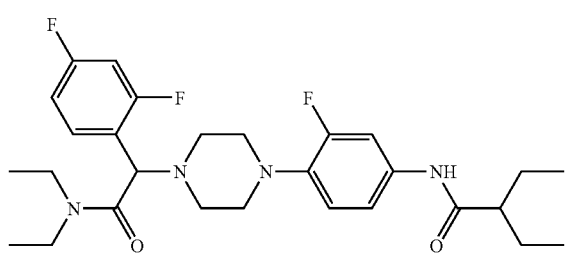

Example 197

N-(4-{4-[Diethylcarbamoyl-(2,4-difluoro-phenyl)-methyl]-piperazin-1-yl}-3-fluoro-phenyl)-2-ethyl-butyramide MS: 519.4. $^1$H NMR (CDCl$_3$): 7.52-7.27 (m, 2H), 7.25-7.04 (m, 4H), 6.50-6.82 (m, 1H), 4.2 (s, 1H), 3.50-3.15 (m, 4H), 3.10-2.90 (m, 3H), 2.80-2.40 (m, 3H), 2.05-1.96 (m, 1H), 1.76-1.62 (m, 4H), 1.58-1.48 (m, 2H), 1.18-1.02 (m, 6H), 1.02-0.88 (m, 6H).

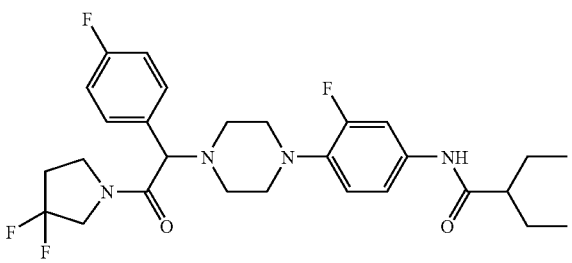

Example 198

N-(4-{4-[2-(3,3-Difluoro-pyrrolidin-1-yl)-1-(4-fluoro-phenyl)-2-oxo-ethyl]-piperazin-1-yl}-3-fluoro-phenyl)-2-ethyl-butyramide MS: 535.4. $^1$H NMR (CDCl$_3$): 7.52-7.36 (m, 3H), 7.30-7.20 (m, 1H), 7.12-7.00 (m, 3H), 6.88-6.80 (m, 1H), 4.04-3.82 (m, 2H), 3.80-3.66 (m, 2H), 3.66-3.36 (m, 2H), 3.12-2.90 (m, 4H), 2.70-2.56 (m, 1H), 2.48-2.18 (m, 2H), 2.04-1.94 (m, 1H), 1.80-1.60 (m, 4H), 1.60-1.48 (m, 2H), 0.97-0.88 (m, 6H).

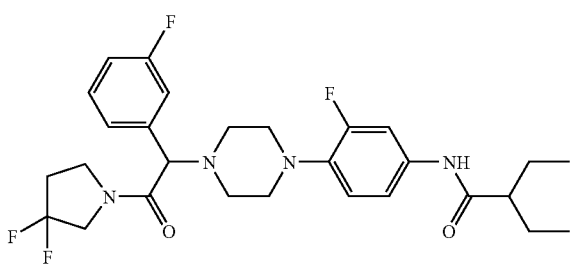

Example 199

N-(4-{4-[2-(3,3-Difluoro-pyrrolidin-1-yl)-1-(3-fluoro-phenyl)-2-oxo-ethyl]-piperazin-1-yl}-3-fluoro-phenyl)-2-ethyl-butyramide MS: 535.4. $^1$H NMR (CDCl$_3$): 7.52-7.27 (m, 2H), 7.25-7.95 (m, 5H), 6.90-6.80 (m, 1H), 4.00-3.82 (m, 2H), 3.80-3.55 (m, 4H), 3.25-2.80 (m, 3H), 2.70-2.60 (m, 2H), 2.50-2.20 (m, 2H), 2.05-1.95 (m, 1H), 1.80-1.50 (m, 6H), 0.98-0.90 (m, 6H).

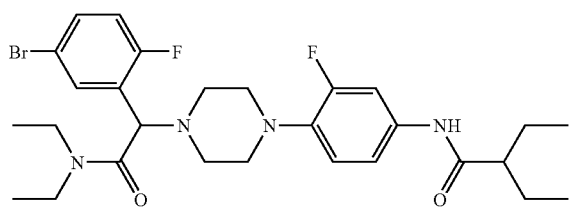

Example 200

N-(4-{4-[(5-Bromo-2-fluoro-phenyl)-diethylcarbamoyl-methyl]-piperazin-1-yl}-3-fluoro-phenyl)-2-ethyl-butyramide MS: 539.4. $^1$H NMR (mixture of rotamers; CDCl$_3$): 7.91-7.80 (m, 0.7H), 7.76-7.68 (m, 0.3H), 7.52-7.46 (m, 1H), 7.42-7.34 (m, 1H), 7.20 (s, 1H), 7.10-7.04 (m, 1H), 7.04-6.90 (m, 1H), 6.90-6.82 (1H), 5.40 (s, 0.2H), 4.68 (s, 0.8H), 3.44-3.22 (m, 4H), 3.14-3.02 (m, 3H), 2.74-2.66 (m, 3H), 2.04-1.95 (m, 1H), 1.74-1.82 (m, 4H), 1.58-1.48 (m, 2H), 1.18-1.04 (m, 6H), 1.04-0.88 m, 6H).

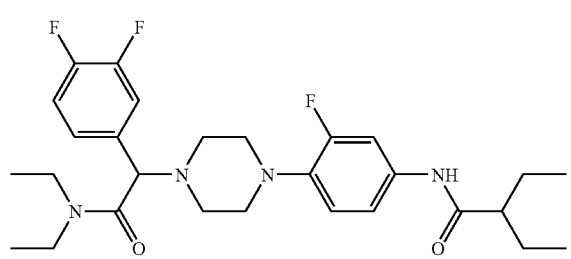

Example 201

N-(4-{4-[Diethylcarbamoyl-(3,4-difluoro-phenyl)-methyl]-piperazin-1-yl}-3-fluoro-phenyl)-2-ethyl-butyramide MS: 519.4. $^1$H NMR (CDCl$_3$): 7.48-7.42 (m, 1H), 7.36-7.26 (m, 4H), 7.10-7.03 (m, 1H), 6.86 (t, J=9.0, 1H), 3.97-3.52 (m, 5H), 3.42-3.32 (m, 1H), 3.31-3.09 (m, 2H), 2.76-2.62 (m, 1H), 2.56-2.16 (m, 4H), 2.12-1.90 (m, 3H), 1.75-1.63 (m, 2H), 1.58-1.50 (m, 2H), 1.47-1.40 (m, 1H), 1.37-1.21 (m, 3H), δ 0.99 (t, J=7.4, 6H).

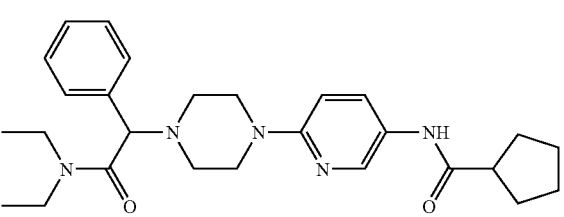

Example 202

Cyclopentanecarboxylic acid {6-[4-(diethylcarbamoyl-phenyl-methyl)-piperazin-1-yl]-pyridin-3-yl}-amide

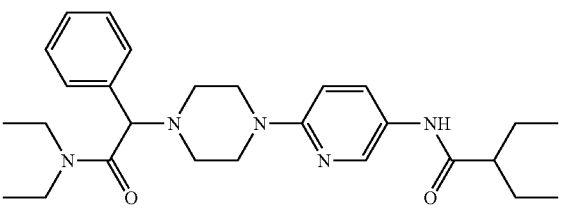

Example 203

N-{6-[4-(Diethylcarbamoyl-phenyl-methyl)-piperazin-1-yl]-pyridin-3-yl}-2-ethyl-butyramide

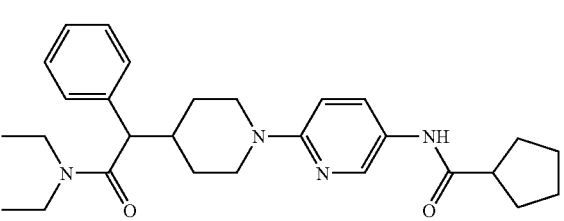

Example 204

Cyclopentanecarboxylic acid [4-(diethylcarbamoyl-phenyl-methyl)-3,4,5,6-tetrahydro-2H-[1,2']bipyridinyl-5'-yl]-amide MS: 463.4. $^1$H NMR (CDCl$_3$): 8.06 (d, J=2.7, 1H), 7.83 (dd, J=9.1, 2.7, 1H), 7.35-7.27 (m, 4H), 7.25-7.22 (m 1H), 7.17 (s, 1H), 6.59 (d, J=9.1, 1H), 4.26-4.18 (m, 1H), 4.14-4.06 (m, 1H), 3.44-3.26 (m, 4H), 3.20-3.10 (m, 1H), 2.89-2.80 (m, 1H), 2.73-2.60 (m, 1H), 2.42-2.32 (m, 1H), 2.00-1.83 (m, 5H), 1.81-1.69 (m, 5H), 1.65-1.55 (m, 3H), 1.09-1.02 (m, 6H).

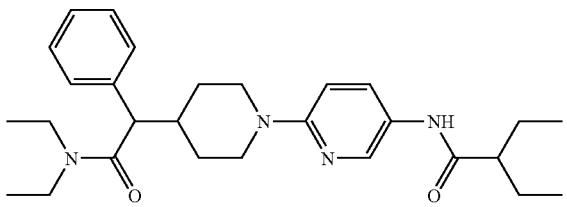

Example 205

N-[4-(Diethylcarbamoyl-phenyl-methyl)-3,4,5,6-tetrahydro-2H-[1,2']bipyridinyl-5'-yl]-2-ethyl-butyramide MS: 465.5. $^1$H NMR (CDCl$_3$): 8.07 (d, J=2.5, 1H), 7.86-7.81 (dd, J=9.1, 2.8, 1H), 7.36-7.27 (m, 4H), 7.25-7.23 (m, 1H), 7.16 (s, 1H), 6.59 (d, J=9.1, 1H), 4.25-4.19 (m, 1H), 4.14-4.07 (m, 1H), 3.45-3.26 (m, 4H), 3.20-3.10 (m, 1H), 2.89-2.81 (m, 1H), 2.72-2.64 (m, 1H), 2.42-2.32 (m, 1H), 2.06-1.93 (m, 2H), 1.78-1.50 (m, 5H), 1.29-1.15 (m, 2H), 1.08-1.02 (m, 6H), 0.98-0.91 (t, J=7.4, 6H).

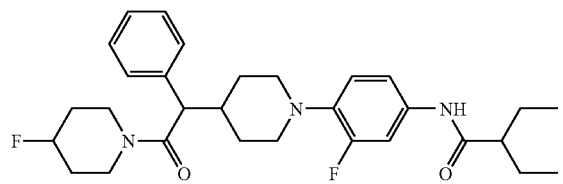

Example 206

2-Ethyl-N-(3-fluoro-4-{4-[2-(4-fluoro-piperidin-1-yl)-2-oxo-1-phenyl-ethyl]-piperidin-1-yl}-phenyl)-butyramide MS: 512.5. $^1$H NMR (CDCl$_3$): 7.49-7.41 (m, 1H), 7.30-7.21 (m, 5H), 7.15 (s, 1H), 7.08-7.03 (m, 1H), 6.86 (t, J=9.0, 1H), 4.87-4.59 (m, 1H), 4.10-4.00 (m, 0.55H), 3.76-3.68 (m, 0.45H), 3.64-3.20 (m, 6H), 2.74-2.64 (m, 1H), 2.57-2.45 (m, 1H), 2.34-2.20 (m, 1H), 2.10-1.92 (m, 2H), 1.80-1.20 (m, 11H), 0.96-0.90 (t, J=7.4, 6H).

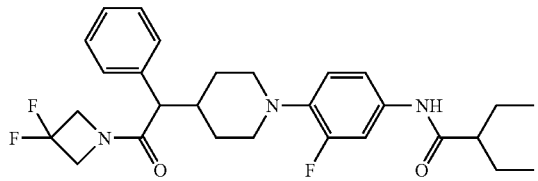

Example 207

N-(4-{4-[2-(3,3-Difluoro-azetidin-1-yl)-2-oxo-1-phenyl-ethyl]-piperidin-1-yl}-3-fluoro-phenyl)-2-ethyl-butyramide MS: 502.4. $^1$H NMR (CDCl$_3$): 7.47-7.41 (dd, J=14.0, 2.4, 1H), 7.37-7.27 (m, 5H), 7.15 (s, 1H), 7.09-7.04 (dd, J=8.6, 1.9, 1H), 6.85 (t, J=9.1, 1H), 4.56-4.44 (m, 1H), 4.36-4.20 (m, 3H), 3.42-3.32 (m, 1H), 3.30-3.22 (m, 1H), 3.10-3.02 (m, 1H), 2.73-2.64 (m, 1H), 2.54-2.46 (m, 1H), 2.28-2.16 (m, 1H), 2.06-1.96 (m, 1H), 1.76-1.38 (m, 6H), 1.32-1.22 (m, 2H), 0.93 (t, J=7.4, 6H).

Example 208

N-(4-{4-[2-(4,4-Difluoro-piperidin-1-yl)-2-oxo-1-phenyl-ethyl]-piperidin-1-yl}-3-fluoro-phenyl)-2-ethyl-butyramide MS: 530.4. $^1$H NMR (CDCl$_3$): 7.45 (dd, J=14.0, 2.4, 1H), 7.35-7.29 (m, 3H), 7.38-7.26 (m, 3H), 7.14 (s, 1H), 7.08-7.04 (m, 1H), 6.85 (t, J=9.1, 1H), 4.05-3.96 (m, 1H), 3.69-3.60 (m, 1H), 3.54-3.38 (m, 3H), 3.38-3.23 (m, 2H), 2.73-2.66 (m, 1H), 2.54-2.46 (m, 1H), 2.32-2.22 (m, 1H), 2.07-1.83 (m, 4H), 1.82-1.61 (m, 4H), 1.59-1.48 (m, 2H), 1.46-1.22 (m, 2H), 0.93 (t, J=7.4, 6H).

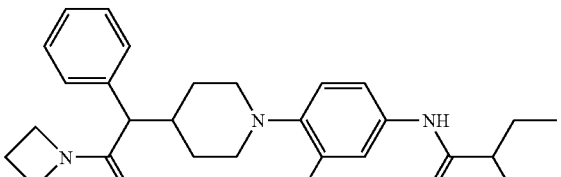

Example 209

N-{4-[4-(2-Azetidin-1-yl-2-oxo-1-phenyl-ethyl)-piperidin-1-yl]-3-fluoro-phenyl}-2-ethyl-butyramide MS: 466.4. $^1$H NMR (CDCl$_3$): 7.46 (dd, J=14.0, 2.4, 1H), 7.36-7.28 (m, 4H), 7.27-7.23 (m, 1H), 7.17 (s, 1H), 7.07-7.03 (m, 1H), 6.85 (t, J=9.0, 1H), 4.28-4.22 (m, 1H), 4.08-3.97 (m, 2H), 3.96-3.90 (m, 1H), 3.39-3.20 (m, 2H), 3.07-3.03 (m, 1H), 2.71-2.64 (m, 1H), 2.52-2.45 (m, 1H), 2.30-2.08 (m, 2H), 2.02-1.95 (m, 2H), 1.75-1.50 (m, 5H), 1.47-1.36 (m, 1H), 1.30-1.24 (m, 2H), 0.92 (t, J=7.4, 6H).

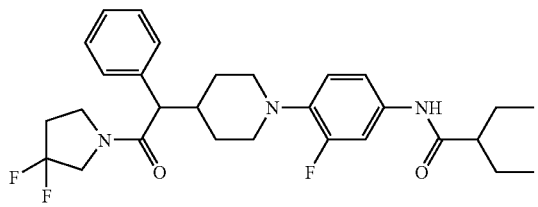

Example 210

N-(4-{4-[2-(3,3-Difluoro-pyrrolidin-1-yl)-2-oxo-1-phenyl-ethyl]-piperidin-1-yl}-3-fluoro-phenyl)-2-ethyl-butyramide MS: 516.4. $^1$H NMR (CDCl$_3$): 7.48-7.42 (m, 1H), 7.36-7.26 (m, 5H), 7.08-7.03 (m, 2H), 6.86 (t, J=9.0, 1H), 3.95-3.55 (m, 5H), 3.40-3.12 (m, 2H), 2.73-2.65 (m, 1H), 2.55-2.15 (m, 4H), 2.08-1.93 (m, 2H), 1.75-1.63 (m, 2H), 1.58-1.39 (m, 3H), 1.33-1.23 (m, 2H), 0.94 (t, J=7.4, 6H).

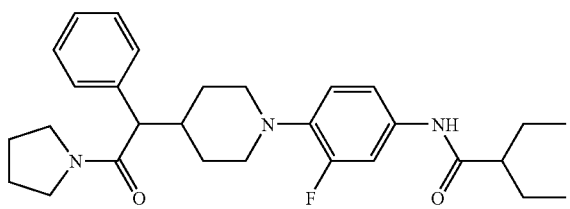

Example 211

2-Ethyl-N-{3-fluoro-4-[4-(2-oxo-1-phenyl-2-pyrrolidin-1-yl-ethyl)-piperidin-1-yl]-phenyl}-butyramide MS: 480.4. $^1$H NMR (CDCl$_3$): 7.46 (dd, J=14.0, 2.4, 1H), 7.39-7.34 (m, 2H), 7.33-7.28 (m, 2H), 7.25-7.22 (m, 1H), 7.13 (s, 1H), 7.07-7.02 (dd, J=8.6, 1.7, 1H), 6.85 (t, J=9.1, 1H), 3.60-3.49 (m, 2H), 3.41-3.21 (m, 5H), 2.72-2.64 (m, 1H), 2.54-2.46 (m, 1H), 2.32-2.22 (m, 1H), 2.10-1.90 (m, 3H), 1.86-1.64 (m, 6H), 1.58-1.40 (m, 3H), 1.34-1.22 (m, 1H), 0.94 (t, J=7.4, 6H).

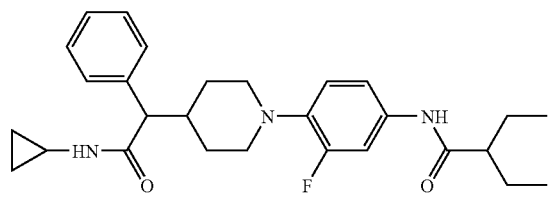

Example 212

N-{4-[4-(Cyclopropylcarbamoyl-phenyl-methyl)-piperidin-1-yl]-3-fluoro-phenyl}-2-ethyl-butyramide MS: 466.4. $^1$H NMR (CDCl$_3$): 7.45 (dd, J=14.0, 2.4, 1H), 7.36-7.23 (m, 5H), 7.30 (s, 1H), 7.07-7.03 (dd, J=8.7, 1.7, 1H), 6.86 (t, J=9.1, 1H), 5.71-5.63 (m, 1H), 3.40-3.34 (m, 1H), 3.29-3.22 (m, 1H), 2.90-2.82 (m, 1H), 2.71-2.63 (m, 2H), 2.55-2.47 (m, 1H), 2.26-2.16 (m, 1H), 2.03-1.94 (m, 1H), 1.76-1.65 (m, 2H), 1.57-1.50 (m, 2H), 1.35-1.20 (m, 4H), 0.94 (t, J=7.4, 6H), 0.81-0.66 (m, 2H), 0.50-0.35 (m, 2H).

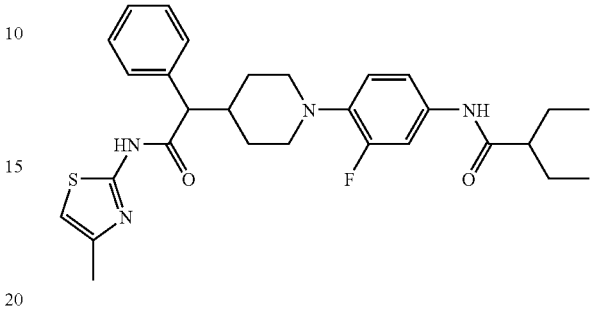

Example 213

2-Ethyl-N-(3-fluoro-4-{4-[(4-methyl-thiazol-2-ylcarbamoyl)-phenyl-methyl]-piperidin-1-yl}-phenyl)-butyramide MS: 522.4. $^1$H NMR (CDCl$_3$): 9.5 (s, 1H), 7.45-7.40 (dd, J=13.9, 2.4, 1H), 7.32-7.27 (m, 2H), 7.25-7.24 (m, 2H), 7.15 (s, 1H), 7.10-7.06 (m, 1H), 6.85 (t, J=9.0, 1H), 6.52 (s, 1H), 3.38-3.22 (m, 2H), 3.21-3.16 (m, 1H), 2.70-2.62 (m, 1H), 2.56-2.48 (1H), 2.34-2.26 (m, 4H), 2.04-1.92 (m, 2H), 1.76-1.64 (m, 3H), 1.58-1.44 (m, 3H), 1.38-1.22 (m, 2H), 0.93 (t, J=7.4, 6H).

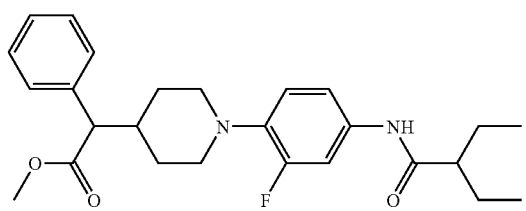

Example 214

{1-[4-(2-Ethyl-butyrylamino)-2-fluoro-phenyl]-piperidin-4-yl}-phenyl-acetic acid methyl ester

MS: 441.4.

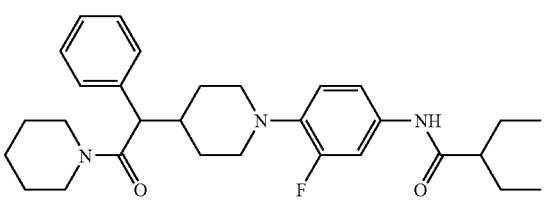

Example 215

2-Ethyl-N-{3-fluoro-4-[4-(2-oxo-1-phenyl-2-piperidin-1-yl-ethyl)-piperidin-1-yl]-phenyl}-butyramide MS: 494.4. $^1$H NMR (CDCl$_3$): 7.47 (dd, J=14.0, 2.4, 1H), 7.36-7.28 (m, 5H), 7.27-7.22 (m, 1H), 7.09-7.03 (m, 1H), 6.85 (t, J=9.1, 1H), 4.29-4.21 (m, 1H), 4.08-3.98 (m, 2H), 3.97-3.89 (m, 1H), 3.40-3.32 (m, 1H), 3.29-3.20 (m, 1H), 3.08-3.03 (m, 1H), 2.72-2.62 (m, 1H), 2.53-2.45 (m, 1H), 2.31-2.07 (m, 3H), 2.00-1.96 (m, 2H), 1.79-1.60 (m, 5H), 1.51-1.38 (m, 4H), 1.32-1.22 (m, 2H), 0.93 (t, J=7.4, 6H).

Example 216

2-Ethyl-N-(3-fluoro-4-{4-[2-(4-methyl-piperazin-1-yl)-2-oxo-1-phenyl-ethyl]-piperidin-1-yl}-phenyl)-butyramide

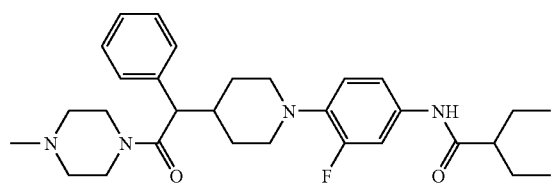

Example 217

N-{3-Cyano-4-[4-(diethylcarbamoyl-phenyl-methyl)-piperidin-1-yl]-phenyl}-2-ethyl-butyramide MS: 489.3. $^1$H NMR (CDCl$_3$): 7.80 (d, J=2.5, 1H), 7.62 (dd, J=8.9, 2.6, 1H), 7.41-7.35 (m, 2H), 7.34-7.30 (m, 2H), 7.29-7.21 (m, 1H), 6.95 (d, J=8.9, 1H), 3.51-3.32 (m, 6H), 3.26-3.18 (m, 1H), 2.82-2.75 (m, 1H), 2.64-2.56 (m, 1H), 2.32-2.23 (m, 1H), 2.09-2.00 (m, 2H), 1.77-1.67 (m, 2H), 1.61-1.52 (m, 2H), 1.52-1.46 (m, 1H), 1.40-1.33 (m, 1H), 1.29-1.22 (m, 1H), 1.12 (t, J=7.1, 3H), 1.08 (t, J=7.1, 3H), 0.95 (t, J=7.4, 6H).

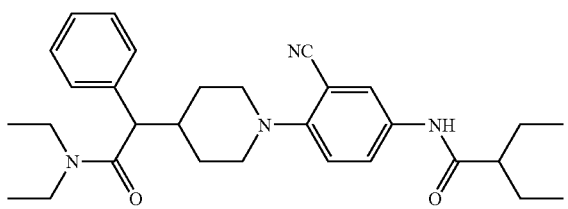

Example 218

N-{3-Cyano-4-[4-(diethylcarbamoyl-phenyl-methyl)-piperidin-1-yl]-phenyl}-2-methyl-butyramide MS: 476.5. $^1$H NMR (CDCl$_3$): 7.92-7.85 (m, 1H), 7.68-7.60 (m, 2H), 7.48-7.41 (m, 2H), 7.37-7.28 (m, 3H), 6.65 (d, J=8.9, 1H), 4.21 (s, 1H), 3.49-3.38 (m, 2H), 3.35-3.10 (m, 6H), 2.75-2.60 (m, 4H), 2.32-2.20 (m, 1H), 1.80-1.69 (m, 2H), 1.55-1.42 (m, 1H), 1.20 (t, J=6.7, 3H), 1.08 (t, J=7.0, 6H), 0.94 (t, J=7.3, 3H).

Example 219

N-{3-Bromo-4-[4-(diethylcarbamoyl-phenyl-methyl)-piperidin-1-yl]-phenyl}-2-ethyl-butyramide MS: 542.2/544.2. $^1$H NMR (CDCl$_3$): 7.84 (d, J=2.5, 1H), 7.40-7.34 (m, 4H), 7.31-7.27 (m, 2H), 7.25-7.21 (m, 1H), 6.94 (d, J=8.7, 1H), 3.48-3.30 (m, 4H), 3.28-3.14 (m, 3H), 2.64-2.58 (m, 1H), 2.45-2.38 (m, 1H), 2.28-2.20 (m, 1H), 2.04-1.96 (m, 2H), 1.73-1.64 (m, 2H), 1.58-1.48 (m, 1H), 1.47-1.38 (m, 1H), 1.34-1.25 (m, 1H), 1.22-1.15 (m, 1H), 1.12 (t, J=7.1, 3H), 1.06 (t, J=7.1, 3H), 0.93 (t, J=7.3, 6H).

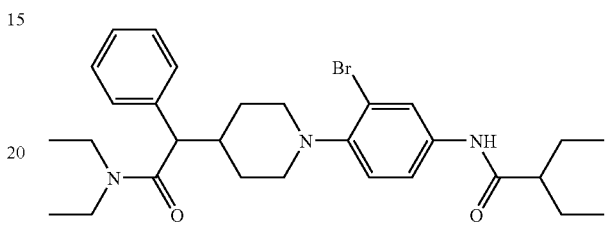

Example 220

Cyclopentanecarboxylic acid {4-[4-(diethylcarbamoyl-phenyl-methyl)-piperidin-1-yl]-3-fluoro-phenyl}-amide MS: 480.3. $^1$H NMR (CDCl$_3$): 7.44 (dd, J=14.1, 2.3, 1H), 7.40-7.21 (m, 6H), 7.03 (dd, J=8.5, 1.7, 1H), 6.83 (dd, J=9.1, 9.0, 1H), 3.51-3.39 (m, 1H), 3.38-3.28 (m, 4H), 3.27-3.21 (m, 1H), 3.20-3.12 (m, 1H), 2.68-2.56 (m, 2H), 2.50-2.40 (m, 1H), 2.28-2.16 (m, 1H), 2.05-1.96 (m, 1H), 1.94-1.80 (m, 4H), 1.79-1.66 (m, 2H), 1.64-1.51 (m, 2H), 1.51-1.36 (m, 1H), 1.35-1.16 (m, 2H), 1.10 (t, J=7.1, 3H), 1.06 (t, J=7.1, 3H).

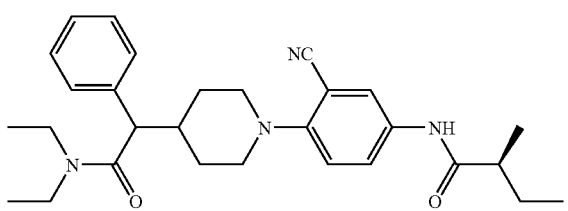

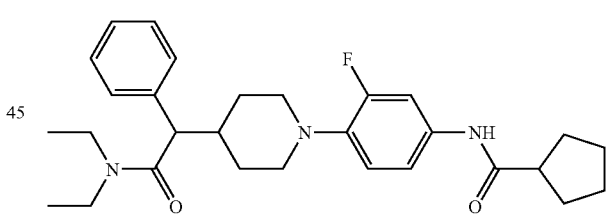

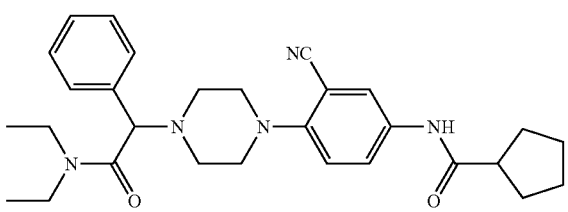

Example 221

Cyclopentanecarboxylic acid {3-cyano-4-[4-(diethylcarbamoyl-phenyl-methyl)-piperazin-1-yl]-phenyl}-amide MS: 488.5. $^1$H NMR (CDCl$_3$): 7.91-7.79 (m, 2H), 7.63 (dd, J=8.9, 2.5, 1H), 7.45-7.42 (m, 2H), 7.36-7.27 (m, 3H), 6.91 (d, J=8.9, 1H), 4.19 (s, 1H), 3.47-3.34 (m, 2H), 3.32-3.23 (m, 1H), 3.24-3.15 (m, 1H), 3.15-3.07 (m, 4H), 2.72-2.58 (m, 5H), 1.95-1.79 (m, 4H), 1.80-1.67 (m, 2H), 1.64-1.50 (m, 2H), 1.06 (t, J=7.1, 6H).

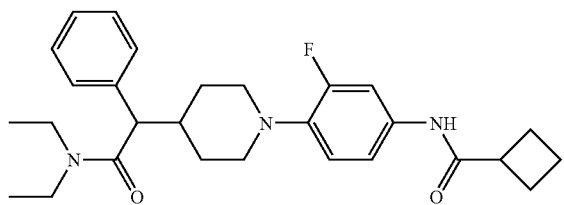

Example 222

Cyclobutanecarboxylic acid {4-[4-(diethylcarbamoyl-phenyl-methyl)-piperidin-1-yl]-3-fluoro-phenyl}-amide MS: 488.5. $^1$H NMR (CDCl$_3$): 7.43 (dd, J=14.0, 2.3, 1H), 7.37-7.33 (m, 2H), 7.32-7.27 (m, 2H), 7.25-7.20 (m, 1H), 7.01 (dd, J=8.4, 1.7, 1H), 6.84 (t, J=9.1, 1H), 3.48-3.39 (m, 1H), 3.38-3.22 (m, 5H), 3.21-3.04 (m, 2H), 2.71-2.62 (m, 1H), 2.52-2.44 (m, 1H), 2.40-2.30 (m, 2H), 2.29-2.14 (m, 1H), 2.06-1.83 (m, 3H), 1.50-1.38 (m, 1H), 1.36-1.20 (m, 2H), 1.10 (t, J=7.1, 3H), 1.06 (t, J=7.1, 3H).

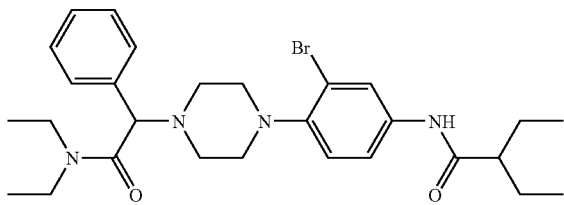

Example 223

N-{3-Bromo-4-[4-(diethylcarbamoyl-phenyl-methyl)-piperazin-1-yl]-phenyl}-2-ethyl-butyramide MS: 545.6. $^1$H NMR (CDCl$_3$): 7.96 (d, J=2.3, 1H), 7.76 (s, 1H), 7.50-7.45 (m, 3H), 7.37-7.27 (m, 3H), 7.00 (d, J=8.7, 1H), 4.22 (s, 1H), 3.52-3.37 (m, 2H), 3.32-3.17 (m, 2H), 3.07-2.92 (m, 4H), 2.77-2.62 (m, 4H), 2.11-1.99 (m, 1H), 1.96-1.85 (m, 1H), 1.75-1.58 (m, 2H), 1.58-1.39 (m, 2H), 1.12-1.04 (m, 6H), 0.91 (t, J=7.4, 6H).

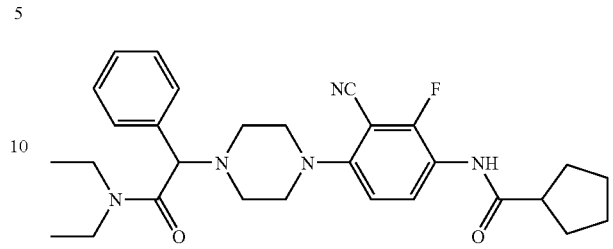

Example 224

Cyclopentanecarboxylic acid {3-cyano-4-[4-(diethylcarbamoyl-phenyl-methyl)-piperazin-1-yl]-2-fluoro-phenyl}-amide MS: 508.6. $^1$H NMR (CDCl$_3$): 8.34 (t, J=9.0, 1H), 7.47-7.42 (m, 2H), 7.39-7.31 (m, 3H), 7.21 (s, 1H), 6.72 (dd, J=9.2, 1.0, 1H), 4.22 (s, 1H), 3.51-3.12 (m, 8H), 2.77-2.65 (m, 5H), 2.01-1.73 (m, 6H), 1.68-1.59 (m, 2H), 1.08 (t, J=6.5, 3H), 1.05 (t, J=6.5, 3H).

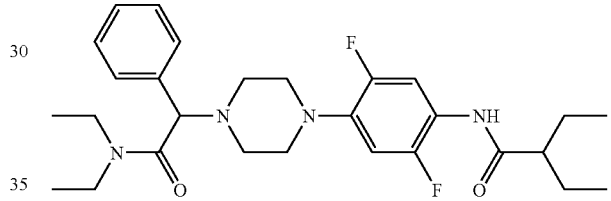

Example 225

N-{4-[4-(Diethylcarbamoyl-phenyl-methyl)-piperazin-1-yl]-2,5-difluoro-phenyl}-2-ethyl-butyramide MS: 501.6. $^1$H NMR (CDCl$_3$): 8.07 (dd, J=14.0, 7.4, 1H), 7.47-7.41 (m, 2H), 7.38-7.29 (m, 3H), 7.18 (s, 1H), 6.65 (dd, J=12.5, 7.6, 1H), 4.22 (s, 1H), 3.52-3.33 (m, 2H), 3.32-3.23 (m, 1H), 3.22-3.13 (m, 1H), 3.11-3.00 (m, 4H), 2.76-2.58 (m, 4H), 2.10-1.98 (m, 1H), 1.74-1.63 (m, 2H), 1.62-1.49 (m, 2H), 1.08 (t, J=7.1, 3H), 1.03 (t, J=7.1, 3H), 0.94 (t, J=7.4, 1H).

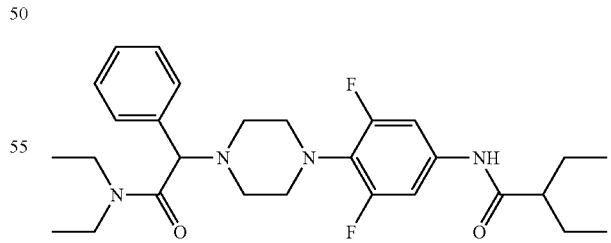

Example 226

N-{4-[4-(Diethylcarbamoyl-phenyl-methyl)-piperazin-1-yl]-3,5-difluoro-phenyl}-2-ethyl-butyramide MS: 501.3. $^1$H NMR (CDCl$_3$): 7.70-7.60 (m, 1H), 7.49 (dd, J=7.8, 1.6, 2H), 7.42-7.35 (m, 3H), 7.17 (d, J=10.8, 2H), 4.65

(br s, 1H), 3.50-3.28 (m, 4H), 3.27-3.17 (m, 1H), 3.12-2.87 (m, 2H), 2.87-2.70 (m, 2H), 2.10-2.00 (m, 1H), 1.75-1.62 (m, 2H), 1.59-1.49 (m, 2H), 1.10 (t, J=7.1, 3H), 1.02 (t, J=7.1, 3H), 0.92 (t, J=7.4, 6H).

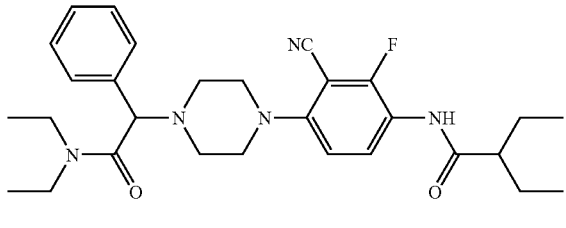

Example 227

N-{3-Cyano-4-[4-(diethylcarbamoyl-phenyl-methyl)-piperazin-1-yl]-2-fluoro-phenyl}-2-ethyl-butyramide MS: 506.6. ¹H NMR (CDCl₃): 8.32 (t, J=9.0, 1H), 7.45-7.42 (m, 2H), 7.37-7.29 (m, 3H), 7.22 (s, 1H), 6.72 (d, J=9.1, 1H), 4.23-4.21 (m, 1H), 3.48-3.33 (m, 2H), 3.32-3.10 (m, 6H), 2.69 (t, J=4.7, 4H), 2.12-2.05 (m, 1H), 1.63-1.46 (m, 1H), 1.75-1.63 (m, 2H), 1.08 (t, J=7.1, 3H), 1.04 (t, J=7.2, 3H), 0.94 (t, J=7.4, 6H).

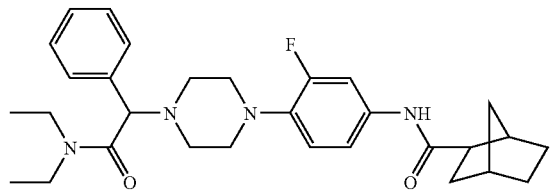

Example 228

Bicyclo[2.2.1]heptane-2-carboxylic acid {4-[4-(diethylcarbamoyl-phenyl-methyl)-piperazin-1-yl]-3-fluoro-phenyl}-amide MS: 506.3. ¹H NMR (CDCl₃): 7.49-7.38 (m, 1H), 7.37-7.33 (m, 2H), 7.32-7.27 (m, 2H), 7.24-7.22 (m, 1H), 7.05-6.96 (m, 2H), 6.87-6.81 (m, 1H), 3.49-3.38 (m, 1H), 3.38-3.29 (m, 4H), 3.25 (d, J=11.1, 1H), 3.21-3.12 (m, 1H), 2.77-2.70 (m, 1H), 2.70-2.62 (m, 1H), 2.52-2.43 (m, 2H), 2.31-2.16 (m, 1H), 2.09-1.88 (m, 2H), 1.78-1.73 (m, 1H), 1.54-1.27 (m, 6H), 1.27-1.14 (m, 3H), 1.10 (t, J=7.1, 3H), 1.06 (t, J=7.1, 3H).

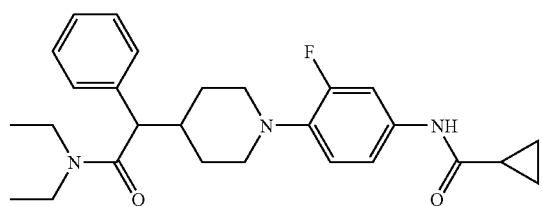

Example 229

Cyclopropanecarboxylic acid {4-[4-(diethylcarbamoyl-phenyl-methyl)-piperidin-1-yl]-3-fluoro-phenyl}-amide ¹H NMR (CDCl₃): 7.44-7.33 (m, 4H), 7.32-7.27 (m, 2H), 7.25-7.22 (m, 1H), 7.01 (d, J=8.1, 1H), 6.84 (t, J=9.0, 1H), 3.48-3.38 (m, 1H), 3.38-3.29 (m, 4H), 3.25 (d, J=11.5, 1H), 3.21-3.10 (m, 1H), 2.65 (t, J=11.6, 1H), 2.47 (t, J=11.5, 1H), 2.32-2.16 (m, 1H), 2.06-1.95 (m, 1H), 1.51-1.37 (m, 2H), 1.35-1.18 (m, 2H), 1.12-1.03 (m, 8H), 0.81 (dd, J=7.6, 3.0, 2H).

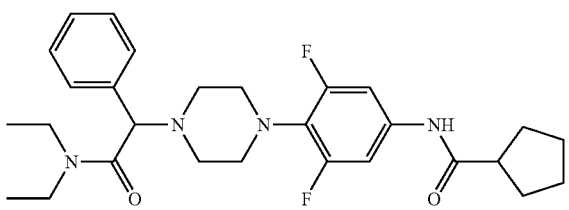

Example 230

Cyclopentanecarboxylic acid {4-[4-(diethylcarbamoyl-phenyl-methyl)-piperazin-1-yl]-3,5-difluoro-phenyl}-amide MS: 499.3. ¹H NMR (CDCl₃): 7.63 (s, 1H), 7.52-7.47 (m, 2H), 7.45-7.39 (m, 3H), 7.14 (d, J=10.7, 2H), 5.06 (s, 1H), 3.49-3.11 (m, 10H), 3.03-2.89 (m, 2H), 2.71-2.63 (m, 1H), 1.98-1.71 (m, 6H), 1.65-1.53 (m, 1H), 1.11 (t, J=7.1, 3H), 0.99 (t, J=7.1, 3H).

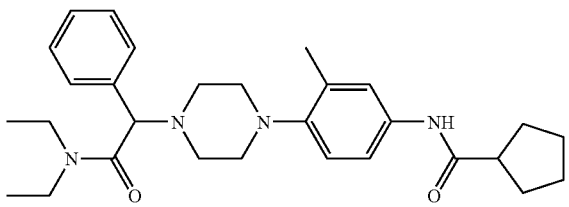

Example 231

Cyclopentanecarboxylic acid {4-[4-(diethylcarbamoyl-phenyl-methyl)-piperazin-1-yl]-3-methyl-phenyl}-amide MS: 477.3. ¹H NMR (CDCl₃): 7.51-7.05 (m, 7H), 6.96 (d, J=8.5, 1H), 4.27 (s, 1H), 3.53-3.35 (m, 2H), 3.32-3.15 (m, 2H), 2.92-2.85 (m, 4H), 2.73-2.56 (m, 5H), 2.24 (s, 3H), 1.97-1.52 (m, 8H), 1.09 (t, J=5.6, 3H), 1.06 (t, J=5.7, 3H).

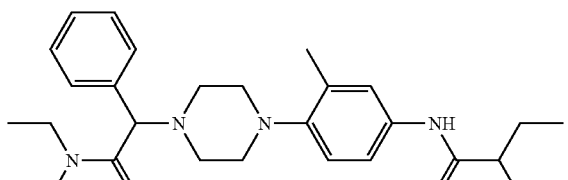

Example 232

N-{4-[4-(Diethylcarbamoyl-phenyl-methyl)-piperazin-1-yl]-3-methyl-phenyl}-2-ethyl-butyramide MS: 479.4. ¹H NMR (CDCl₃): 7.51-7.41 (m, 3H), 7.39-7.21 (m, 4H), 6.97 (d, J=8.6, 1H), 4.27 (s, 1H), 3.55-3.35 (m, 2H), 3.33-3.15 (m, 2H), 2.93-2.86 (m, 4H), 2.73-2.58 (m, 4H), 2.24 (s, 3H), 2.05-1.93 (m, 1H), 1.77-1.62 (m, 2H), 1.59-1.46 (m, 2H), 1.11-1.03 (m, 6H), 0.93 (t, J=7.4, 6H).

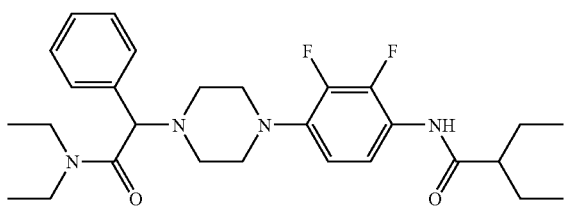

Example 233

N-{4-[4-(Diethylcarbamoyl-phenyl-methyl)-piperazin-1-yl]-2,3-difluoro-phenyl}-2-ethyl-butyramide MS: 501.0. ¹H NMR (CDCl₃): 7.89-7.82 (m, 1H), 7.46-7.43 (m, 2H), 7.39-7.30 (m, 3H), 7.20 (s, 1H), 6.65 (dt, J=8.9, 2.1, 1H), 4.24 (s, 1H), 3.51-3.34 (m, 2H), 3.33-3.14 (m, 2H), 3.12-3.06 (m, 4H), 2.76-2.61 (m, 4H), 2.14-2.02 (m, 1H), 1.77-1.64 (m, 2H), 1.62-1.51 (m, 2H), 1.08 (t, J=7.1, 3H), 1.04 (t, J=7.2, 3H), 0.95 (t, J=7.4, 6H).

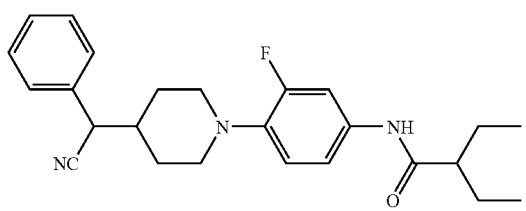

Example 234

N-{4-[4-(Cyano-phenyl-methyl)-piperidin-1-yl]-3-fluoro-phenyl}-2-ethyl-butyramide MS: 408.2. ¹H NMR (CDCl₃): 7.47-7.30 (m, 6H), 7.17 (s, 1H), 7.12 (dd, J=8.6, 2.4, 1H), 6.87 (t, J=9.0, 1H), 3.67 (d, J=7.7, 1H), 3.48-3.75 (m, 2H), 2.63 (dt, J=11.8, 2.4, 1H), 2.57 (dt, J=11.6, 3.0, 1H), 2.05-1.96 (m, 2H), 1.95-1.84 (m, 1H), 1.78-1.48 (m, 7H), 0.95 (t, J=7.4, 6H).

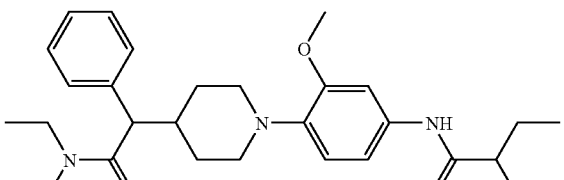

Example 235

N-{4-[4-(Diethylcarbamoyl-phenyl-methyl)-piperazin-1-yl]-3-methoxy-phenyl}-2-ethyl-butyramide

MS: 495.7.

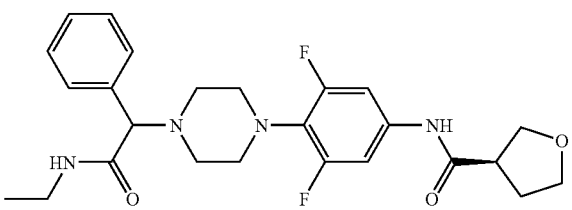

Example 236

(R)-Tetrahydro-furan-3-carboxylic acid {4-[4-(ethyl-carbamoyl-phenyl-methyl)-piperazin-1-yl]-3,5-difluoro-phenyl}-amide

MS: 472.3.

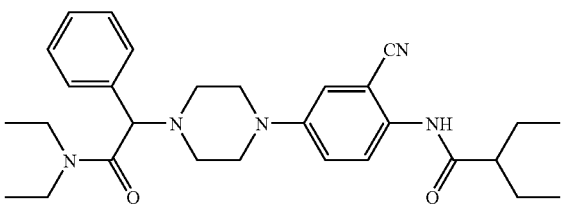

Example 237

N-{2-Cyano-4-[4-(diethylcarbamoyl-phenyl-methyl)-piperazin-1-yl]-phenyl}-2-ethyl-butyramide

MS: 490.7.

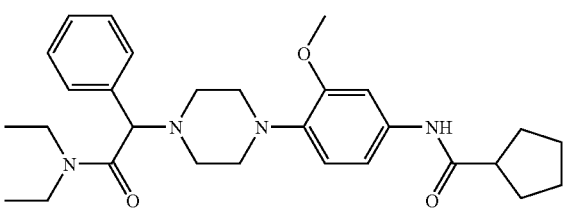

Example 238

Cyclopentanecarboxylic acid {4-[4-(diethylcarbamoyl-phenyl-methyl)-piperazin-1-yl]-3-methoxy-phenyl}-amide

MS: 493.6.

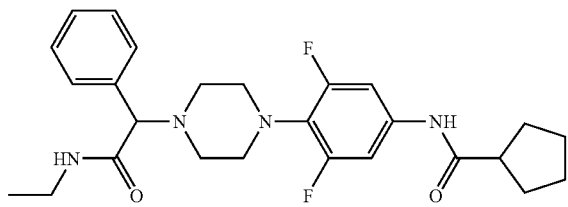

Example 239

Cyclopentanecarboxylic acid {4-[4-(ethylcarbamoyl-phenyl-methyl)-piperazin-1-yl]-3,5-difluoro-phenyl}-amide

MS: 470.3.

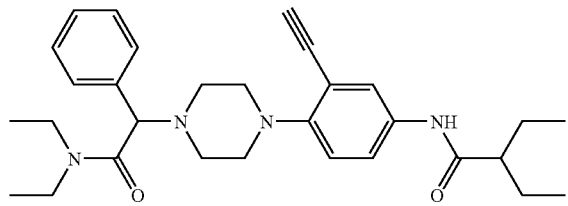

Example 240

N-{4-[4-(Diethylcarbamoyl-phenyl-methyl)-piperazin-1-yl]-3-ethynyl-phenyl}-2-ethyl-butyramide To a solution of N-{3-bromo-4-[4-(diethylcarbamoyl-phenyl-methyl)-piperazin-1-yl]-phenyl}-2-ethyl-butyramide (66 mg, 0.12 mmol) in DMF (1.5 mL) was added CuI (1.3 mg, 0.01 mmol), triphenylphosphine (73 mg, 0.28 mmol), diethylamine (220 µL, 2.1 mmol), trimethylsilylacetylene (22 µL, 0.15 mmol) and dichlorobis(triphenylphosphine)palladium (II) (5.0 mg, 0.01 mmol). This solution was heated in a focused microwave reactor at 120° C. for 5 min, after which the solution was concentrated and purified by reverse phase HPLC to provide N-{4-[4-(diethylcarbamoyl-phenyl-methyl)-piperazin-1-yl]-3-trimethylsilanylethynyl-phenyl}-2-ethylbutyramide (10.5 mg, 16%). This compound (18 mg, 0.03 mmol) was dissolved in MeOH and treated with $K_2CO_3$ (9.0 mg, 0.06 mmol). After 1 h, the solids were filtered off, the filtrate concentrated, and the product purified by reverse phase HPLC to afford the title compound (10 mg, 63%). MS: 489.4.

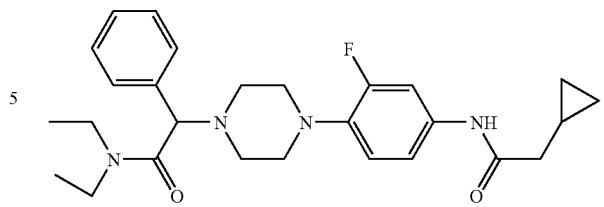

Example 241

2-{4-[4-(2-Cyclopropyl-acetylamino)-2-fluoro-phenyl]-piperazin-1-yl}-N,N-diethyl-2-phenyl-acetamide MS: 467.4. $^1$H NMR (CDCl$_3$): 7.55 (br s, 1H), 7.49-7.45 (m, 3H), 7.39-7.33 (m, 3H), 7.08-7.06 (m, 1H), 6.91-6.87 (m, 1H), 5.32 (s, 1H), 4.25 (m, 1H), 3.51-3.41 (m, 2H), 3.31-3.27 (m, 1H), 3.24-3.20 (m, 1H), 3.12-3.09 (m, 4H), 2.72-2.68 (m, 4H), 2.19 (d, J=1.3, 2H), 1.12-1.05 (m, 6H), 0.73-0.70 (m, 2H), 0.31-0.28 (m, 2H).

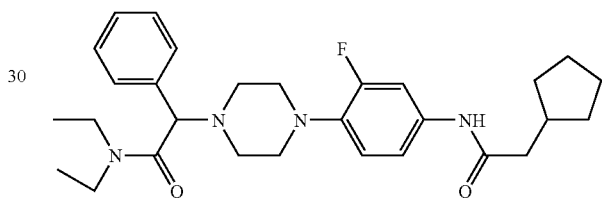

Example 242

2-{4-[4-(2-Cyclopentyl-acetylamino)-2-fluoro-phenyl]-piperazin-1-yl}-N,N-diethyl-2-phenyl-acetamide

MS: 495.4.

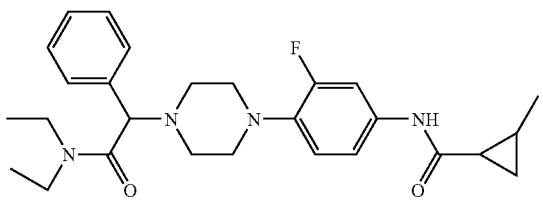

Example 243

2-Methyl-cyclopropanecarboxylic acid {4-[4-(diethylcarbamoyl-phenyl-methyl)-piperazin-1-yl]-3-fluoro-phenyl}-amide MS: 467.4. $^1$H NMR (CDCl$_3$): 7.49-7.46 (m, 3H), 7.39-7.31 (m, 3H), 7.04-7.02 (m, 1H), 6.87 (t, J=9.1, 1H), 4.24 (s, 1H), 3.49-3.41 (m, 2H), 3.33-3.26 (m, 1H), 3.25-3.18 (m, 1H), 3.12-3.06 (m, 4H), 2.73-2.67 (m, 4H), 1.48-1.44 (m, 1H), 1.28-1.24 (m, 2H), 1.19-1.17 (m, 1H), 1.15 (d, J=6.0, 3H), 1.12-1.05 (m, 6H), 0.70-0.66 (m, 1H).

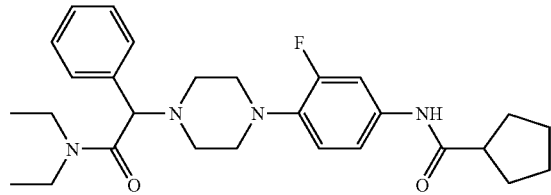

Example 244

Cyclopentanecarboxylic acid {4-[4-(diethylcarbamoyl-phenyl-methyl)-piperazin-1-yl]-3-fluoro-phenyl}-amide MS: 481.4. $^1$H NMR (CDCl$_3$): 7.49-7.45 (m, 3H), 7.39-7.31 (m, 3H), 7.08-7.03 (m, 2H), 6.88 (t, J=9.0, 1H), 4.24 (s, 1H), 3.51-3.40 (m, 3H), 3.31-3.26 (m, 1H), 3.25-3.18 (m, 1H), 3.13-3.06 (m, 4H), 2.74-2.62 (m, 5H), 1.96-1.86 (m, 4H), 1.83-1.78 (m, 2H), 1.67-1.63 (m, 1H), 1.12-1.05 (m, 6H).

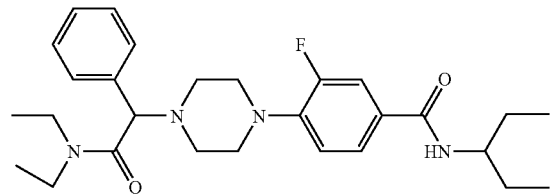

Example 245

4-[4-(Diethylcarbamoyl-phenyl-methyl)-piperazin-1-yl]-N-(1-ethyl-propyl)-3-fluoro-benzamide

MS: 483.4.

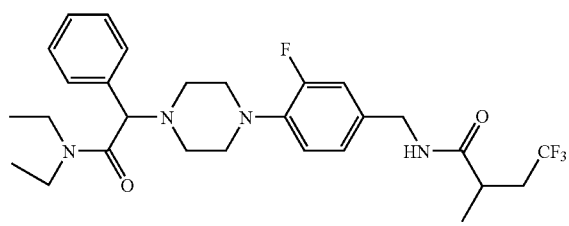

Example 246

N-{4-[4-(Diethylcarbamoyl-phenyl-methyl)-piperazin-1-yl]-3-fluoro-benzyl}-4,4,4-trifluoro-2-methyl-butyramide

MS: 537.6.

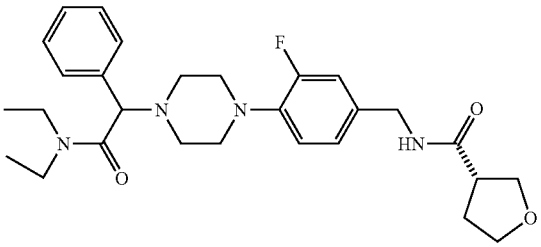

Example 247

(S)-Tetrahydro-furan-3-carboxylic acid 4-[4-(diethylcarbamoyl-phenyl-methyl)-piperazin-1-yl]-3-fluoro-benzylamide

MS: 497.6.

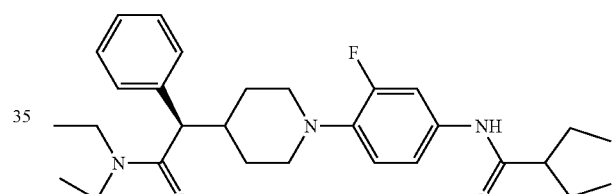

Example 248

(R)-(−)-N-{4-[4-(Diethylcarbamoyl-phenyl-methyl)-piperidin-1-yl]-3-fluoro-phenyl}-2-ethyl-butyramide MS: 482.3. $^1$H NMR (CDCl$_3$): 7.46 (dd, J=14.0, 2.4, 1H), 7.36-7.34 (m, 2H), 7.30 (t, J=7.3, 2H), 7.25-7.22 (m, 1H), 7.15 (br s, 1H), 7.05 (dd, J=8.7, 2.0, 1H), 6.86 (t, J=9.0, 1H), 3.47-3.39 (m, 1H), 3.38-3.29 (m, 3H), 3.28-3.24 (m, 1H), 3.21-3.13 (m, 1H), 2.69-2.64 (m, 1H), 2.51-2.45 (m, 1H), 2.28-2.21 (m, 1H), 2.04-1.95 (m, 2H), 1.73-1.64 (m, 3H), 1.57-1.49 (m, 2H), 1.48-1.40 (m, 1H), 1.35-1.27 (m, 1H), 1.24-1.21 (m, 1H), 1.10 (t, J=7.1, 3H), 1.06 (t, J=7.1, 3H), 0.93 (t, J=7.4, 6H).

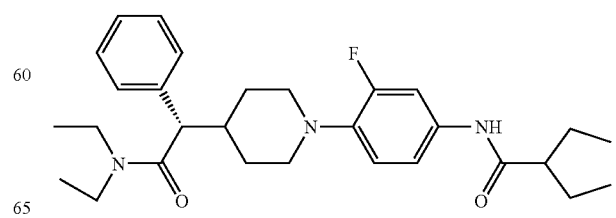

Example 249

(S)—(+)-N-{4-[4-(Diethylcarbamoyl-phenyl-methyl)-piperidin-1-yl]-3-fluoro-phenyl}-2-ethyl-butyramide MS: 482.3. ¹H NMR (CDCl₃): 7.47-7.41 (m, 2H), 7.36-7.34 (m, 2H), 7.30 (t, J=7.3, 1H), 7.25-7.22 (m, 1H), 7.17 (br s, 1H), 7.05 (dd, J=8.7, 1.7, 1H), 6.85 (t, J=9.0, 1H), 3.47-3.39 (m, 1H), 3.38-3.29 (m, 3H), 3.27-3.24 (m, 1H), 3.21-3.13 (m, 1H), 2.69-2.63 (m, 1H), 2.50-2.45 (m, 1H), 2.26-2.21 (m, 1H), 2.04-1.96 (m, 2H), 1.74-1.66 (m, 3H), 1.58-1.51 (m, 2H), 1.48-1.39 (m, 1H), 1.33-1.21 (m, 2H), 1.10 (t, J=7.1, 3H), 1.06 (t, J=7.1, 3H), 0.95-0.91 (m, 6H).

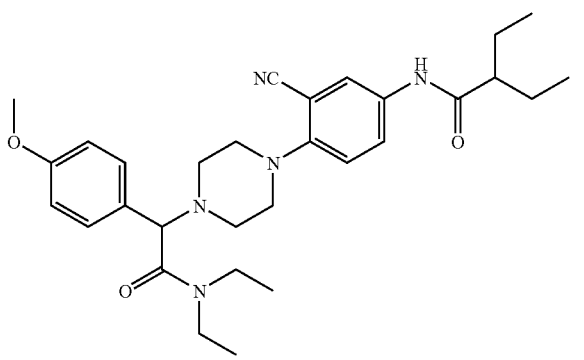

Example 250

N-(3-Cyano-4-{4-[diethylcarbamoyl-(4-methoxy-phenyl)-methyl]-piperazin-1-yl}-phenyl)-2-ethyl-butyramide MS: 520.7. ¹H NMR (CDCl₃): 8.19 (s, 1H), 7.97 (d, J=2.5, 1H), 7.70 (dd, J=9.0, 2.5, 1H), 7.36 (d, J=9.0, 2H), 6.92 (d, J=8.5, 1H), 6.86 (d, J=8.5, 2H), 3.79 (s, 3H), 3.46-3.39 (m, 2H), 3.30-3.11 (m, 6H), 2.66 (bs, 4H), 2.12-2.10 (m, 1H), 1.72-1.66 (m, 2H), 1.55-1.49 (m, 2H), 1.10-1.05 (m, 6H), 0.93-0.90 (m, 6H).

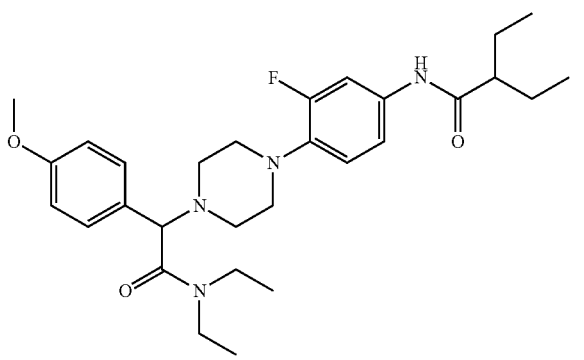

Example 251

N-(4-{4-[Diethylcarbamoyl-(4-methoxy-phenyl)-methyl]-piperazin-1-yl}-3-fluoro-phenyl)-2-ethyl-butyramide MS: 513.7. ¹H NMR (CDCl₃): 7.74 (s, 1H), 7.57 (d, J=11.8, 1H), 7.38 (d, J=8.6, 2H), 7.12 (d, J=8.6, 1H), 6.88-6.85 (m, 3H), 3.78 (s, 3H), 3.46-3.40 (m, 2H), 3.29-3.05 (m, 4H), 2.68 (bs, 4H), 2.06-2.04 (m, 1H), 1.71-1.66 (m, 2H), 1.54-1.50 (m, 2H), 1.09-1.06 (m, 6H), 0.94-0.91 (m, 6H).

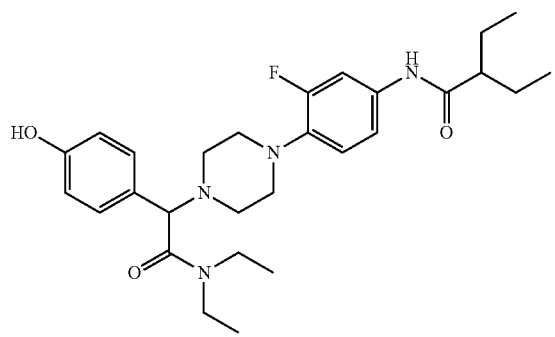

Example 252

N-(4-{4-[Diethylcarbamoyl-(4-hydroxy-phenyl)-methyl]-piperazin-1-yl}-3-fluoro-phenyl)-2-ethyl-butyramide MS: 499.6. ¹H NMR (CDCl₃): 7.73 (s, 1H), 7.50 (d, J=11.0, 1H), 7.29 (d, J=8.6, 2H), 7.08 (d, J=8.6, 1H), 6.89-6.86 (m, 3H), 3.46-3.40 (m, 2H), 3.29-3.05 (m, 4H), 3.09-3.06 (m, 4H), 2.70-2.67 (m, 4H), 2.06-2.04 (m, 1H), 1.70-1.65 (m, 2H), 1.54-1.50 (m, 2H), 1.09-1.06 (m, 6H), 0.94-0.91 (m, 6H).

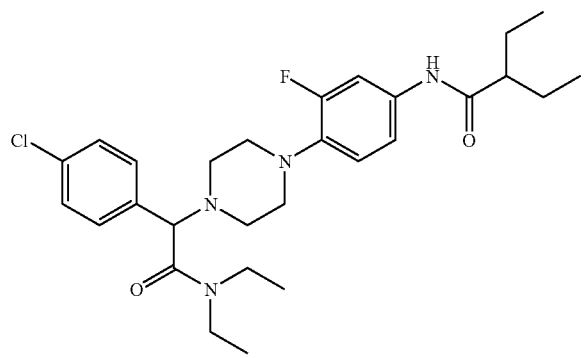

Example 253

N-(4-{4-[(4-Chloro-phenyl)-diethylcarbamoyl-methyl]-piperazin-1-yl}-3-fluoro-phenyl)-2-ethyl-butyramide MS: 517.4. ¹H NMR (CDCl₃): 7.53-7.45 (m, 3H), 7.37-7.31 (m, 3H), 7.09-7.07 (m, 1H), 6.88-6.84 (m, 1H), 3.45-

3.39 (m, 2H), 3.31-3.22 (m, 2H), 3.07 (bs, 4H), 2.74-2.73 (m, 4H), 2.03-2.00 (m, 1H), 1.72-1.67 (m, 2H), 1.57-1.52 (m, 2H), 1.11-1.08 (m, 6H), 0.95-0.92 (m, 6H).

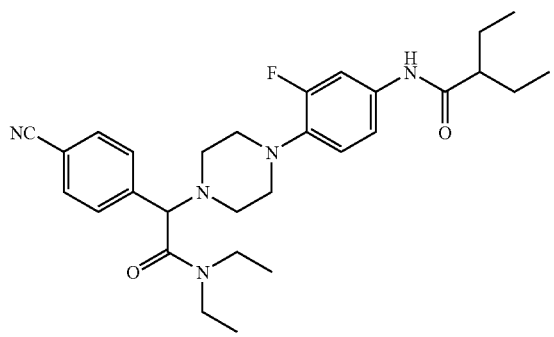

Example 254

N-(4-{4-[(4-Cyano-phenyl)-diethylcarbamoyl-methyl]-piperazin-1-yl}-3-fluoro-phenyl)-2-ethyl-butyramide MS: 508.4. $^1$H NMR (CDCl$_3$): 7.68-7.67 (m, 4H), 7.52-7.49 (m, 1H), 7.14 (bs, 1H), 7.08-7.06 (m, 1H), 6.88-6.85 (m, 1H), 3.43-3.31 (m, 4H), 3.12 (bs, 2H), 2.76-2.74 (m, 2H), 2.01-1.99 (m, 1H), 1.74-1.52 (m, 8H), 1.14-1.09 (m, 6H), 0.95-0.93 (m, 6H).

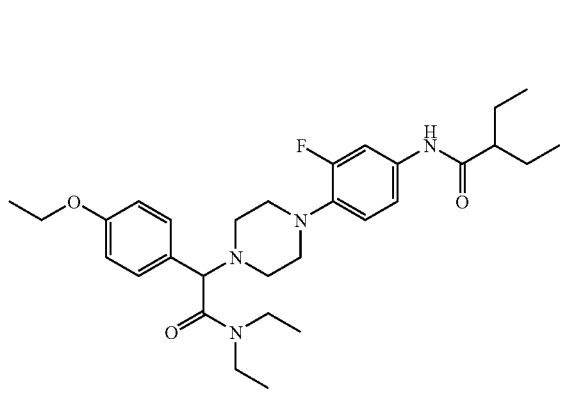

Example 255

N-(4-{4-[Diethylcarbamoyl-(4-ethoxy-phenyl)-methyl]-piperazin-1-yl}-3-fluoro-phenyl)-2-ethyl-butyramide MS: 527.6. $^1$H NMR (CDCl$_3$): 7.74 (s, 1H), 7.54 (d, J=11.4, 1H), 7.38 (d, J=8.4, 2H), 7.12 (d, J=8.4, 1H), 6.88-6.85 (m, 3H), 3.98-3.96 (m, 2H) 3.46-3.40 (m, 2H), 3.29-3.05 (m, 4H), 2.68 (bs, 4H), 2.06-2.04 (m, 1H), 1.71-1.66 (m, 2H), 1.54-1.50 (m, 2H), 1.34-1.32 (m, 3H) 1.09-1.06 (m, 6H), 0.94-0.91 (m, 6H).

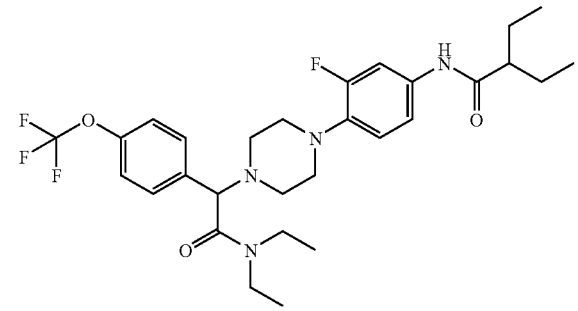

Example 256

N-(4-{4-[Diethylcarbamoyl-(4-trifluoromethoxy-phenyl)-methyl]-piperazin-1-yl}-3-fluoro-phenyl)-2-ethyl-butyramide MS: 567.6. $^1$H NMR (CDCl$_3$): 7.55-7.51 (m, 3H), 7.43 (bs, 1H), 7.20-7.19 (m, 2H), 7.10-7.09 (m, 1H), 6.87-6.84 (m, 1H), 3.43-3.37 (m, 2H), 3.33-3.30 (m, 2H), 3.07-3.06 (m, 4H), 2.67-2.66 (m, 4H), 2.05-2.01 (m, 1H), 1.72-1.66 (m, 2H), 1.56-1.51 (m, 2H), 1.13-1.08 (m, 6H), 0.94-0.91 (m, 6H).

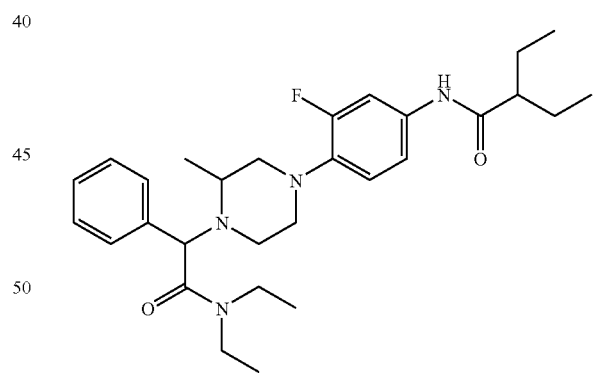

Example 257

N-{4-[4-(Diethylcarbamoyl-phenyl-methyl)-3-methyl-piperazin-1-yl]-3-fluoro-phenyl}-2-ethyl-butyramide MS: 497.5. $^1$H NMR (CDCl$_3$): 7.53-7.45 (m, 3H), 7.38-7.31 (m, 3H), 7.10-7.07 (m, 1H), 6.89-6.84 (m, 1H), 3.50-3.37 (m, 2H), 3.30-3.25 (m, 2H), 3.15-3.10 (m, 3H), 2.70 (bs, 4H), 2.05-2.01 (m, 1H), 1.75-1.68 (m, 2H), 1.60-1.52 (m, 2H), 1.24 (s, 3H) 1.09-1.02 (m, 6H), 0.97-0.91 (m, 6H).

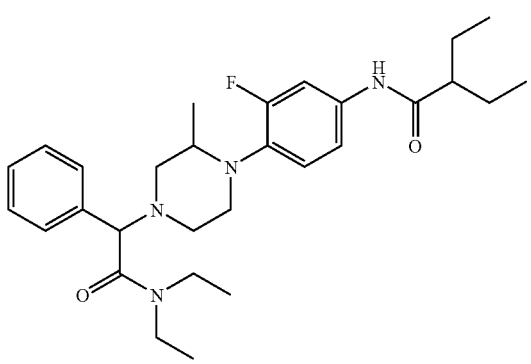

Example 258

N-{4-[4-(Diethylcarbamoyl-pyridin-2-yl-methyl)-2-methyl-piperazin-1-yl]-3-fluoro-phenyl}-2-ethyl-butyramide MS: 497.4. $^1$H NMR (CDCl$_3$): 7.63 (bs, 1H), 7.59 (dd, J=13.4, 2.2, 1H), 7.48-7.46 (m, 2H), 7.37-7.30 (m, 2H), 7.18-7.16 (m, 1H), 7.06-7.02 (m, 2H), 3.50-3.43 (m, 2H), 3.30-3.19 (m, 2H), 3.10-2.81 (m, 4H), 2.70-2.63 (m, 1H), 2.46-2.31 (m, 1H), 2.06-2.03 (m, 1H), 1.82-1.48 (m, 6H), 1.10-1.06 (m, 3H), 0.96-0.91 (m, 12H).

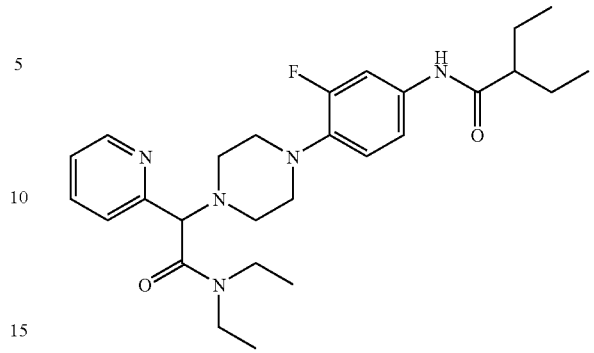

Example 260

N-{4-[4-(Diethylcarbamoyl-pyridin-2-yl-methyl)-piperazin-1-yl]-3-fluoro-phenyl}-2-ethyl-butyramide MS: 484.4. $^1$H NMR (CDCl$_3$): 8.59 (d, J=4.8, 1H), 7.77-7.66 (m, 2H), 7.50-7.43 (m, 2H), 7.25-7.18 (m, 2H), 7.13-7.08 (m, 1H), 3.39-3.35 (m, 2H), 3.10-3.09 (m, 4H), 2.80-2.62 (m, 4H), 2.06-2.04 (m, 1H), 1.74-1.67 (m, 2H), 1.57-1.53 (m, 2H), 1.17-1.15 (m, 2H), 1.09-1.07 (m, 2H), 0.96-0.92 (m, 12H).

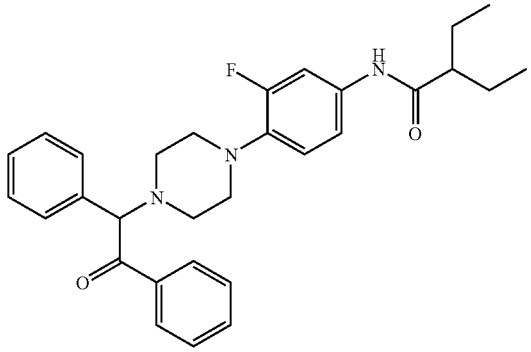

Example 259

2-Ethyl-N-{3-fluoro-4-[4-(2-oxo-1,2-diphenyl-ethyl)-piperazin-1-yl]-phenyl}-butyramide MS: 488.4. $^1$H NMR (CDCl$_3$): 8.05-8.02 (m, 2H), 7.53-7.26 (m, 9H), 7.11-7.07 (m, 2H), 6.89 (t, J=9.1, 1H), 3.17-3.09 (m, 4H), 2.71 (bs, 4H), 2.02-1.97 (m, 1H), 1.56-1.51 (m, 2H), 1.31-1.25 (m, 2H), 0.98-0.86 (m, 6H).

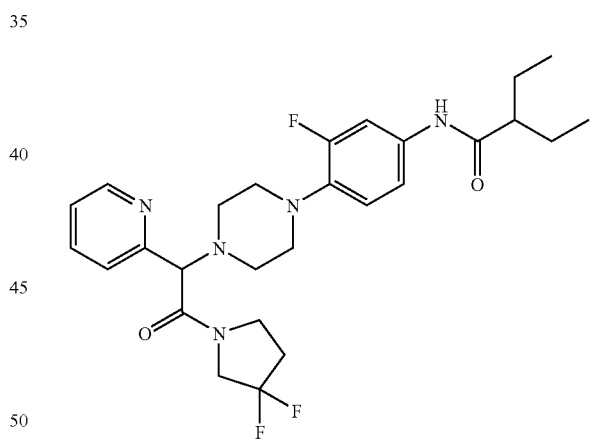

Example 261

N-(4-{4-[2-(3,3-Difluoro-pyrrolidin-1-yl)-2-oxo-1-pyridin-2-yl-ethyl]-piperazin-1-yl}-3-fluoro-phenyl)-2-ethyl-butyramide MS: 518.4. $^1$H NMR (CDCl$_3$): 8.55-8.53 (m, 1H), 7.73-7.69 (m, 2H), 7.49-7.48 (m, 1H), 7.25-7.24 (m, 2H), 7.11-7.09 (m, 1H), 6.89-6.84 (m, 1H), 4.16-3.68 (m, 3H), 3.13-3.06 (m, 4H), 2.76-2.62 (m, 4H), 2.38-2.28 (m, 2H), 2.02-1.98 (m, 1H), 1.73-1.66 (m, 2H), 1.57-1.50 (m, 2H), 0.98-0.96 (m, 6H).

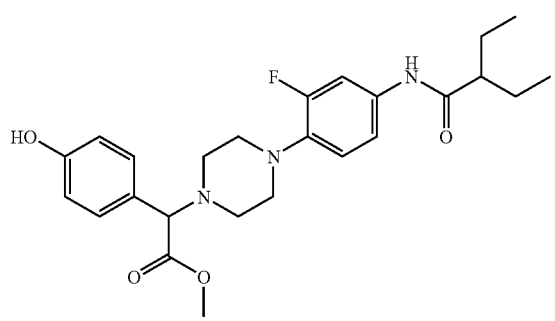

Example 262

{4-[4-(2-Ethyl-butyrylamino)-2-fluoro-phenyl]-piperazin-1-yl}-(4-hydroxy-phenyl)-acetic acid methyl ester MS: 458.6. $^1$H NMR (CDCl$_3$): 7.47-7.44 (m, 1H), 7.32-7.31 (m, 2H), 7.20 (bs, 1H), 7.10-7.08 (m, 1H), 6.88-6.82 (m, 3H), 3.72 (s, 3H), 3.10 (bs, 4H), 2.66 (bs, 4H), 2.02-2.00 (m, 1H), 1.74-1.68 (m, 2H), 1.57-1.54 (m, 2H), 0.96-0.93 (m, 6H).

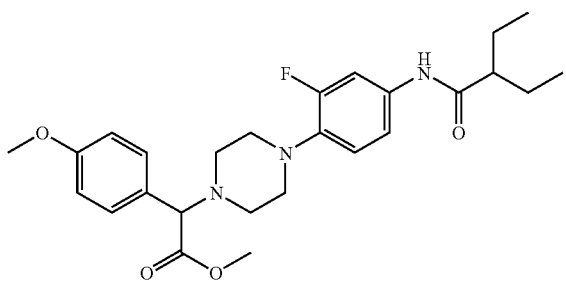

Example 263

{4-[4-(2-Ethyl-butyrylamino)-2-fluoro-phenyl]-piperazin-1-yl}-(4-methoxy-phenyl)-acetic acid methyl ester MS: 472.5. $^1$H NMR (CDCl$_3$): 7.49-7.48 (m, 1H), 7.40-7.38 (m, 2H), 7.22 (s, 1H), 7.10-7.08 (m, 1H), 6.90-6.85 (m, 3H), 3.81 (s, 3H), 3.71 (s, 3H), 3.10 (bs, 4H), 2.65 (bs, 4H), 2.02-1.99 (m, 1H), 1.71-1.69 (m, 2H), 1.56-1.54 (m, 2H), 0.96-0.92 (m, 6H).

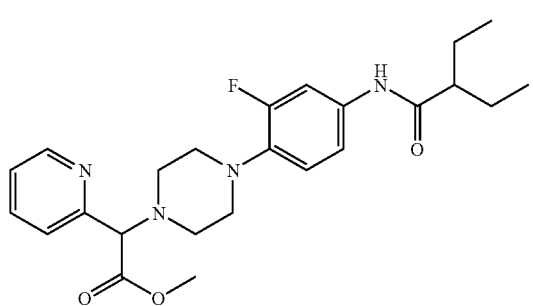

Example 264

{4-[4-(2-Ethyl-butyrylamino)-2-fluoro-phenyl]-piperazin-1-yl}-pyridin-2-yl-acetic acid methyl ester MS: 443.4. $^1$H NMR (CDCl$_3$): 8.60-8.59 (m, 1H), 7.74-7.70 (m, 1H), 7.57-7.55 (m, 1H), 7.47-7.42 (m, 1H), 7.26-7.23 (m, 2H), 7.12-7.10 (m, 1H), 6.89-6.85 (m, 1H), 3.75 (s, 3H), 3.11-3.09 (m, 4H), 2.76-2.74 (m, 4H), 2.05-1.98 (m, 1H), 1.80 (s, 2H), 1.73-1.66 (m, 2H), 1.56-1.51 (m, 2H), 0.95-0.91 (m, 6H).

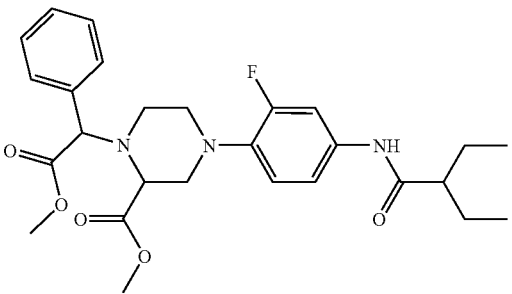

Example 265

4-[4-(2-Ethyl-butyrylamino)-2-fluoro-phenyl]-1-(methoxycarbonyl-phenyl-methyl)-piperazine-2-carboxylic acid methyl ester (diastereomer 2)

The title compound was separated by FCC to give diastereomer 2 and diastereomer 1 (Example 269). MS: 500.4. $^1$H NMR (CDCl$_3$): 7.46-7.41 (m, 3H), 7.35-7.33 (m, 3H), 7.16 (s, 1H), 7.10-7.07 (m, 1H), 6.88-6.84 (m, 1H), 3.70-3.63 (m, 6H), 3.55-3.50 (m, 1H), 3.25-3.08 (m, 2H), 2.97-2.85 (m, 4H), 2.00-1.97 (m, 1H), 1.73-1.51 (m, 4H), 0.96-0.92 (m, 6H).

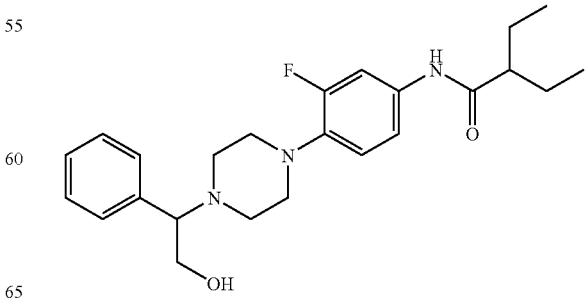

Example 266

2-Ethyl-N-{3-fluoro-4-[4-(2-hydroxy-1-phenyl-ethyl)-piperazin-1-yl]-phenyl}-butyramide

MS: 414.4.

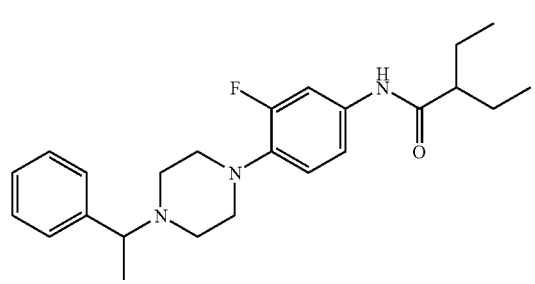

Example 267

2-Ethyl-N-{3-fluoro-4-[4-(1-phenyl-ethyl)-piperazin-1-yl]-phenyl}-butyramide

MS: 398.4.

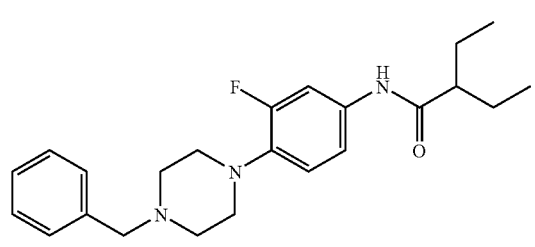

Example 268

N-[4-(4-Benzyl-piperazin-1-yl)-3-fluoro-phenyl]-2-ethyl-butyramide

MS: 384.27.

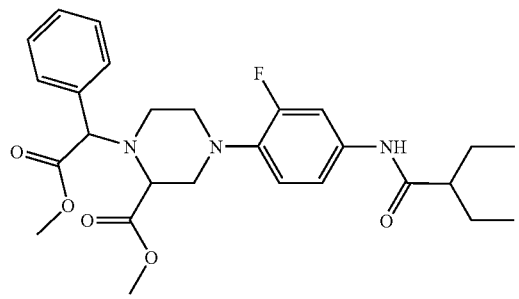

Example 269

4-[4-(2-Ethyl-butyrylamino)-2-fluoro-phenyl]-1-(methoxycarbonyl-phenyl-methyl)-piperazine-2-carboxylic acid methyl ester (diastereomer 1)

MS: 500.4.

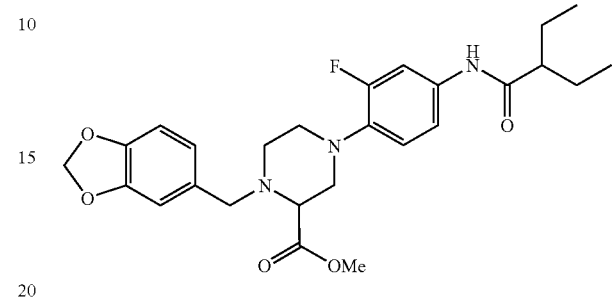

Example 270

1-Benzo[1,3]dioxol-5-ylmethyl-4-[4-(2-ethyl-butyrylamino)-2-fluoro-phenyl]-piperazine-2-carboxylic acid methyl ester

MS: 486.4.

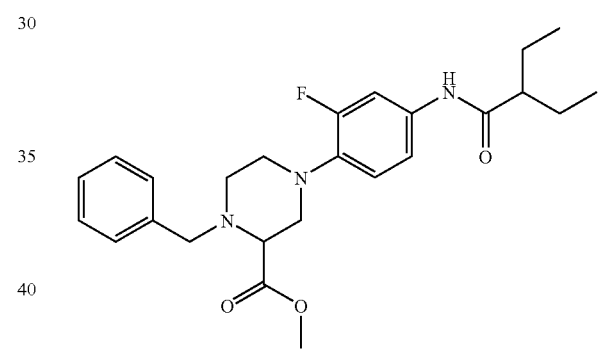

Example 271

1-Benzyl-4-[4-(2-ethyl-butyrylamino)-2-fluoro-phenyl]-piperazine-2-carboxylic acid methyl ester

MS: 442.4.

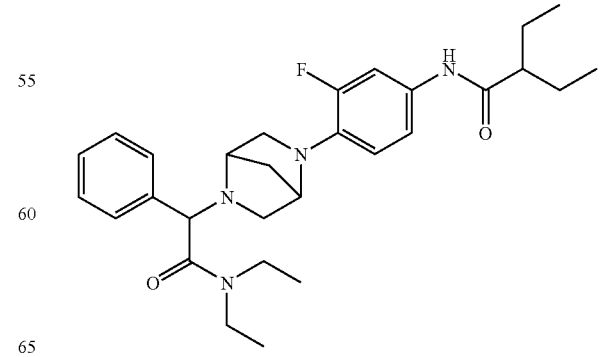

Example 272

N-{4-[5-(Diethylcarbamoyl-phenyl-methyl)-2,5-diaza-bicyclo[2.2.1]heptyl]-3-fluoro-phenyl}-2-ethyl-butyramide

MS: 495.6.

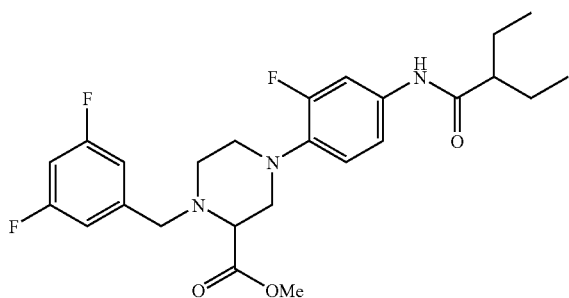

Example 273

1-(3,5-Difluoro-benzyl)-4-[4-(2-ethyl-butyrylamino)-2-fluoro-phenyl]-piperazine-2-carboxylic acid methyl ester

MS: 478.4.

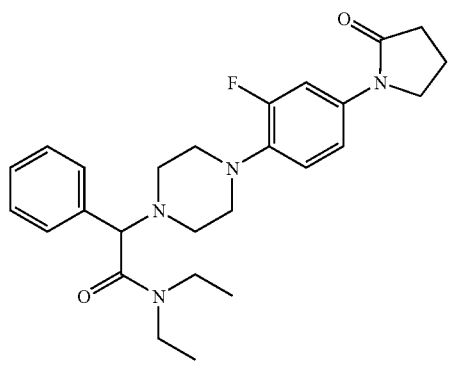

Example 274

N,N-Diethyl-2-{4-[2-fluoro-4-(2-oxo-pyrrolidin-1-yl)-phenyl]-piperazin-1-yl}-2-phenyl-acetamide

MS: 453.4.

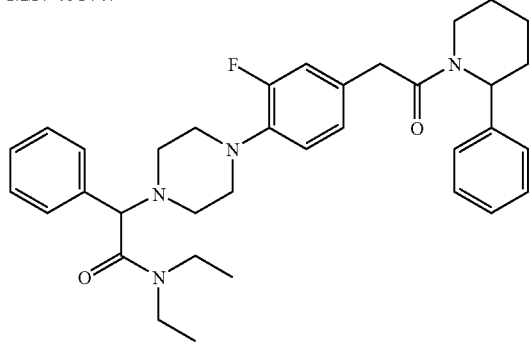

Example 275

N,N-Diethyl-2-(4-{2-fluoro-4-[2-oxo-2-(2-phenyl-piperidin-1-yl)-ethyl]-phenyl}-piperazin-1-yl)-2-phenyl-acetamide Step A. 2-(4-Chloro-3-fluoro-phenyl)-1-(2-phenyl-piperidin-1-yl)-ethanone. A solution of 4-chloro-3-fluoro phenyl acetic acid (0.30 g, 1.60 mmol), 2-phenyl piperidine (0.28 g, 1.76 mmol), and EDCI (0.36 g, 1.90 mmol) in DCM (15 mL) was stirred for 15 h. The mixture was diluted with 1 N NaHCO$_3$ (20 mL) and extracted with DCM (20 mL×3). The combined organic layers were dried (Na$_2$SO$_4$) and concentrated. The residue was purified by SiO$_2$ column chromatography (EtOAc:hexanes) to provide the title compound (0.35 g, 66%).

Step B. A solution of 2-(4-chloro-3-fluoro-phenyl)-1-(2-phenyl-piperidin-1-yl)-ethanone (0.25 g, 0.75 mmol), N,N-diethyl-2-phenyl-2-piperazin-1-yl-acetamide (0.23 g, 0.82 mmol), Pd$_2$(dba)$_3$ (0.01 g, 0.0075 mmol), XPhos (0.01 g, 0.015 mmol), and sodium t-butoxide (0.11 g, 1.05 mmol) in toluene (2 mL) was irradiated by microwave at 120° C. for 20 min. The solution was allowed to cool, filtered through diatomaceous earth, washing with DCM (10 mL). The filtrate was concentrated and the residue was purified by SiO$_2$ column chromatography (2 M NH$_3$ in MeOH:DCM) to provide the title compound (0.07 g, 16%). MS: 571.7. $^1$H NMR (CDCl$_3$): 7.48-7.46 (m, 2H), 7.38-7.35 (m, 4H), 7.28-7.23 (m, 2H), 7.19-7.15 (m, 4H), 6.90-6.89 (m, 2H), 3.70 (bs, 2H), 3.49-3.40 (m, 6H), 3.31-3.12 (m, 8H), 2.70-2.69 (m, 4H), 1.60-1.59 (m, 3H), 1.10-1.04 (m, 6H).

Examples 276 to 291 were prepared using methods similar to those described in Example 275, with the appropriate substituent changes.

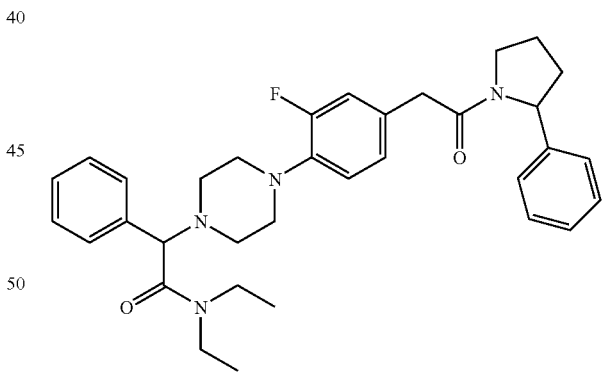

Example 276

N,N-Diethyl-2-(4-{2-fluoro-4-[2-oxo-2-(2-phenyl-pyrrolidin-1-yl)-ethyl]-phenyl}-piperazin-1-yl)-2-phenyl-acetamide MS: 557.7. $^1$H NMR (CDCl$_3$): 7.48 (bs, 1H), 7.38-7.36 (m, 4H), 7.28-7.22 (m, 2H), 7.20-7.18 (m, 4H), 6.79-6.69 (m, 2H), 3.72-3.70 (m, 2H), 3.49-3.40 (m, 6H), 3.31-3.12 (m, 6H), 2.70 (bs, 4H), 1.62-1.58 (m, 3H), 1.10-1.03 (m, 6H).

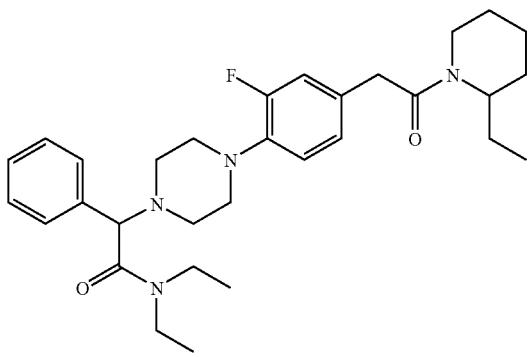

Example 277

N,N-Diethyl-2-(4-{4-[2-(2-ethyl-piperidin-1-yl)-2-oxo-ethyl]-2-fluoro-phenyl}-piperazin-1-yl)-2-phenyl-acetamide MS: 523.7. $^1$H NMR (CDCl$_3$): 7.46-7.45 (m, 2H), 7.36-7.30 (m, 3H), 6.92-6.85 (m, 3H), 3.63-3.61 (m, 2H), 3.45-3.43 (m, 2H), 3.29-3.19 (m, 2H), 3.11 (bs, 4H), 2.71-2.68 (m, 4H), 1.63-1.53 (m, 5H), 1.09-1.02 (m, 6H).

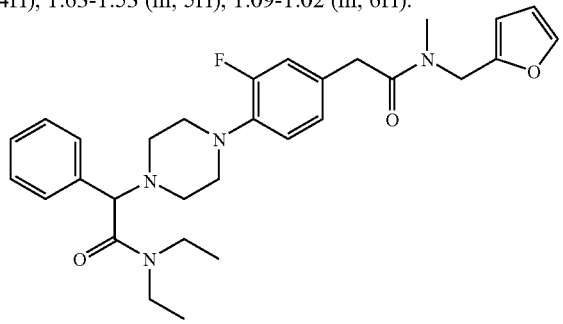

Example 278

N,N-Diethyl-2-(4-{2-fluoro-4-[(furan-2-yl methyl-methyl-carbamoyl)-methyl]-phenyl}-piperazin-1-yl)-2-phenyl-acetamide MS: 521.6. $^1$H NMR (CDCl$_3$): 7.49-7.48 (m, 2H), 7.38-7.33 (m, 4H), 6.93-6.85 (m, 4H), 6.33-6.30 (m, 1H), 4.57 (s, 1H), 4.40 (s, 1H), 3.76 (s, 1H), 3.64 (s, 1H), 3.48-3.38 (m, 2H), 3.29-3.13 (m, 6H), 2.96-2.95 (m, 3H), 1.27-1.25 (m, 2H), 1.10-1.03 (m, 6H).

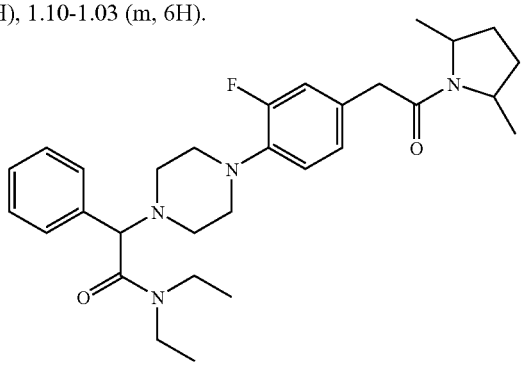

Example 279

2-(4-{4-[2-(2,5-Dimethyl-pyrrolidin-1-yl)-2-oxo-ethyl]-2-fluoro-phenyl}-piperazin-1-yl)-N,N-diethyl-2-phenyl-acetamide MS: 509.7. $^1$H NMR (CDCl$_3$): 7.46 (d, J=7.21, 2H), 7.36-7.30 (m, 3H), 6.95-6.90 (m, 2H), 6.86-6.83 (m, 1H), 4.13-4.04 (m, 4H), 3.56-3.36 (m, 4H), 3.30-3.16 (m, 2H), 3.10 (bs, 4H), 2.69 (bs, 4H), 1.65-1.59 (m, 5H), 1.31-1.21 (m, 12H).

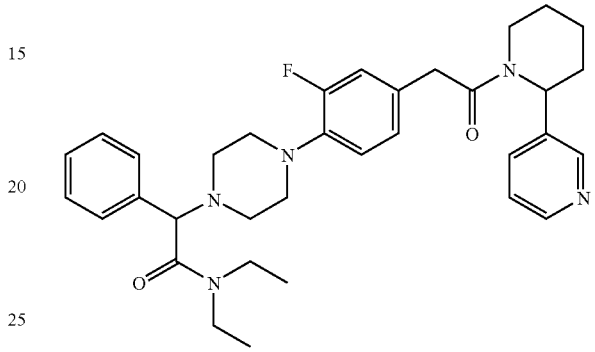

Example 280

N,N-Diethyl-2-(4-{2-fluoro-4-[2-oxo-2-(3,4,5,6-tetrahydro-2H-[2,3']bipyridinyl-1-yl)-ethyl]-phenyl}-piperazin-1-yl)-2-phenyl-acetamide MS: 572.7. $^1$H NMR (CDCl$_3$): 8.47 (s, 1H), 7.50-7.48 (m, 1H), 7.44-7.31 (m, 6H), 7.00-6.89 (m, 4H), 3.70 (bs, 2H), 3.54-3.48 (m, 6H), 3.30-3.16 (m, 8H), 2.70-2.64 (m, 4H), 1.61-1.59 (m, 3H), 1.10-1.04 (m, 6H).

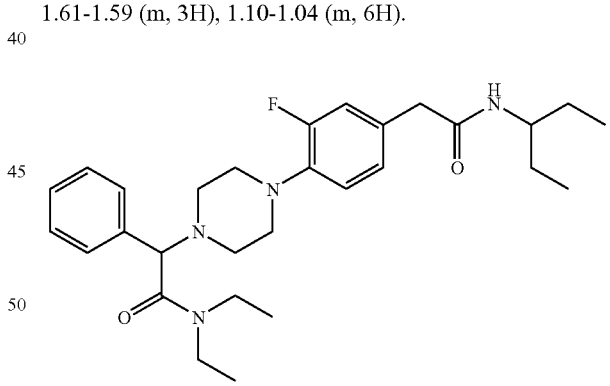

Example 281

N,N-Diethyl-2-(4-{4-[(1-ethyl-propylcarbamoyl)-methyl]-2-fluoro-phenyl}-piperazin-1-yl)-2-phenyl-acetamide MS: 497.6. $^1$H NMR (CDCl$_3$): 7.47-7.46 (m, 2H), 7.37-7.32 (m, 3H), 6.93-6.88 (m, 3H), 5.73-5.52 (m, 2H), 5.12-5.10 (m, 1H), 3.75-3.72 (m, 1H), 3.47-3.39 (m, 4H), 3.29-3.14 (m, 4H), 2.72 (bs, 4H), 1.48-1.45 (m, 2H), 1.28-1.24 (m, 2H), 1.09-1.02 (m, 6H), 0.81-0.78 (m, 6H).

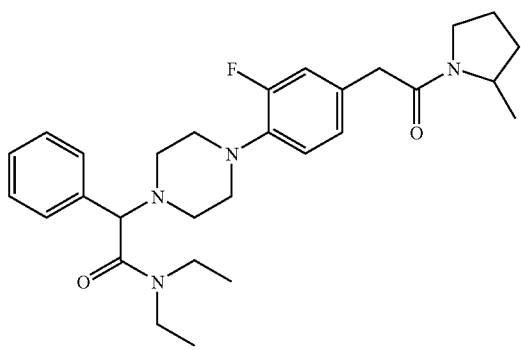

Example 282

N,N-Diethyl-2-(4-{2-fluoro-4-[2-(2-methyl-pyrrolidin-1-yl)-2-oxo-ethyl]-phenyl}-piperazin-1-yl)-2-phenyl-acetamide

MS: 495.7.

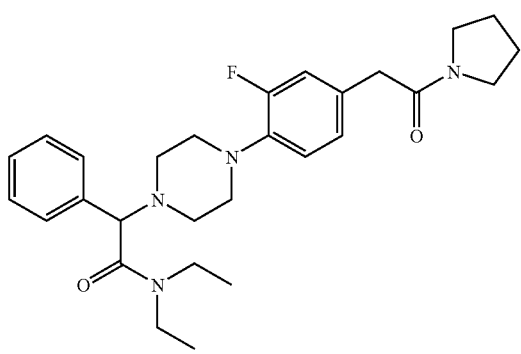

Example 283

N,N-Diethyl-2-{4-[2-fluoro-4-(2-oxo-2-pyrrolidin-1-yl-ethyl)-phenyl]-piperazin-1-yl}-2-phenyl-acetamide

MS: 481.7.

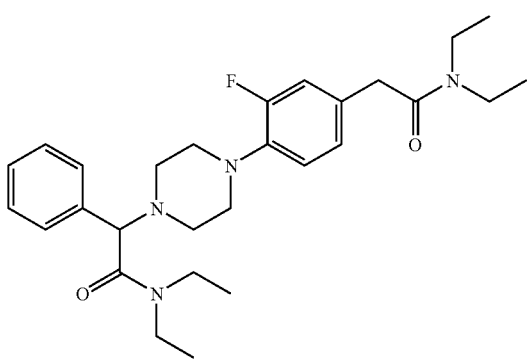

Example 284

N,N-Diethyl-2-{4-[4-(3-ethyl-2-oxo-1-phenyl-pentyl)-piperazin-1-yl]-3-fluoro-phenyl}-acetamide

MS: 483.7.

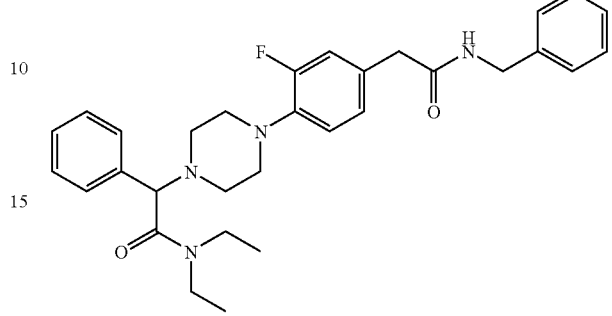

Example 285

N-Benzyl-2-{4-[4-(3-ethyl-2-oxo-1-phenyl-pentyl)-piperazin-1-yl]-3-fluoro-phenyl}-acetamide

MS: 517.4.

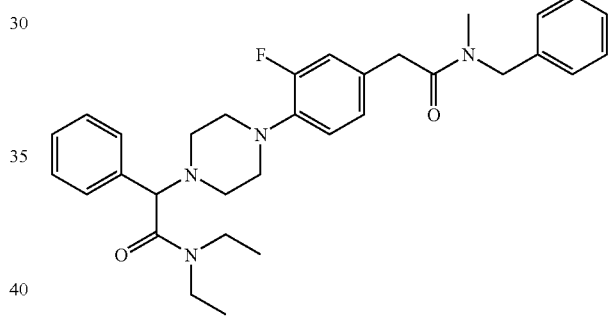

Example 286

N-Benzyl-2-{4-[4-(3-ethyl-2-oxo-1-phenyl-pentyl)-piperazin-1-yl]-3-fluoro-phenyl}-N-methyl-acetamide

MS: 531.6.

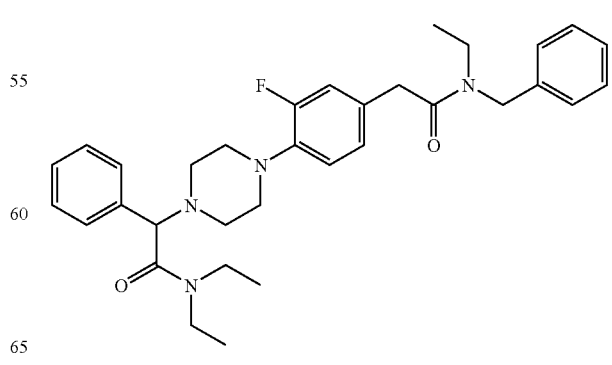

Example 287

N-Benzyl-N-ethyl-2-{4-[4-(3-ethyl-2-oxo-1-phenyl-pentyl)-piperazin-1-yl]-3-fluoro-phenyl}-acetamide

MS: 545.7.

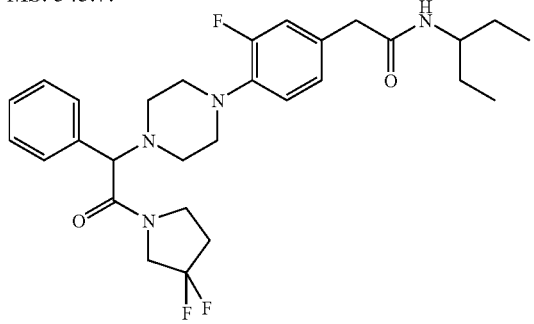

Example 288

2-(4-{4-[2-(3,3-Difluoro-pyrrolidin-1-yl)-2-oxo-1-phenyl-ethyl]-piperazin-1-yl}-3-fluoro-phenyl)-N-(1-ethyl-propyl)-acetamide

MS: 531.7.

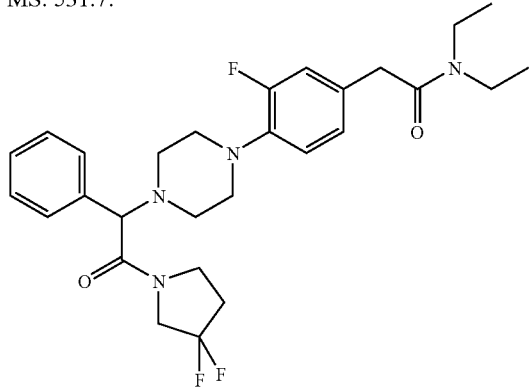

Example 289

2-(4-{4-[2-(3,3-Difluoro-pyrrolidin-1-yl)-2-oxo-1-phenyl-ethyl]-piperazin-1-yl}-3-fluoro-phenyl)-N,N-diethyl-acetamide

MS: 517.6.

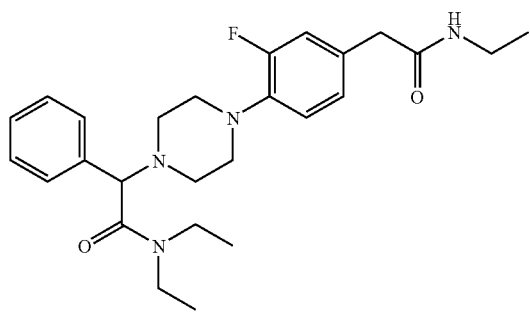

Example 290

N,N-Diethyl-2-[4-(4-ethylcarbamoylmethyl-2-fluoro-phenyl)-piperazin-1-yl]-2-phenyl-acetamide

MS: 455.4.

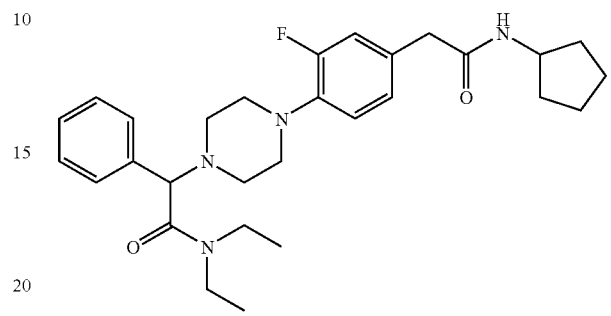

Example 291

2-[4-(4-Cyclopentylcarbamoylmethyl-2-fluoro-phenyl)-piperazin-1-yl]-N,N-diethyl-2-phenyl-acetamide

MS: 495.7.

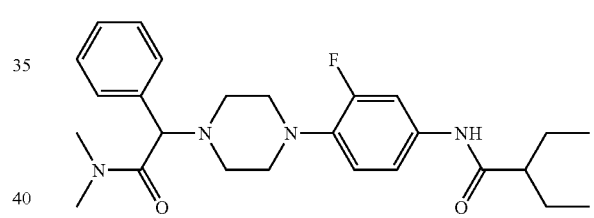

Example 292

N-{4-[4-(Dimethylcarbamoyl-phenyl-methyl)-piperazin-1-yl]-3-fluoro-phenyl}-2-ethyl-butyramide The title compound was prepared using methods analogous to those described in the preceding examples. MS: 455.3.

The compounds in Examples 293-296 may be prepared using methods analogous to those described in the preceding examples.

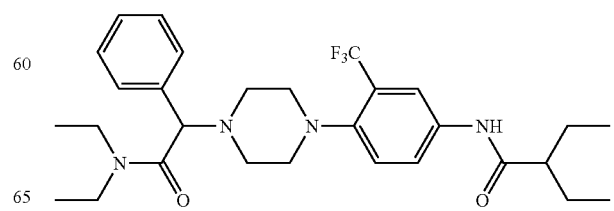

Example 293

N-{4-[4-(Diethylcarbamoyl-phenyl-methyl)-piperazin-1-yl]-3-trifluoromethyl-phenyl}-2-ethyl-butyramide

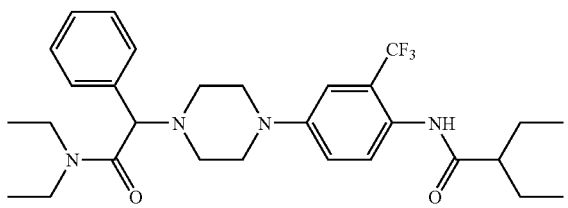

Example 294

N-{4-[4-(Diethylcarbamoyl-phenyl-methyl)-piperazin-1-yl]-2-trifluoromethyl-phenyl}-2-ethyl-butyramide

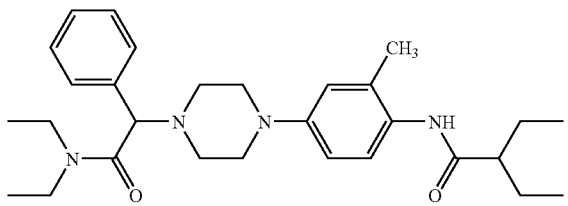

Example 295

N-{4-[4-(Diethylcarbamoyl-phenyl-methyl)-piperazin-1-yl]-2-methyl-phenyl}-2-ethyl-butyramide

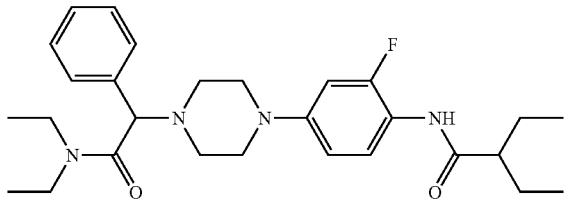

Example 296

N-{4-[4-(Diethylcarbamoyl-phenyl-methyl)-piperazin-1-yl]-2-fluoro-phenyl}-2-ethyl-butyramide Biological Methods
Radioligand Binding Assay KAN-Ts endogenously expressing Y2 receptors were used for the radioligand binding assay. Cells were grown to confluence on 150 cm² tissue culture plates, washed with phosphate-buffered saline (PBS), and scraped into 50 mL tubes. After centrifugation, the supernatant was aspirated, and the pellets frozen and stored at −80° C. Thawed pellets were homogenized with a polytron tissue grinder for 15 sec in 20 mM Tris-HCl, 5 mM EDTA. The homogenate was centrifuged at 800×g for 5 min and the collected supernatant was recentrifuged at 25000×g for 25 min. The resulting pellet was resuspended in binding buffer (20 mM HEPES, 120 mM NaCl, 0.22 mM $KH_2PO_4$, 1.3 mM $CaCl_2$, 0.8 mM $MgSO_4$). Membranes were incubated with [$^{125}$I]PYY (80 pM) in the presence or absence of test compound for 1 h at rt. The reaction was stopped by filtration through GF/C filter plates pre-soaked in 0.3% polyethylenimine and subsequently washed with Tris 50 mM, 5 mM EDTA buffer. Plates were dried for 1 h in a 55° C. oven, scintillation fluid was added and the radioactivity was counted in a Packard TopCount. Specific binding to the NPY receptor subtypes was determined by radioactivity that was bound in the presence of 1 mM NPY. Each binding experiment was repeated three to eight times, each in duplicate. $IC_{50}$ values (i.e. concentration of unlabelled peptide or antagonist required to compete for 50% of specific binding to the radioligand) were calculated using the GraphPad Prism software (GraphPad Software Inc., San Diego Calif.) with a fit to a sigmoidal dose response curve. Data for compounds tested are presented in Tables 1 and 2 as an average of results obtained.

TABLE 1

| EX | $IC_{50}$ (nM) |
|---|---|
| 1 | 58 |
| 2 | 2350 |
| 3 | 560 |
| 4 | 370 |
| 5 | 1900 |
| 6 | 71 |
| 7 | 377 |
| 8 | 10 |
| 9 | 14 |
| 10 | 15 |
| 11 | 12 |
| 12 | 26 |
| 13 | 58 |
| 14 | 112 |
| 15 | 162 |
| 16 | 280 |
| 17 | 1000 |
| 18 | 4000 |
| 19 | 10000 |
| 20 | 16 |
| 21 | 20 |
| 22 | 26 |
| 23 | 42 |
| 24 | 176 |
| 25 | 260 |
| 26 | 2000 |
| 27 | 30000 |
| 28 | 2900 |
| 29 | 65 |
| 30 | 570 |
| 31 | 24 |
| 32 | 180 |
| 33 | 180 |
| 34 | 40 |
| 35 | 33 |
| 36 | 210 |
| 37 | 56 |
| 38 | 440 |
| 39 | 800 |
| 40 | 110 |
| 41 | 77 |
| 42 | 4833 |
| 43 | 14 |
| 44 | 131 |
| 45 | 4000 |
| 46 | 6000 |
| 47 | 10000 |
| 48 | 30000 |
| 49 | 1300 |

TABLE 1-continued

| EX | IC$_{50}$ (nM) |
|---|---|
| 50 | 1800 |
| 51 | 1850 |
| 52 | 1400 |
| 53 | 12600 |
| 54 | 30000 |
| 55 | 30000 |
| 56 | 4000 |
| 57 | 30000 |
| 58 | 3000 |
| 59 | 13100 |
| 60 | 527 |
| 61 | 2500 |
| 62 | 1300 |
| 63 | 600 |
| 64 | 1000 |
| 65 | 1300 |
| 66 | 30000 |
| 67 | 30000 |
| 68 | 1400 |
| 69 | 25000 |
| 70 | 30000 |
| 71 | 30000 |
| 72 | 6000 |
| 73 | 30000 |
| 74 | 30000 |
| 75 | 30000 |
| 76 | 30000 |
| 77 | 30000 |
| 78 | 230 |
| 79 | 100 |
| 80 | 30000 |
| 81 | 30000 |
| 82 | 400 |
| 83 | 3600 |
| 84 | 3350 |
| 85 | 1300 |
| 86 | 4800 |
| 87 | 1700 |
| 88 | 1000 |
| 89 | 1035 |
| 90 | 9700 |
| 91 | 10000 |
| 92 | 5100 |
| 93 | 5000 |
| 94 | 10000 |
| 95 | 10000 |
| 96 | 9000 |
| 97 | 1100 |
| 98 | 12000 |
| 99 | 250 |
| 100 | 890 |
| 101 | 20000 |
| 102 | 20000 |
| 103 | 2500 |
| 104 | 7000 |
| 105 | 30000 |
| 106 | 12000 |
| 107 | 30000 |
| 108 | 26000 |
| 109 | 6100 |
| 110 | 2400 |
| 111 | 340 |
| 112 | 450 |
| 113 | 5750 |
| 114 | 10000 |
| 115 | 3200 |
| 116 | 10000 |
| 117 | 10000 |
| 118 | 3400 |
| 119 | 300 |
| 120 | 2400 |
| 121 | 610 |
| 122 | 8 |
| 123 | 17 |
| 124 | 15 |
| 125 | 20 |
| 126 | 25 |
| 127 | 20 |

TABLE 1-continued

| EX | IC$_{50}$ (nM) |
|---|---|
| 128 | 35 |
| 129 | 40 |
| 130 | 40 |
| 131 | 50 |
| 132 | 55 |
| 133 | 60 |
| 134 | 80 |
| 135 | 60 |
| 136 | 70 |
| 137 | 70 |
| 138 | 70 |
| 139 | 72 |
| 140 | 80 |
| 141 | 80 |
| 142 | 75 |
| 143 | 80 |
| 144 | 100 |
| 145 | 100 |
| 146 | 115 |
| 147 | 100 |
| 148 | 120 |
| 149 | 110 |
| 150 | 120 |
| 151 | 140 |
| 152 | 170 |
| 153 | 142 |
| 154 | 220 |
| 155 | 200 |
| 156 | 230 |
| 157 | 235 |
| 158 | 240 |
| 159 | 250 |
| 160 | 260 |
| 161 | 300 |
| 162 | 300 |
| 163 | 300 |
| 164 | 300 |

TABLE 2

| EX | IC$_{50}$ (nM) |
|---|---|
| 165 | 1100 |
| 166 | 560 |
| 167 | 3300 |
| 168 | 740 |
| 169 | 410 |
| 170 | 260 |
| 171 | 270 |
| 172 | 520 |
| 173 | 590 |
| 174 | 4000 |
| 175 | 10000 |
| 176 | 10000 |
| 177 | 10000 |
| 178 | 2900 |
| 179 | 540 |
| 180 | 770 |
| 181 | 9300 |
| 182 | 1650 |
| 183 | 4500 |
| 184 | 870 |
| 185 | 2400 |
| 186 | 210 |
| 187 | 148 |
| 188 | 200 |
| 189 | 10000 |
| 190 | 5700 |
| 191 | 380 |
| 192 | 5000 |
| 193 | 140 |
| 194 | 100 |
| 195 | 50 |
| 196 | 107 |
| 197 | 150 |

TABLE 2-continued

| EX | IC$_{50}$ (nM) |
|---|---|
| 198 | 350 |
| 199 | 148 |
| 200 | 15 |
| 201 | 330 |
| 202 | 900 |
| 203 | 735 |
| 204 | 400 |
| 205 | 300 |
| 206 | 20 |
| 207 | 70 |
| 208 | 20 |
| 209 | 100 |
| 210 | 25 |
| 211 | 26 |
| 212 | 55 |
| 213 | 30 |
| 214 | 40 |
| 215 | 100 |
| 216 | 10000 |
| 217 | 10 |
| 218 | 30 |
| 219 | 37 |
| 220 | 40 |
| 221 | 48 |
| 222 | 63 |
| 223 | 80 |
| 224 | 92 |
| 225 | 107 |
| 226 | 95 |
| 227 | 116 |
| 228 | 120 |
| 229 | 120 |
| 230 | 150 |
| 231 | 200 |
| 232 | 210 |
| 233 | 270 |
| 234 | 280 |
| 235 | 810 |
| 236 | 900 |
| 237 | 1100 |
| 238 | 1300 |
| 239 | 2500 |
| 240 | 18 |
| 241 | 300 |
| 242 | 3000 |
| 243 | 120 |
| 244 | 80 |
| 245 | 3000 |
| 246 | 2200 |
| 247 | 10000 |
| 248 | 13 |
| 249 | 100 |
| 250 | 9 |
| 251 | 18 |
| 252 | 104 |
| 253 | 102 |
| 254 | 44 |
| 255 | 44 |
| 256 | 26 |
| 257 | 68 |
| 258 | 145 |
| 259 | 70 |
| 260 | 100 |
| 261 | 130 |
| 262 | 162 |
| 263 | 250 |
| 264 | 550 |
| 265 | 600 |
| 266 | 785 |
| 267 | 1271 |
| 268 | 1400 |
| 269 | 2300 |
| 270 | 3000 |
| 271 | 4000 |
| 272 | 4000 |
| 273 | 7000 |
| 274 | 1600 |
| 275 | 142 |
| 276 | 200 |
| 277 | 320 |
| 278 | 320 |
| 279 | 540 |
| 280 | 570 |
| 281 | 560 |
| 282 | 940 |
| 283 | 1200 |
| 284 | 1500 |
| 285 | 1900 |
| 286 | 2100 |
| 287 | 2200 |
| 288 | 2100 |
| 289 | 3450 |
| 290 | 4300 |
| 291 | 8700 |
| 292 | 104 |

[$^{35}$S] GTPγS binding assay in KAN-Ts cells

Membranes from KAN-Ts cells were prepared as described above. Membranes were thawed on ice and diluted in 50 mM Tris-HCl buffer, pH 7.4 containing 10 mM MgCl$_2$, 1 mM EDTA, 100 mM NaCl, 5 mM GDP, 0.25% BSA. Assay mixture (150 mL) were preincubated with compounds for 30 min at rt. Then, 50 mL of [$^{35}$S]GTPγS in assay buffer was added to a final concentration of 200 pM and the assay mixtures were incubated for 1 h at rt. Reactions were terminated by rapid filtration thought GF/C filters. Filters were washed twice with ice cold 50 mM Tris-HCl, pH 7.4 containing 10 mM MgCl$_2$. Basal [$^{35}$S]GTPγS was measured in the absence of compounds. In initial experiments, nonspecific binding was measured in the presence of 100 mM GTPγS. This nonspecific binding never exceeded 10% of basal binding and was thus not subtracted from experimental data. Stimulation of [$^{35}$S]GTPγS is presented as percentage over basal and was calculated as one hundred times the difference between stimulated and basal binding (in cpm). Agonist concentration-response curves for increases in [$^{35}$S]GTPγS binding and antagonist inhibition curves for inhibition of PYY (300 nM)-stimulated [$^{35}$S]GTPγS binding were analyzed by non-linear regression using GraphPad Prism software (GraphPad Software Inc., San Diego Calif.). EC$_{50}$ (concentration of compound at which 50% of its own maximal stimulation is obtained) and IC$_{50}$ (concentration of its own maximal inhibition of PYY-stimulated [$^{35}$S]GTPγS binding is obtained) were derived from the curves. IC$_{50}$ values were corrected as follows: corrected IC$_{50}$ (IC$_{50}$corr)=IC$_{50}$/(1+[PYY]/EC$_{50}$ (PYY)) and pIC$_{50}$corr=−log IC$_{50}$corr. Example 10 was tested in this assay and was found to behave as an antagonist, with an pIC$_{50}$ of 5 nM.

What is claimed is:

1. A compound having NPY Y2 inhibitory activity of Formula (I):

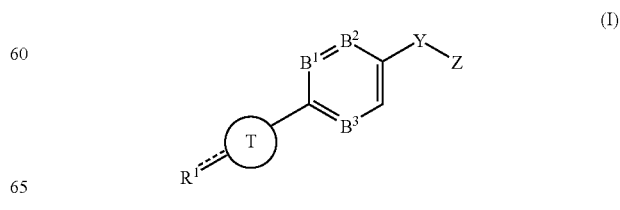

wherein

B¹, B², and B³ are each independently CH, or CR²;
where each R² is independently —C₁₋₄alkyl, -ethynyl, —OC₁₋₄alkyl, halo, —CF₃, or —CN;

Ring T is

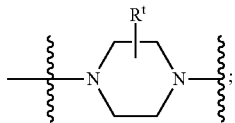

where R$^t$ is —H, —C₁₋₄alkyl, or —CO₂C₁₋₄alkyl;

R¹ is

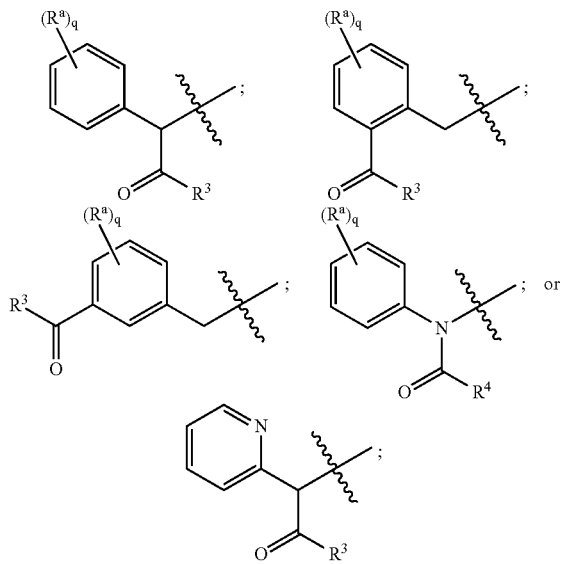

where q is 0, 1, 2, or 3;

each R$^a$ is independently —C₁₋₄alkyl, —C₃₋₈cycloalkyl, —OC₁₋₄alkyl, —OH, halo, —NO₂, —N(R$^u$)R$^v$, —CF₃, —OCF₃, —C(O)—C₁₋₄alkyl, —C(O)OC₁₋₄alkyl, —CN, —S(O)₁₋₂-C₁₋₆alkyl, —N(R$^u$)S(O)₁₋₂—C₁₋₆alkyl, —S(O)₁₋₂—N(R$^u$)R$^v$, or a 4- to 7-membered monocyclic heterocycloalkyl, or two adjacent R$^a$ substituents taken together form —O(CH₂)₁₋₂—O—:
where R$^u$ and R$^v$ are each independently —H or —C₁₋₄alkyl;

R³ is selected from the group consisting of:
i) —OC₁₋₄alkyl, —OC₁₋₄alkenyl, —O-benzyl, —O-phenyl, —NHNH₂, phenyl;
ii) —NR$^b$R$^c$, where R$^b$ is —H or —C₁₋₄alkyl and R$^c$ is a —C₁₋₄alkyl, —C₃₋₄-alkenyl, monocyclic cycloalkyl optionally fused to phenyl, or monocyclic heterocycloalkyl group, each optionally substituted with R$^d$;
where R$^d$ is —C₁₋₄alkyl, —OC₁₋₄alkyl, —OH, —CF₃, —OCF₃, halo, —NO₂, N(R$^e$)R$^f$, —C(O)—C₁₋₄alkyl, —C(O)phenyl, —C(O)OC₁₋₄alkyl, —CN, —S(O)₁₋₂—C₁₋₆alkyl, —N(R$^e$)—S(O)₁₋₂—C₁₋₆alkyl, or —S(O)₁₋₂—N(R$^e$)R$^f$, or a 4- to 7-membered monocyclic heterocycloalkyl group optionally substituted with —C₁₋₄alkyl, fluoro, or —CF₃;

where R$^e$ is —H or —C₁₋₄alkyl and R$^f$ is —C₁₋₄alkyl;
iii) —NR$^g$R$^h$, where R$^g$ is —H or —C₁₋₄alkyl and R$^h$ is —(CH₂)₀₋₂-phenyl or —(CH₂)₀₋₂-(monocyclic heteroaryl);
where each phenyl or heteroaryl is optionally substituted with R$^i$;
R$^i$ is —C₁₋₄alkyl, —OC₁₋₄alkyl, —OH, —CF₃, —OCF₃, halo, —CN, or —NR$^j$R$^k$;
where R$^j$ and R$^k$ are independently —H or —C₁₋₄alkyl, or R$^j$ and R$^k$ taken together with their nitrogen of attachment form a 4- to 7-membered monocyclic heterocycloalkyl; and
iv) a nitrogen-linked 4- to 7-membered monocyclic heterocycloalkyl, optionally substituted with —C₁₋₄alkyl, —OC₁₋₄alkyl, —OH, —CF₃, —OCF₃, halo, —CN, —C(O)—OC₁₋₄alkyl, or —NR$^j$R$^k$;

R⁴ is —C₁₋₈alkyl, phenyl, or monocyclic heteroaryl, where each phenyl or heteroaryl is optionally substituted with —C₁₋₄alkyl, —C₃₋₈cycloalkyl, —OC₁₋₄alkyl, —OH, halo, —NO₂, —N(R$^w$)R$^x$, —CF₃, —C(O)OC₁₋₄alkyl, or —CN;
where R$^w$ and R$^x$ are each independently —H or —C₁₋₄alkyl;

Y is selected from the group consisting of —CH(OH)—, —C(O)—, —CH₂C(O)—, —C(=N—OH)—, —CO₂—, —C(O)N(R$^L$)—, —CH₂C(O)N(R$^L$)—, —N(R$^L$)—, —N(R$^L$)C(O)—, —N(R$^y$)C(O)—, —CH₂N(R$^L$)C(O)—, —N(R$^L$)C(O)N(R$^L$)—, N(R$^L$)SO₂—, —N(SO₂C₁₋₄alkyl)SO₂—, —N(R$^L$)SO₂N(R$^L$)—, —N(R$^L$)SO₂NH—, and —N(R$^L$)SO₂N(R$^L$)CO₂—;
where each R$^L$ is —H, —C₁₋₄alkyl, or phenyl; or, alternatively, two R$^L$ groups taken together form —CH₂CH₂—, wherein Y is not

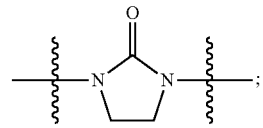

R$^y$ and Z together form —(CH₂)₃— or —(CH₂)₄—, optionally substituted with —C₁₋₄alkyl; and
R$^z$ and Z together form —(CH₂)₂— or —(CH₂)₃—, each optionally substituted with —C₁₋₄alkyl;

Z is selected from the group consisting of:
a) RingA, where RingA is phenyl, optionally mono-, di-, or tri-substituted with R$^m$;
where each R$^m$ is independently selected from the group consisting of —C₁₋₆alkyl, —C₁₋₆alkyl-OH, —CF₃, —C₂₋₆alkenyl, —C₂₋₆alkynyl, —C₃₋₈cycloalkyl, —CN, —NO₂, —N(R$^n$)R$^o$, —C(O)C₁₋₆alkyl, —C(O)OH, —C(O)OC₁₋₆alkyl, —C(O)N(R$^n$)R$^o$, —S—C₁₋₆alkyl, —S(O)₁₋₂—C₁₋₆alkyl, —SCF₃, halo, —OH, —OC₁₋₆alkyl, —OCF₃, —OC₃₋₆alkenyl, and —OC₃₋₆alkynyl;
where R$^n$ and R$^o$ are each independently —H or —C₁₋₆alkyl;
b) RingB, where RingB is monocyclic or fused bicyclic heteroaryl, optionally mono-, di-, or tri-substituted with R$^m$;
c) RingC, where RingC is heterocycloalkyl, optionally mono- or di-substituted with —C₁₋₄alkyl, —C₃₋₈cycloalkyl, halo, phenyl, or pyridyl;

d) RingD, where RingD is monocyclic cycloalkyl, optionally substituted with —OH, halo, or —C$_{1-4}$alkyl, and optionally fused to phenyl;

e) —C(R$^q$)$_2$-RingA, —C(R$^q$)$_2$-RingB, —CH$_2$-RingC, —CH$_2$-RingD;

where each R$^q$ is —H or —C$_{1-4}$alkyl, or two R$^q$ substituents taken together form a C$_{3-6}$cycloalkyl;

f) —C$_{1-8}$alkyl, optionally substituted with —OH, halo, or —CF$_3$;

g) -ethyl substituted with RingA, RingB, monocyclic heterocycloalkyl, or —N(R$^r$)R$^s$, and optionally further substituted with —OH or —CF$_3$;

where R$^r$ and R$^s$ are each independently —H or —C$_{1-4}$alkyl;

h) —CH═CH-RingA, —CH═CH-RingB; and i) bicyclo[2.2.1]heptan-2-yl;

or a pharmaceutically acceptable salt or pharmaceutically acceptable prodrug of such compound;

with the proviso that when Z is RingA or a monocyclic RingB, Y is —N(H)C(O)—, and one R$^m$ is attached at the ortho-position relative to the attachment point of Y to RingA or RingB, then said ortho-positional R$^m$ is not iodo or bromo.

2. A compound according to claim 1, wherein B$^1$, B$^2$ and B$^3$ are CH.

3. A compound according to claim 1, wherein Ring T is

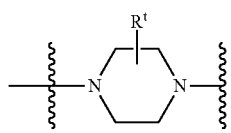

and is —H or —CH$_3$.

4. A compound according to claim 1, wherein R$^1$ is

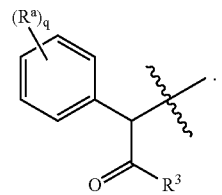

5. A compound according to claim 1, wherein Y is —N(H)C(O)— or —C(O)N(H)—.

6. A compound according to claim 1, wherein Y is —C(O)—.

7. A compound according to claim 1, wherein Z is piperidin-1-yl or pyrrolidin-1-yl, optionally substituted with methyl, ethyl, phenyl, or pyridinyl.

8. A compound according to claim 1, wherein Z is selected from the group consisting of isopropyl, 1-methylpropyl, isopentyl, cyclopropyl, cyclobutyl, cyclopentyl, or cyclohexyl.

9. A compound having NPY Y2 inhibitory activity of Formula (II):

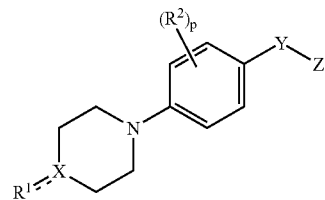

wherein X is N and R$^1$ is

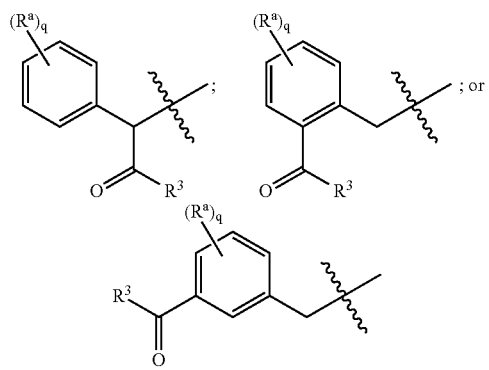

where q is 0, 1, 2, or 3;

each R$^a$ is independently —C$_{1-4}$alkyl, —C$_{1-4}$cycloalkyl, —OH, halo, —NO$_2$, —N(R$^u$)R$^v$, —CF$_3$, —C(O)—C$_{1-4}$alkyl, —C(O)OC$_{1-4}$alkyl, —CN, —S(O)$_{1-2}$—C$_{1-6}$alkyl, —N(R$^u$)—S(O)$_{1-2}$—C$_{1-6}$alkyl, —S(O)$_{1-2}$—N(R$^u$)R$^v$, or a 4- to 7-membered monocyclic heterocycloalkyl, or two adjacent R$^a$ substituents taken together form —O(CH$_2$)$_{1-2}$—O—;

where R$^u$ and R$^v$ are each independently —H or —C$_{1-4}$alkyl;

R$^3$ is selected from the group consisting of;

i) —OC$_{1-4}$alkyl, —OC$_{3-4}$alkenyl, —O-benzyl, —O-phenyl, phenyl;

ii) —NR$^b$R$^c$, where R$^b$ is —H or —C$_{1-4}$alkyl and R$^c$ is a —C$_{1-4}$alkyl, —C$_{3-4}$alkenyl, monocyclic cycloalkyl optionally fused to phenyl, or monocyclic heterocycloalkyl group, each optionally substituted with R$^d$;

where R$^d$ is —C$_{1-4}$alkyl, —OC$_{1-4}$alkyl, —OH, —CF$_3$, —OCF$_3$, halo, —NO$_2$, —N(R$^e$)R$^f$, —C(O)—C$_{1-4}$alkyl, —C(O)phenyl, —C(O)OC$_{1-4}$alkyl, —CN, —S(O)$_{1-2}$—C$_{1-6}$alkyl, —N(R$^e$)—S(O)$_{1-2}$—C$_{1-6}$alkyl, or —S(O)$_{1-2}$—N(R$^e$)R$^f$, or a 4- to 7-membered monocyclic heterocycloalkyl group optionally substituted with —C$_{1-4}$alkyl, fluoro, or —CF$_3$;

where R$^e$ is —H or —C$_{1-4}$alkyl and R$^f$ is —C$_{1-4}$alkyl;

iii) —NR$^g$R$^h$, where R$^g$ is —H or —C$_{1-4}$alkyl and R$^h$ is —(CH$_2$)$_{0-2}$-phenyl or —(CH$_2$)$_{0-2}$-(monocyclic heteroaryl);

where each phenyl or heteroaryl is optionally substituted with R$^i$;

R$^i$ is —C$_{3-4}$alkyl, —OC$_{1-4}$alkyl, —OH, —CF$_3$, —OCF$_3$, halo, —CN, or —NR$^j$R$^k$;

where R$^j$ and R$^k$ are independently —H or —C$_{1-4}$alkyl, or R$^j$ and R$^k$ taken together with their nitrogen of attachment form a 4- to 7-membered monocyclic heterocycloalkyl; and iv) a nitrogen-linked 4- to 7-membered monocyclic heterocycloalkyl, optionally substituted with —$C_{1-4}$alkyl, —$OC_{1-4}$alkyl, —OH, —$CF_3$, —$OCF_3$, halo, —CN, —C(O)O$C_{1-4}$alkyl, or —NR$^j$R$^k$;

p is 0, 1, or 2;

each R$^2$ is independently —$C_{1-4}$alkyl, —$C_{3-8}$cycloalkyl, —$OC_{1-4}$alkyl, halo, —$CF_3$, or —CN;

Y is selected from the group consisting of —N(R$^L$)C(O)—, —C(O)N(R$^L$)—, and —N(R$^L$)C(O)N(R$^L$)—;
where each R$^L$ is —H, —$C_{1-4}$alkyl, or phenyl;

Z is selected from the group consisting of:
a) RingA, where RingA is phenyl, optionally mono-, di-, or tri-substituted with R$^m$;
where each R$^m$ is independently selected from the group consisting of —$C_{1-6}$alkyl, —$C_{1-6}$alkyl-OH, —$CF_3$, —$C_{2-6}$alkenyl, —$C_{2-6}$alkynyl, —$C_{3-8}$cycloalkyl, —CN, —$NO_2$, —N(R$^n$)R$^o$, —C(O)$C_{1-6}$alkyl, —C(O)OH, —C(O)O$C_{1-6}$alkyl, —C(O)N(R$^n$)R$^o$, —S—$C_{1-6}$alkyl, —S(O)$_{1-2}$—$C_{1-6}$alkyl, —$SCF_3$, halo, —OH, —O$C_{1-6}$alkyl, —$OCF_3$, —$OC_{3-6}$alkenyl, and —$OC_{3-6}$alkynyl;
where R$^n$ and R$^o$ are each independently —H or —$C_{1-8}$alkyl;
b) RingB, where RingB is monocyclic or fused bicyclic heteroaryl, optionally mono-, di-, or tri-substituted with R$^m$;
c) RingC, where RingC is heterocycloalkyl, optionally substituted with —$C_{1-4}$alkyl, —$C_{3-8}$cycloalkyl, or halo;
d) RingD, where RingD is monocyclic cycloalkyl, optionally substituted with —OH, halo, or —$C_{1-4}$alkyl, and optionally fused to phenyl;
e) —C(R$^q$)$_2$-RingA, —C(R$^q$)$_2$-RingB, —$CH_2$-RingC, —$CH_2$-RingD;
where each R$^q$ is —H or —$C_{1-4}$alkyl, or two R$^q$ substituents taken together form a $C_{3-8}$cycloalkyl;
f) —$C_{1-8}$alkyl, optionally substituted with —OH, halo, or —$CF_3$;
g) -ethyl substituted with RingA, RingB, monocyclic heterocycloalkyl, or —N(R$^r$)R$^s$, and optionally further substituted with —OH or —$CF_3$;
where R$^r$ and R$^s$ are each independently —H or —$C_{1-4}$alkyl;
h) —CH═CH-RingA, and —CH═CH-RingB,
or a pharmaceutically acceptable salt, or a pharmaceutically acceptable prodrug of such compound;

with the proviso that when Z is RingA or a monocyclic RingB, Y is —N(H)C(O)—, and one R$^m$ is attached at the ortho-position relative to the attachment point of Y to RingA or RingB, then said ortho-positional R$^m$ is not iodo or bromo.

10. A compound according to claim 9, wherein R$^1$ is

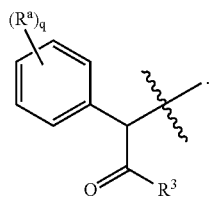

11. A compound according to claim 9, wherein q is 0.
12. A compound according to claim 9, wherein q is 1 or 2.
13. A compound according to claim 9, wherein R$^a$ is methyl, ethyl, propyl, isopropyl, tert-butyl, cyclopropyl, cyclobutyl, cyclopentyl, cyclohexyl, methoxy, ethoxy, isopropoxy, sec-butyloxy, hydroxy, fluoro, bromo, chloro, iodo, nitro, amino, methylamino, dimethylamino, ethylamino, ethylmethylamino, diethylamino, dipropylamino, trifluoromethyl, acetyl, propionyl, methoxycarbonyl, ethoxycarbonyl, cyano, methylsulfonyl, methanesulfonylamino, methylsulfamoyl, pyrrolidinyl, piperidinyl, morpholinyl, or thiomorpholinyl.

14. A compound according to claim 9, wherein two R$^a$ substituents form methylenedioxy.

15. A compound according to claim 9, wherein R$^a$ is methyl, methoxy, fluoro, chloro, bromo, difluoro, dichloro, methoxy, trifluoromethyl, nitro, or cyano.

16. A compound according to claim 9, wherein R$^a$-substituted phenyl groups are selected from the group consisting of phenyl, 4-methylphenyl, 3-methoxyphenyl, 4-methoxyphenyl, 2-fluorophenyl, 3-fluorophenyl, 4-fluorophenyl, 3-chlorophenyl, 4-chlorophenyl, 4-bromophenyl, 2,3-difluorophenyl, 2-fluoro-5-bromophenyl, 3,5-difluorophenyl, 3,4-dichlorophenyl, 2-chloro-4-fluorophenyl, 4-trifluoromethylphenyl, 4-nitrophenyl, 4-cyanophenyl, and benzo[1,3]dioxolanyl.

17. A compound according to claim 9, wherein R$^3$ is selected from the group consisting of:
i) methoxy, ethoxy, propoxy, isopropoxy, butoxy, allyloxy, benzyloxy, or phenyloxy;
ii) —NR$^b$R$^c$, where R$^b$ is —H, methyl, ethyl, propyl, isopropyl, or butyl; and R$^c$ is methyl, ethyl, propyl, isopropyl, butyl, tert-butyl, allyl, cyclopropyl, cyclobutyl, cyclopentyl, cyclohexyl, indanyl, azetidinyl, pyrrolidinyl, piperidinyl, homopiperidinyl, tetrahydrofuranyl, tetrahydropyranyl, piperazinyl, morpholinyl, thiomorpholinyl, dioxothiomorpholinyl, or thiazolidinyl;
iii) —NR$^g$R$^h$, where R$^g$ is —H, methyl, ethyl, propyl, isopropyl, or butyl; and R$^h$ is phenyl, pyridyl, pyrimidinyl, pyrazinyl, indolyl, furanyl, thiophenyl, pyrazolyl, imidazolyl, oxazolyl, isoxazolyl, thiazolyl, benzyl, pyridylmethyl, pyrimidinylmethyl, pyrazinylmethyl, indolylmethyl, furanylmethyl, thiophenylmethyl, pyrazolylmethyl, imidazolylmethyl, oxazolylmethyl, isoxazolylmethyl, thiazolylmethyl, phenethyl, or pyridylethyl; and
iv) azetidinyl, pyrrolidinyl, piperidinyl, homopiperidinyl, morpholinyl, thiomorpholinyl, tetrahydrofuranyl, tetrahydropyranyl, or thiazolidinyl;
where each of i)-iv) is optionally substituted.

18. A compound according to claim 9, wherein R$^3$ is selected from the group consisting of methoxy, ethoxy, phenoxy, benzyloxy, hydroxy, ethylamino, diethylamino, propylamino, methylamino, dipropylamino, ethyl-methylamino, allylamino, cyclopropylamino, indanylamino, piperidinylamino, tetrahydropyranylamino, morpholinylamino, thiazolidinylamino, phenylamino, pyridylamino, isoxazolylamino, thiazolylamino, benzyl, thiophenylmethyl, furanylmethyl, pyridylmethyl, phenethyl, pyridylethyl, pyrrolidinyl, piperidinyl, piperazinyl, and morpholinyl, each optionally substituted.

19. A compound according to claim 9, wherein R$^3$ is selected from the group consisting of:
i) methoxy;
ii) ethylamino, diethylamine, ethyl-methylamino, dipropylamino, 3-methoxypropylamino, 2,2,2-trifluoroethylamino, 2-fluoroethylamino, 2-ethoxyethylamino, 2-diethylaminoethylamino, methoxycarbonylmethylamino, —$NHCH_2C(O)$phenyl, allylamino, indan-1-ylamino, 2-pyrrolidin-1-yl-ethylamino, 2-morpholin-4-ylethylamino, tetrahydropyran-4-ylamino, 4,5-dihydro-thiazol-2-ylamino, 1-methyl-piperidin-4-ylamino, 1-isopropyl-piperidin-4-ylamino, morpholin-4-ylamino;

iii) phenylamine, 3-methoxyphenylamino, 4-morpholin-4-yl-phenylamino, 4-methylthiazol-2-ylamino, 5-methyl-thiazol-2-ylamino, isoxazol-3-ylamino, 6-methoxy-pyridin-3-ylamino, 4,6-dimethyl-pyridin-2-ylamino, benzylamino, 3-fluorobenzylamino, 4-methoxybenzylamino, pyridin-2-ylmethylamino, thiophen-2-ylmethylamino, furan-2-ylmethylamino, phenethylamino, 2-pyridin-4-yl-ethylamino; and iv) pyrrolidinyl, 3,3-difluoropyrrolidinyl, piperidinyl, 4-methyl-piperidin-1-yl, 4,4-difluoropiperidin-1-yl, piperazinyl, 4-methyl-piperazin-1-yl, 4-isopropyl-piperazin-1-yl, 4-(2-morpholin-4-yl-2-oxo-ethyl)-piperazin-1-yl, and morpholin-4-yl.

20. A compound according to claim 9, wherein $R^3$ is 4-fluoro-piperidin-1-yl, 3,3-difluoro-azetidin-1-yl, azetidin-1-yl, or phenyl.

21. A compound according to claim 9, wherein $R^2$ is independently methyl, ethyl, propyl, isopropyl, butyl, cyclopropyl, cyclobutyl, cyclopentyl, cyclohexyl, methoxy, ethoxy, propoxy, isopropoxy, butyloxy, fluoro, bromo, chloro, odo, trifluoromethyl, or cyano.

22. A compound according to claim 9, wherein each $R^2$ is independently methyl, fluoro, chloro, bromo, trifluoromethyl, or cyano.

23. A compound according to claim 9, wherein $R^2$ is ethynyl or methoxy.

24. A compound according to claim 9, wherein each $R^L$ is independently —H, methyl, ethyl, propyl, isopropyl, butyl, tert-butyl, or phenyl.

25. A compound according to claim 9, wherein Y is —N(H)C(O), —N(phenyl)C(O)—, —C(O)N(H)—, —N(H)C(O)N(H)—, or —N(ethyl)C(O)N(ethyl)-.

26. A compound according to claim 9, wherein Y is —N(H)C(O)—.

27. A compound according to claim 9, wherein Z is selected from the group consisting of:
a) RingA, where RingA is phenyl, indanyl, or tetrahydronaphthalenyl;
b) RingB, where RingB is pyridyl, pyrimidinyl, pyrazinyl, indolyl, furanyl, thiophenyl, pyrazolyl, imidazolyl, oxazolyl, isoxazolyl, thiazolyl, indolyl, benzofuranyl, benzothiophenyl, benzimidazolyl, benzoxazolyl, benzothiazolyl, pyrrolopyridinyl, imidazopyridinyl, quinolinyl, isoquinolinyl, or naphthyridinyl;
c) RingC, where RingC is azetidinyl, pyrrolidinyl, piperidinyl, homopiperidinyl, tetrahydrofuranyl, tetrahydropyranyl, piperazinyl, morpholinyl, thiomorpholinyl, dioxothiomorpholinyl, thiazolidinyl, or dihydroindolyl;
d) RingD, where RingD is cyclopropyl, cyclobutyl, cyclopentyl, cyclohexyl, cycloheptyl, cyclooctyl, indanyl, bicyclo[4.2.0]octa-1,3,5-triene, or tetrahydronaphthyl;
e) —CH$_2$-RingA, —CH$_2$-RingB, —CH$_2$-RingC, —CH$_2$-RingD, —CH(CH$_3$)-RingA, —CH(CH$_3$)-RingB, —C(CH$_3$)$_2$-RingA, —C(CH$_3$)$_2$-RingB,

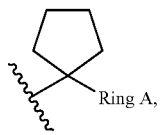 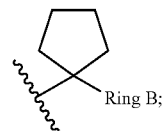

f) methyl, ethyl, propyl, isopropyl, butyl, sec-butyl, tert-butyl, pentyl, isopentyl, hexyl, heptyl, octyl;
g) -ethyl-RingA, -ethyl-RingB, -ethyl-(monocyclic heterocycloalkyl), —CH(RingA)CH$_3$, —CH(RingB)CH$_3$, —CH(monocyclic heterocycloalkyl)CH$_3$, -ethyl-N(R$^r$)R$^s$, —CH[N(R$^r$)R$^s$]CH$_3$; and
h) —CH═CH-RingA, and —CH═CH-RingB;
where each of a)-h) is optionally substituted.

28. A compound according to claim 9, wherein Z is selected from the group consisting of:
a) phenyl, 2-methylphenyl, 3-methylphenyl, 4-methylphenyl, 2-ethylphenyl, 3-ethylphenyl, 4-ethylphenyl, 2-isopropylphenyl, 3-isopropylphenyl, 4-tert-butylphenyl, 2,5-dimethylphenyl, 2,6-dimethylphenyl, 4-hydroxymethylphenyl, 3-vinylphenyl, 4-vinylphenyl, 2-cyclohexylphenyl, 2-methoxyphenyl, 3-methoxyphenyl, 4-methoxyphenyl, 2-fluorophenyl, 3-fluorophenyl, 4-fluorophenyl, 2-chlorophenyl, 3-chlorophenyl, 4-chlorophenyl, 2-bromophenyl, 4-bromophenyl, 2-iodophenyl, 2,3-difluorophenyl, 2-fluoro-5-bromophenyl, 3,5-difluorophenyl, 3,4-dichlorophenyl, 2-chloro-4-fluorophenyl, 2-trifluoromethylphenyl, 4-trifluoromethylphenyl, 4-nitrophenyl, 2-aminophenyl, 2-methylaminophenyl, 2-cyanophenyl, 4-cyanophenyl;
b) 2-pyrrolyl, 2-furanyl, 3-furanyl, 2-thiophenyl, 3-thiophenyl, triazol-5-yl, 1H-methyl-pyrrol-2-yl, 2-ethyl-pyrazol-3-yl, 2-tert-butyl-pyrazol-3-yl, 2-methyl-thiophen-3-yl, 5-methyl-isoxazol-4-yl, 3,5-dimethyl-isoxazol-3-yl, 2-pyridyl, 3-pyridyl, 4-pyridyl, pyrimidin-5-yl, 2-bromo-pyridin-3-yl, 2-methyl-pyridin-3-yl, 2-methylsulfanyl-pyridin-3-yl;
c) tetrahydrofuran-3-yl, 1-cyclohexyl-azetidin-2-yl;
d) cyclopropyl, cyclobutyl, cyclopentyl, cyclohexyl, 2-methyl-2,2,3,3-tetramethylcyclopropyl, 1-methylcyclohexyl, bicyclo[4.2.0]octa-1,3,5-triene;
e) benzyl, 4-fluorobenzyl, 2,5-dimethylbenzyl, 2,6-difluorobenzyl, 2-methoxybenzyl, 1-(4-chloro-phenyl)-1-methyl-ethyl, 1-(4-fluoro-phenyl)-ethyl, 1-phenylethyl, 1-phenylcyclopentyl, 4-methyl-thiophen-3-yl-methyl, 3,5-dimethyl-isoxazol-4-ylmethyl, 4-pyridylmethyl, cyclopropylmethyl, cyclohexylmethyl, 4-isopropyl-piperazin-1-ylmethyl;
f) methyl, ethyl, propyl, isopropyl, butyl, 1-methylpropyl, 2-methylpropyl, isopentyl, pentyl, 1-methylbutyl, 3-methylbutyl, 1-ethylpentyl, 1-propylbutyl,
g) phenethyl, 2-diethylaminoethyl, 2,2,2-trifluoro-1-pyrrolidin-2-ylmethyl-ethyl 2,2,2-trifluoro-1-piperidin-2-ylmethyl-ethyl; and
h) styryl, and 2-(2-methoxy-phenyl)-vinyl.

29. A compound according to claim 9, wherein Z is selected from the group consisting of isopropyl, 1-methypropyl, isopentyl, cyclopropyl, cyclobutyl, cyclopentyl, and cyclohexyl.

30. A compound according to claim 9, wherein Z is piperidin-1-yl or pyrrolidin-1-yl, optionally substituted with methyl, ethyl, phenyl, or pyridinyl.

31. A compound selected from the group consisting of:
2-Ethyl-N-{3-fluoro-4-[4-(2-oxo-1-phenyl-2-pyrrolidin-1-yl-ethyl)-piperazin-1-yl]-phenyl}-butyramide;
2-{4-[4-(2-Ethyl-butyrylamino)-2-fluoro-phenyl]-piperazin-1-ylmethyl}-benzoic acid methyl ester;
2-Ethyl-N-(3-fluoro-4-{4-[3-(morpholin-4-carbonyl)-benzyl]-piperazin-1-yl}-phenyl)-butyramide;
N,N-Diethyl-2-{4-[4-(2-ethyl-butyrylamino)-2-fluoro-phenyl]-piperazin-1-ylmethyl}-benzamide;
2-Ethyl-N-(3-fluoro-4-{4-[2-(morpholine-4-carbonyl)-benzyl]-piperazin-1-yl}-phenyl)-butyramide;
N-{4-[4-(Diethylcarbamoyl-phenyl-methyl)-piperazin-1-yl]-3-fluoro-phenyl}-2-ethyl-butyramide;
2-Ethyl-N-{4-[4-(ethylcarbamoyl-phenyl-methyl)-piperazin-1-yl]-3-fluoro-phenyl}-butyramide;

2-(4-{4-[3-(3,5-Dimethyl-isoxazol-4-yl)-ureido]-2-fluoro-phenyl}-piperazin-1-yl)-N,N-diethyl-2-phenyl-acetamide;
2-(4-{4-[2-(3,5-Dimethyl-isoxazol-4-yl)-acetylamino]-2-fluoro-phenyl}-piperazin-1-yl)-N,N-diethyl-2-phenyl-acetamide;
3,5-Dimethyl-isoxazole-4-carboxylic acid {4-[4-(diethylcarbamoyl-phenyl-methyl)-piperazin-1-yl]-3-fluoro-phenyl}-amide;
2-(4-{4-[3-(3,5-Dimethyl-isoxazol-4-yl)-ureido]-2-fluoro-phenyl}-piperazin-1-yl)-N-ethyl-2-phenyl-acetamide;
2-(4-{4-[2-(3,5-Dimethyl-isoxazol-4-yl)-acetylamino]-2-fluoro-phenyl}-piperazin-1-yl)-N-ethyl-2-phenyl-acetamide;
2-(4-{4-[3-(2,5-Dimethyl-phenyl)-ureido]-2-fluoro-phenyl}-piperazin-1-yl)-N-ethyl-2-phenyl-acetamide;
N-Ethyl-2-(4-{2-fluoro-4-[3-(4-fluoro-benzyl)-ureido]-phenyl}-piperazin-1-yl)-2-phenyl-acetamide;
Phenyl-{4-[4-(3-phenyl-acryloylamino)-phenyl]-piperazin-1-yl}-acetic acid methyl ester;
N-Ethyl-2-[4-(2-fluoro-4-{3-[(S)-1-(4-fluoro-phenyl)-ethyl]-ureido}-phenyl)-piperazin-1-yl]-2-phenyl-acetamide;
(S)-Tetrahydro-furan-3-carboxylic acid {4-[4-(diethylcarbamoyl-phenyl-methyl)-piperazin-1-yl]-3-fluoro-phenyl}-amide;
2-(4-{4-[3-(3,5-Dimethyl-isoxazol-4-yl)-1,3-diethyl-ureido]-2-fluoro-phenyl}-piperazin-1-yl)-N,N-diethyl-2-phenyl-acetamide;
4-[4-(Diethylcarbamoyl-phenyl-methyl)-piperazin-1-yl]-N-(3,5-dimethyl-isoxazol-4-ylmethyl)-3-fluoro-benzamide;
{4-[4-(2-Ethyl-butyrylamino)-2-fluoro-phenyl]-piperazin-1-yl}-(3-fluoro-phenyl)-acetic acid methyl ester;
N-(4-{[Diethylcarbamoyl-(3-fluoro-phenyl)-methyl]-piperazin-1-yl}-3-fluoro-phenyl)-2-ethyl-butyramide;
(4-Cyano-phenyl)-{4-[4-(2-ethyl-butyrylamino)-2-fluoro-phenyl]-piperazin-1-yl}-acetic acid methyl ester;
(3-Chloro-phenyl)-{4-[4-(2-ethyl-butyrylamino)-2-fluoro-phenyl]-piperazin-1-yl}-acetic acid methyl ester;
(2,3-Difluoro-phenyl)-{4-[4-(2-ethyl-butyrylamino)-2-fluoro-phenyl]-piperazin-1-yl}-acetic acid methyl ester;
{4-[2-Chloro-4-(2-methyl-benzoylamino)-phenyl]-piperazin-1-yl}-phenyl-acetic acid methyl ester;
{4-[4-(2-Ethyl-butyrylamino)-2,6-difluoro-phenyl]-piperazin-1-yl}-phenyl-acetic acid methyl ester;
{4-[2,6-Dichloro-4-(2-ethyl-butyrylamino)-phenyl]-piperazin-1-yl}-phenyl-acetic acid methyl ester;
2-Ethyl-N-{4-[4-(ethylcarbamoyl-phenyl-methyl)-piperazin-1-yl]-2-fluoro-phenyl}-butyramide;
{4-[4-(2-Ethyl-butyrylamino)-2-fluoro-phenyl]-piperazin-1-yl}-phenyl-acetic acid methyl ester;
(4-{4-[(Bicyclo[4.2.0]octa-1(6),2,4-triene-7-carbonyl)-amino]phenyl}-piperazin-1-yl)-phenyl-acetic acid methyl ester;
[4-(4-Benzoylamino-phenyl)-piperazin-1-yl]-phenylacetic acid methyl ester;
{4-[4-(Cyclohexanecarbonyl-amino)-phenyl]-piperazin-1-yl}-phenyl-acetic acid methyl ester;
{4-[4-(2-Cyclohexyl-benzoylamino)-phenyl]-piperazin-1-yl}-phenyl-acetic acid methyl ester;
{4-[4-(2-Methyl-benzoylamino)-phenyl]-piperazin-1-yl}-phenyl-acetic acid methyl ester;
{4-[4-(2-Ethyl-benzoylamino)-phenyl]-piperazin-1-yl}-phenyl-acetic acid methyl ester;
{4-[4-(2-Isopropyl-benzoylamino)-phenyl]-piperazin-1-yl}-phenyl-acetic acid methyl ester;
{4-[4-(2-Chloro-benzoylamino)-phenyl]-piperazin-1-yl}-phenyl-acetic acid methyl ester;
{4-[4-(2-Cyano-benzoylamino)-phenyl]-piperazin-1-yl}-phenyl-acetic acid methyl ester;
{4-[4-(2-Fluoro-benzoylamino)-phenyl]-piperazin-1-yl}-phenyl-acetic acid methyl ester;
{4-[4-(2-Methoxy-benzoylamino)-phenyl]-piperazin-1-yl}-phenyl-acetic acid methyl ester;
Phenyl-{4-[4-(2-trifluoromethyl-benzoylamino)-phenyl]-piperazin-1-yl}-acetic acid methyl ester;
{4-[4-(2-Methylamino-benzoylamino)-phenyl]-piperazin-1-yl}-phenyl-acetic acid methyl ester;
{4-[4-(Cyclopentanecarbonyl-amino)-phenyl]-piperazin-1-yl}-phenyl-acetic acid methyl ester;
{4-[4-(2-Ethyl-butyrylamino)-phenyl]-piperazin-1-yl}-phenyl-acetic acid methyl ester;
[4-(4-Benzoylamino-2-fluoro-phenyl)-piperazin-1-yl]-phenyl-acetic acid methyl ester;
{4-[2-Fluoro-4-(2-methyl-benzoylamino)-phenyl]-piperazin-1-yl}-phenyl-acetic acid methyl ester;
{4-[4-(2-Ethyl-benzoylamino)-2-fluoro-phenyl]-piperazin-1-yl}-phenyl-acetic acid methyl ester;
{4-[2-Fluoro-4-(2-isopropyl-benzoylamino)-phenyl]-piperazin-1-yl}-phenyl-acetic acid methyl ester;
{4-[2-Fluoro-4-(2-methoxy-benzoylamino)-phenyl]-piperazin-1-yl}-phenyl-acetic acid methyl ester;
[4-(4-Acetylamino-phenyl)-piperazin-1-yl]-phenyl-acetic acid methyl ester;
[4-(4-Acetylamino-2-fluoro-phenyl)-piperazin-1-yl]-phenyl-acetic acid methyl ester;
{4-[2-Fluoro-4-(2-methylamino-benzoylamino)-phenyl]-piperazin-1-yl}-phenyl-acetic acid methyl ester;
{4-[4-(3-Ethyl-benzoylamino)-phenyl]-piperazin-1-yl}-phenyl-acetic acid methyl ester;
{4-[4-(4-Ethyl-benzoylamino)-phenyl]-piperazin-1-yl}-phenyl-acetic acid methyl ester;
{4-[4-(4-Isopropyl-benzoylamino)-phenyl]-piperazin-1-yl}-phenyl-acetic acid methyl ester;
{4-[4-(3-Methyl-benzoylamino)-phenyl]-piperazin-1-yl}-phenyl-acetic acid methyl ester;
{4-[4-(4-Methyl-benzoylamino)-phenyl]-piperazin-1-yl}-phenyl-acetic acid methyl ester;
Phenyl-(4-{4-[(thiophene-2-carbonyl)-amino]-phenyl}piperazin-1-yl)-acetic acid methyl ester;
{4-[4-(4-Hydroxymethyl-benzoylamino)-phenyl]-piperazin-1-yl}-phenyl-acetic acid methyl ester;
Phenyl-{4-[4-(3-vinyl-benzoylamino)-phenyl]-piperazin-1-yl}-acetic acid methyl ester;
Phenyl-{4-[4-(4-vinyl-benzoylamino)-phenyl]-piperazin-1-yl}-acetic acid methyl ester;
{4-[2-Fluoro-4-(4-methyl-pentanoylamino)-phenyl]-piperazin-1-yl}-phenyl-acetic acid methyl ester;
{4-[4-(2-Ethyl-hexanoylamino)-2-fluoro-phenyl]-piperazin-1-yl}-phenyl-acetic acid methyl ester;
{4-[4-(4-tert-Butyl-benzoylamino)-phenyl]-piperazin-1-yl}-phenyl-acetic acid methyl ester;
[4-(4-Butyrylamino-phenyl)-piperazin-1-yl]-phenyl-acetic acid methyl ester;
{4-[4-(2-Ethyl-hexanoylamino)-phenyl]-piperazin-1-yl}-phenyl-acetic acid methyl ester;
[4-(4-Hexanoylamino-phenyl)-piperazin-1-yl]-phenyl-acetic acid methyl ester;
Phenyl-{4-[4-(3-phenyl-propionylamino)-phenyl]-piperazin-1-yl}-acetic acid methyl ester;

{4-[4-(2-Methyl-pentanoylamino)-phenyl]-piperazin-1-yl}-phenyl-acetic acid methyl ester;
[4-(4-Pentanoylamino-phenyl)-piperazin-1-yl]-phenyl-acetic acid methyl ester;
{4-[4-(4-Methyl-pentanoylamino)-phenyl]-piperazin-1-yl}-phenyl-acetic acid methyl ester;
4-Methyl-pentanoic acid {4-[4-(ethylcarbamoyl-phenyl-methyl)-piperazin-1-yl]-3-fluoro-phenyl}-amide;
2-Ethyl-hexanoic acid {4-[4-(ethylcarbamoyl-phenyl-methyl)-piperazin-1-yl]-3-fluoro-phenyl}-amide;
N-{4-[4-(Ethylcarbamoyl-phenyl-ethyl)-piperazin-1-yl]-3-fluoro-phenyl}-3-phenyl-propionamide;
3-Diethylamino-N-{4-[4-(ethylcarbamoyl-phenyl-methyl)-piperazin-1-yl]-3-fluoro-phenyl}-propionamide;
N-Ethyl-2-{4-[2-fluoro-4-(2-pyridin-4-yl-acetylamino)-phenyl]-piperazin-yl}-2-phenyl-acetamide;
N-{4-[4-(Ethylcarbamoyl-phenyl-methyl)-piperazin-1-yl]-3-fluoro-phenyl}-3,3,3-trifluoro-2-pyrrolidin-2-yl-methyl-propionamide;
N-{4-[4-(Ethylcarbamoyl-phenyl-methyl)-piperazin-1-yl]-3-fluoro-phenyl}-3,3,3-trifluoro-2-piperidin-2-yl-methyl-propionamide;
N-Ethyl-2-(4-{2-fluoro-4-[2-(4-isopropyl-piperazin-1-yl)-acetylamino]-phenyl}-piperazin-1-yl)-2-phenyl-acetamide;
1-Cyclohexyl-azetidine-2-carboxylic acid {4-[4-(ethylcarbamoyl-phenyl-methyl)-piperazin-1-yl]-3-fluoro-phenyl}-amide;
(Z)—N-{4-[4-(Ethylcarbamoyl-phenyl-methyl)-piperazin-1-yl]-3-fluoro-phenyl}-3-(2-methoxy-phenyl)-acryl amide;
Phenyl-(4-{4-[(pyridine-3-carbonyl)-amino]-phenyl}-piperazin-1-yl)-acetic acid methyl ester;
2-Bromo-N-{4-[4-(ethylcarbamoyl-phenyl-methyl)-piperazin-1-yl]-3-fluoro-phenyl}-nicotinamide;
(4-{4-[(Furan-2-carbonyl)-amino]-phenyl}-piperazin-1-yl)-phenyl-acetic acid methyl ester;
(4-{4-[(Furan-3-carbonyl)-amino]-phenyl}-piperazin-1-yl)-phenyl-acetic acid methyl ester;
Phenyl-(4-{4-[(thiophene-3-carbonyl)-amino]-phenyl}-piperazin-1-yl)-acetic acid methyl ester;
Phenyl-(4-{4-[(1H-pyrrole-2-carbonyl)-amino]-phenyl}-piperazin-1-yl)-acetic acid methyl ester;
Phenyl-(4-{4-[(pyridine-4-carbonyl)-amino]-phenyl}-piperazin-1-yl)-acetic acid methyl ester;
Phenyl-(4-{4-[(pyridine-2-carbonyl)-amino]-phenyl}-piperazin-1-yl)-acetic acid methyl ester;
Phenyl-(4-{4-[(1H-pyrazole-4-carbonyl)-amino]-phenyl}-piperazin-1-yl)-acetic acid methyl ester;
Phenyl-(4-{4-[(pyrimidine-5-carbonyl)-amino]-phenyl}-piperazin-1-yl)-acetic acid methyl ester;
{4-[4-(3-Methyl-butyrylamino)-phenyl]-piperazin-1-yl}-phenyl-acetic acid methyl ester;
2-Bromo-N-{4-[4-(diethylcarbamoyl-phenyl-methyl)-piperazin-1-yl]-3-fluoro-phenyl}-benzamide;
N-{4-[4-(Diethylcarbamoyl-phenyl-methyl)-piperazin-1-yl]-fluoro-phenyl}-2-ethyl-N-methyl-butyramide;
4-[4-(Ethylcarbamoyl-phenyl-methy)-piperazin-1-yl]-N-(1-ethyl-propyl)-3-fluoro-benzamide;
Phenyl-[4-(4-phenylcarbamoyl-phenyl)-piperazin-1-yl]-acetic acid methyl ester;
{4-[4-(1-Ethyl-propylcarbamoyl)-2-fluoro-phenyl]-piperazin-1-yl}-phenyl-acetic acid methyl ester;
{4-[4-(1-Ethyl-propylcarbamoyl)-phenyl]-piperazin-1-yl}-phenyl-acetic acid methyl ester;
2-{4-[4-(Acetyl-phenyl-amino)-phenyl]-piperazin-1-yl}-N-indan-5-yl-2-phenyl-acetamide;
2-{4-[4-(3-Ethyl-1-phenyl-ureido)-phenyl]-piperazin-1-yl}-N-indan-5-yl-2-phenyl-acetamide;
(S)-Tetrahydro-furan-3-carboxylic acid {3-cyano-4-[4-(diethylcarbaoyl-phenyl-methyl)-piperazin-1-yl]-phenyl}-amide;
(R)-Tetrahydro-furan-3-carboxylic acid {3-cyano-4-[4-(diethylcarbamoyl-phenyl-methyl)-piperazin-1-yl]-phenyl}-amide;
N-(4-{4-[(5-Bromo-2-fluoro-phenyl)-diethylcarbamoyl-methyl]-piperazin-1-yl}-3-fluoro-phenyl)-2-ethyl-butyramide;
1-Phenyl-cyclopentanecarboxylic acid {4-[4-(diethylcarbamoyl-phenyl-methyl)-piperazin-1-yl]-3-fluoro-phenyl}-amide;
{4-[4-(2-Ethyl-butyrylamino)-2-fluoro-phenyl]-piperazin-1-yl}-phenyl-acetic acid ethyl ester;
2-Ethyl-2H-pyrazole-3-carboxylic acid {4-[4-(diethylcarbamoyl-phenyl-methyl)-piperazin-1-yl]-3-fluoro-phenyl}-amide;
N-(4-{4-[Diethylcarbamoyl-(3-methoxy-phenyl)-methyl]-piperazin-1-yl}-3-fluoro-phenyl)-2-ethyl-butyramide;
Cyclobutanecarboxylic acid {4-[4-(diethylcarbamoyl-phenyl-methyl)-piperazin-1-yl]-3-fluoro-phenyl}-amide;
1-Methyl-cyclohexanecarboxylic acid {4-[4-(diethylcarbamoyl-phenyl-methyl)-piperazin-1-yl]-3-fluoro-phenyl}-amide:
(S)—N-{4-[4-(Diethylcarbamoyl-phenyl-methyl)-piperazin-1-yl]-3-fluoro-phenyl}-2-methyl-butyramide;
2-(4-Chloro-phenyl)-N-{4-[4-(diethylcarbamoyl-phenyl-methyl)-piperazin-1-yl]-3-fluoro-phenyl}-isobutyramide;
Cyclopentanecarboxylic acid {4-[4-(diethylcarbamoyl-phenyl-methyl)-piperazin-1-yl]-3-fluoro-phenyl}-amide;
3,5-Difluoro-phenyl)-{4-[4-(2-ethyl-butyrylamino)-2-fluoro-phenyl]-piperazin-1-yl}-acetic acid methyl ester;
2-Methyl-cyclopropanecarboxylic acid {4-[4-(diethylcarbmoyl-phenyl-methyl)-piperazin-1-yl]-3-fluoro-phenyl}-amide;
(S)-Tetrahydro-furan-3-carboxylic acid (4-{4-[2-(3,3-difluoro-pyrrolidin-1-yl)-2-oxo-1-phenyl-ethyl]-piperazin-1-yl}-3-fluoro-phenyl)-amide;
2,2,3,3-Tetramethyl-cyclopropanecarboxylic acid {4-[4-(diethylcarbamoyl-phenyl-methyl)-piperazin-1-yl]-3-fluoro-phenyl}-amide;
N-(4-{4-[(2-Bromo-5-fluoro-phenyl)-diethylcarbamoyl-methyl]-piperazin-1-yl}-3-fluoro-phenyl)-2-ethyl-butyramide;
N-(4-{4-[Diethylcarbamoyl-(4-fluoro-phenyl)-methyl]-piperazin-1-yl}-fluoro-phenyl)-2-ethyl-butyramide;
N-(4-{4-[2-(4,4-Difluoro-piperidin-1-yl)-1-(4-fluoro-phenyl)-2-oxo-ethyl]-piperazin-1-yl}-3-fluoro-phenyl)-2-ethyl-butyramide;
2-Ethyl-N-(4-{4-[ethylcarbamoyl-(3-fluoro-phenyl)-methyl]-piperazin-1-yl}-3-fluoro-phenyl)-butyramide;
2-{4-[4-(2-Cyclopropyl-acetylamino)-2-fluoro-phenyl]-piperazin-1-yl}-N,N-diethyl-2-phenyl-acetamide;
N,N-Diethyl-2-(4-{2-fluoro-4-[2-(2-methoxy-phenyl)-acetylamino]-phenyl}-piperazin-1-yl)-2-phenyl-acetamide;
2-tert-Butyl-5-methyl-2H-pyrazole-3-carboxylic acid {4-[4-(diethylcarbamoyl-phenyl-methyl)-piperazin-1-yl]-3-fluoro-phenyl}-amide;
diastereomers and pharmaceutically acceptable salts thereof.

32. A compound selected from the group consisting of:
4-[4-(Diethylcarbamoyl-phenyl-methyl)-piperazin-1-yl]-N-(1-ethyl-propyl)-3-fluoro-benzamide;
N-(4-{4-[(3-Chloro-phenyl)-diethylcarbamoyl-methyl]-piperazin-1-yl}-3-fluoro-phenyl)-2-ethyl-butyramide;
N-(4-{4-[2-(4,4-Difluoro-piperidin-1-yl)-1-(3-fluoro-phenyl)-2-oxo-ethyl]-piperazin-1-yl}-3-fluoro-phenyl)-2-ethyl-butyramide;
N-(4-{4-[Diethylcarbamoyl-(2,4-difluoro-phenyl)-methyl]-piperazin-1-yl}-3-fluoro-phenyl)-2-ethyl-butyramide;
N-(4-{4-[2-(3,3-Difluoro-pyrrolidin-1-yl)-1-(4-fluoro-phenyl)-2-oxo-ethyl]-piperazin-1-yl}-3-fluoro-phenyl)-2-ethyl-butyramide;
N-(4-{4-[2-(3,3-Difluoro-pyrrolidin-1-yl)-1-(3-fluoro-phenyl)-2-oxo-ethyl]-piperazin-1-yl}-3-fluoro-phenyl)-2-ethyl-butyramide;
N-(4-{4-[(5-Bromo-2-fluoro-phenyl)-diethylcarbamoyl-methyl]-piperazin-1-yl}-3-fluoro-phenyl)-2-ethyl-butyramide;
N-(4-{4-[Diethylcarbamoyl-(3,4-difluoro-phenyl)-ethyl]-piperazin-1-yl}-3-fluoro-phenyl)-2-ethyl-butyramide;
Cyclopentanecarboxylic acid {3-cyano-4-[4-(diethylcarbamoyl-phenyl-methyl]-piperazin-1-yl}-phenyl)-amide;
N-{3-Bromo-4-[4-(diethylcarbamoyl-phenyl-methyl)-piperazin-1-yl]-phenyl}-2-ethyl-butyramide;
Cyclopentanecarboxylic acid {3-cyano-4-[4-(diethylcarbamoyl-phenyl-methyl)-piperazin-1-yl]-2-fluoro-phenyl}-amide;
N-{4-[4-(Diethylcarbamoyl-phenyl-methyl)-piperazin-1-yl]-2,5-difluoro-phenyl}-2-ethyl-butyramide;
N-{4-[4-(Diethylcarbamoyl-phenyl-methyl)-piperazin-1-yl]-3,5-difluoro-phenyl}-2-ethyl-butyramide;
N-{3-Cyano-4-[4-(diethylcarbamoyl-phenyl-ethyl)-piperazin-1-yl]-2-fluoro-phenyl}-2-ethyl-butyramide;
Cyclopentanecarboxylic acid {4-[4-(diethylcarbamoyl-phenyl-methyl)-piperazin-1-yl]-3,5-difluoro-phenyl}amide;
Cyclopentanecarboxylic acid {4-[4-(diethylcarbamoyl-phenyl-methyl)-piperazin-1-yl]-3-methyl-phenyl}-amide;
N-{4-[4-(Diethylcarbamoyl-phenyl-methyl)-piperazin-1-yl]-3-methyl-phenyl}-2-ethyl-butyramide;
N-{4-[4-(Diethylcarbamoyl-phenyl-methyl)-piperazin-1-yl]-2,3-difluoro-phenyl}-2-ethyl-butyramide;
N-{4-[4-(Diethylcarbamoyl-phenyl-methyl)-piperazin-1-yl]-3-methoxy-phenyl}-2-ethyl-butyramide:
(R)-Tetrahydro-furan-3-carboxylic acid {4-[4-(ethylcarbamoyl-phenyl-methyl)-piperazin-1-yl]-3,5-difluoro-phenyl}-amide;
N-{2-Cyano-4-[4-(diethylcarbamoyl-phenyl-methyl)-piperazin-1-yl]-phenyl}-2-ethyl-butyramide;
Cyclopentanecarboxylic acid {4-[4-(diethylcarbamoyl-phenyl-methyl)-piperazin-1-yl]-3-methoxy-phenyl}-amide;
Cyclopentanecarboxylic acid {4-[4-(ethylcarbamoyl-phenyl-methyl)-piperazin-1-yl]-3,5-difluoro-phenyl}-amide;
2-{4-[4-(2-Cyclopropyl-acetylamino)-2-fluoro-phenyl]-piperazin-1-yl}N,N-diethyl-2-phenyl-acetamide;
2-{4-[4-(2-Cyclopentyl-acetylamino)-2-fluoro-phenyl]-piperazin-1-yl}-N,N-diethyl-2-phenyl-acetamide;
2-Methyl-cyclopropanecarboxylic acid {4-[4-(diethylcarbamoyl-phenyl-methyl)-piperazin-1-yl]-3-fluoro-phenyl}-amide;
Cyclopentanecarboxylic acid {4-[4-(diethylcarbamoyl-phenyl-methyl)-piperazin-1-yl]-3-fluoro-phenyl}-amide;
4-[4-(Diethylcarbamoyl-phenyl-methyl)-piperazin-1-yl]-N-(1-ethyl-propyl)-3-fluoro-benzamide;
N-(3-Cyano-4-{4-[diethylcarbamoyl-(4-methoxy-phenyl)-methyl]-piperazin-1-yl}-phenyl)-2-ethyl-butyramide;
N-(4-{4-[Diethylcarbamoyl-(4-methoxy-phenyl)-ethyl]-piperazin-1-yl}-3-fluoro-phenyl)-2-ethyl-butyramide;
N-(4-{4-[Diethylcarbamoyl-(4-hydroxy-phenyl)-methyl]-piperazin-1-yl}-3-fluoro-phenyl)-2-ethyl-butyramide;
N-(4-{(4-[(4-Chloro-phenyl)-diethylcarbamoyl-methyl]-piperazin-1-yl}-3-fluoro-phenyl)-2-ethyl-butyramide;
N-(4-{4-[(4-Cyano-phenyl)-diethylcarbamoyl-methyl]-piperazin-1-yl}-3-fluoro-phenyl)-2-ethyl-butyramide;
N-(4-{4-[Diethylcarbamoyl-(4-ethoxy-phenyl)-methyl]-piperazin-1-yl}-3-fluoro-phenyl)-2-ethyl-butyramide;
{4-[4-(2-Ethyl-butyrylamino)-2-fluoro-phenyl]-piperazin-1-yl}-(4-hydroxy-phenyl)-acetic acid methyl ester;
{4-[4-(2-Ethyl-butyrylamino)-2-fluoro-phenyl]-piperazin-1-yl}-(4-methoxy-phenyl)-acetic acid methyl ester;
N-{4-[4-(Dimethylcarbamoyl-phenyl-methyl)-piperazin-1-yl]-3-fluoro-phenyl}-2-ethyl-butyramide;
N-{4-[4-(Diethylcarbamoyl-phenyl-methyl)-piperazin-1-yl]-3-fluoromethyl-phenyl}-2-ethyl-butyramide;
N-{4-[4-(Diethylcarbamoyl-phenyl-methyl)-piperazin-1-yl]-2-trifluoromethyl-phenyl}-2-ethyl-butyramide;
N-{4-[4-(Diethylcarbamoyl-phenyl-methyl)-piperazin-1-yl]-2-methyl-phenyl}-2-ethyl-butyramide; and
N-{4-[4-(Diethylcarbamoyl-phenyl-methyl)-piperazin-1-yl]-2-fluoro-phenyl}-2-ethyl-butyramide;
diastereomers and pharmaceutically acceptable salts thereof.

33. A compound selected from the group consisting of:
N,N-Diethyl-2-{-4-[2-fluoro-4-(propane-1-sulfonylamino)-phenyl]-piperazin-1-yl}-2-phenyl-acetamide;
N-{4-[4-(Diethylcarbamoyl-phenyl-methyl)-piperazin-1-yl]-3-fluoro-phenyl)}-N-dipropanesulfonanilide;
2-[4-(4-Cyclopentanecarbonyl-2-fluoro-phenyl)-piperazin-1-yl]-N,N-diethyl-2-phenyl-acetamide;
2-{4-[4-(Cyclopentyl-hydroxyimino-ethyl)-2-fluoro-phenyl]-piperazin-1-yl}-N,N-diethyl-2-phenyl-acetamide;
N,N-Diethyl-2-{4-[2-fluoro-4-(2-methyl-butyryl)-phenyl]-piperazin-1-yl}-2-phenyl-acetamide;
N-{4-[4-(Diethylcarbamoyl-phenyl-methyl)-piperazin-1-yl]-3-fluoro-benzyl}-2-ethyl-butyramide;
{4-[2-Fluoro-4-(5-(3-pentyl)-1,2,5-thiadiazolidine-2-yl, 11-dioxide)-phenyl]-piperazin-1-yl}-phenyl-acetic acid ethyl ester;
2-{4-[4-(1,3-Dipropyl-sulfamoyl)-2-fluoro-phenyl]-piperazin-1-yl}-N,N-diethyl-2-phenyl-acetamide;
3-{4-[4-(Diethylcarbamoyl-phenyl-methyl)-piperazin-1-yl]-3-fluoro-phenyl}-1,2,5-thiadiazolidine, 1,1-dioxide-2-carboxylic acid methyl ester;
N,N-Diethyl-2-{4-[2-fluoro-4-(1,2,5-thiadiazolidine-2-yl,1,1-dioxide)-phenyl]-piperazin-1-yl}-2-phenyl-acetamide;
3-{4-[4-(Ethoxycarbonyl-phenyl-methyl)-piperazin-1-yl]-3-fluoro-phenyl}-1,2,5-thiadiazolidine, 1,1-dioxide-2-carboxylic acid methyl ester;
{4-[2-Fluoro-4-(1,2,5-thiadiazolidine-2-yl,1,1-dioxide)-phenyl]-piperazin yl}-phenyl-acetic acid ethyl ester;

{4-[2-Fluoro-4-(5-(1-Ethyl-pyrrolidin-3-yl)-1,2,5-thiadiazolidine-2-yl,1,1-dioxide)-phenyl]-piperazin-1-yl}-phenyl-acetic acid ethyl ester;
{4-[2-Fluoro-4-(5-(tetrahydro-furan-3-yl)-1,2,5-thiadiazolidine-2-yl,1,1-dioxide)-phenyl]-piperazin-1-yl}-phenyl-acetic acid ethyl ester;
{4-[2-Fluoro-4-(5-propyl-1,2,5-thiadiazolidine-2-yl,1,1-dioxide)-phenyl]-piperazin-1-yl}-phenyl-acetic acid ethyl ester;
{4-[2-Fluoro-4-(5-cyclopentyl-1,2,5-thiadiazolidine-2-yl,1,1-dioxide)-phenyl]-piperazin-1-yl}-phenyl-acetic acid ethyl ester;
2-Ethyl-N-{3-fluoro-4-[4-(hydrazinocarbonyl-phenyl-methyl)-piperazin-1-yl]-phenyl}-butyramide;
4-[4-(Diethylcarbamoyl-phenyl-methyl)-piperazin-1-yl]-3-fluoro-benzoic acid methyl ester;
N,N-Diethyl-2-{4-[2-fluoro-4-(pyridin-2-ylamino)-phenyl]-piperazin-1-yl}-2-phenyl-acetamide;
N,N-Diethyl-2-{4-[2-fluoro-4-(3-methyl-pyridin-2-ylamino)-phenyl]-piperazin-1-yl}-2-phenyl-acetamide;
Bicyclo[2.2.1]heptane-2-carboxylic acid {4-[4-(diethylcarbamoyl-phenyl-methyl)-piperazin-1-yl]-3-fluoro-phenyl}-amide;
N-{4-[4-(Diethylcarbamoyl-phenyl-methyl)-piperazin-1-yl]-3-ethynyl-phenyl}-2-ethyl-butyramide;
N-{4-[4-(Diethylcarbamoyl-phenyl-methyl)-piperazin-1-yl]-3-fluoro-benzyl}-4,4,4-trifluoro-2-methyl-butyramide;
(S)-Tetrahydro-furan-3-carboxylic acid 4-[4-(diethylcarbamoyl-phenyl-methyl)-piperazin-1-yl]-3-fluoro-benzylamide;
N-(4-{4-[Diethylcarbamoyl-(4-trifluoromethoxy-phenyl)-methyl]-piperazin-1-yl}-3-fluoro-phenyl)-2-ethyl-butyramide;
N-{4-[4-(Diethylcarbamoyl-phenyl-methyl)-3-methyl-piperazin-1-yl]-3-fluoro-phenyl}-2-ethyl-butyramide;
N-{4-[4-(Diethylcarbamoyl-pyridin-2-yl-methyl)-2-methyl-piperazin-1-yl]-3-fluoro-phenyl}-2-ethyl-butyramide;
2-Ethyl-N-{3-fluoro-4-[4-(2-oxo-1,2-diphenyl-ethyl)-piperazin-1-yl]-phenyl}-butyramide;
N-{4-[4-(Diethylcarbamoyl-pyridin-2-yl-methyl)-piperazin-1-yl]-3-fluoro-phenyl}-2-ethyl-butyramide;
N-(4-{4-[2-(3,3-Difluoro-pyrrolidin-1-yl)-2-oxo-1-pyridin-2-yl-ethyl]-piperazin-1-yl}-3-fluoro-phenyl)-2-ethyl-butyramide;
{4-[4-(2-Ethyl-butyrylamino)-2-fluoro-phenyl]-piperazin-1-yl}-pyridin-2-yl-acetic acid methyl ester;
4-[4-(2-Ethyl-butyrylamino)-2-fluoro-phenyl]-1-(methoxycarbonyl-phenyl-methyl)-piperazine-2-carboxylic acid methyl ester
2-Ethyl-N-{3-fluoro-4-[4-(2-hydroxy-1-phenyl-ethyl)-piperazin-1-yl]-phenyl}-butyramide;
2-Ethyl-N-{3-fluoro-4-[4-(1-phenyl-ethyl)-piperazin-1-yl]-phenyl}-butyramide;
N-[4-(4-Benzyl-piperazin-1-yl)-3-fluoro-phenyl]-2-ethyl-butyramide;
1-Benzo[1,3]dioxol-5-ylmethyl-4-[4-(2-ethyl-butyrylamino)-2-fluoro-phenyl]-piperazine-2-carboxylic acid methyl ester;
1-Benzyl-4-[4-(2-ethyl-butyrylamino)-2-fluoro-phenyl]-piperazine-2-carboxylic acid methyl ester;
1-(3,5-Difluoro-benzyl)-4-[4-(2-ethyl-butyrylamino)-2-fluoro-phenyl]-piperazine-2-carboxylic acid methyl ester;
N,N-Diethyl-2-{4-[2-fluoro-4-(2-oxo-pyrrolidin-1-yl)-phenyl]-piperazin-1-yl}-2-phenyl-acetamide;
N,N-Diethyl-2-(4-{2-fluoro-4-[2-oxo-2-(2-phenyl-piperidin-1-yl)-ethyl]-phenyl}-piperazin-1-yl)-2-phenyl-acetamide;
N,N-Diethyl-2-(4-{2-fluoro-4-[2-oxo-2-(2-phenyl-pyrrolidin-1-yl)-ethyl]-phenyl}-piperazin-1-yl)-2-phenyl-acetamide;
N,N-Diethyl-2-(4-{4-[2-(2-ethyl-piperidin-1-yl)-2-oxo-ethyl]-2-fluoro-phenyl}-piperazin-1-yl)-2-phenyl-acetamide;
N,N-Diethyl-2-(4-{2-fluoro-4-[(furan-2-ylmethyl-methyl-carbamoyl)-methyl]-phenyl}-piperazin-1-yl)-2-phenyl-acetamide;
2-(4-{4-[2-(2,5-Dimethyl-pyrrolidin-1-yl)-2-oxo-ethyl]-2-fluoro-phenyl}-piperazin-1-yl)-N,N-diethyl-2-phenyl-acetamide;
N,N-Diethyl-2-(4-{2-fluoro-4-[2-oxo-2-(3,4,5,6-tetrahydro-2H-[2,3']bipyridinyl-1-yl)-ethyl]-phenyl}-piperazin-1-yl)-2-phenyl-acetamide;
N,N-Diethyl-2-(4-{4-[(1-ethyl-propylcarbamoyl)-methyl]-2-fluoro-phenyl}-piperazin-1-yl)-2-phenyl-acetamide;
N,N-Diethyl-2-(4-{2-fluoro-4-[2-(2-methyl'-pyrrolidin-1-yl)-2-oxo-ethyl]-phenyl}-piperazin-1-yl)-2-phenyl-acetamide;
N,N-Diethyl-2-{4-[2-fluoro-4-(2-oxo-2-pyrrolidin-1-yl-ethyl)-phenyl]-piperazin-1-yl}-2-phenyl-acetamide;
N,N-Diethyl-2-{4-[4-(3-ethyl-2-oxo-1-phenyl-pentyl)-piperazin-1-yl]-3-fluoro-phenyl}-acetamide,
N-Benzyl-2-{4-[4-(3-ethyl-2-oxo-1-phenyl-pentyl)-piperazin-1-yl]-3-fluoro-phenyl}-acetamide;
N-Benzyl-2-{4-[4-(3-ethyl-2-oxo-1-phenyl-pentyl)-piperazin-1-yl]-3-fluoro-phenyl}-N-methyl-acetamide;
N-Benzyl-N-ethyl-2-{4-[4-(3-ethyl-2-oxo-1-phenyl-pentyl)-piperazin-1-yl]-3-fluoro-phenyl}-acetamide;
2-(4-{4-[2-(3,3-Difluoro-pyrrolidin-1-yl)-2-oxo-1-phenyl-ethyl]piperazin-1-yl}-3-fluoro-phenyl)-N-(1-ethyl-propyl)-acetamide;
2-(4-{4-[2-(3,3-Difluoro-pyrrolidin-1-yl)-2-oxo-1-phenyl-ethyl]-piperazin-1-yl}-3-fluoro-phenyl)-N,N-diethyl-acetamide;
N,N-Diethyl-2-[4-(4-ethylcarbamoylmethyl-2-fluoro-phenyl)-piperazin-1-yl]-2-phenyl-acetamide; and
2-[4-(4-Cyclopentylcarbamoylmethyl-2-fluoro-phenyl)-piperazin-yl]-N,N-diethyl-2-phenyl-acetamide:
diastereomers and pharmaceutically acceptable salts thereof.

34. A pharmaceutical composition for treating a disease, disorder, or medical condition mediated by NPY Y2 activity, comprising:
(a) an effective amount of an agent selected from the group consisting of compounds of Formula (I):

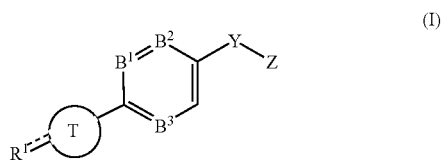

wherein
$B^1$, $B^2$, and $B^3$ are each independently CH, or $CR^2$;
where each $R^2$ is independently —$C_{1-4}$alkyl, -ethynyl, —$C_{3-8}$cycloalkyl, —$OC_{1-4}$alkyl, halo, —$CF_3$, or —CN;

Ring T is

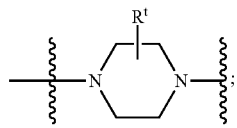

where $R^t$ is —H, —$C_{1-4}$alkyl, or —$CO_2C_{1-4}$alkyl,
$R^1$ is

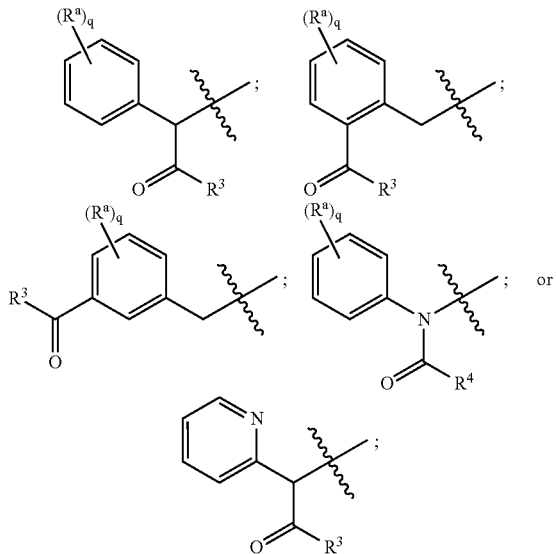

where q is 0, 1, 2, or 3;
each $R^a$ is independently —$C_{1-4}$alkyl, —$C_{3-8}$cycloalkyl, —OH, halo, —$NO_2$, —$N(R^u)R^v$, —$CF_3$, —$OCF_3$, —C(O)—$C_{1-4}$alkyl, —C(O)O$C_{1-4}$alkyl, —CN, —$S(O)_{1-2}$—$C_{1-6}$alkyl, —$N(R^u)$—$S(O)_{1-2}$—$C_{1-6}$alkyl, —$S(O)_{1-2}$—$N(R^u)R^v$, or a 4- to 7-membered monocyclic heterocycloalkyl, or two adjacent $R^a$ substituents taken together form —$O(CH_2)_{1-2}$—O—;
where $R^u$ and $R^v$ are each independently —H or —$C_{1-4}$alkyl;
$R^3$ is selected from the group consisting of:
i) —$OC_{1-4}$alkyl, —$OC_{3-4}$alkenyl, —O-benzyl, —O-phenyl, —$NHNH_2$, phenyl;
ii) —$NR^bR^c$, where $R^b$ is —H or —$C_{1-4}$alkyl and $R^c$ is a —$C_{1-4}$alkyl, —$C_{3-4}$alkenyl, monocyclic cycloalkyl optionally fused to phenyl, or monocyclic heterocycloalkyl group, each optionally substituted with $R^d$;
where $R^d$ is —$C_{1-4}$alkyl, —$OC_{1-4}$alkyl, —OH, —$CF_3$, —$OCF_3$, halo, —$NO_2$, —$N(R^e)R^f$, —C(O)—$C_{1-4}$alkyl, —C(O)phenyl, —C(O)O$C_{1-4}$alkyl, —CN, —$S(O)_{1-2}$—$C_{1-6}$alkyl, —$N(R^e)$—$S(O)_{1-2}$—$C_{1-6}$alkyl, or —$S(O)_{1-2}$—N($R^e)R^f$, or a 4- to 7-membered monocyclic heterocycloalkyl group optionally substituted with —$C_{1-4}$alkyl, fluoro, or —$CF_3$;
where $R^e$ is —H or —$C_{1-4}$alkyl and $R^f$ is —$C_{1-4}$alkyl;
iii) —$NR^gR^h$, where $R^g$ is —H or —$C_{1-4}$alkyl and $R^h$ is —$(CH_2)_{0-2}$-phenyl or —$(CH_2)_{0-2}$-(monocyclic heteroaryl);
where each phenyl or heteroaryl is optionally substituted with $R^i$;

$R^i$ is —$C_{1-4}$alkyl, —$OC_{1-4}$alkyl, —OH, —$CF_3$, —$OCF_3$, halo, —CN, or —$NR^jR^k$,
where $R^j$ and $R^k$ are independently —H or —$C_{1-4}$alkyl, or $R^j$ and $R^k$ taken together with their nitrogen of attachment form a 4- to 7-membered monocyclic heterocycloalkyl; and
iv) a nitrogen-linked 4- to 7-membered monocyclic heterocycloalkyl, optionally substituted with —$C_{1-4}$alkyl, —$OC_{1-4}$alkyl, —OH, —$CF_3$, —$OCF_3$, halo, —CN, —C(O)—$C_{1-4}$alkyl, —C(O)O$C_{1-4}$alkyl, or —$NR^jR^k$;
$R^4$ is —$C_{1-8}$alkyl, phenyl, or monocyclic heteroaryl, where each phenyl or heteroaryl is optionally substituted with —$C_{1-4}$alkyl, —$C_3$cycloalkyl, —$OC_{1-4}$alkyl, —OH, halo, —$NO_2$, —$N(R^w)R^x$, —$CF_3$, —C(O)O$C_{1-4}$alkyl, or —CN;
where and $R^x$ are each independently —H or —$C_{1-4}$alkyl:
Y is selected from the group consisting of —CH(OH)—, —C(O)—, —$CH_2$C(O)—, —C(=N—OH)—, —$CO_2$—, —C(O)N($R^L$)—, —$CH_2$C(O)N($R^L$)—, —N($R^L$)—, N($R^L$)C(O), —N($R^y$)C(O)—, —$CH_2$N($R^L$)C(O)—, —N($R^L$)C(O)N($R^L$)—, —N($R^L$)$SO_2$—, —N($SO_2C_{1-4}$alkyl)$SO_2$—, —N($R^L$)$SO_2$N($R^L$)—, —N($R^z$)$SO_2$NH—, and —N($R^L$)$SO_2$N($R^L$)$CO_2$—:
where each $R^L$ is —H, —$C_{1-4}$alkyl, or phenyl; or, alternatively, two $R^L$ groups taken together form —$CH_2CH_2$—, wherein Y is not

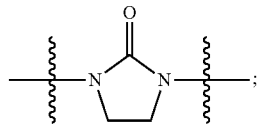

$R^y$ and Z together form —$(CH_2)_3$— or —$(CH_2)_4$—, optionally substituted with —$C_{1-4}$alkyl; and
$R^z$ and Z together form —$(CH_2)_2$— or —$(CH_2)_3$—, each optionally substituted with —$C_{1-4}$alkyl;
Z is selected from the group consisting of:
a) RingA, where RingA is phenyl, optionally mono-, di-, or tri-substituted with $R^m$;
where each $R^m$ is independently selected from the group consisting of —$C_{1-6}$alkyl, —$C_{1-6}$alkyl-OH, —$CF_3$, —$C_{2-6}$alkenyl, —$C_{2-6}$alkynyl, —$C_{3-8}$cycloalkyl, —CN, —$NO_2$, —$N(R^n)R^o$, —C(O)$C_{1-6}$alkyl, —C(O)OH, —C(O)O$C_{1-6}$alkyl, —C(O)N($R^n)R^o$, —S—$C_{1-6}$alkyl, —$S(O)_{1-2}$—$C_{1-6}$alkyl, —$SCF_3$, halo, —OH, —$OC_{1-6}$alkyl, —$OCF_3$, —$OC_{3-6}$alkenyl, and —$OC_{3-6}$alkynyl;
where $R^n$ and $R^o$ are each independently —H or —$C_{1-6}$alkyl;
b) RingB, where RingB is monocyclic or fused bicyclic heteroaryl, optionally mono-, di-, or tri-substituted with $R^m$;
c) RingC, where RingC is heterocycloalkyl, optionally mono- or di-substituted with —$C_{1-4}$alkyl, —$C_{3-8}$cycloalkyl, halo, phenyl, or pyridyl;
d) RingD, where RingD is monocyclic cycloalkyl, optionally substituted with —OH, halo, or —$C_{1-4}$alkyl, and optionally fused to phenyl;
e) —C($R^q)_2$-RingA, —C($R^q)_2$-RingB, —$CH_2$-RingC, —$CH_2$-RingD;
where each $R^q$ is —H or —$C_{1-4}$alkyl, or two $R^q$ substituents taken together form a $C_{3-6}$cycloalkyl;

f) —C$_{1-8}$alkyl, optionally substituted with —OH, halo, or —CF$_3$;
g) -ethyl substituted with RingA, RingB, monocyclic heterocycloalkyl, or —N(R$^r$)R$^s$, and optionally further substituted with —OH or —CF$_3$;
  where R$^r$ and R$^s$ are each independently —H or —C$_{1-4}$alkyl;
h) —CH=CH-RingA, —CH=CH-RingB; and
i) bicyclo[2.2.1]heptan-2-yl;
or a pharmaceutically acceptable salt, or a pharmaceutically acceptable prodrug of such compound; and
(b) a pharmaceutically acceptable excipient.

35. A pharmaceutical composition for treating a disease, disorder, or medical condition mediated by NPY Y2 activity, comprising:
(a) an effective amount of an agent selected from the group consisting of compounds of Formula (II):

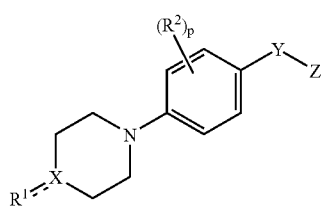

(II)

wherein X is N and R$^1$ is

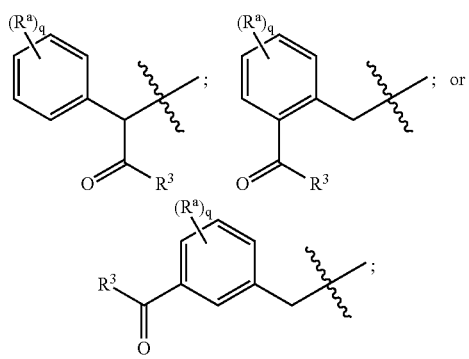

; or where q is 0, 1, 2, or 3;
  each R$^a$ is independently —C$_{1-4}$alkyl, —C$_{3-8}$cycloalkyl, —OC$_{1-4}$alkyl, —OH, halo, —NO$_2$, —N(R$^u$)R$^v$, —CF$_3$, —C(O)—C$_{1-4}$alkyl, —C(O)OC$_{1-4}$alkyl, —CN, —S(O)$_{1-2}$—C$_{1-6}$alkyl, —N(R$^u$)—S(O)$_{1-2}$—C$_{1-6}$alkyl, —S(O)$_{1-2}$—N(R$^u$)R$^v$, or a 4- to 7-membered, monocyclic heterocycloalkyl, or two adjacent R$^a$ substituents taken together form —O(CH$_2$)$_{1-2}$—O—;
  where R$^u$ and R$^v$ are each independently —H or —C$_{1-4}$alkyl;
R$^3$ is selected from the group consisting of:
  i) —OC$_{1-4}$alkyl, —OC$_{3-4}$alkenyl, —O-benzyl, —O-phenyl, phenyl;
  ii) —NR$^b$R$^c$, where R$^b$ is —H or —C$_{1-4}$alkyl and R$^c$ is a —C$_{1-4}$alkyl, —C$_{3-4}$alkenyl, monocyclic cycloalkyl optionally fused to phenyl, or monocyclic heterocycloalkyl group, each optionally substituted with R$^d$;
    where R$^d$ is —C$_{1-4}$alkyl, —OC$_{1-4}$alkyl, —OH, —CF$_3$, —OCF$_3$, halo, —NO$_2$, —N(R$^e$)R$^f$, —C(O)—C$_{1-4}$alkyl, —C(O)phenyl, —C(O)OC$_{1-4}$alkyl, —CN, —S(O)$_{1-2}$—C$_{1-6}$alkyl, —N(R$^e$)—S(O)$_{1-2}$—C$_{1-6}$alkyl, or —S(O)$_{1-3}$—N(R$^e$)R$^f$, or a 4- to 7-membered monocyclic heterocycloalkyl group optionally substituted with —C$_{1-4}$alkyl, fluoro, or —CF$_3$;
    where R$^e$ is —H or —C$_{1-4}$alkyl and R$^f$ is —C$_{1-4}$alkyl;
  iii) —NR$^g$R$^h$, where R$^g$ is —H or —C$_{1-4}$alkyl and R$^h$ is —(CH$_2$)$_{0-2}$-phenyl or —(CH$_2$)$_{0-2}$-(monocyclic heteroaryl);
    where each phenyl or heteroaryl is optionally substituted with R$^i$;
      R$^i$ is —C$_{1-4}$alkyl, —OC$_{1-4}$alkyl, —OH, —CF$_3$, —OCF$_3$, halo, —CN, or —NR$^j$R$^k$;
      where R$^j$ and R$^k$ are independently —H or —C$_{1-4}$alkyl, or R$^j$ and R$^k$ taken together with their nitrogen of attachment form a 4- to 7-membered monocyclic heterocycloalkyl; and
  iv) a nitrogen-linked 4- to 7-membered monocyclic heterocycloalkyl, optionally substituted with —C$_{1-4}$alkyl, —OC$_{1-4}$alkyl, —OH, —CF$_3$—OCF$_3$, halo, —CN, —C(O)OC$_{1-4}$alkyl, or —NR$^j$R$^k$;
p 0, 1, or 2;
each R$^2$ is independently —C$_{1-4}$alkyl, —C$_{3-8}$cycloalkyl, —OC$_{1-4}$alkyl, halo, —CF$_3$, or —CN;
Y is selected from the group consisting of —N(R$^L$)C(O)—, —C(O)N(R$^L$)—, and —N(R$^L$)C(O)N(R$^L$)—;
  where each R$^L$ is —H, —C$_{1-4}$alkyl, or phenyl;
Z is selected from the group consisting of:
a) RingA, where RingA is phenyl, optionally mono-, di-, or tri-substituted with R$^m$;
  where each R$^m$ is independently selected from the group consisting of —C$_{1-6}$alkyl, —C$_{1-6}$alkyl-OH, —CF$_3$, —C$_{2-6}$alkenyl, —C$_{2-6}$alkynyl, —C$_{3-8}$cycloalkyl, —CN, —NO$_2$, —N(R$^n$)R$^o$, —C(O)C$_{1-6}$alkyl, —C(O)OH, —C(O)OC$_{1-6}$alkyl, —C(O)N(R$^n$)R$^o$, —S—C$_{1-6}$alkyl, —S(O)$_{1-2}$—C$_{1-6}$alkyl, —SCF$_3$, halo, —OH, —OC$_{1-6}$alkyl, —OCF$_3$, —OC$_{3-6}$alkenyl, and —OC$_{3-6}$alkynyl;
    where R$^n$ and R$^o$ are each independently —H or —C$_{1-6}$alkyl;
b) RingB, where RingB is monocyclic or fused bicyclic heteroaryl, optionally mono-, di-, or tri-substituted with R$^m$;
c) RingC, where RingC is heterocycloalkyl, optionally substituted with —C$_{1-4}$alkyl, —C$_{3-8}$cycloalkyl, or halo;
d) Ring, where RingD is monocyclic cycloalkyl, optionally substituted with —OH, halo, or —C$_{1-4}$alkyl, and optionally fused to phenyl;
e) —C(R$^q$)$_2$—RingA, —C(R$^q$)$_2$-RingB, —CH$_2$-RingC, —CH$_2$-RingD;
  where each R$^q$ is —H or —C$_{1-4}$alkyl, or two R$^q$ substituents taken together form a C$_{3-6}$cycloalkyl;
f) —C$_{1-8}$alkyl, optionally substituted with —OH, halo, or —CF$_3$;
g) -ethyl substituted with RingA, RingB, monocyclic heterocycloalkyl, or —N(R$^r$)R$^s$, and optionally further substituted with —OH or —CF$_3$;
  where R$^r$ and R$^s$ are each independently —H or —C$_{1-4}$alkyl;
h) —CH=CH—RingA, and —CH=CH-RingB;
or a pharmaceutically acceptable salt, or a pharmaceutically acceptable prodrug of such compound; and
(b) a pharmaceutically acceptable excipient.

* * * * *